(12) United States Patent
Kruegel et al.

(10) Patent No.: US 11,840,541 B2
(45) Date of Patent: Dec. 12, 2023

(54) OPIOID RECEPTOR MODULATORS

(71) Applicants: Andrew C. Kruegel, New York, NY (US); Madalee G. Wulf, Beverly, MA (US); Jonathan A. Javitch, Dobbs Ferry, NY (US); Dalibor Sames, New York, NY (US)

(72) Inventors: Andrew C. Kruegel, New York, NY (US); Madalee G. Wulf, Beverly, MA (US); Jonathan A. Javitch, Dobbs Ferry, NY (US); Dalibor Sames, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/528,339

(22) PCT Filed: Nov. 25, 2015

(86) PCT No.: PCT/US2015/062726
§ 371 (c)(1),
(2) Date: May 19, 2017

(87) PCT Pub. No.: WO2016/086158
PCT Pub. Date: Jun. 2, 2016

(65) Prior Publication Data
US 2017/0334923 A1    Nov. 23, 2017

Related U.S. Application Data

(60) Provisional application No. 62/084,994, filed on Nov. 26, 2014, provisional application No. 62/204,318, filed on Aug. 12, 2015.

(51) Int. Cl.
| | | |
|---|---|---|
| *C07D 491/12* | (2006.01) | |
| *C07D 491/18* | (2006.01) | |
| *A61P 25/24* | (2006.01) | |
| *A61P 25/04* | (2006.01) | |
| *C07D 495/18* | (2006.01) | |
| *C07D 471/18* | (2006.01) | |
| *A61K 9/00* | (2006.01) | |
| *A61K 9/70* | (2006.01) | |
| *A61K 31/485* | (2006.01) | |
| *A61K 47/38* | (2006.01) | |

(52) U.S. Cl.
CPC .......... *C07D 491/18* (2013.01); *A61K 9/0073* (2013.01); *A61K 9/7092* (2013.01); *A61K 31/485* (2013.01); *A61P 25/04* (2018.01); *A61P 25/24* (2018.01); *C07D 471/18* (2013.01); *C07D 495/18* (2013.01); *A61K 9/0002* (2013.01); *A61K 47/38* (2013.01)

(58) Field of Classification Search
CPC .. C07D 491/18; C07D 471/18; C07D 495/18; C07D 491/12; A61P 25/04; A61K 31/485
USPC ......................................................... 549/200
See application file for complete search history.

(56) References Cited

U.S. PATENT DOCUMENTS

| | | |
|---|---|---|
| 3,716,528 A | 2/1973 | Nagata et al. |
| 5,869,672 A | 2/1999 | Kozikowski et al. |
| 8,337,941 B2 | 12/2012 | Gubernator et al. |
| 8,741,891 B1 | 6/2014 | Mash |
| 9,075,014 B2 | 7/2015 | Sames et al. |
| 9,988,377 B2 | 6/2018 | Sames et al. |
| 10,183,919 B2 | 1/2019 | Kruegel et al. |
| 2008/0194522 A1 | 8/2008 | Chen et al. |
| 2010/0035279 A1 | 2/2010 | Gubernator et al. |
| 2013/0171664 A1 | 7/2013 | Sames et al. |
| 2013/0190497 A1 | 7/2013 | Gubernator et al. |
| 2015/0056699 A1 | 2/2015 | Sames et al. |
| 2017/0217913 A1 | 8/2017 | Kruegel et al. |
| 2019/0047970 A1 | 2/2019 | Kruegel et al. |
| 2019/0084983 A1 | 3/2019 | Kruegel et al. |

FOREIGN PATENT DOCUMENTS

| | | |
|---|---|---|
| EP | 0 468 562 A1 | 1/1992 |
| WO | WO 2006/023821 A2 | 3/2006 |
| WO | WO 2006/026368 A2 | 3/2006 |
| WO | WO 2007/022263 A1 | 2/2007 |
| WO | WO 2008/013997 A2 | 1/2008 |
| WO | WO 2011/094560 A1 | 8/2011 |

(Continued)

OTHER PUBLICATIONS

Synthesis of a new series of iboga analogues. Sibasish Paul et al. (Year: 2011).*
Conoliferine and isoconoliferine, structually novel alkaloid-lignan conjugates from Tabernarmontana corymbosa. Kuan-Hon Lim et al. (Year: 2009).*

(Continued)

*Primary Examiner* — John S Kenyon
(74) *Attorney, Agent, or Firm* — Gary J. Gershik

(57) ABSTRACT

The present invention provides a compound having the structure wherein A is a ring structure, with or without substitution; X1 is C or N; X2 is N, O, or S; Y1 is H, -(alkyi), -(alkenyl), -(alkynyl), -(cycloalkyi), (haloalkyi), -(alkyl)-O-(alkyl or -(alkyl)-(cycloalkyl); Y 2 is H, -(alkyi), -(alkenyl), -(alkynyl), -(cycloalkyi), (haloalkyi), -(alkyl)-O-(alkyl) or -(alkyl)-(cycloalkyl); Y3 is H-(alkyi), -(alkenyl), -(alkynyl), -(cycloalkyi), (haloalkyi), -(alkyl)-O-(alkyl) or -(alkyl)-(cycloalkyl); Y 4 is H-(alkyi), -(alkenyl), -(alkynyl), -(cycloalkyi), (haloalkyi), -(alkyl)-O-(alkyl) or -(alkyl)-(cycloalkyl); Y5 is H, -(alkyi), -(alkenyl), -(alkynyl), -(cycloalkyi), (haloalkyi), -(alkyl)-O-(alkyl) or -(alkyl)-(cycloalkyl); a and P are each present or absent and when present each is a bond.

27 Claims, 4 Drawing Sheets

(56) References Cited

FOREIGN PATENT DOCUMENTS

| WO | WO 2013/028999 A1 | 2/2013 |
| WO | WO 2013/112757 A1 | 8/2013 |
| WO | WO 2015/138791 A1 | 9/2015 |
| WO | WO 2016/086158 A1 | 6/2016 |
| WO | WO 2017/049158 A1 | 3/2017 |
| WO | WO 2017/165738 A1 | 9/2017 |
| WO | WO 2018/170275 A1 | 9/2018 |

OTHER PUBLICATIONS

Kruegel, A., et al. "Constructing Iboga Alkaloids via C-H Bond Functionalization: Examination of the Direct and Catalytic Union of Heteroarenes and Isoquinuclidine Alkenes." J. Org. Chem. (2015), vol. 80, pp. 2062-2071. (Year: 2015).*

Paul, Sibasish, et al. "Synthesis of new series of iboga analogues." Tetrahedron Letters. (2011), vol. 52, pp. 6166-6169. (Year: 2011).*

International Search Report dated Oct. 26, 2012 in connection with International Application PCT/US2012/052327.

Notification of Transmittal of the International Search Report and the Written Opinion of the International Searching Authority, or Declaration dated Oct. 26, 2012 in connection with International Application PCT/US2012/052327.

Written Opinion of the International Search Authority dated Oct. 26, 2012 in connection with International Application PCT/US2012/052327.

International Preliminary Report on Patentability dated Feb. 25, 2014 in connection with International Application PCT/US2012/052327.

Office Action dated Aug. 4, 2016 in connection with U.S. Appl. No. 14/240,681.

Office Action dated Feb. 8, 2017 in connection with U.S. Appl. No. 14/240,681.

Office Action dated Jun. 6, 2017 in connection with U.S. Appl. No. 14/240,681.

Notification of Transmittal of the International Search Report and the Written Opinion of the International Searching Authority, or Declaration dated Feb. 5, 2016 in connection with International Application PCT/US2015/062726.

Eketjall, S. et al. "Distinct structural elements in GDNF mediate binding to the GFRa1 and activation of the GFRa1-c-Ret receptor complex." EMBO Journal 1999, 18, 5901-5910.

Johnstone, R. et al. "A rapid, simple, and mild procedure for alkylation of phenols, alcohols, amides and acids" Tetrahedron 1979 vol. 35, 2169-2173.

Nakano et al. "A novel chiral oxazolidine organocatalyst for the synthesis of an oseltamivir intermediate using a highly enantioselective Diels-Alder reaction of 1,2-dihydropyridine" Chemical Communications. 2010, vol. 46, 4827-4829.

Jana et al. (2010) Tet. Lett. 51, 1441-1443.

Caplus Document No. 143:248545 (2005).

Caplus Document No. 92:6781 (1979).

Registry No. 663195-14-0 (2004).

Kruegel et al. "Constructing Iboga Alkaloids via C-H Bond Functionalization: Examination of the Direct and Catalytic Union of Heteroarenes and Isoquinuclidine Alkenes" J. Org. Chem. 2015, 80, 2062-2071.

S. Paul, et al., "Synthesis of new series of iboga analogues", Tetrahedron Letters 52(2011) pp. 6166-6169.

International Search Report in connection with PCT International Application No. PCT/US2015/062726.

Written Opinion of the International Searching Authority in connection with PCT International Application No. PCT/US2015/062726.

Extended European Search Report dated Apr. 13, 2018 in connection with European Patent Application EP15863352.9.

Amendment filed Nov. 13, 2018 in connection with European Patent Application EP15863352.9.

Office Action dated Jun. 17, 2019 in connection with European Patent Application EP15863352.

Kruegel, A.C., "Chemical and Biological Explorations of Novel Opioid Receptor Modulators" PhD Thesis, Columbia University, Aug. 26, 2015; 1-930.

Office Action dated Mar. 2, 2020 in connection with European Patent Application EP15863352.

Office Action dated Feb. 2, 2021 in connection with European Patent Application EP15863352.

Office Action dated Sep. 30, 2021 in connection with European Patent Application EP15863352.

Sames, D., "Chemistry and Pharmacology of Iboga Alkaloids" Abstract Text, from Project No. 1R01DA050613-01, Awarded by National Institute on Drug Abuse, Jun. 3, 2020.

Amendment in Response to Aug. 4, 2016 Office Action filed on Nov. 4, 2016, in connection with U.S. Appl. No. 14/240,681.

Amendment in Response to Feb. 8, 2017 Office Action filed on May 8, 2017, in connection with U.S. Appl. No. 14/240,681.

Amendment in Response dated Jun. 6, 2017 Office Action filed on Nov. 6, 2017, in connection with U.S. Appl. No. 14/240,681.

Response to Communication Pursuant to Article 94(3) EPC dated Jun. 17, 2019, filed on Oct. 17, 2019, in connection with European Patent Application No. EP 15 863 352.9.

Response to Communication Pursuant to Article 94(3) EPC dated Mar. 2, 2020, filed on Sep. 14, 2020, in connection with European Patent Application No. EP 15 863 352.9.

Response to Communication Pursuant to Article 94(3) EPC dated Feb. 2, 2021, filed on Jun. 9, 2021, in connection with European Patent Application No. EP 15 863 352.9.

Response to Communication Pursuant to Article 94(3) EPC dated Sep. 30, 2021, filed on Mar. 30, 2022, in connection with European Patent Application No. EP 15 863 352.9.

File history of U.S. Pat. No. 9,988,377 B2, dated Jun. 5, 2018, to Sames et al.

* cited by examiner

OPIOID RECEPTOR MODULATORS

CROSS-REFERENCE TO RELATED APPLICATIONS

This application is a § 371 national stage of PCT International Application No. PCT/US2015/062726, filed Nov. 25, 2015, claiming the benefit of U.S. Provisional Applications Nos. 62/204,318, filed Aug. 12, 2015 and 62/084,994, filed Nov. 26, 2014, the contents of each of which are hereby incorporated by reference into the application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

The mu-opioid receptor (MOR) has been a significant molecular target for treatment of pain for several decades. However, the vast majority of MOR agonists used clinically today are structurally related to, or derived from, alkaloids of the opium poppy (e.g. morphine). These compounds suffer from various drawbacks, including rapid development of tolerance (increased dosing is required to achieve the same analgesic effects), high addiction liability, and other side effects (e.g., respiratory depression, nausea, and constipation) (Williams, J. T. et al. 2013). Agonists of the related kappa-opioid receptor (KOR) have also been explored as potential analgesics. However, existing KOR agonists also suffer from significant disadvantages, including profound dysphoric and dissociative effects at high doses (Chavkin, C. 2011). Accordingly, there is continuing interest in the development of novel pain medications, including new MOR and/or KOR modulators with improved therapeutic profile (Corbett, A. D. et al. 2006).

Both KOR agonists and antagonists have also been suggested as potential treatments for drug addiction or abuse. For example, KOR agonists reduce self-administration of cocaine in addicted monkeys (Negus, S. S. et al. 1997) and inhibit reinstatement of cocaine self-administration in rats (Schenk, S. et al. 2000).

Furthermore, there is both historical and growing interest in the use of MOR modulators as medicaments for depression. Prior to the adoption of tricyclic antidepressants and electroshock therapy as favored treatments for depression, opiates were among the only options available. More recently, studies in rodents (Besson, A. et al. 1996) have suggested that MOR activation may lead to antidepressant and/or anxiolytic effects. On the molecular level, MORs are extensively expressed in the hippocampus and have been shown to exert a variety of indirect modulatory effects on glutamatergic neurons in this brain region (Xie, C. W. et al. 1997; Svoboda, K. R. et al. 1999). Normalization and modulation of glutamate signaling has been strongly associated with the actions of antidepressants (Paul, I. A. and Skolnick, P. 2003) and indeed, the N-methyl-D-aspartate receptor antagonist ketamine, shows rapid and efficacious antidepressant activity in human clinical trials (Zarate, C. A. Jr et al. 2006). Therefore, indirect modulation of glutamate signaling represents a potential molecular mechanism of action for MOR-mediated antidepressant and axiolytic effects. Further, agonists of the related delta-opioid receptor (DOR) have been demonstrated to show robust antidepressant efficacy (Jutkiewicz, E. M. 2006).

SUMMARY OF THE INVENTION

The present invention provides a compound having the structure:

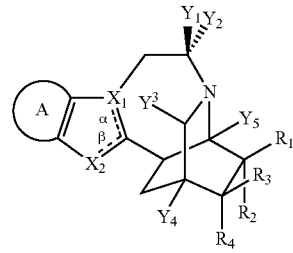

wherein
A is a ring structure, with or without substitution;
$X_1$ is C or N;
$X_2$ is N, O, or S;
$Y_1$ is H, -(alkyl), -(alkenyl), -(alkynyl), -(cycloalkyl), -(haloalkyl), -(alkyl)-O-(alkyl) or -(alkyl)-(cycloalkyl);
$Y_2$ is H, -(alkyl), -(alkenyl), -(alkynyl), -(cycloalkyl), -(haloalkyl), -(alkyl)-O-(alkyl) or -(alkyl)-(cycloalkyl);
$Y_3$ is H, -(alkyl), -(alkenyl), -(alkynyl), -(cycloalkyl), -(haloalkyl), -(alkyl)-O-(alkyl) or -(alkyl)-(cycloalkyl);
$Y_4$ is H, -(alkyl), -(alkenyl), -(alkynyl), -(cycloalkyl), -(haloalkyl), -(alkyl)-O-(alkyl) or -(alkyl)-(cycloalkyl);
$Y_5$ is H, -(alkyl), -(alkenyl), -(alkynyl), -(cycloalkyl), -(haloalkyl), -(alkyl)-O-(alkyl) or -(alkyl)-(cycloalkyl);
$\alpha$ and $\beta$ are each present or absent and when present each is a bond,
wherein either $\alpha$ or $\beta$ is present, and
when $\alpha$ is present, then $X_1$ is C and $X_2$ is S or O, or
when $\beta$ is present, then $X_1$ is N and $X_2$ is N; and
$R_1$, $R_2$, $R_3$ and $R_4$ are each independently —H, -(alkyl), -(alkenyl), -(alkynyl), -(haloalkyl), -(cycloalkyl), -(aryl), -(heteroaryl), -(heteroalkyl), -(hydroxyalkyl), -(alkyl)-(aryl), -(alkyl)- (heteroaryl), -(alkyl)-(cycloalkyl), -(alkyl)-OH, -(alkyl)-O-(alkyl), —OH, —NH$_2$, —OAc, —CO$_2$H, —CN, OCF$_3$, halogen, —CO$_2$—($C_2$-$C_{12}$ alkyl), C(O)—NH$_2$, —C(O)—NH-(alkyl), C(O)—NH-(aryl), —O-alkyl, —O-alkenyl, —O-alkynyl, —O-aryl, —O-(heteroaryl), —NH-alkyl, —NH-alkenyl, —NH-alkynyl, —NH-aryl, —NH-(heteroaryl), —O—C(O)(alkyl), or —C(O)—N(alkyl)$_2$,
or a pharmaceutically acceptable salt or ester thereof.

DETAILED DESCRIPTION OF THE INVENTION

Figure 1:
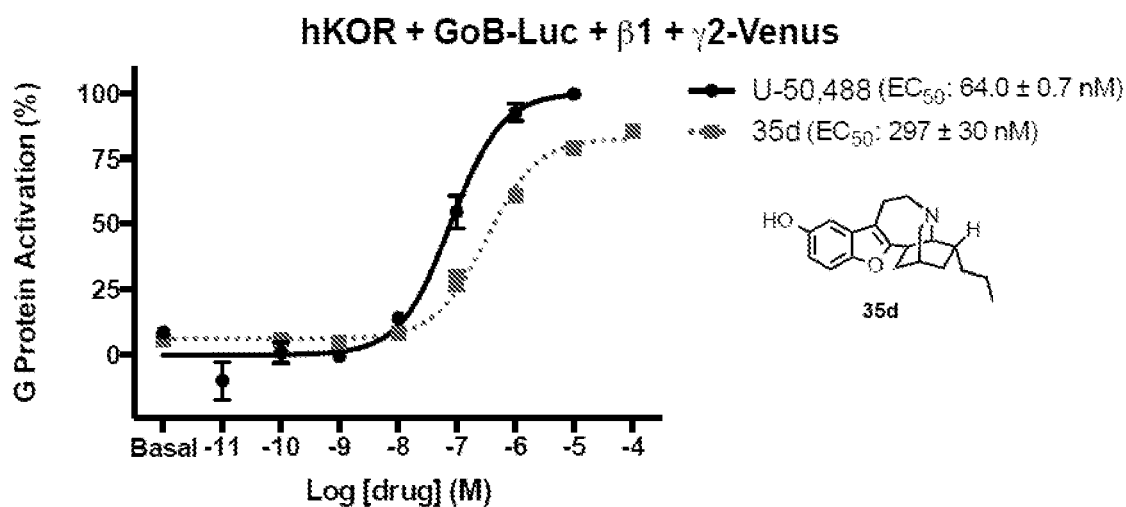
FIG. 1: Human KOR was co-expressed with $G\alpha_{oB}$-RLuc8, $\beta_1$, and mVenus-$\gamma_2$. The induced BRET signal by either 35d (EC$_{50}$: 297±30 nM) or control agonist U-50,488 (EC$_{50}$: 64.0±0.7 nM) was measured at 5 minutes. Data represent mean±SEM of 2 independent experiments.

The present invention provides a compound having the structure:

wherein
A is a ring structure, with or without substitution;
X$_1$ is C or N;
X$_2$ is N, O, or S;
Y$_1$ is H, -(alkyl), -(alkenyl), -(alkynyl), -(cycloalkyl), -(haloalkyl), -(alkyl)-O-(alkyl) or -(alkyl)-(cycloalkyl);
Y$_2$ is H, -(alkyl), -(alkenyl), -(alkynyl), -(cycloalkyl), -(haloalkyl), -(alkyl)-O-(alkyl) or -(alkyl)-(cycloalkyl);
Y$_3$ is H, -(alkyl), -(alkenyl), -(alkynyl), -(cycloalkyl), -(haloalkyl), -(alkyl)-O-(alkyl) or -(alkyl)-(cycloalkyl);
Y$_4$ is H, -(alkyl), -(alkenyl), -(alkynyl), -(cycloalkyl), -(haloalkyl), -(alkyl)-O-(alkyl) or -(alkyl)-(cycloalkyl);
Y$_5$ is H, -(alkyl), -(alkenyl), -(alkynyl), -(cycloalkyl), -(haloalkyl), -(alkyl)-O-(alkyl) or -(alkyl)-(cycloalkyl);
α and β are each present or absent and when present each is a bond,
  wherein either α or β is present, and
  when α is present, then X$_1$ is C and X$_2$ is S or O, or
  when β is present, then X$_1$ is N and X$_2$ is N; and
R$_1$, R$_2$, R$_3$ and R$_4$ are each independently —H, -(alkyl), -(alkenyl), -(alkynyl), -(haloalkyl), -(cycloalkyl), -(aryl), -(heteroaryl), -(heteroalkyl), -(hydroxyalkyl), -(alkyl)-(aryl), -(alkyl)-(heteroaryl), -(alkyl)-(cycloalkyl), -(alkyl)-OH, -(alkyl)-O-(alkyl), —OH, —NH$_2$, —OAc, —CO$_2$H, —CN, —OCF$_3$, halogen, —CO$_2$—(C$_2$-C$_{12}$ alkyl), C(O)—NH$_2$, —C(O)—NH-(alkyl), C(O)—NH-(aryl), —O-alkyl, —O-alkenyl, —O-alkynyl, —O-aryl, —O-(heteroaryl), —NH-alkyl, —NH-alkenyl, —NH-alkynyl, —NH-aryl, —NH-(heteroaryl), —O—C(O)(alkyl), or —C(O)—N(alkyl)$_2$, or a pharmaceutically acceptable salt or ester thereof.

In some embodiments of the above compound, A is other than

In some embodiments, R$_1$, R$_2$, R$_3$ and R$_4$ are each independently —H, -(alkyl), -(alkenyl), -(alkynyl), -(fluoroalkyl), -(cycloalkyl), -(aryl), -(heteroaryl), -(heteroalkyl), -(hydroxyalkyl), - (alkyl)-(aryl), -(alkyl)-(heteroaryl), -(alkyl)-(cycloalkyl), -(alkyl)-OH, -(alkyl)-O-(alkyl), —OH, —NH$_2$, —OAc, —CO$_2$H, —CN, —OCF$_3$, halogen, —CO$_2$—(C$_2$-C$_{12}$ alkyl), C(O)—NH$_2$, —C(O)—NH-(alkyl), C(O)—NH-(aryl), —O-alkyl, —O-alkenyl, —O-alkynyl, —O-aryl, —O-(heteroaryl), —NH-alkyl, —NH-alkenyl, —NH-alkynyl, —NH-aryl, —NH-(heteroaryl), —O—C(O)(alkyl), or —C(O)—N(alkyl)$_2$.

In some embodiments, R$_1$, R$_2$, R$_3$ and R$_4$ are each independently —H, (alkyl), -(alkenyl), -(alkynyl), -(fluoroalkyl), -(cycloalkyl), -(aryl), -(heteroaryl), -(heteroalkyl), -(hydroxyalkyl), -(alkyl)-(aryl), -(alkyl)-(heteroaryl), -(alkyl)-(cycloalkyl), -(alkyl)-OH, -(alkyl)-O-(alkyl), —OH, —NH$_2$, —OAc, —CO$_2$H, —CN, —CF$_3$, —CH$_2$F, —OCF$_3$, halogen, —CO$_2$—(C$_2$-C$_{12}$ alkyl), C(O)—NH$_2$, —C(O)—NH-(alkyl), C(O)—NH-(aryl), —O-alkyl, —O-alkenyl, —O-alkynyl, —O-aryl, —O-(heteroaryl), —NH-alkyl, —NH-alkenyl, —NH-alkynyl, —NH-aryl, —NH-(heteroaryl), —O—C(O)(alkyl), or —C(O)—N(alkyl)$_2$.

The present invention provides a compound having the structure:

wherein
A is a ring structure, with or without substitution;
X$_1$ is C or N;
X$_2$ is N, O, or S;
Y$_1$ is H, -(alkyl), -(alkenyl), -(alkynyl), -(cycloalkyl) or -(alkyl)-(cycloalkyl);
Y$_2$ is H, -(alkyl), -(alkenyl), -(alkynyl), -(cycloalkyl) or -(alkyl)-(cycloalkyl);

$Y_3$ is H, -(alkyl), -(alkenyl), -(alkynyl), -(cycloalkyl) or -(alkyl)-(cycloalkyl);

$Y_4$ is H, -(alkyl), -(alkenyl), -(alkynyl), -(cycloalkyl) or -(alkyl)-(cycloalkyl);

$Y_5$ is H, -(alkyl), -(alkenyl), -(alkynyl), -(cycloalkyl) or -(alkyl)-(cycloalkyl);

α and β are each present or absent and when present each is a bond,
  wherein either α or β is present, and
  when α is present, then $X_1$ is C and $X_2$ is S or O, or
  when β is present, then $X_1$ is N and $X_2$ is N; and $R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), or —C(O)—NH-(alkyl), or a pharmaceutically acceptable salt or ester thereof.

The present invention further provides a compound having the structure:

wherein
A is a ring structure, with or without substitution;
$X_1$ is C or N;
$X_2$ is N, O, or S;
α and β are each present or absent and when present each is a bond,
  wherein either α or β is present, and
  when α is present, then $X_1$ is C and $X_2$ is S or O, or
  when β is present, then $X_1$ is N and $X_2$ is N; and $R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), —C(O)—NH$_2$ or —C(O)—NH-(alkyl), or a pharmaceutically acceptable salt or ester thereof.

In some embodiments, $R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), - (alkyl)-OH, -(alkyl)-O-(alkyl), —OH, —NH$_2$, —CO$_2$H, —CO$_2$-(alkyl), —C(O)—NH$_2$ or —C(O)—NH-(alkyl), In some embodiments, when A is phenyl, $X_1$ is C, $X_2$ is O and α is present, $R_1$ is other than —CO$_2$Me.

In some embodiments, when A is phenyl, $X_1$ is C, $X_2$ is O and α is present, $R_2$ is other than —CO$_2$Me.

In some embodiments, the compound having the structure:

wherein
A is an aryl or heteroaryl;
$X_1$ is C or N;
$X_2$ is N, O, or S;
α and β are each present or absent and when present each is a bond,
  wherein either α or β is present,
  when α is present, then $X_1$ is C and $X_2$ is S or O, and
  when β is present, then $X_1$ is N and $X_2$ is N;

$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), or —C(O)—NH-(alkyl); and $R_5$, $R_6$, $R_7$, $R_8$ are each independently —H, halogen, —CN, —CF$_3$, —OCF$_3$, -(alkyl), -(alkenyl), -(alkynyl), -(aryl), -(heteroaryl), -(heteroalkyl), -(hydroxyalkyl), —NH$_2$, —NH-(alkyl), —NH-(alkenyl), —NH-(alkynyl)-NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), or C(O)—NH-(aryl), or a pharmaceutically acceptable salt or ester thereof.

In some embodiments, the compound having the structure:

wherein
$X_1$ is C or N;
$X_2$ is N, O, or S;
α and β are each present or absent and when present each is a bond,
  wherein either α or β is present,
  when α is present, then $X_1$ is C and $X_2$ is S or O, and
  when β is present, then $X_1$ is N and $X_2$ is N;

$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), or —C(O)—NH-(alkyl); and $R_5$, $R_6$, $R_7$, $R_8$ are each independently —H, halogen, —CN, —CF$_3$, —OCF$_3$, -(alkyl), -(alkenyl), -(alkynyl), -(aryl), -(heteroaryl), -(heteroalkyl), -(hydroxyalkyl), —NH$_2$, —NH-(alkyl), —NH-(alkenyl), —NH-(alkynyl)-NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), or C(O)—NH-(aryl), or a pharmaceutically acceptable salt or ester thereof.

In some embodiments of the above compounds, R$_5$ is —H.

In some embodiments of the above compounds, R$_5$ is other than —OH.

In some embodiments, the compound having the structure:

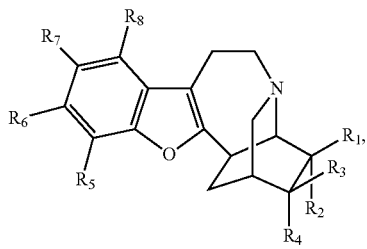

or a pharmaceutically acceptable salt or ester thereof.

In some embodiments of the above compounds, R$_5$ is —H.

In some embodiments of the above compounds, R$_5$ is other than —OH.

In some embodiments, the compound having the structure:

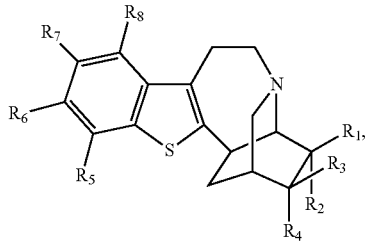

or a pharmaceutically acceptable salt or ester thereof.

In some embodiments, the compound having the structure:

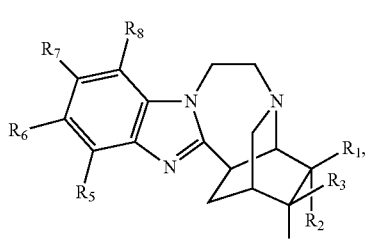

or a pharmaceutically acceptable salt or ester thereof.

In some embodiments, the compound having the structure:

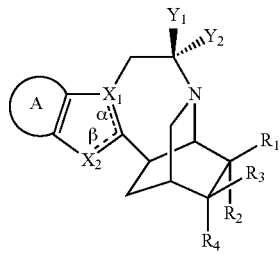

wherein
A is a ring structure, with or without substitution;
X$_1$ is C or N;
X$_2$ is N, O, or S;
Y$_1$ is H, -(alkyl), -(alkenyl) or -(alkynyl);
Y$_2$ is H, -(alkyl), -(alkenyl) or -(alkynyl);
α and β are each present or absent and when present each is a bond,
  wherein either α or β is present, and
  when α is present, then X$_1$ is C and X$_2$ is S or O, or
  when β is present, then X$_1$ is N and X$_2$ is N; and
R$_2$, R$_2$, R$_3$ and R$_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), or —C(O)—NH-(alkyl), or a pharmaceutically acceptable salt or ester thereof.

In some embodiments of the above compound, A is other than

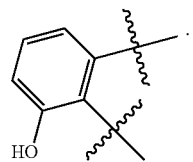 [SMILES: *c1cccc(O)c1*]

In some embodiments, the compound having the structure:

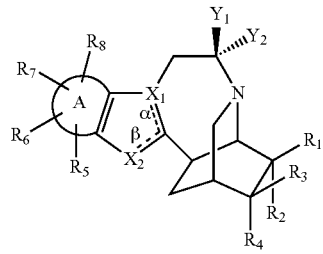

wherein
A is an aryl or heteroaryl;
X$_1$ is C or N;
X$_2$ is N, O, or S;
Y$_1$ is H, -(alkyl), -(alkenyl), -(alkynyl), -(cycloalkyl), -(haloalkyl), -(alkyl)-O-(alkyl) or -(alkyl)-(cycloalkyl);
Y$_2$ is H, -(alkyl), -(alkenyl), -(alkynyl), -(cycloalkyl), -(haloalkyl), -(alkyl)-O-(alkyl) or -(alkyl)-(cycloalkyl);

α and β are each present or absent and when present each
is a bond,
wherein either α or β is present,
when α is present, then $X_1$ is C and $X_2$ is S or O, and
when β is present, then $X_1$ is N and $X_2$ is N;
$R_1$, $R_2$, $R_3$ and $R_4$ are each independently —H, -(alkyl), -(alkenyl), -(alkynyl), -(haloalkyl), -(cycloalkyl), -(aryl), -(heteroaryl), -(heteroalkyl), -(hydroxyalkyl), -(alkyl)-(aryl), -(alkyl)- (heteroaryl), -(alkyl)-(cycloalkyl), -(alkyl)-OH, -(alkyl)-O-(alkyl), —OH, —$NH_2$, —OAc, —$CO_2H$, —CN, $OCF_3$, halogen, —$CO_2$—($C_2$-$C_{12}$ alkyl), C(O)—$NH_2$, —C(O)—NH-(alkyl), C(O)—NH-(aryl), —O-alkyl, —O-alkenyl, —O-alkynyl, —O-aryl, —O-(heteroaryl), —NH-alkyl, —NH-alkenyl, —NH-alkynyl, —NH-aryl, —NH-(heteroaryl), —O—C(O)(alkyl), or —C(O)—N(alkyl)$_2$; and
$R_5$, $R_6$, $R_7$, and $R_8$ are each independently —H, halogen, —CN, —$CF_3$, —$OCF_3$, -(alkyl), -(alkenyl), -(alkynyl), -(haloalkyl), -(cycloalkyl), -(aryl), -(heteroaryl), -(heteroalkyl), -(hydroxyalkyl), —$NH_2$, —NH-(alkyl), —NH-(alkenyl), —NH-(alkynyl) —NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), or C(O)—NH-(aryl),
or a pharmaceutically acceptable salt or ester thereof.

In some embodiments, $R_5$, $R_6$, $R_7$ and $R_8$ are each independently —H, halogen, —CN, —$CF_3$, —$OCF_3$, -(alkyl), -(alkenyl), -(alkynyl), -(fluoroalkyl), -(cycloalkyl), -(aryl), -(heteroaryl), -(heteroalkyl), -(hydroxyalkyl), —$NH_2$, —NH-(alkyl), —NH-(alkenyl), —NH-(alkynyl)-NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), or C(O)—NH-(aryl).

In some embodiments, $R_5$, $R_6$, $R_7$ and $R_8$ are each independently —H, halogen, —CN, —$CF_3$, —$OCF_3$, -(alkyl), -(alkenyl), -(alkynyl), (cycloalkyl), -(aryl), -(heteroaryl), -(heteroalkyl), -(hydroxyalkyl), —$NH_2$, —NH-(alkyl), —NH-(alkenyl), —NH-(alkynyl)-NH-(aryl), —NH-(heteroaryl), —OH, —OAc, —$CO_2H$, —$CF_3$, —$CH_2F$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), or C(O)—NH-(aryl).

In some embodiments, the compound having the structure:

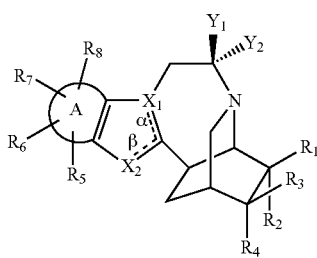

wherein
A is an aryl or heteroaryl;
$X_1$ is C or N;
$X_2$ is N, O, or S;
$Y_1$ is H, -(alkyl), -(alkenyl) or -(alkynyl);
$Y_2$ is H, -(alkyl), -(alkenyl) or -(alkynyl);
α and β are each present or absent and when present each
is a bond,
wherein either α or β is present,
when α is present, then $X_1$ is C and $X_2$ is S or O, and
when β is present, then $X_1$ is N and $X_2$ is N;
$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —$NH_2$, —$CO_2H$, —$CO_2$—($C_2$-$C_{12}$ alkyl), or —C(O)—NH-(alkyl); and
$R_5$, $R_6$, $R_7$, $R_8$ are each independently —H, halogen, —CN, —$CF_3$, —$OCF_3$, -(alkyl), -(alkenyl), -(alkynyl), -(aryl), -(heteroaryl), -(heteroalkyl), -(hydroxyalkyl), —$NH_2$, —NH-(alkyl), —NH-(alkenyl), —NH-(alkynyl)-NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), or C(O)—NH-(aryl),
or a pharmaceutically acceptable salt or ester thereof.

In some embodiments, the compound having the structure:

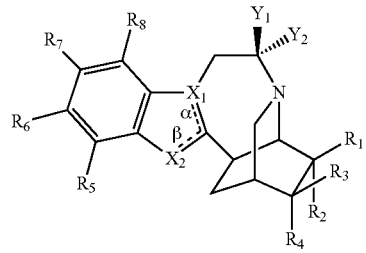

wherein
$X_1$ is C or N;
$X_2$ is N, O, or S;
$Y_1$ is H, -(alkyl), -(alkenyl) or -(alkynyl);
$Y_2$ is H, -(alkyl), -(alkenyl) or -(alkynyl);
α and β are each present or absent and when present each
is a bond,
wherein either α or β is present,
when α is present, then $X_1$ is C and $X_2$ is S or O, and
when β is present, then $X_1$ is N and $X_2$ is N;
$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —$NH_2$, —$CO_2H$, —$CO_2$—($C_2$-$C_{12}$ alkyl), or —C(O)—NH-(alkyl); and
$R_5$, $R_6$, $R_7$, $R_6$ are each independently —H, halogen, —CN, —$CF_3$, —$OCF_3$, -(alkyl), -(alkenyl), -(alkynyl), -(aryl), -(heteroaryl), -(heteroalkyl), -(hydroxyalkyl), —$NH_2$, —NH-(alkyl), —NH-(alkenyl), —NH-(alkynyl)-NH-(aryl), —NH-(heteroaryl), —OH, —OAc, —$CO_2H$, —$CO_2$-(alkyl), —O—C(O)(alkyl), —O-(alkyl), —O-(alkenyl), —O-(alkynyl), —O-(aryl), —O-(heteroaryl), C(O)—$NH_2$, C(O)—NH-(alkyl), or C(O)—NH-(aryl),
or a pharmaceutically acceptable salt or ester thereof.

In some embodiments of the above compounds, $R_5$ is —H.

In some embodiments of the above compounds, $R_5$ is other than —OH.

In some embodiments, the compound having the structure:

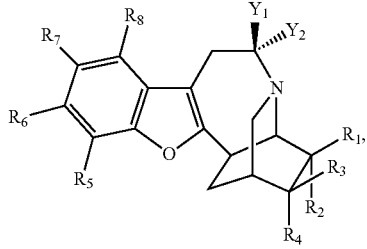

or a pharmaceutically acceptable salt or ester thereof.

In some embodiments, the compound having the structure:

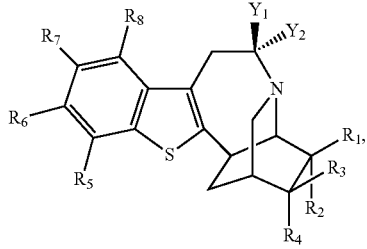

or a pharmaceutically acceptable salt or ester thereof.

In some embodiments of the above compounds, $R_5$ is —H.

In some embodiments of the above compounds, $R_5$ is other than —OH.

In some embodiments, the compound having the structure:

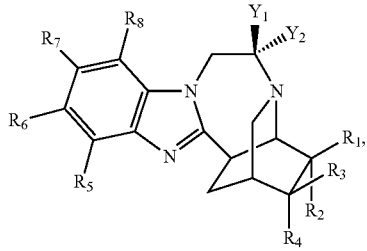

or a pharmaceutically acceptable salt or ester thereof.

In some embodiments, the compound wherein $R_1$ is —H and $R_2$ is -(alkyl), -(alkenyl), -(alkynyl), -(aryl), -(heteroaryl), -(alkyl)-OH, -(alkyl)-(aryl), -(alkyl)-O-(alkyl), —OH, —NH$_2$, —CO$_2$-(alkyl), or —C(O)—NH-(alkyl).

In some embodiments, the compound wherein $R_1$ is —H and $R_2$ is —CH$_2$CH$_3$.

In some embodiments, the compound wherein $R_1$ is —H and $R_2$ is —CH$_2$CH$_3$, —CH$_2$CH$_2$CH$_3$, —CH$_2$CH$_2$CH$_2$CH$_3$, —CH$_2$C$_6$H$_5$, —CH(CH$_3$)$_2$, —CO$_2$CH$_2$CH$_3$, —CH$_2$OCH$_3$, —C$_6$H$_5$ or —CH$_2$OH.

In some embodiments, the compound wherein $R_1$ is —H and $R_2$ is —CH$_3$, —CH$_2$CH$_3$, —CH$_2$CH$_2$CH$_3$—CH$_2$CH$_2$CH$_2$CH$_3$, —CH$_2$C$_6$H$_5$, —CH(CH$_3$)$_2$, —CO$_2$CH$_2$CH$_3$—CH$_2$OCH$_3$, —C$_6$H$_5$ or —CH$_2$OH.

In some embodiments, the compound wherein $R_2$ is —H and $R_1$ is -(alkyl), -(alkenyl), -(alkynyl), -(aryl), -(heteroaryl), -(alkyl)-OH, -(alkyl)-(aryl), -(alkyl)-O-(alkyl), —OH, —NH$_2$, —CO$_2$-(alkyl), or —C(O)—NH-(alkyl).

In some embodiments, the compound wherein $R_2$ is —H and $R_1$ is —CH$_2$CH$_3$.

In some embodiments, the compound wherein $R_2$ is —H and $R_1$ is —CH$_2$CH$_3$, —CH$_2$CH$_2$CH$_3$, —CH$_2$CH$_2$CH$_2$CH$_3$, —CH$_2$C$_6$H$_5$, —CH(CH$_3$)$_2$, —CO$_2$CH$_2$CH$_3$—CH$_2$OCH$_3$—C$_6$H$_5$ or CH$_2$OH.

In some embodiments, the compound wherein $R_2$ is —H and $R_1$ is —CH$_3$, —CH$_2$CH$_3$, —CH$_2$CH$_2$CH$_3$, —CH$_2$CH$_2$CH$_2$CH$_3$, —CH$_2$C$_6$H$_5$, —CH(CH$_3$)$_2$, —CO$_2$CH$_2$CH$_3$, —CH$_2$OCH$_3$, —C$_6$H$_5$ or CH$_2$OH.

In some embodiments, the compound wherein $R_3$ is —H and $R_4$ is -(alkyl), -(alkenyl), -(alkynyl), -(aryl), -(heteroaryl), -(alkyl)-OH, -(alkyl)-(aryl), -(alkyl)-O-(alkyl), —OH, —NH$_2$, —CO$_2$-(alkyl), or —C(O)—NH-(alkyl).

In some embodiments, the compound wherein $R_3$ is —H and $R_4$ is —CH$_2$CH$_3$.

In some embodiments, the compound wherein $R_3$ is —H and $R_4$ is —CH$_2$CH$_3$, —CH$_2$CH$_2$CH$_3$—CH$_2$CH$_2$CH$_2$CH$_3$—CH$_2$C$_6$H$_5$, —CH(CH$_3$)$_2$, —CO$_2$CH$_2$CH$_3$, —CH$_2$OCH$_3$, —C$_6$H$_5$ or —CH$_2$OH.

In some embodiments, the compound wherein $R_3$ is —H and $R_4$ is —CH$_3$, —CH$_2$CH$_3$, —CH$_2$CH$_2$CH$_3$, —CH$_2$CH$_2$CH$_2$CH$_3$, —CH$_2$C$_6$H$_5$, —CH(CH$_3$)$_2$, —CO$_2$CH$_2$CH$_3$, —CH$_2$OCH$_3$, —C$_6$H$_5$ or —CH$_2$OH.

In some embodiments, the compound wherein $R_4$ is —H and $R_3$ is -(alkyl), -(alkenyl), -(alkynyl), -(aryl), -(heteroaryl), -(alkyl)-OH, -(alkyl)-(aryl), -(alkyl)-O-(alkyl), —OH, —NH$_2$, —CO$_2$-(alkyl), or —C(O)—NH-(alkyl).

In some embodiments, the compound wherein $R_4$ is —H and $R_3$ is —CH$_2$CH$_3$.

In some embodiments, the compound wherein $R_4$ is —H and $R_3$ is —CH$_2$CH$_3$—CH$_2$CH$_2$CH$_3$—CH$_2$CH$_2$CH$_2$CH$_3$, —CH$_2$C$_6$H$_5$, —CH(CH$_3$)$_2$, —CO$_2$CH$_2$CH$_3$—CH$_2$OCH$_3$, —C$_6$H$_5$ or —CH$_2$OH.

In some embodiments, the compound wherein $R_4$ is —H and $R_3$ is —CH$_3$, —CH$_2$CH$_3$, —CH$_2$CH$_2$CH$_3$—CH$_2$CH$_2$CH$_2$CH$_3$, —CH$_2$C$_6$H$_5$, —CH(CH$_3$)$_2$, —CO$_2$CH$_2$CH$_3$, —CH$_2$OCH$_3$, —C$_6$H$_5$ or —CH$_2$OH.

In some embodiments, the compound wherein $R_1$ and $R_2$ are each —H.

In some embodiments, the compound wherein $R_3$ and $R_4$ are each —H.

In some embodiments, the compound wherein $R_1$, $R_2$, $R_3$ and $R_4$ are each —H.

In some embodiments, the compound wherein $R_5$, $R_6$, $R_7$ and $R_8$ are each —H.

In some embodiments, the compound wherein $R_5$, $R_6$ and $R_7$ are each —H and $R_8$ is halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), or —O-(heteroaryl).

In some embodiments, the compound wherein $R_5$, $R_6$ and $R_7$ are each —H and $R_8$ is halogen, —OH or —O-(alkyl).

In some embodiments, the compound wherein $R_5$, $R_6$ and $R_7$ are each —H and $R_8$ is halogen, —OH—OAc, or —O-(alkyl).

In some embodiments, the compound wherein
$R_5$, $R_6$ and $R_7$ are each —H and $R_8$ is —F, —OH or —OCH$_3$.

In some embodiments, the compound wherein
$R_5$, $R_6$ and $R_8$ are each —H and $R_7$ is halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), or —O-(heteroaryl).

In some embodiments, the compound wherein
$R_5$, $R_6$ and $R_8$ are each —H and $R_7$ is halogen, —OH or —O-(alkyl).

In some embodiments, the compound wherein
$R_5$, $R_6$ and $R_8$ are each —H and $R_7$ is halogen, —OH, —OAc or —O-(alkyl).

In some embodiments, the compound wherein
$R_5$, $R_6$ and $R_8$ are each —H and $R_7$ is —F, —OH or —OCH$_3$.

In some embodiments, the compound wherein
$R_5$, $R_7$ and $R_8$ are each —H and $R_6$ is halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), —O-(heteroaryl).

In some embodiments, the compound wherein
$R_5$, $R_7$ and $R_8$ are each —H and $R_6$ is halogen, —OH or —O-(alkyl).

In some embodiments, the compound wherein
$R_5$, $R_7$ and $R_8$ are each —H and $R_6$ is halogen, —OH, —OAc or —O-(alkyl).

In some embodiments, the compound wherein
$R_5$, $R_7$ and $R_8$ are each —H and $R_6$ is —F, —OH or —OCH$_3$.

In some embodiments, the compound wherein
$R_6$, $R_7$ and $R_8$ are each —H and $R_5$ is halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), or —O-(heteroaryl).

In some embodiments, the compound wherein
$R_6$, $R_7$ and $R_8$ are each —H and $R_5$ is halogen, —OH or —O-(alkyl).

In some embodiments, the compound wherein
$R_6$, $R_7$ and $R_8$ are each —H and $R_5$ is halogen, —OH, —OAc or O-(alkyl).

In some embodiments, the compound wherein
$R_6$, $R_7$ and $R_8$ are each —H and $R_5$ is —F, —OH or —OCH$_3$.

In some embodiments, the compound wherein
$R_5$ and $R_8$ are each —H and $R_6$ and $R_7$ are each independently halogen, —CN, —CF$_3$, —OCF$_3$, -(alkyl), -(alkenyl), -(alkynyl), -(aryl), -(heteroaryl), —NH$_2$, —NH-(alkyl), —NH-(alkenyl), —NH-(alkynyl)-NH-(aryl), —NH-(heteroaryl), —OH, —OAc, —O—C(O)(alkyl), —O-(alkyl), —O-(alkenyl), —O-(alkynyl), —O-(aryl), or —O-(heteroaryl).

In some embodiments, the compound wherein
$R_5$ and $R_8$ are each —H and $R_6$ and $R_7$ are each independently halogen, —OH or —O-(alkyl).

In some embodiments, the compound wherein
$R_5$ and $R_8$ are each each —H and and $R_6$ and $R_7$ are each independently —F, —OH or —OCH$_3$.

In some embodiments, the compound wherein
$R_5$ and $R_8$ are each each —H and and $R_6$ and $R_7$ are each independently —F, —OH or —OCH$_3$.

In some embodiments, the compound wherein
$R_5$ and $R_8$ are each —H and $R_6$ and $R_7$ are each independently -(alkyl) or —O-(alkyl).

In some embodiments, the compound wherein
$R_5$ and $R_8$ are each —H and $R_6$ and $R_7$ are each independently -(alkyl), —OH or —O-(alkyl).

In some embodiments, the compound wherein
$R_5$ and $R_8$ are each each —H and and $R_6$ and $R_7$ are each independently —CH$_3$ or —OCH$_3$.

In some embodiments, the compound wherein
$R_5$ and $R_8$ are each each —H and and $R_6$ and $R_7$ are each independently —CH$_3$, —OH or —OCH$_3$.

In some embodiments, the compound having the structure:

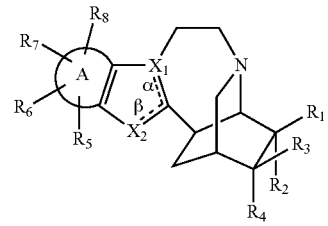

wherein
A is phenyl;
$X_1$ is C or N;
$X_2$ is N, O, or S;
α and β are each present or absent and when present each is a bond,
  wherein either α or β is present,
  when α is present, then $X_1$ is C and $X_2$ is S or O, and
  when β is present, then $X_1$ is N and $X_2$ is N;
$R_1$, $R_2$, $R_3$ and $R_4$ are each independently H, -(alkyl), -(aryl), -(alkyl)-OH, -(alkyl)-(aryl), or -(alkyl)-O-(alkyl),
$R_5$, $R_6$, $R_7$ and $R_6$ are each independently —H, halogen, —OH, or —O-(alkyl),
or a pharmaceutically acceptable salt or ester thereof.

In some embodiments, the compound having the structure:

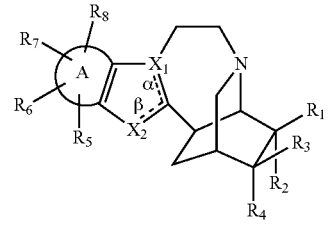

wherein
A is phenyl;
$X_1$ is C or N;
$X_2$ is N, O, or S;
α and β are each present or absent and when present each is a bond,
  wherein either α or β is present,
  when α is present, then $X_1$ is C and $X_2$ is S or O, and
  when β is present, then $X_1$ is N and $X_2$ is N;

R$_1$, R$_2$, R$_3$ and R$_4$ are each independently H, -(alkyl), -(aryl), -(alkyl)-OH, -(alkyl)-(aryl), or -(alkyl)-O-(alkyl), R$_5$, R$_6$, R$_7$ and R$_8$ are each independently —H, -(alkyl), halogen, —OH, or —O-(alkyl), or a pharmaceutically acceptable salt or ester thereof.

In some embodiments, the compound having the structure:

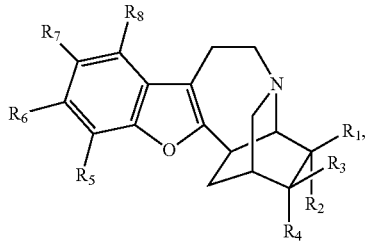

or a pharmaceutically acceptable salt or ester thereof.

In some embodiments of the above compounds, R$_5$ is —H.

In some embodiments of the above compounds, R$_5$ is other than —OH.

In some embodiments, the compound having the structure:

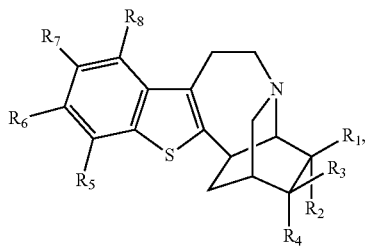

or a pharmaceutically acceptable salt or ester thereof.

In some embodiments, the compound having the structure:

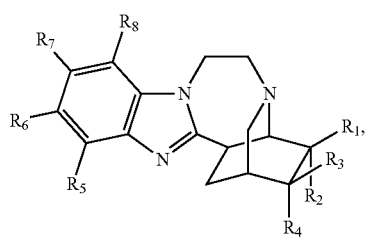

or a pharmaceutically acceptable salt or ester thereof.

In some embodiments, the compound having the structure:

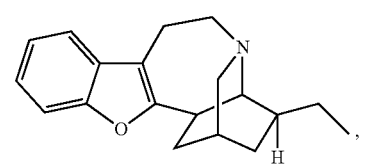

-continued

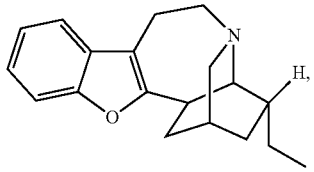

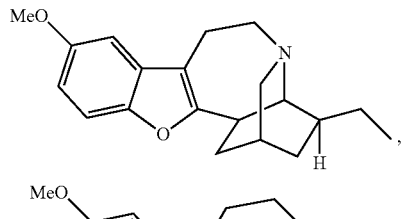

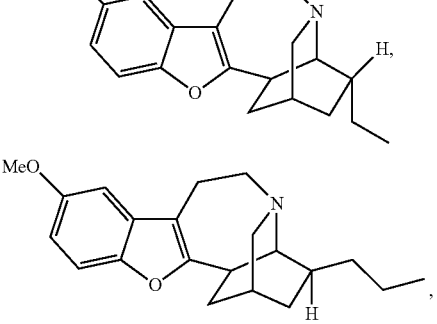

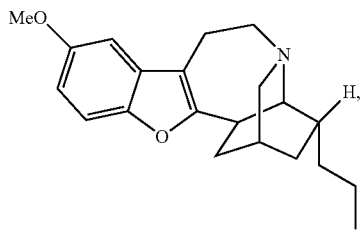

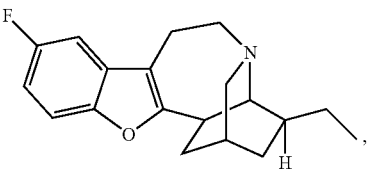

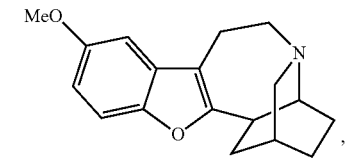

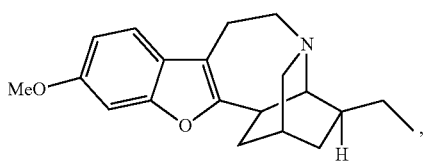

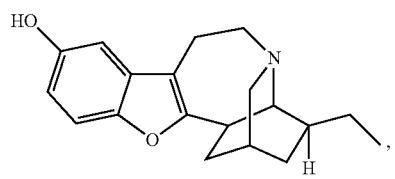

-continued
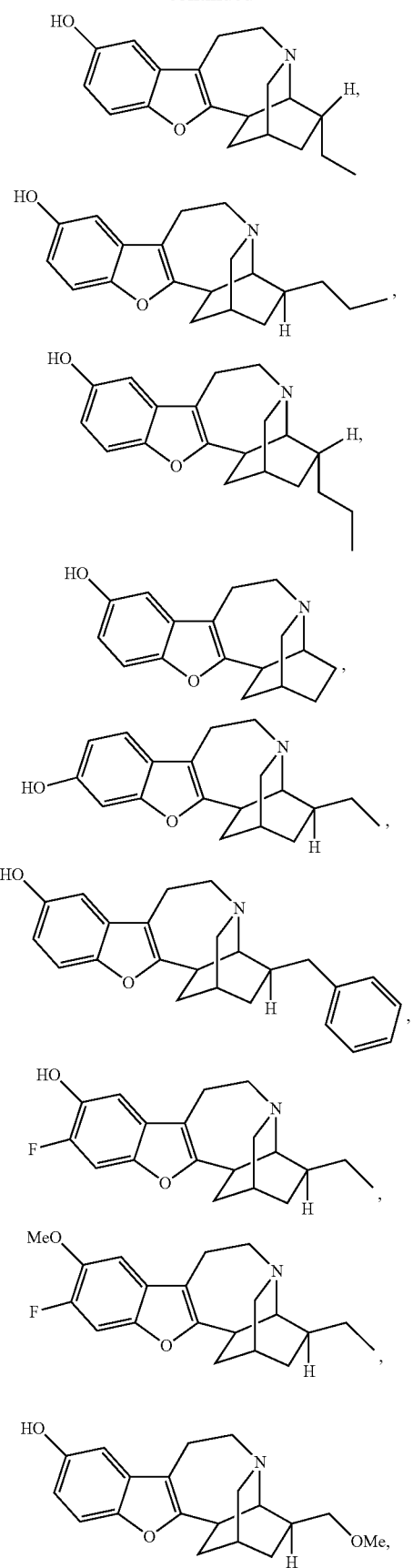
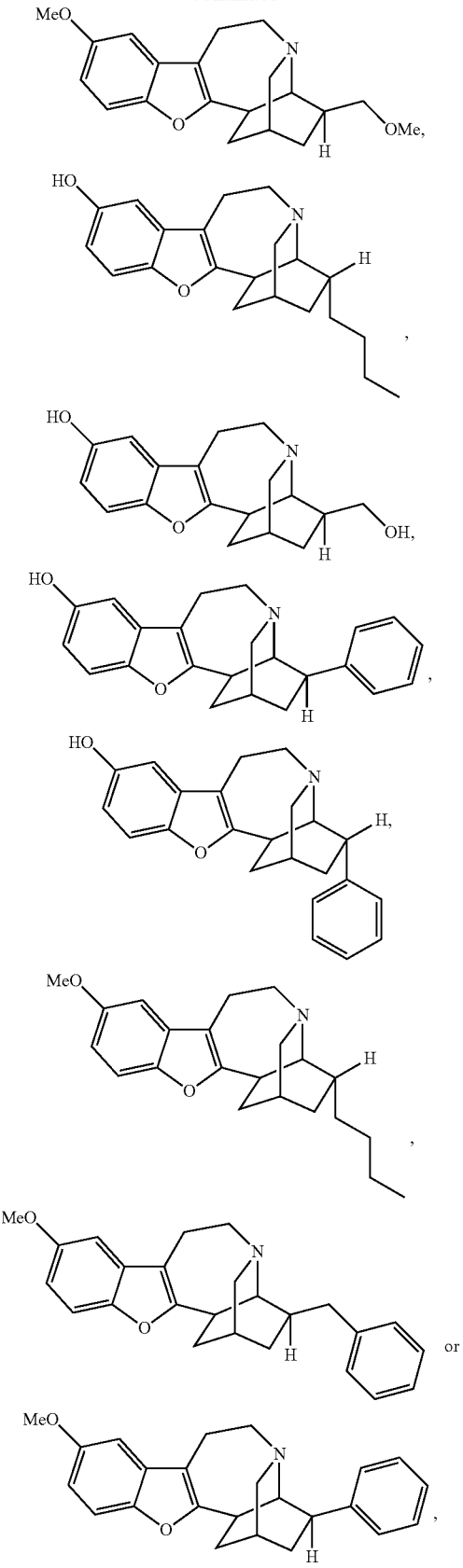
or a pharmaceutically acceptable salt or ester thereof.

In some embodiments, the compound having the structure:
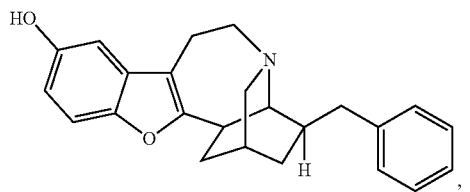
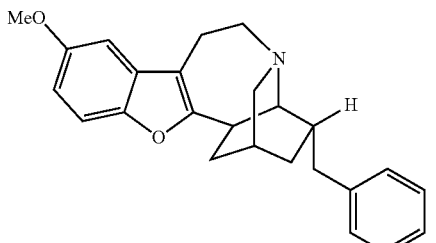
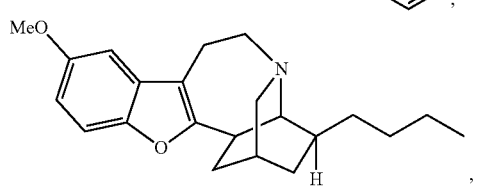
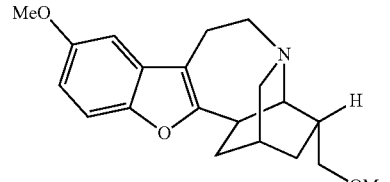
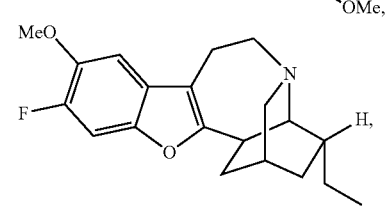
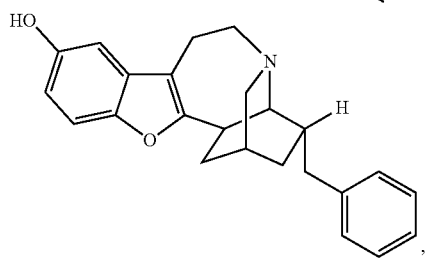
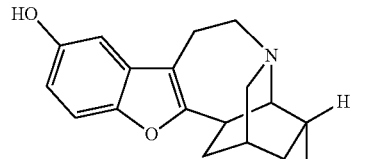
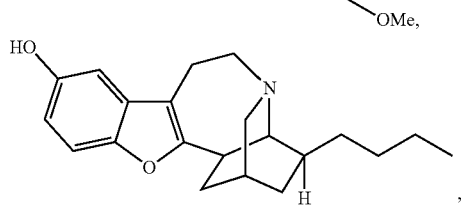
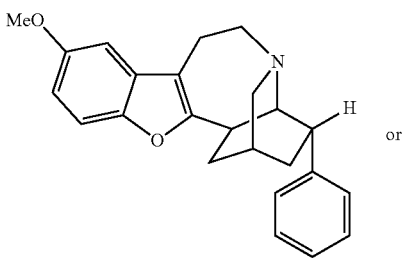
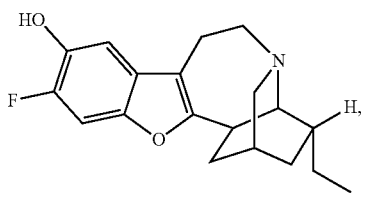
or a pharmaceutically acceptable salt or ester thereof.
In some embodiments, the compound having the structure:
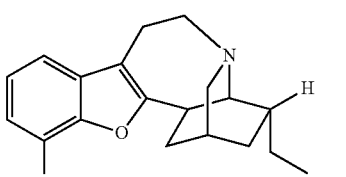
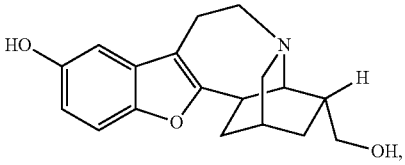
or a pharmaceutically acceptable salt or ester thereof.
In some embodiments, the compound having the structure:
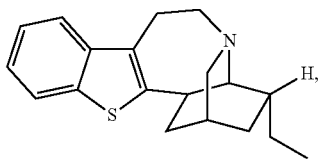
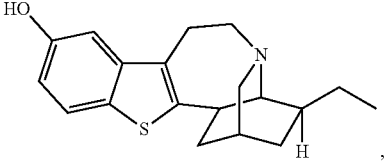
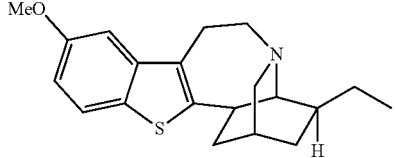
or a pharmaceutically acceptable salt thereof.-

In some embodiments, the compound having the structure:

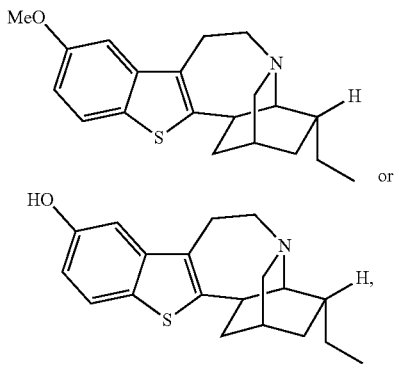

or a pharmaceutically acceptable salt or ester thereof.

In some embodiments, the compound having the structure:

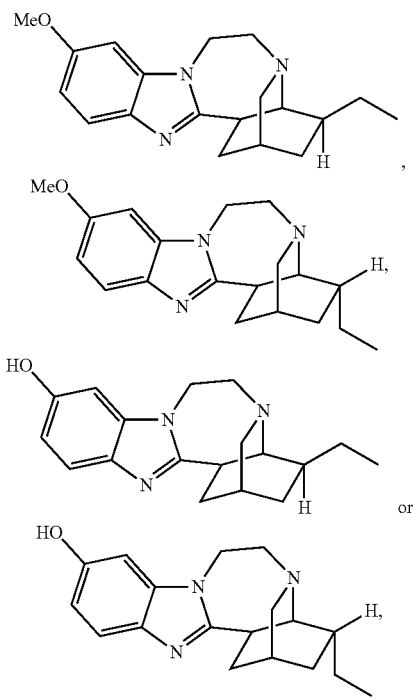

or a pharmaceutically acceptable salt or ester thereof.

In some embodiments, the compound having the structure:

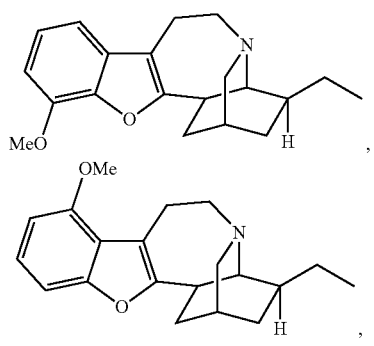

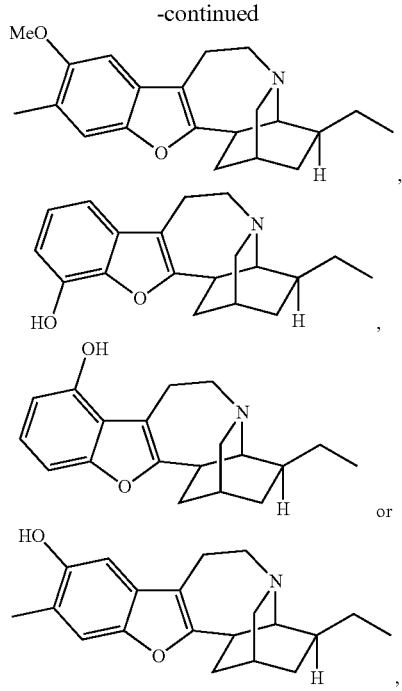

or a pharmaceutically acceptable salt or ester thereof.

In some embodiments of any of the above compounds, wherein
$Y_1$ is H or -(alkyl); and
$Y_2$ is H or -(alkyl).

In some embodiments of any of the above compounds, wherein
$Y_1$ is H or -(alkyl);
$Y_2$ is H or -(alkyl);
$Y_3$ is H or -(alkyl);
$Y_4$ is H or -(alkyl); and
$Y_5$ is H or -(alkyl).

In some embodiments, the compound wherein
$Y_1$ is H, —CH$_3$ or —CH$_2$CH$_3$; and
$Y_2$ is H, —CH$_3$ or —CH$_2$CH$_3$.

In some embodiments, the compound wherein
$Y_1$ is H; and
$Y_2$ is —CH$_3$ or —CH$_2$CH$_3$.

In some embodiments, the compound wherein
$Y_1$ is —CH$_3$ or —CH$_2$CH$_3$; and
$Y_2$ is H.

In some embodiments, the compound wherein
$Y_1$ is H; and
$Y_2$ is —CH$_2$CH$_3$.

In some embodiments, the compound wherein
$Y_1$ is —CH$_2$CH$_3$; and
$Y_2$ is H.

In some embodiments, the compound wherein
$R_1$, $R_2$, $R_3$ and $R_4$ are each —H;
$R_5$, $R_6$, $R_8$ are each H;
$R_7$ is OH;
$Y_1$ is —CH$_2$CH$_3$; and
$Y_2$ is H.

In some embodiments, the compound wherein
$R_2$, $R_3$ and $R_4$ are each —H;
$R_5$, $R_6$, $R_8$ are each H;
$R_7$ is OH;
$Y_1$ is H; and
$Y_2$ is —CH$_2$CH$_3$.

In some embodiments, the compound having the structure:
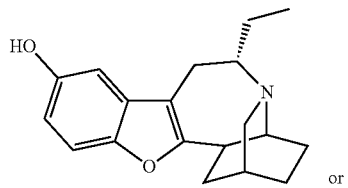
or
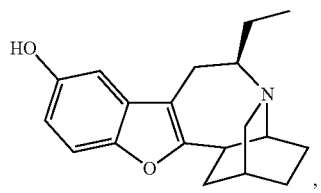
or a pharmaceutically acceptable salt or ester thereof.
In some embodiments, the compound having the structure:
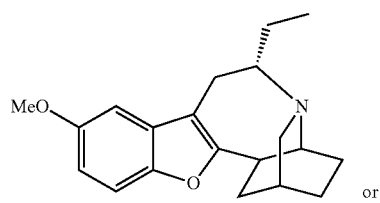
or
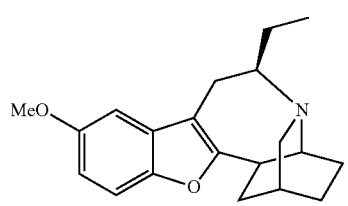
or a pharmaceutically acceptable salt or ester thereof.
In some embodiments, the compound having the structure:
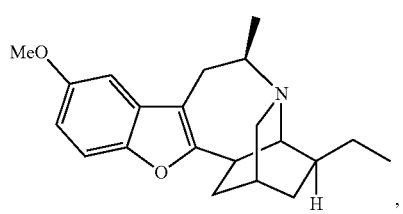
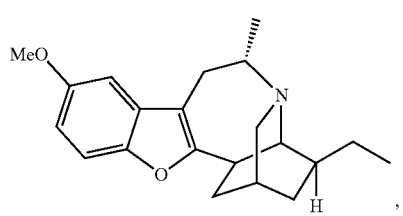
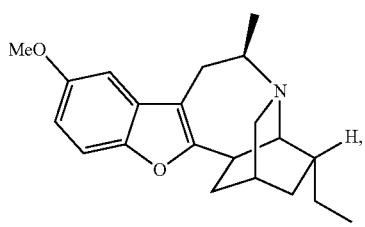
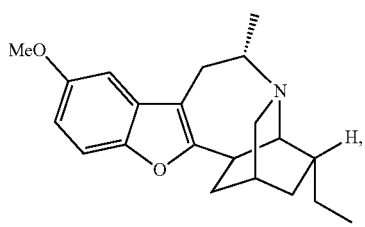
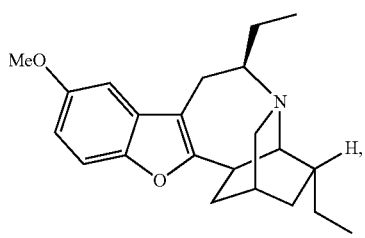
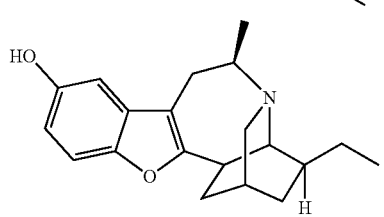
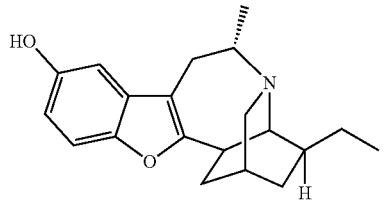
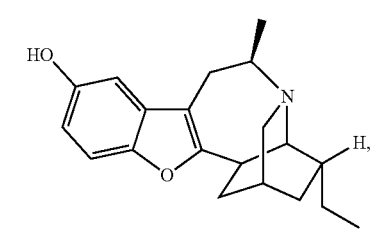
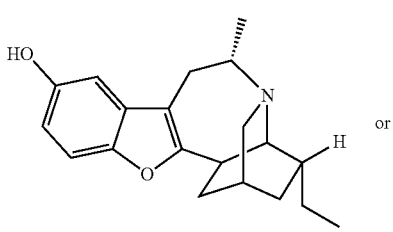
or -continued

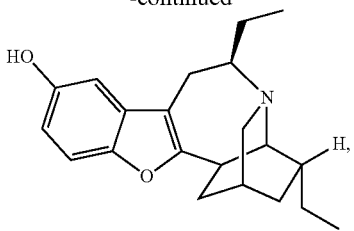

or a pharmaceutically acceptable salt or ester thereof.

In some embodiments, the compound having the structure:

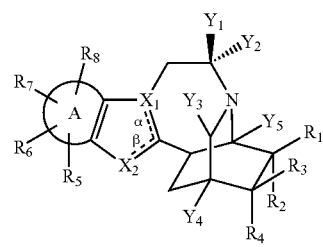

wherein

A is a ring structure, with or without substitution;
$X_1$ is C or N;
$X_2$ is N, O, or S;
$Y_1$ is H, -(alkyl), -(alkenyl), -(alkynyl), -(cycloalkyl), -(haloalkyl), -(alkyl)-O-(alkyl) or -(alkyl)-(cycloalkyl);
$Y_2$ is H, -(alkyl), -(alkenyl), -(alkynyl), -(cycloalkyl), -(haloalkyl), -(alkyl)-O-(alkyl) or -(alkyl)-(cycloalkyl);
$Y_3$ is H, -(alkyl), -(alkenyl), -(alkynyl), -(cycloalkyl), -(haloalkyl), -(alkyl)-O-(alkyl) or -(alkyl)-(cycloalkyl);
$Y_4$ is H, -(alkyl), -(alkenyl), -(alkynyl), -(cycloalkyl), -(haloalkyl), -(alkyl)-O-(alkyl) or -(alkyl)-(cycloalkyl);
$Y_5$ is H, -(alkyl), -(alkenyl), -(alkynyl), -(cycloalkyl), -(haloalkyl), -(alkyl)-O-(alkyl) or -(alkyl)-(cycloalkyl);
α and β are each present or absent and when present each is a bond,
wherein either α or β is present, and
when α is present, then $X_1$ is C and $X_2$ is S or O, or
when β is present, then $X_1$ is N and $X_2$ is N; and
$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —$NH_2$, —$CO_2H$, —$CO_2$—($C_2$-$C_{12}$ alkyl), or —C(O)—NH-(alkyl),
or a pharmaceutically acceptable salt or ester thereof.

In some embodiments of the above compound A is other than

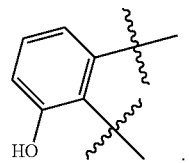 [SMILES: *c1cccc(O)c1*]

In some embodiments, the compound having the structure:

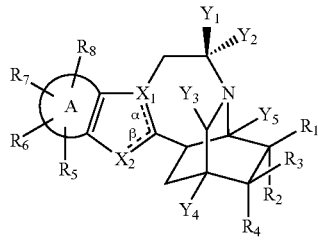

wherein

A is a ring structure, with or without substitution;
$X_1$ is C or N;
$X_2$ is N, O, or S;
$Y_1$ is H, -(alkyl), -(alkenyl), -(alkynyl), -(cycloalkyl) or -(alkyl)-(cycloalkyl);
$Y_2$ is H, -(alkyl), -(alkenyl), -(alkynyl), -(cycloalkyl) or -(alkyl)-(cycloalkyl);
$Y_3$ is H, -(alkyl), -(alkenyl), -(alkynyl), -(cycloalkyl) or -(alkyl)-(cycloalkyl);
$Y_4$ is H, -(alkyl), -(alkenyl), -(alkynyl), -(cycloalkyl) or -(alkyl)-(cycloalkyl);
$Y_5$ is H, -(alkyl), -(alkenyl), -(alkynyl), -(cycloalkyl) or -(alkyl)-(cycloalkyl);
α and β are each present or absent and when present each is a bond,
wherein either α or β is present, and
when α is present, then $X_1$ is C and $X_2$ is S or O, or
when β is present, then $X_1$ is N and $X_2$ is N; and
$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —$NH_2$, —$CO_2H$, —$CO_2$—($C_2$-$C_{12}$ alkyl), or —C(O)—NH-(alkyl),
or a pharmaceutically acceptable salt or ester thereof.

In some embodiments, the compound having the structure:

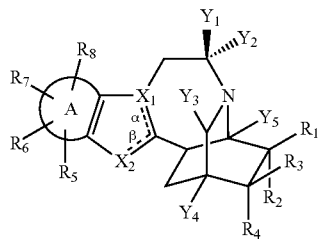

wherein

A is an aryl or heteroaryl;
$X_1$ is C or N;
$X_2$ is N, O, or S;
$Y_1$ is H, -(alkyl), -(alkenyl), -(alkynyl), -(cycloalkyl) or -(alkyl)-(cycloalkyl);
$Y_2$ is H, -(alkyl), -(alkenyl), -(alkynyl), -(cycloalkyl) or -(alkyl)-(cycloalkyl);
$Y_3$ is H, -(alkyl), -(alkenyl), -(alkynyl), -(cycloalkyl) or -(alkyl)-(cycloalkyl);
$Y_4$ is H, -(alkyl), -(alkenyl), -(alkynyl), -(cycloalkyl) or -(alkyl)-(cycloalkyl);

$Y_5$ is H, -(alkyl), -(alkenyl), -(alkynyl), -(cycloalkyl) or -(alkyl)-(cycloalkyl);

α and β are each present or absent and when present each is a bond,
wherein either α or β is present,
when α is present, then $X_1$ is C and $X_2$ is S or O, and
when β is present, then $X_1$ is N and $X_2$ is N;

$R_1$, $R_2$, $R_3$ and $R_4$ are each independently H, -(alkyl), -(alkenyl), -(alkynyl), -(aryl), -(heteroaryl), -(heteroalkyl), -(hydroxyalkyl), -(alkyl)-(aryl), -(alkyl)-(heteroaryl), -(alkyl)-OH, -(alkyl)- O-(alkyl), —OH, —NH$_2$, —CO$_2$H, —CO$_2$—(C$_2$-C$_{12}$ alkyl), or —C(O)—NH-(alkyl); and $R_5$, $R_6$, $R_7$, $R_8$ are each independently —H, halogen, —CN, —CF$_3$, —OCF$_3$, -(alkyl), -(alkenyl), -(alkynyl), -(aryl), -(heteroaryl), -(heteroalkyl), -(hydroxyalkyl), —NH$_2$, —NH-(alkyl), —NH-(alkenyl), —NH-(alkynyl)-NH-(aryl), —NH-(heteroaryl), —OH, —OAc, —CO$_2$H, —CO$_2$-(alkyl), —O—C(O)(alkyl), —O-(alkyl), —O-(alkenyl), —O-(alkynyl), —O-(aryl), —O-(heteroaryl), C(O)—NH$_2$, C(O)—NH-(alkyl), or C(O)—NH-(aryl), or a pharmaceutically acceptable salt or ester thereof.

In some embodiments, the compound having the structure:

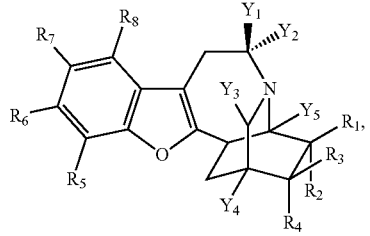

or a pharmaceutically acceptable salt or ester thereof.

In some embodiments of the above compounds, $R_5$ is —H.

In some embodiments of the above compounds, $R_5$ is other than —OH.

In some embodiments, the compound having the structure:

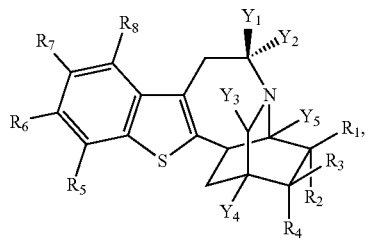

or a pharmaceutically acceptable salt or ester thereof.

In some embodiments, the compound having the structure:

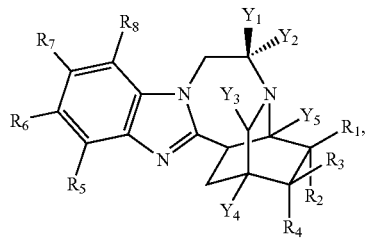

or a pharmaceutically acceptable salt or ester thereof.

In some embodiments, the compound wherein $Y_1$ and $Y_2$ are each —H.

In some embodiments, the compound wherein $R_5$, $R_6$ and $R_8$ are each —H; and $R_7$ is —OH or —OCH$_3$.

In some embodiments, the compound wherein $Y_3$, $Y_4$ and $Y_5$ are each, independently, H or -(alkyl).

In some embodiments, the compound wherein $Y_3$, $Y_4$ and $Y_5$ are each, independently, H or —CH$_3$.

In some embodiments, the compound having the structure:

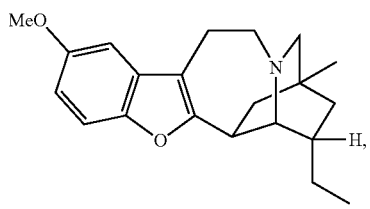

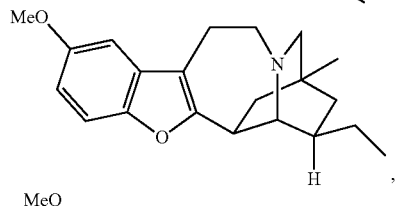

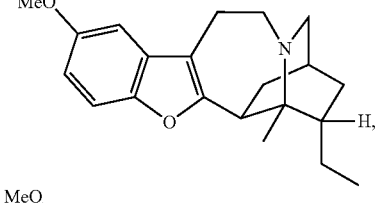

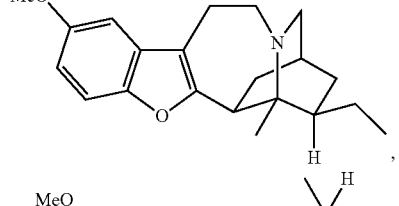

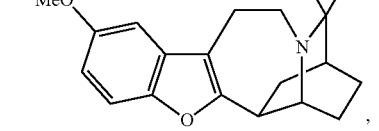

-continued

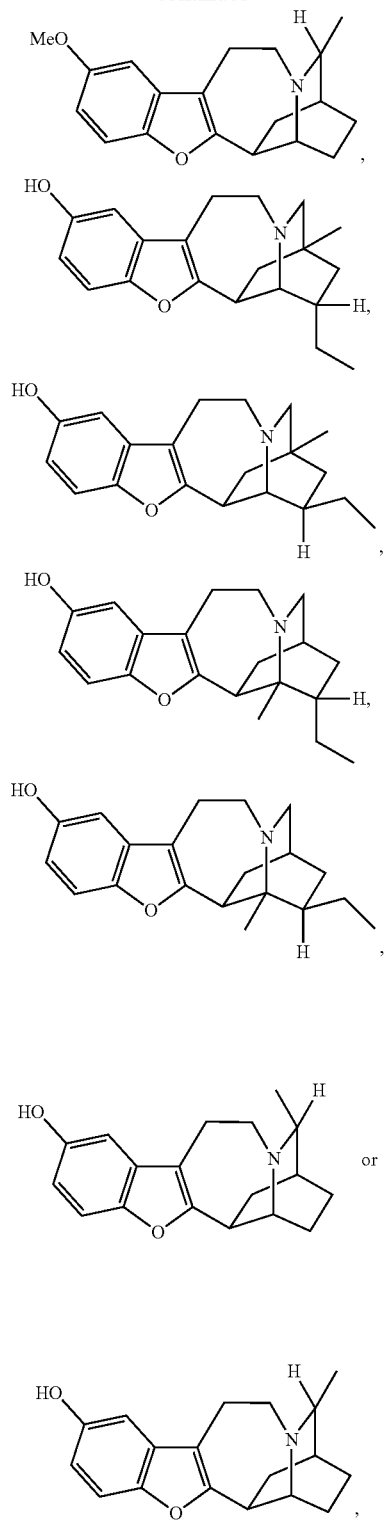

or a pharmaceutically acceptable salt or ester thereof.

In some embodiments of any of the above compounds, $R_5$ is other than —OH.

In some embodiments of any of the above compounds, $R_5$ is —H.

In some embodiments, the compound having the structure:

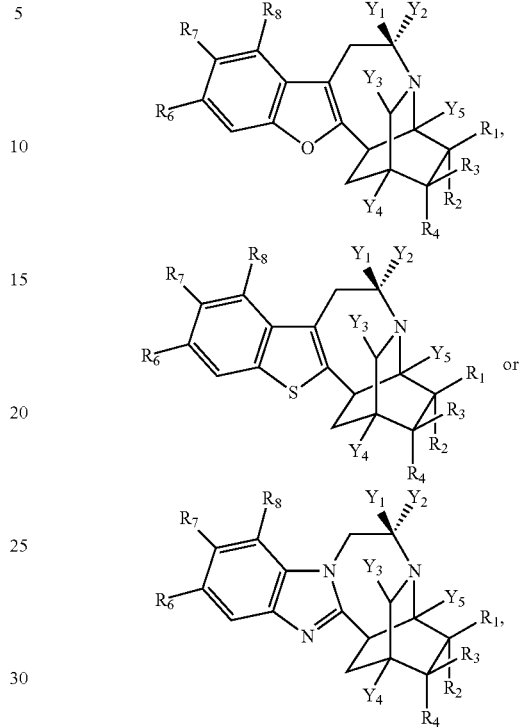

wherein the $R_1$, $R_2$, $R_3$, $R_4$, $R_6$, $R_7$, $R_8$, $Y_1$, $Y_2$, $Y_3$, $Y_4$ and $Y_5$ are defined according any of the above embodiments or combination thereof.

The present invention also provides a pharmaceutical composition comprising the compound of the present application and a pharmaceutically acceptable carrier.

The present invention also provides a method of activating mu-opioid receptor comprising contacting the mu-opioid receptor with the compound of the present application.

The present invention also provides a method of activating delta-opioid receptor comprising contacting the delta-opioid receptor with the compound of the present application.

The present invention also provides a method of activating kappa-opioid receptor comprising contacting the kappa-opioid receptor with the compound of the present application.

The present invention also provides a method of inhibiting mu-opioid receptor comprising contacting the mu-opioid receptor with the compound of the present application.

The present invention also provides a method of inhibiting delta-opioid receptor comprising contacting the delta-opioid receptor with the compound of the present application.

The present invention also provides a method of inhibiting kappa-opioid receptor comprising contacting the kappa-opioid receptor with the compound of the present application.

The present invention also provides a method of treating a subject afflicted with depression or major depression comprising administering an effective amount of the compound of the present application to the subject so as to treat the depression or major depression.

The present invention also provides a method of treating a subject afflicted with pain comprising administering an effective amount of the compound of the present application to the subject so as to treat the pain.

The present invention also provides a method of treating a subject afflicted with an anxiety disorder comprising administering an effective amount of the compound of the present application to the subject so as to treat the anxiety disorder.

The present invention also provides a method of treating a subject afflicted with obsessive-compulsive disorder (OCD) comprising administering an effective amount of the compound of the present application to the subject so as to treat the obsessive-compulsive disorder (OCD).

The present invention also provides a method of treating a subject afflicted with a stress disorder comprising administering an effective amount of the compound of the present application to the subject so as to treat the stress disorder.

In some embodiments of any of the above methods, the compound activates mu-opioid, delta-opioid, or kappa-opioid receptors or any combination thereof in the subject.

In some embodiments of any of the above methods, the compound is an agonist of mu-opioid, delta-opioid, or kappa-opioid receptors or any combination thereof in the subject.

In some embodiments of any of the above methods, the compound inhibits mu-opioid, delta-opioid, or kappa-opioid receptors or any combination thereof in the subject.

In some embodiments of any of the above methods, the compound is an antagonist of mu-opioid, delta-opioid, or kappa-opioid receptors or any combination thereof in the subject.

The present invention further provides a process for producing the compound having the structure:

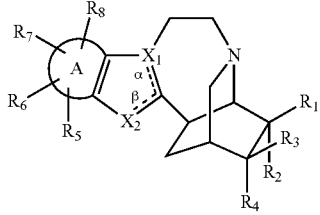

comprising
(a) contacting the compound having the structure:

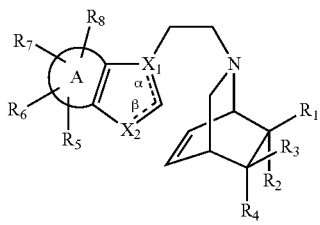

with a preformed palladium (II) catalyst in a first suitable solvent;
(b) adding a second suitable solvent to the reaction mixture; and
(c) adding a reducing agent to the reaction mixture to produce the compound having the structure:

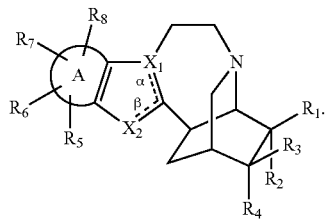

The present invention further provides a process for producing the compound having the structure:

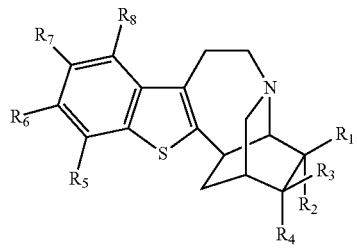

comprising
(a) contacting the compound having the structure:

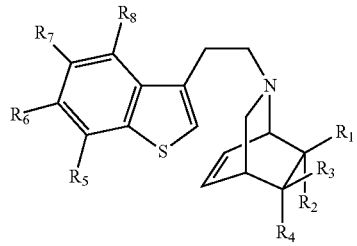

with a preformed palladium (II) catalyst in a first suitable solvent;
(b) adding a second suitable solvent to the reaction mixture; and
(c) adding a reducing agent to the reaction mixture to produce the compound having the structure:

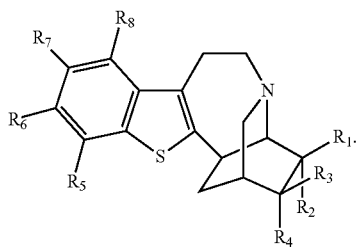

In some embodiments, the process wherein the palladium (II) catalyst is $Pd(CH_3CN)_4(BF_4)_2$.

In some embodiments, the process wherein the first suitable solvent is acetonitrile.

In some embodiments, the process wherein the second suitable solvent is methanol.

In some embodiments, the process wherein the reducing agent is sodium borohydride.

The present invention further provides a process for producing the compound having the structure:

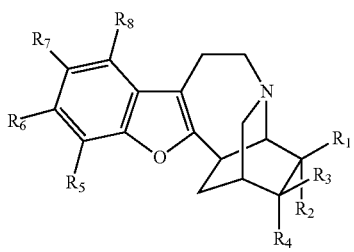

comprising (a) contacting the compound having the structure:

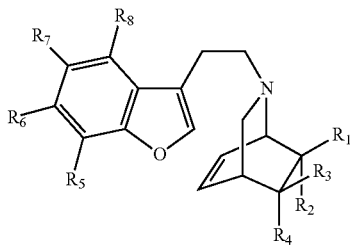

with a nickel (0) catalyst in the presence of an N-heterocyclic carbene in a first suitable solvent to produce a compound having the structure:

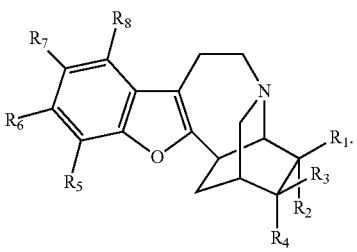

The present invention further provides a process for producing the compound having the structure:

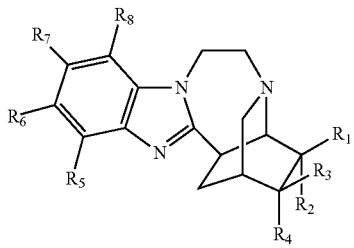

comprising (a) contacting the compound having the structure:

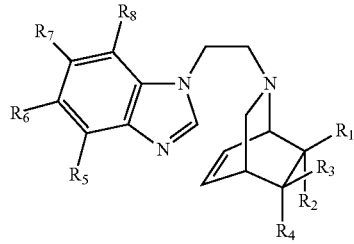

with a nickel (0) catalyst in the presence of an N-heterocyclic carbene in a first suitable solvent to produce a compound having the structure:

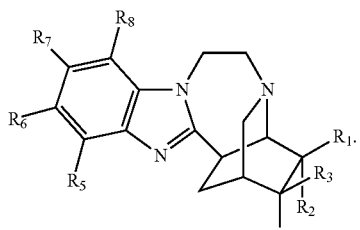

In some embodiments, the process wherein the nickel (0) catalyst is bis(1,5-cyclooctadiene)nickel(0).

In some embodiments, the process wherein the first suitable solvent is heptane.

In some embodiments, the process wherein the first suitable solvent is toluene, hexane, and dodecane.

In some embodiments, the process wherein the first suitable solvent is a non-polar hydrocarbon solvent.

In some embodiments, the process wherein the N-heterocyclic carbene is 1,3-bis(2,4,6-trimethylphenyl)-1,3-2H-imidazol-2-ylidene (IMes).

In some embodiments of any of the above processes, the compound contacted in step (a) is

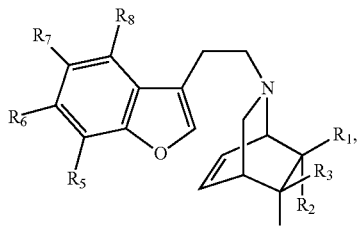

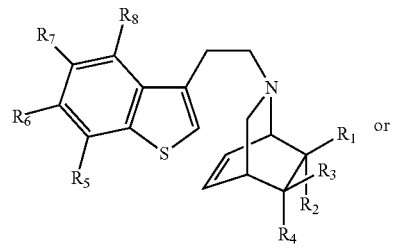

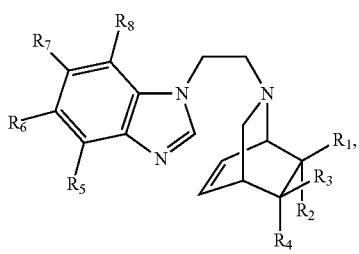
and the compound produced is
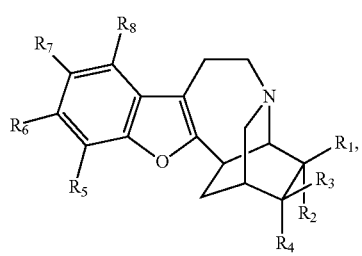
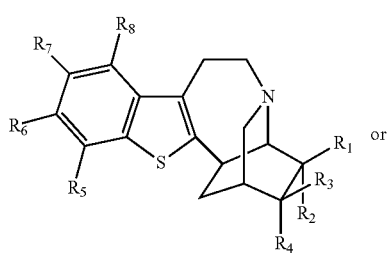
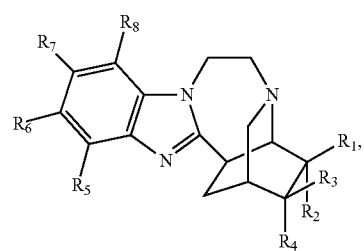
respectively.
In some embodiments of any of the above palladium (II) or nickel (0) cyclization processes, the compound contacted in step (a) is
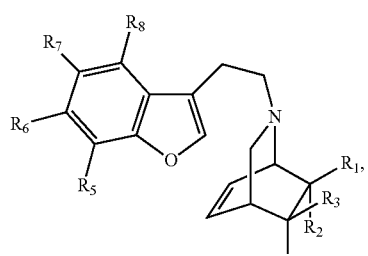
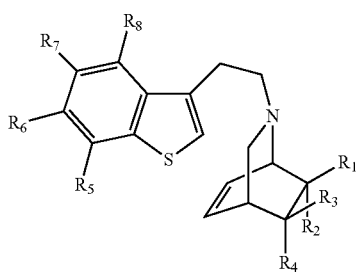
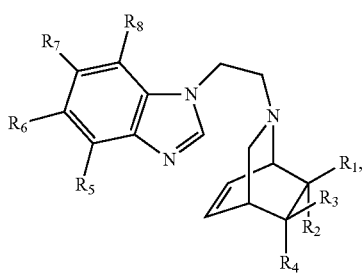
and the compound produced is
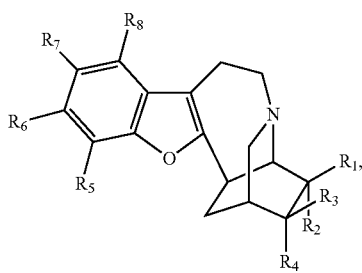
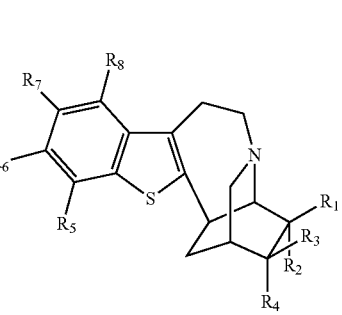
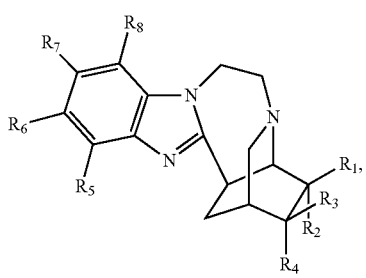
respectively.

In some embodiments of any of the above processes, the compound contacted in step (a) is

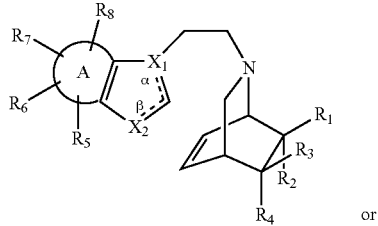

or

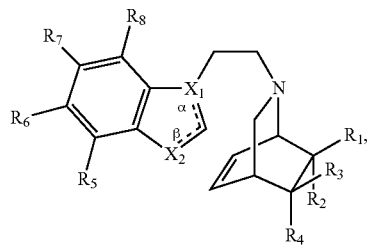

and the compound produced is

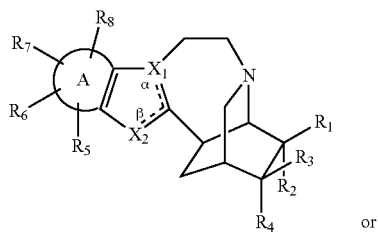

or

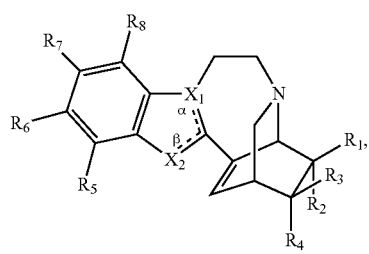

respectively.

In some embodiments of any of the above palladium (II) or nickel (0) processes, the compound contacted in step (a) is

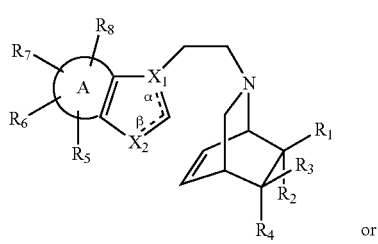

or

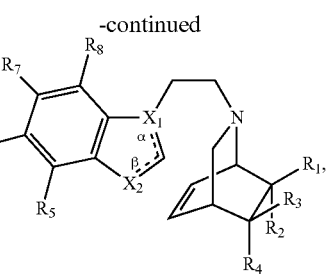

and the compound produced is

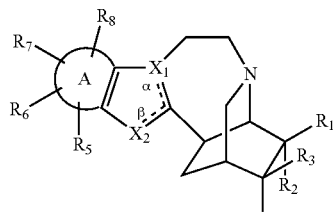

or

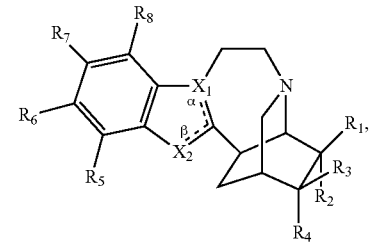

respectively.

The present invention yet further provides a process for producing a compound having the structure:

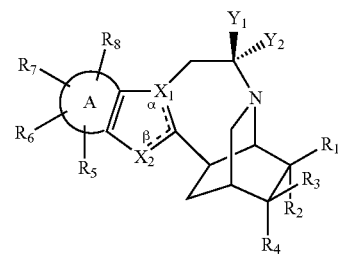

comprising
(a) contacting the compound having the structure:

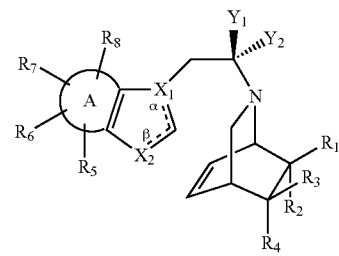

with a preformed palladium (II) catalyst in a first suitable solvent;

(b) adding a second suitable solvent to the reaction mixture; and (c) adding a reducing agent to the reaction mixture to produce the compound having the structure:

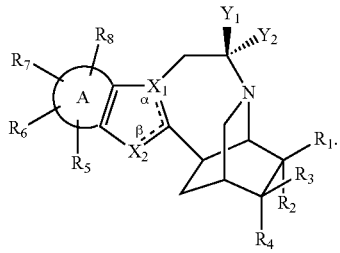

The present invention yet further provides a process for producing the compound having the structure:

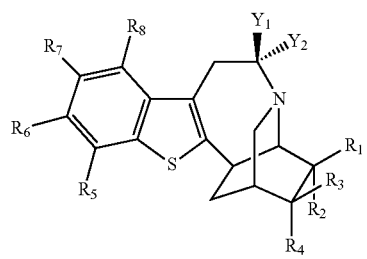

comprising
(a) contacting the compound having the structure:

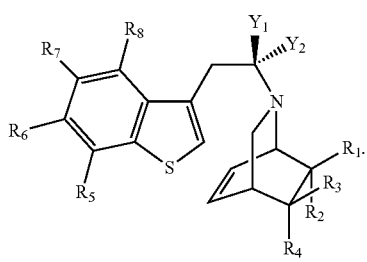

with a preformed palladium (II) catalyst in a first suitable solvent;

(b) adding a second suitable solvent to the reaction mixture; and (c) adding a reducing agent to the reaction mixture to produce the compound having the structure:

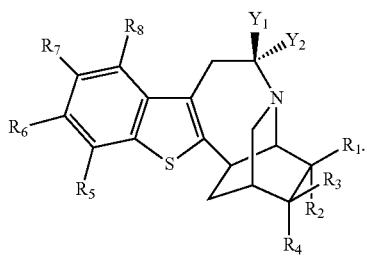

The present invention yet further provides a process for producing the compound having the structure:

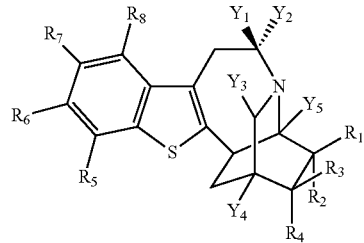

comprising
(a) contacting the compound having the structure:

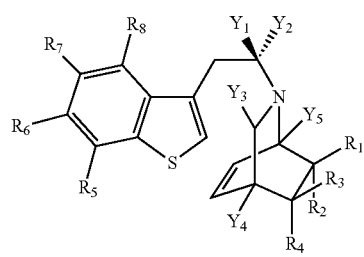

with a preformed palladium (II) catalyst in a first suitable solvent;

(b) adding a second suitable solvent to the reaction mixture; and (c) adding a reducing agent to the reaction mixture to produce the compound having the structure:

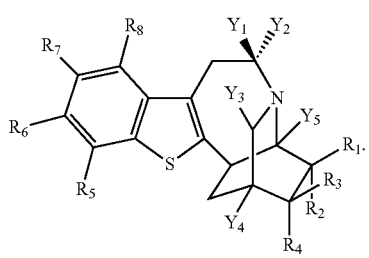

In some embodiments, the above process wherein the palladium (II) catalyst is $Pd(CH_3CN)_4(BF_4)_2$.

In some embodiments, the above process wherein the first suitable solvent is acetonitrile.

In some embodiments, the above process wherein the second suitable solvent is methanol.

In some embodiments, the above process wherein the reducing agent is sodium borohydride.

The present invention yet further provides a process for producing the compound having the structure:

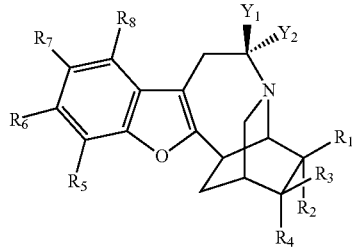

comprising
(a) contacting the compound having the structure:

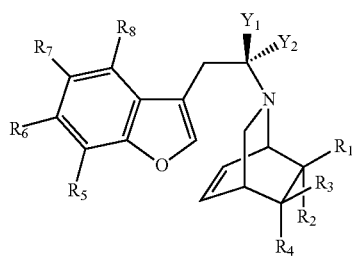

with a nickel (0) catalyst in the presence of an N-heterocyclic carbene in a first suitable solvent to produce a compound having the structure:

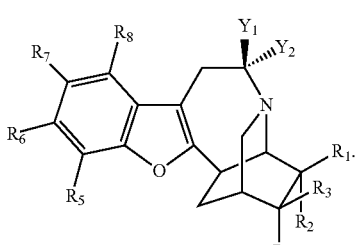

The present invention yet further provides a process for producing the compound having the structure:

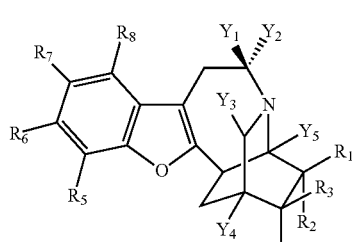

comprising
(a) contacting the compound having the structure:

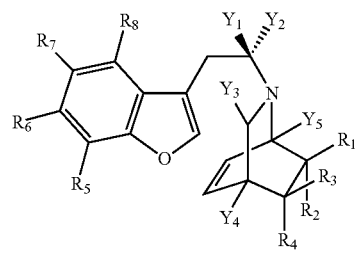

with a nickel (0) catalyst in the presence of an N-heterocyclic carbene in a first suitable solvent to produce a compound having the structure:

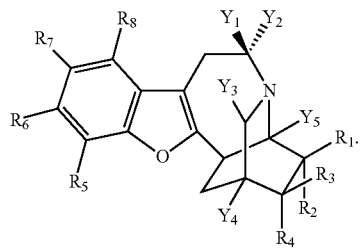

The present invention yet further a process for producing the compound having the structure:

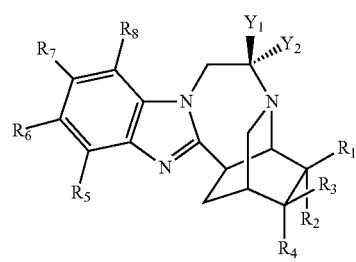

comprising
(a) contacting the compound having the structure:

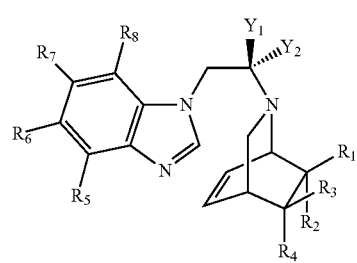

with a nickel (0) catalyst in the presence of an N-heterocyclic carbene in a first suitable solvent to produce a compound having the structure:

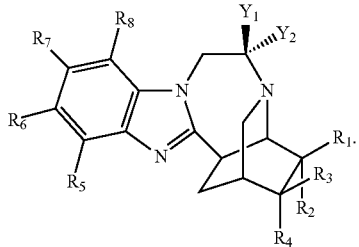

The present invention yet further a process for producing the compound having the structure:

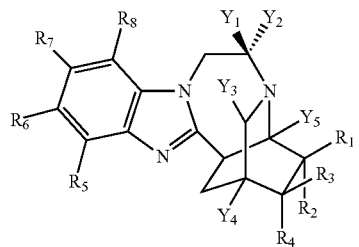

comprising
(a) contacting the compound having the structure:

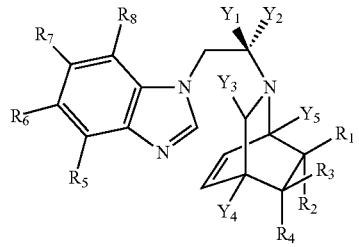

with a nickel (0) catalyst in the presence of an N-heterocyclic carbene in a first suitable solvent to produce a compound having the structure:

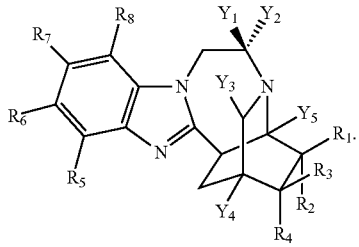

In some embodiments, the above process wherein the nickel (0) catalyst is bis(1,5-cyclooctadiene)nickel(0).

In some embodiments, the above process wherein the first suitable solvent is heptane.

In some embodiments, the process wherein the first suitable solvent is toluene, hexane, and dodecane.

In some embodiments, the process wherein the first suitable solvent is a non-polar hydrocarbon solvent.

In some embodiments, the above process wherein the N-heterocyclic carbene is 1,3-bis(2,4,6-trimethylphenyl)-1,3-2H-imidazol-2-ylidene (IMes).

The present invention provides a pharmaceutical composition comprising the compound of the present invention and a pharmaceutically acceptable carrier.

The present invention provides a method of activating mu-opioid receptor comprising contacting the mu-opioid receptor with the compound of the present invention.

The present invention provides a method of activating delta-opioid receptor comprising contacting the delta-opioid receptor with the compound of the present invention.

The present invention provides a method of activating kappa-opioid receptor comprising contacting the kappa-opioid receptor with the compound of the present invention.

The present invention provides a method of treating a subject afflicted with depression or major depression comprising administering an effective amount of the compound of the present invention to the subject so as to treat the depression or major depression.

The present invention provides a method of treating a subject afflicted with pain comprising administering an effective amount of the compound of the present invention to the subject so as to treat the pain.

The present invention provides a method of treating a subject afflicted with anxiety comprising administering an effective amount of the compound of the present invention to the subject so as to treat the anxiety.

The present invention provides a method of treating a subject afflicted with stress related disorders comprising administering an effective amount of the compound of the present invention to the subject so as to treat the stress related disorder.

In some embodiments, the mu-opioid, delta-opioid or kappa-opioid receptors are in a human subject.

In some embodiments, the stress disorder is post-traumatic stress disorder (PTSD) or acute stress disorder.

In some embodiments, the anxiety disorder is panic disorder, social anxiety disorder, generalized anxiety disorder or a specific phobia.

In some embodiments, a pharmaceutically acceptable salt of any of the above compounds of the present invention.

In some embodiments, any of the above compounds for use in activating the mu-opioid receptor, delta-opioid receptor and/or kappa-opioid receptor.

In some embodiments, any of the above compounds for use in inhibiting the mu-opioid receptor, delta-opioid receptor and/or kappa-opioid receptor.

In some embodiments, any of the above compounds for use in treating a subject afflicted with depression, major depression, pain, anxiety disorder, obsessive-compulsive disorder (OCD) or stress disorder.

In some embodiments, any of the above compounds for use in treating depression, major depression, pain, anxiety disorder, obsessive-compulsive disorder (OCD) or stress disorder.

In some embodiments, use of any of the above compounds for activating the mu-opioid receptor, delta-opioid receptor and/or kappa-opioid receptor.

In some embodiments, use of any of the above compounds for inhibiting the mu-opioid receptor, delta-opioid receptor and/or kappa-opioid receptor.

In some embodiments, use of any of the above compounds for treating a subject afflicted with depression, major depression, pain, anxiety disorder, obsessive-compulsive disorder (OCD) or stress disorder.

In some embodiments, use of any of the above compounds for treating depression, major depression, pain, anxiety disorder, obsessive-compulsive disorder (OCD) or stress disorder.

In some embodiments, a pharmaceutical composition comprising any of the above compounds for treating a subject afflicted with depression, major depression, pain, anxiety disorder, obsessive-compulsive disorder (OCD) or stress disorder.

In some embodiments, a pharmaceutical composition comprising any of the above compounds for treating depression, major depression, pain, anxiety disorder, obsessive-compulsive disorder (OCD) or stress disorder.

Various $R_1$-$R_8$ groups replace the $R_1$-$R_8$ groups found on the compounds of Table 3. Compounds with such $R_1$-$R_8$ groups act as KOR, DOR and/or MOR agonists with similar activity to the compounds of Table 3.

Various $R_1$-$R_8$ groups replace the $R_1$-$R_8$ groups found on the compounds of Tables 4 and 5. Compounds with such $R_1$-$R_8$ groups act as KOR, DOR and/or MOR agonists with similar activity to the compounds of Table 4 and 5.

Various $R_1$-$R_8$ groups replace the $R_1$-$R_8$ groups found on the compounds of Tables 3-5. Compounds with such $R_1$-$R_8$ groups act as KOR, DOR and/or MOR antagonists with similar activity to the compounds of Table 3-5.

An additional aspect of the invention provides synthetic methods that are used to modify or encompass chemical space around the core structure of 35d. Additional compounds are synthesized according to the protocols described in Schemes 1-13, and function analogously to 35d.

An additional aspect of the invention provides synthetic methods that are used to modify or encompass chemical space around the core structure of 35d. Additional compounds are synthesized according to the protocols described in Schemes 1-13, and function analogously to the compounds of Tables 3-5.

Embodiments of the compounds disclosed herein include compounds where $R_1$, $R_2$, $R_3$ or $R_4$ are H, methyl, ethyl, propyl, butyl, pentyl or hexyl.

The term "MOR agonist" is intended to mean any compound or substance that activates the mu-opioid receptor (MOR). The agonist may be a partial, full, super, or biased agonist.

The term "DOR agonist" is intended to mean any compound or substance that activates the delta-opioid receptor (DOR). The agonist may be a partial, full, super, or biased agonist.

The term "KOR agonist" is intended to mean any compound or substance that activates the kappa-opioid receptor (KOR). The agonist may be a partial, full, super, or biased agonist.

The term "MOR antagonist" is intended to mean any compound or substance that blocks or inhibits the mu-opioid receptor (MOR). The antagonist may be a competitive, non-competitive, uncompetitive or silent antagonist.

The term "DOR antagonist" is intended to mean any compound or substance that blocks or inhibits the delta-opioid receptor (DOR). The antagonist may be a competitive, non-competitive, uncompetitive or silent antagonist.

The term "KOR antagonist" is intended to mean any compound or substance that blocks or inhibits the kappa-opioid receptor (KOR). The antagonist may be a competitive, non-competitive, uncompetitive or silent antagonist.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers.

By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^1H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_2$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon-to-carbon double bond, and up to the maximum possible number of non-aromatic carbon-carbon double bonds may be present. Thus, $C_2$-$C_n$ alkenyl is defined to include groups having 1,2 . . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon-to-carbon triple bond, and up to the maximum possible number of non-aromatic carbon-carbon triple bonds may be present. Thus, $C_2$-$C_n$ alkynyl is defined to include groups having 1, 2 . . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl.

As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "heteroalkyl" includes both branched and straight-chain saturated aliphatic hydrocarbon groups having the specified number of carbon atoms and at least 1 heteroatom within the chain or branch.

In some embodiments, the haloalkyl is fluoroalkyl. In some embodiments, the fluoroalkyl is —$CF_3$ or —$CH_2F$.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to tenmembered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons.

The term "benzyl" is intended to mean a —CH$_2$R$_1$ group wherein the R$_1$ is a phenyl group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5$^{th}$ ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Those having ordinary skill in the art of organic synthesis will appreciate that modifications to general procedures and synthetic routes contained in this application can be used to yield additional derivatives and structurally diverse compounds. Suitable organic transformations are described in the forthcoming Figures and Schemes or in March's Advanced Organic Chemistry: Reactions, Mechanisms, and Structure (Wiley-Interscience; $6^{th}$ edition, 2007), the content of which is hereby incorporated by reference.

General Considerations

Reagents and solvents (including anhydrous solvents) were obtained from commercial sources and were used without further purification unless otherwise stated. All compounds were prepared in racemic form. All reactions were performed in flame-dried glassware under argon atmosphere unless otherwise stated and monitored by TLC using solvent mixtures appropriate to each reaction. All column chromatography was performed on silica gel (40-63 µm) and preparative TLC on 20×20 cm plates coated in a 1 mm silica layer. Nuclear magnetic resonance spectra were recorded on Bruker 300, 400, or 500 MHz instruments as indicated. Chemical shifts are reported as δ values in ppm referenced to $CDCl_3$ ($^1$H NMR=7.26 and $^{13}$C NMR=77.16), Methanol-$d_4$ ($^1$H NMR=3.31 and $^{13}$C NMR=49.00), or DMSO-$d_6$ ($^1$H NMR=2.50 and $^{13}$C NMR=39.52). Multiplicity is indicated as follows: s (singlet); d (doublet); t (triplet); q (quartet); p (pentet); h (heptet); dd (doublet of doublets); ddd (doublet of doublet of doublets); dt (doublet of triplets); td (triplet of doublets); dtd (doublet of triplet of doublets); ddt (double of doublet of triplets); m (multiplet); br (broad). For those described compounds containing a carbamate group, complex spectra with split peaks are observed. This effect can be ascribed to the presence of conformers about the carbamate group. Furthermore, compounds containing fluorine are subject to F—C coupling, resulting in splitting of some carbon peaks. As a result of these effects, multiple peaks may correspond to the same proton group or carbon atom. In some cases, this is indicated by an "and" joining two peaks or spectral regions. Alternatively, certain carbon peaks overlap and thus represent two carbons (indicated by (2C) designation). In all cases the assignments of these complex peaks were determined by COSY, HSQC, and/or DEPT-135 experiments. All carbon peaks are rounded to one decimal place unless such rounding would cause two close peaks to become identical. In these cases, two decimal places are retained. Low-resolution mass spectra (LR-MS) were recorded on a JEOL LCmate (ionization mode: APCI+). High-resolution mass spectra (HRMS) were acquired on a high-resolution sector-type double-focusing mass spectrometer (ionization mode: FAB+). In calculated high-resolution masses, the mass difference for loss of one electron has been taken into account for positive ions.

Preparation of Ethyltrichlorosilane Treated Silica Gel

Deactivated silica was prepared as follows. To a suspension of silica gel (40-63 µm, 50 g) in $CH_2Cl_2$ (200 mL) was added ethyltrichlorosilane (4.0 mL) (gas evolution occurs) and the resulting mixture was stirred for 15 min. At this time the treated silica was collected by filtration, washed with $CH_2Cl_2$ (2×100 mL) and MeOH (3×100 mL), and dried in vacuo with gentle warming. Treated TLC plates were prepared in the same manner. However, these were UV opaque and thus were developed in an iodine chamber.

EXAMPLE 1

Initial Studies: Heteroarene C—H Bond Functionalization by Electrophilic Approach Initially, a catalytic electrophilic activation strategy was attempted under acidic conditions to allow formation of the central 7-membered ring in the desired heteroarylazepine scaffold. Electrophilic palladium(II) species are known to activate arenes for addition to olefins in oxidative couplings (effectively stoichiometric Heck reactions) (Fujiwara, Y. et al. 1969; Baran, P. S. et al. 2003). Likewise, Trost (Trost, B. M. et al. 1978; Trost, B. M. et al. 1979; Trost, B. M. et al. 1982) and others (Artman, G. D. et al. 2007) have shown that the intermediate alkyl-palladium species in these reactions can be reduced to afford a reductive coupling process. Therefore, it was hoped that where oxidative cyclization is not feasible due to strain considerations, the intermediate alkyl-palladium species would be susceptible to protonolysis. In such a reaction, an electrophilic palladium (or other metal) species would activate the system either through direct metalation of the heteroarene or through coordination to the olefin. Following C—C bond formation, protonative removal of the metal could regenerate the electrophilic catalyst.

Unfortunately, a variety of Pd(II) salts under protic/acidic conditions failed to effect cyclization. A large variety of other electrophilic transition metal conditions were examined, including platinum and ruthenium catalysts effective for intramolecular indole-alkene hydroarylation reactions (Liu, C. et al. 2007; Youn, S. W. et al. 2004). Several gold-catalyzed conditions were also attempted as well as the non-metallic electrophilic reagent N-phenylselenophthalimide (Wang, M-Z. et al. 2008; Rozenman, M. M. et al. 2007; Zhao, X. et al. 2007). However, in all cases, none or only a trace of the desired product was detected. A frequent problem in many trials was the rapid reduction and precipitation of the electrophilic metal species as the corresponding neutral metal (e.g. palladium black). It is suspected that reduction by the tertiary amine of the substrate is a primary driver of these difficulties. Furthermore, addition of a variety of oxidants did not successfully prevent reduction and precipitation of the metal in the case of palladium.

In contrast, it was found that the palladium tetrafluoroborate salt $Pd(CH_3CN)_4(BF_4)_2$ provided modest yields of the desired heteroarylazepines following sodium borohydride reduction of the resulting organopalladium intermediate (Table 1).

TABLE 1

Preparation of Heteroarylazepines via Electrophilic Palladation-Cyclization[a]

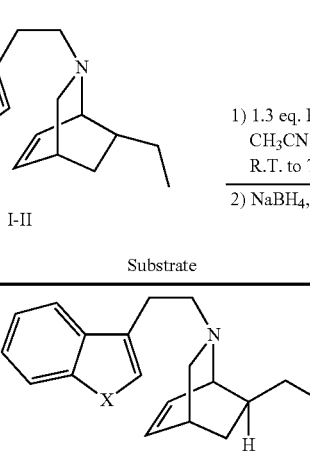

| Entry | Substrate | Result[b] |
|---|---|---|
| 1 | 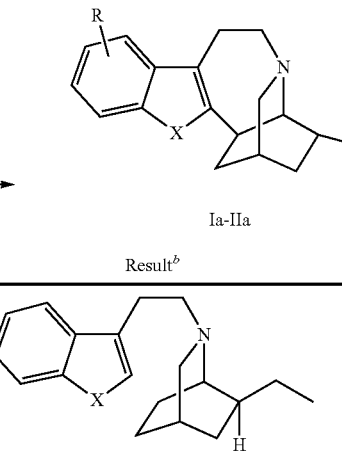 I | (11%) Ia |
| 2[c] | 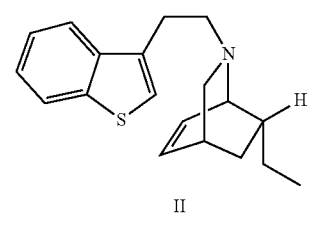 II | 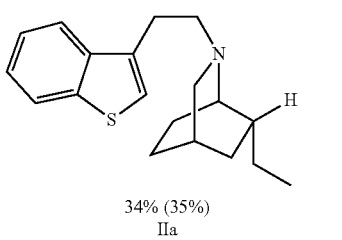 [SMILES: CCC1CC2CCC1N(CCc1csc3ccccc13)C2 ; "34% (35%)IIa"] 34% (35%) IIa |

[a]Reactions run at 0.250 mmol scale,
[b]Isolated yields from representative examples of 2 or more independent trials, NMR yields in parentheses, trial-to-trial variation typically <5%,
[c]Run at 0.060 mmol scale In all cases, the primary side products were the hydrogenated starting materials (olefin reduced), which were often observed in comparable yields to the desired products. Presumably, these side products result from residual starting material that is hydrogenated by liberated hydrogen during the sodium borohydride quench.

General Procedure for Preparation of Heteroarylazepines by $Pd(CH_3CN)_4(BF_4)_2$ Mediated Cyclization of N-arylalkylisoquinuclidines (Ia to IIa). In a glovebox, a Schlenk flask was charged with $Pd(CH_3CN)_4(BF_4)_2$ (144 mg, 0.325 mmol). It was then sealed and removed from the glovebox and anhydrous $CH_3CN$ (3.5 mL) was added to form a yellow solution. To this solution was added a solution of the substrate (0.250 mmol) in anhydrous $CH_3CN$ (9.0 mL) resulting in a color change (ranging from orange to deep-red depending on substrate). The reaction mixture was stirred for 2 h at room temperature and then warmed to 70° C. and stirred for a further 16 h. At this time, the reaction was cooled to 0° C. and anhydrous MeOH (2.25 mL) was added followed by NaBH₄ (30.3 mg, 0.800 mmol), causing the immediate precipitation of palladium black. The resulting black mixture was stirred for 20 min. at 0° C., then diluted with Et₂O (50 mL), filtered through celite, and the filter cake washed with additional Et₂O (4×10 mL). The combined filtrate and washings were concentrated to afford the crude product. The NMR yield was then determined using mesitylene (10 μL) as an internal standard and the product was purified by column chromatography with an appropriate solvent mixture (as described below for each compound).

7-ethyl-6,6a,7,8,9,10,12,13-octahydro-6,9-methanobenzofuro[2,3-d] pyrido[1,2-a]azepine (Ia). The product was not isolated due to low yield. NMR yield was calculated as 11% in two independent trials. For spectral data, see Ni-catalyzed preparation below.

7-ethyl-6,6a,7,8,9,10,12,13-octahydro-6,9-methanobenzo [4,5] thieno[2,3-d]pyrido[1,2-a]azepine (IIa). The reaction was run on 0.060 mmol scale. The product IIa was purified by column chromatography (9:1 hexanes:EtOAc+2% Et₃N, 4 column volumes→8:2 hexanes:EtOAc+2% Et₃N, 2 column volumes) and obtained as a pale-yellow oil (6.0 mg, 34%). ¹H NMR (500 MHz, CDCl₃) δ 7.74 (d, J=7.9 Hz, 1H), 7.62 (d, J=8.1 Hz, 1H), 7.35 (t, J=7.6 Hz, 1H), 7.26 (t, J=7.6 Hz, 1H), 3.46-3.30 (m, 3H), 3.28-3.18 (m, 1H), 3.18-3.09 (m, 2H), 2.92 (s, 1H), 2.82 (d, J=14.7 Hz, 1H), 2.13 (t, J=12.5 Hz, 1H), 2.02-1.90 (m, 3H), 1.75 (dd, J=13.4, 6.6 Hz, 1H), 1.46-1.36 (m, 2H), 1.11-1.00 (m, 1H), 0.94 (t, J=7.4 Hz, 3H); ¹³C NMR (126 MHz, CDCl₃) δ 145.3, 141.6, 138.2, 131.0, 124.0, 123.5, 122.2, 120.9, 57.7, 54.6, 50.7, 42.2, 35.6, 35.2, 31.6, 28.0, 26.5, 23.5, 12.2; HRMS (FAB+) m/z: [M+H]⁺ Calcd for C₁₉H₂₄NS⁺ 298.1624; found 298.1620.

EXAMPLE 2

Initial Studies: Low-Valent Metal Insertion Approach

An alternative cyclization strategy employing a direct C—H insertion mechanism was also explored. It was envisioned that oxidative addition of a low-valent transition metal into the 2-position heteroaryl C—H bond might provide a metal hydride species that could then add directly to the olefin to provide the cyclized product following reductive elimination to regenerate the catalyst. Applying 20 mol % Ni(COD)₂ and 24 mol % IMes (1,3-Bis(2,4,6-trimethylphenyl)-1,3-dihydro-2H-imidazol-2-ylidene) in toluene at 130° C. to benzofuran substrate I, good yields of the cyclized product Ia could be obtained (Table 2). Interestingly, yields with the endo-epimer substrate III were not as high. After some optimization, it was found that heptane was a slightly superior solvent for this transformation, and yields of ~40% were obtained (Table 2). This disparity may result from an increase in steric shielding of the olefin in endo-substrate III. Yields for these transformations could not be further improved.

TABLE 2

Ni-catalyzed C—H Activation[a]

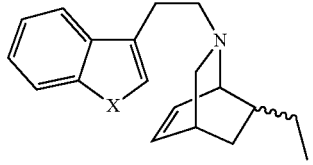

| Entry | Substrate | Result[b] |
|---|---|---|
| 1 | 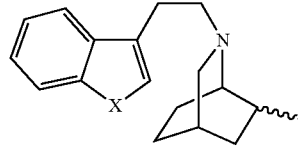 I | 74% (86%) Ia |
| 2 | 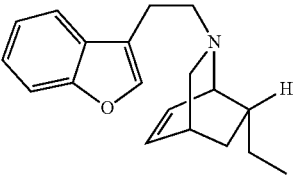 III | 38% (42%) IIIa |
| 3[c] | II | No Conversion |

[a]Reactions run at 0.500 mmol scale,
[b]Isolated yields from representative examples of 2 or more independent trials, NMR yields in parentheses, trial-to-trial variation typically <5%,
[c]Run at 0.250 mmol scale in toluene General Procedure for Preparation by Ni(0) C—H Insertion. In a glovebox, a vial was charged with Ni(COD)$_2$ (27.5 mg, 0.100 mmol) and 1,3-Bis(2,4,6-trimethylphenyl)-1,3-dihydro-2H-imidazol-2-ylidene (IMes, 36.5 mg, 0.120 mmol) followed by anhydrous heptane (1.0 mL) and the resulting black solution was stirred at room temperature for 15 min. To this mixture was then added a solution of the benzofuran substrate (I or III) (0.500 mmol) in anhydrous heptane (1.5 mL) and the reaction vessel was sealed, removed from the glovebox, and heated at 130° C. for 3 h. After cooling to room temperature the reaction mixture was purified directly by a combination of column chromatography and preparatory TLC as described below for each substrate.

7-ethyl-6,6a,7,8,9,10,12,13-octahydro-6,9-methanobenzofuro[2,3-d] pyrido[1,2-a]azepine (Ia). The crude reaction mixture was purified directly by column chromatography (40:1 hexanes:EtOAc+2% Et$_3$N) to yield several fractions as viscous, pale-yellow oils. The central fractions provided pure product (20.3 mg) while the early (96.1 mg) and later (26.1 mg) fractions were contaminated with co-eluting impurities. The later fractions were purified on a second chromatography column (hexanes+4% Et$_3$N) to provide a colorless oil (14.2 mg). This material was combined with the early fractions from the first column and the whole was purified by preparatory TLC (20×20 cm plate, 1 mm silica layer, 80:1 hexanes:EtOAc+2% Et$_3$N) to provide a second portion of pure product as a viscous, nearly colorless oil (83.8 mg). Overall yield of pure product Ia was 104 mg (74%). $^1$H NMR (500 MHz, CDCl$_3$) δ 7.43-7.39 (m, 1H), 7.39-7.35 (m, 1H), 7.24-7.18 (m, 2H), 3.47-3.39 (m, 1H), 3.28-3.13 (m, 3H), 3.02-2.92 (m, 2H), 2.82 (s, 1H), 2.54 (d, J=15.7 Hz, 1H), 2.05 (t, J=12.4 Hz, 1H), 1.90-1.77 (m, 2H), 1.66 (ddd, J=13.3, 6.4, 3.1 Hz, 1H), 1.62-1.43 (m, 3H), 1.25-1.17 (m, 1H), 0.92 (t, J=7.2 Hz, 3H); $^{13}$C NMR (126 MHz, CDCl$_3$) δ 160.0, 153.7, 130.9, 123.3, 122.1, 118.7, 111.6, 110.6, 57.3, 53.3, 49.7, 41.5, 41.1, 33.0, 32.3, 27.5, 26.5, 19.5, 11.9; HRMS (FAB+) m/z: [M]$^+$ Calcd for C$_{19}$H$_{23}$NO$^+$ 281.1775; found 281.1772.

7-ethyl-6,6a,7,8,9,10,12,13-octahydro-6,9-methanobenzofuro[2,3-d] pyrido[1,2-a]azepine (IIIa). The crude reaction mixture was purified directly by column chromatography (9:1 hexanes:EtOAc+2% Et$_3$N) to yield a viscous, orange-brown oil contaminated with a co-eluting impurity. The NMR yield of product contained in this material (42%) was determined using mesitylene (10 μL) as an internal standard and it was then further purified by preparatory TLC (20×20 cm plate, 1 mm silica layer, Et$_2$O+1% Et$_3$N) to provide the pure product IIIa as a viscous, pale-yellow oil (53.3 mg, 38%). $^1$H NMR (500 MHz, CDCl$_3$) δ 7.43-7.39 (m, 1H), 7.38-7.34 (m, 1H), 7.24-7.18 (m, 2H), 3.44 (ddd, J=13.8, 4.7, 2.3 Hz, 1H), 3.38-3.29 (m, 2H), 3.25 (ddd, J=17.0, 12.3, 4.7 Hz, 1H), 3.12-3.02 (m, 2H), 2.88 (s, 1H), 2.57-2.49 (m, 1H), 2.09-1.94 (m, 3H), 1.92-1.85 (m, 1H), 1.62 (ddd, J=13.3, 6.0, 3.7 Hz, 1H), 1.47-1.34 (m, 2H), 1.18-1.09 (m, 1H), 0.95 (t, J=7.4 Hz, 3H); $^{13}$C NMR (126 MHz, CDCl$_3$) δ 160.7, 153.4, 130.7, 123.3, 122.2, 118.6, 112.1, 110.7, 56.5, 53.5, 49.1, 41.9, 34.3, 34.1, 31.6, 28.5, 26.4, 18.9, 12.3; HRMS (FAB+) m/z: [M+H]$^+$ Calcd for C$_{19}$H$_{24}$NO$^+$ 282.1853; found 282.1859.

EXAMPLE 3

Synthesis of 7-Ethylisoquinuclidines

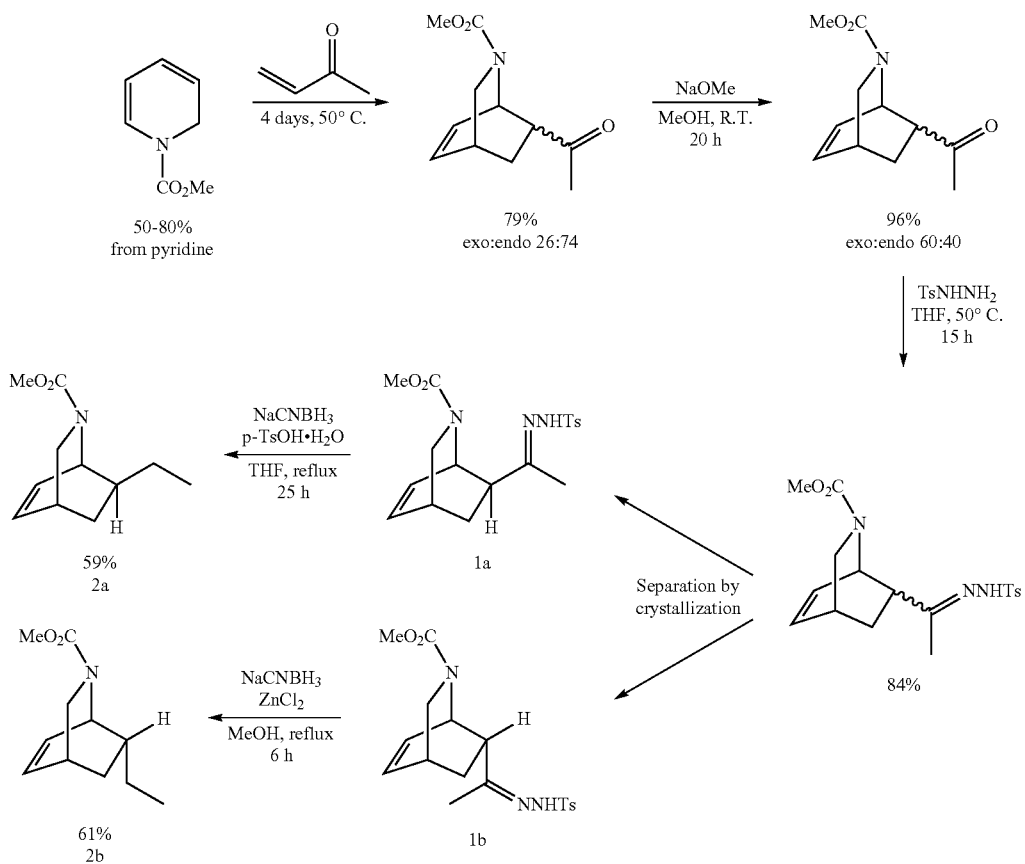

Scheme 1. Synthesis of 7-ethylisoquinuclidines exo-methyl 7-(1-(2-tosylhydrazono)ethyl)-2-azabicyclo[2.2.2]oct-5-ene-2-carboxylate (1a) and endo-methyl 7-(1-(2-tosylhydrazono)ethyl)-2-azabicyclo[2.2.2]oct-5-ene-2-carboxylate (1b). Exo-tosylhydrazone 1a and endo-tosylhydrazone 1b were prepared by the method of Krow (Krow et al. 1988). However, in contrast to this report, crystalline products were obtained for both stereoisomers. Further, the stereochemistry of 1a and 1b has been revised from the initial report as confirmed by 2D NMR experiments and by the reduction of 1a to exo product 2a, the structure of which has been previously assigned by Hodgson using x-ray crystallography (Hodgson, D. M. & Galano, J-M. 2005). For clarification, the preparation of 1a and 1b is described as follows. A mixture of exo/endo-methyl 7-acetyl-2-azabicyclo[2.2.2]oct-5-ene-2-carboxylate (Mariano, P. S. et al. 1979) (60:40 exo:endo ratio, 34.93 g, 167 mmol) and p-toluenesulfonhydrazide (31.10 g, 167 mmol) in anhydrous THF (136 mL) was heated at 50° C. for 15 h, at which time a white precipitate had formed. The reaction mixture was cooled to room temperature and the white precipitate was collected by filtration and washed 3× with ice-cold MeOH, to provide pure endo-tosylhydrazone 1b as a fine white powder (19.55 g, 31%). The filtrate and washings were combined and concentrated to a tan solid, which was recrystallized from MeOH to obtain the pure exo-tosylhydrazone 1a as white plates (33.14 g, 53%).

1a. The exo-tosylhydrazone was prepared by separation of the exo/endo mixture as described above. The spectral data were in agreement with the epimer incorrectly assigned to the endo configuration by Krow (Krow et al. 1988). $^1$H NMR(400 MHz, CDCl$_3$) (spectrum complicated by conformers) δ 7.85 and 7.79 (d, J=8.3 Hz, 2H), 7.35-7.28 (m, 3H), 6.46-6.37 (m, 2H), 4.74-4.68 and 4.61-4.57 (m, 1H), 3.52 and 3.34 (s, 3H), 3.02 and 2.94 (dd, J=9.8, 2.2 Hz, 1H), 2.87 and 2.78 (dt, J=9.8, 2.6 Hz, 1H), 2.73-2.67 (m, 1H), 2.48-2.37 (m, 1H), 2.44 (s, 3H), 2.30 and 2.09 (ddd, J=13.1, 4.4, 2.4 Hz, 1H), 1.89 and 1.80 (s, 3H), 1.42-1.26 (m, 1H); LR-MS calcd. for $C_{18}H_{24}N_3O_4S^+$ [M+H]$^+$ 378.15, found 377.8.

1b. The endo-tosylhydrazone was prepared by separation of the exo/endo mixture as described above. The spectral data were in agreement with the epimer incorrectly assigned to the exo configuration by Krow (Krow et al. 1988). $^1$H NMR (400 MHz, CDCl$_3$) (spectrum complicated by conformers) δ 7.81 (t, J=7.4 Hz, 2H), 7.32 (d, J=8.0 Hz, 2H), 7.12 (s, 1H), 6.19 (q, J=7.5 Hz, 1H), 6.02 (dd, J=12.0, 5.6 Hz, 1H), 4.87 and 4.77 (d, J=4.3 Hz, 1H), 3.69 and 3.66 (s, 3H), 3.23 (d, J=10.1 Hz, 1H), 3.01-2.85 (m, 2H), 2.74 (br s, 1H), 2.45 and 2.44 (s, 3H), 1.87-1.66 (m, 1H), 1.71 and 1.69 (s, 3H), 1.59-1.47 (m, 1H); LR-MS calcd. for $C_{18}H_{24}N_3O_4S^+$ [M+H]$^+$ 378.15, found 377.8.

exo-methyl 7-ethyl-2-azabicyclo[2.2.2]oct-5-ene-2-carboxylate (2a). exo-tosylhydrazone 1a (33.02 g, 87.5 mmol), sodium cyanoborohydride (21.99 g, 350 mmol), and p-toluenesulfonic acid monohydrate (1.40 g, 7.36 mmol) were combined in anhydrous THF (250 mL) and refluxed for 21 h. At this time, additional p-TsOH.H$_2$O (0.35 g, 1.84 mmol) was added and reflux was continued for an additional 4 h. The reaction mixture was then diluted with H$_2$O (250 mL) and extracted with cyclohexane (3×100 mL). The combined organics were washed with H$_2$O (250 mL), saturated aqueous NaHCO$_3$ (250 mL), and H$_2$O again (50 mL), dried over Na$_2$SO$_4$, and concentrated to provide a cloudy, pale-yellow oil. This was washed through a short silica column with 7:3 hexanes:EtOAc and the eluent was concentrated to yield pure exo-isoquinuclidine 2a as a pale-yellow oil (10.12 g, 59%). The spectral data were in agreement with the epimer incorrectly assigned to the endo configuration by Krow and in agreement with the data reported by Hodgson (Krow et al. 1988; Hodgson, D. M. & Galano, J-M. 2005). $^1$H NMR (400 MHz, CDCl$_3$) δ 6.47 and 6.42 (br dd, J=7 Hz, 1H), 6.34 and 6.30 (br dd, J=8 Hz, 1H), 4.59 and 4.44 (d, J=6 Hz, 1H), 3.67 and 3.66 (s, 3H), 3.20 (td, J=10, 2 Hz, 1H), 2.98 and 2.94 (dt, J=10, 3 Hz, 1H), 2.65 (m, 1H), 1.64 and 1.61 (dt, J=10, 3 Hz, 1H), 1.38 (m, 3H), 1.00 (m, 1H), 0.95 and 0.92 (t, J=7 Hz, 3H); $^{13}$C NMR (101 MHz, CDCl$_3$) δ 156.7 and 156.3, 133.8 and 133.7, 133.3 and 133.1, 52.2 and 52.1, 49.1 and 48.8, 48.4 and 48.1, 40.7, 30.8 and 30.6, 29.9, 27.5 and 27.4, 12.1 and 12.0; LR-MS calcd. for $C_{11}H_{18}NO_2^+$ [M+H]$^+$ 196.13, found 195.9.

endo-methyl 7-ethyl-2-azabicyclo[2.2.2]oct-5-ene-2-carboxylate (2b). To a suspension of endo-tosylhydrazone 1b (3.50 g, 9.27 mmol) in anhydrous MeOH (41 mL) was added a solution of sodium cyanoborohydride (833 mg, 13.26 mmol) and ZnCl$_2$ (904 mg, 6.63 mmol) in anhydrous MeOH (28 mL), and the resulting mixture was refluxed for 3 h. The reaction was then quenched with 1% aqueous NaOH (200 mL) and extracted with cyclohexane (3×50 mL). The combined organics were washed with H$_2$O (50 mL) and brine (50 mL), dried over Na$_2$SO$_4$, and concentrated to provide a clear, colorless oil. This was washed through a short silica column with 1:1 hexanes:EtOAc and the eluent was concentrated to yield pure endo-isoquinuclidine 2b as a colorless oil (1.11 g, 61%). The spectral data were in agreement with the epimer incorrectly assigned to the exo configuration by Krow (Krow et al. 1988). $^1$H NMR (400 MHz, CDCl$_3$) δ 6.31 (m, 2H), 4.66 and 4.48 (s, 1H), 3.69 and 3.66 (s, 3H), 3.21 (m, 1H), 2.94 (m, 1H), 2.69 (m, 1H), 1.96 (m, 1H), 1.81 (m, 1H), 1.19 (m, 1H), 1.01-0.84 (m, 5H); $^{13}$C NMR (101 MHz, CDCl$_3$) δ 155.6 and 155.2, 134.4 and 134.0, 130.6 and 130.0, 52.0 and 51.9, 49.3 and 48.9, 46.9 and 46.5, 40.7 and 40.5, 31.0 and 30.8, 30.0, 28.3 and 28.2, 11.2; LR-MS calcd. for $C_{11}H_{18}NO_2^+$ [M+H]$^+$ 196.13, found 195.9.

EXAMPLE 4

Synthesis of 7-Substituted Isoquinuclidines (Method A)

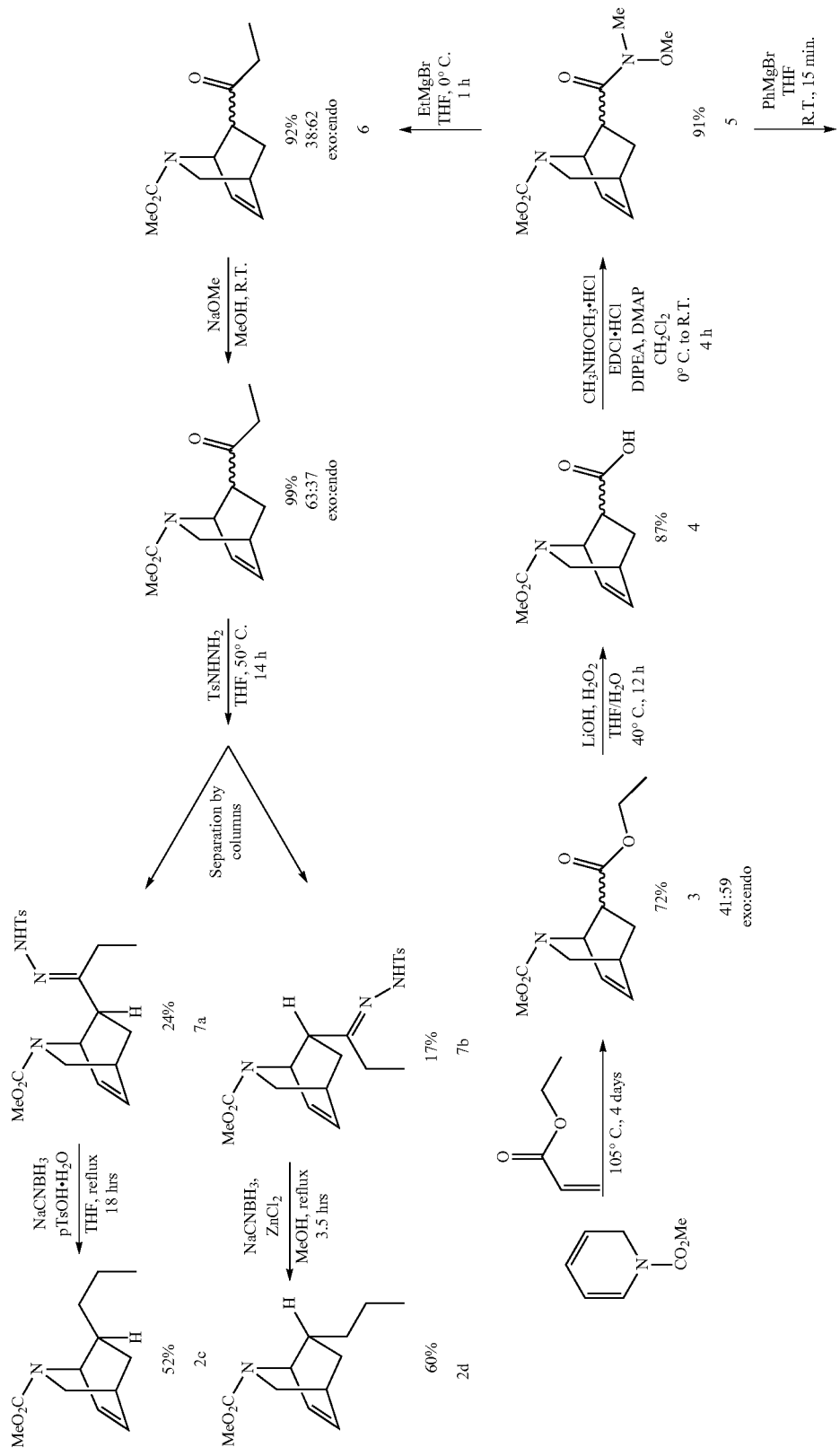
Scheme 2. Synthesis of 7-Substituted isoquinuclidines (Method A)

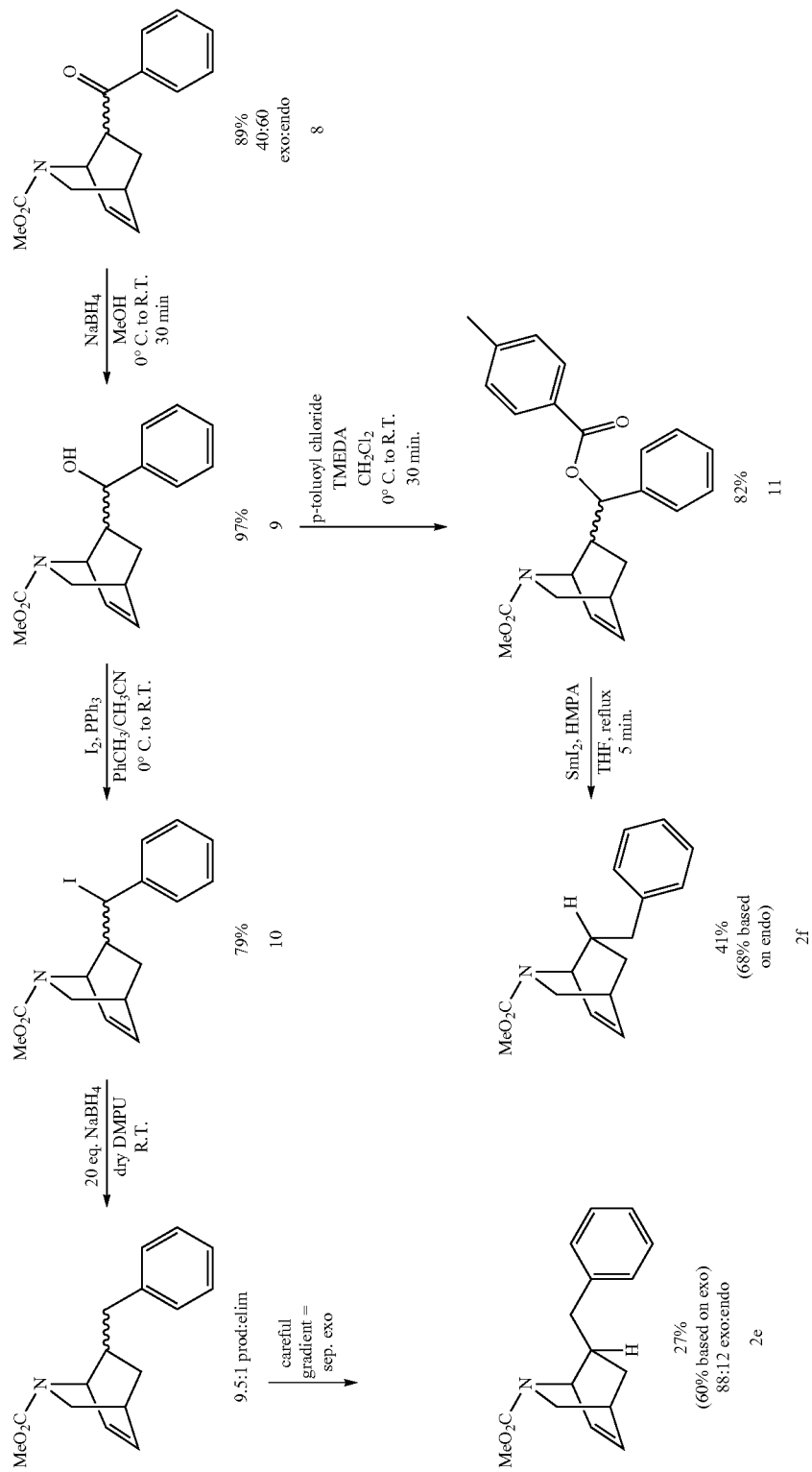

exo/endo-7-ethyl 2-methyl 2-azabicyclo[2.2.2]oct-5-ene-2,7-dicarboxylate (3). N-(methoxycarbonyl)-1,2-dihydropyridine (22.9 g, 165 mmol) was combined with ethyl acrylate (82.6 g, 825 mmol) and the mixture was heated at 105° C. for 4 days. After removing the volatiles in vacuo the resulting yellow oil was purified by column chromatography (3:1 hexanes:EtOAc) to yield ester 3 as a colorless oil (28.6 g, 72%, 41:59 exo:endo determined by $^1$H NMR). $^1$H NMR (400 MHz, CDCl$_3$) (some partial integrals due to conformers and exo/endo mixture) δ 6.54-6.24 (m, 2H), 5.22-4.88 (m, 1H), 4.22-4.02 (m, 2H), 3.67 (m, 3H), 3.41-3.19 (m, 1H), 3.11-3.00 (m, 1H), 3.00-2.88 (m, 1.6H), 2.88-2.74 (m, 1H), 2.53 (tdd, J=10.9, 4.3, 2.1 Hz, 0.4H), 2.10 (tdd, J=6.8, 4.3, 2.5 Hz, 0.4H), 1.92-1.76 (m, 1.2H), 1.58-1.50 (m, 0.4H), 1.26 (m, 3H).

exo/endo-2-(methoxycarbonyl)-2-azabicyclo[2.2.2]oct-5-ene-7-carboxylic acid (4). Ester 3 (28.0 g, 117 mmol) was dissolved in THF (440 mL) and H$_2$O (147 mL) and the solution was cooled to 0° C. H$_2$O$_2$ (34.3 mL of 30% aq. soln., 336 mmol) and LiOH.H$_2$O (9.82 g, 234 mmol) were then added and the mixture was warmed to 40° C. and left to stir for 12 h. After this time, the reaction was cooled to room temperature and the THF was removed in vacuo. The mixture was then diluted with H$_2$O (100 mL) and washed with CH$_2$Cl$_2$ (3×50 mL). The aqueous phase was then acidified with 10% HCl and extracted with CH$_2$Cl$_2$ (4×50 mL). The combined organic extracts were washed with H$_2$O (2×50 mL), dried over Na$_2$SO$_4$, filtered, and concentrated to yield acid 4 as a colorless oil that slowly crystallized into a white, waxy solid (21.5 g, 87%). $^1$H NMR (300 MHz, CDCl$_3$) (some partial integrals due to conformers and exo/endo mixture, OH not observed) δ 6.56-6.27 (m, 2H), 5.25-4.91 (m, 1H), 3.79-3.60 (m, 3H), 3.37 (d, J=10.1 Hz, 0.4H), 3.26 (d, J=10.0 Hz, 0.6H), 3.13 (s, 0.6H), 2.95 (t, J=11.5 Hz, 1H), 2.84 (s, 1H), 2.59 (d, J=8.6 Hz, 0.4H), 2.07 (d, J=12.7 Hz, 0.4H), 1.94-1.78 (m, 1.2H), 1.60 (t, J=11.8 Hz, 0.4H); LR-MS calcd. for $C_{10}H_{14}NO_4^+$ [M+H]$^+$ 212.09, found 212.23.

exo/endo-methyl 7-(methoxy(methyl)carbamoyl)-2-azabicyclo[2.2.2]oct-5-ene-2-carboxylate (5). Acid 4 (15.0 g, 71.0 mmol) was dissolved in anhydrous CH$_2$Cl$_2$ (1.0 L) and cooled to 0° C. DIPEA (14.8 mL, 11.0 g, 85.2 mmol), 1-ethyl-3-(3-dimethylaminopropyl)carbodiimide hydrochloride (14.3 g, 74.6 mmol), N,O-dimethylhydroxylamine hydrochloride (8.31 g, 85.2 mmol), and DMAP (867 mg, 7.10 mmol) were then added and the mixture was stirred for 2 h at 0° C. and 2 h at room temperature before quenching with H$_2$O (700 mL). The organic layer was separated and washed with 1% NaOH (2×150 mL), 2% HCl (3×100 mL), and H$_2$O (150 mL), dried over Na$_2$SO$_4$, filtered through celite, and concentrated to yield amide 5 as a yellow oil (16.5 g, 91%, 41:59 exo:endo determined by $^1$H NMR). $^1$H NMR (300 MHz, CDCl$_3$) (some partial integrals due to conformers and exo/endo mixture) δ 6.52-6.32 (m, 2H), 5.10-4.77 (m, 1H), 3.77-3.58 (m, 6H), 3.44-3.23 (m, 2H), 3.20-3.10 (m, 3H), 3.05-2.86 (m, 1H), 2.86-2.71 (m, 1H), 2.25-2.10 (m, 0.4H), 2.01-1.82 (m, 0.6H), 1.79-1.58 (m, 0.6H), 1.52-1.35 (m, 0.4H); $^{13}$C NMR (126 MHz, CDCl$_3$) (very complex due to conformers and exo/endo mixture) δ 156.3, 155.8, 135.6, 135.3, 134.2, 134.0, 132.3, 131.8, 131.1, 130.9, 61.5, 61.4, 61.2, 52.5, 52.4, 52.3, 47.6, 47.4, 47.11, 47.09, 47.06, 47.0, 46.82, 46.81, 42.4, 41.9, 41.5, 41.2, 33.1 (br), 32.9 (br), 32.5 (br), 30.9, 30.7, 30.3, 30.1, 27.9, 27.4, 24.9, 24.7; LR-MS calcd. for $C_{22}H_{29}N_2O_4^+$ [M+H]$^+$ 255.13, found 255.23.

exo/endo-methyl 7-propionyl-2-azabicyclo[2.2.2]oct-5-ene-2-carboxylate (6, synthesis and epimerization). Amide 5 (5.00 g, 19.7 mmol) was dissolved in anhydrous THF (200 mL) and the solution was cooled to 0° C. EtMgBr (13.1 mL of 3.0 M soln. in Et$_2$O, 39.4 mmol) was then added, and the reaction was left to stir at 0° C. for 1 h. After quenching with ice-cold 5% HCl in 6:1 EtOH:H$_2$O (200 mL), the mixture was diluted with H$_2$O (400 mL) and extracted with CH$_2$Cl$_2$ (3×100 mL). The combined organics were washed with H$_2$O (2×150 mL), dried over Na$_2$SO$_4$, and concentrated to yield ketone 6 as a pale yellow oil (4.06 g, 92%, 38:62 exo:endo determined by $^1$H NMR). To enrich the exo-epimer, this material was dissolved in MeOH (140 mL) under argon, sodium methoxide (5.90 g, 109.2 mmol) was added, and the mixture was stirred at room temperature for 4 h. After removing the MeOH in vacuo, the remaining aqueous was extracted with CH$_2$Cl$_2$ (3×50 mL). The combined organics were washed with water (50 mL) and brine (50 mL), dried over Na$_2$SO$_4$, and concentrated to yield exo-enriched ketone 6 as a yellow oil (4.00 g, 99%, 63:37 exo:endo determined by $^1$H NMR). $^1$H NMR (400 MHz, CDCl$_3$) (some partial integrals due to conformers and exo/endo mixture) δ 6.52-6.42 (m, 1.2H), 6.39 (t, J=7.4 Hz, 0.4H), 6.31-6.25 (m, 0.4H), 5.17-4.80 (m, 1H), 3.66 (m, 3H), 3.35-3.23 (m, 1H), 3.17-3.05 (m, 0.4H), 3.03-2.87 (m, 1H), 2.87-2.72 (m, 1H), 2.72-2.61 (m, 1H), 2.52-2.35 (m, 1.4H), 2.25-2.12 (m, 0.6H), 1.91-1.57 (m, 1H), 1.44-1.27 (m, 0.6H), 1.05 (m, 3H); LR-MS calcd. for $C_{12}H_{18}NO_3^+$ [M+H]$^+$ 224.13, found 224.00.

exo-methyl 7-(1-(2-tosylhydrazono)propyl)-2-azabicyclo[2.2.2]oct-5-ene-2-carboxylate (7a) and endo-methyl 7-(1-(2-tosylhydrazono)propyl)-2-azabicyclo[2.2.2]oct-5-ene-2-carboxylate (7b) (synthesis and separation). Exo-enriched ketone 6 (4.00 g, 17.9 mmol) and tosylhydrazine (3.33 g, 17.9 mmol) were combined in anhydrous THF (15 mL) and the mixture was stirred at 50° C. for 14 h. After removing the volatiles in vacuo, the resulting off-white solid was purified by repeated column chromatography (gradients of Et$_2$O in CH$_2$Cl$_2$) to yield the pure exo (7a, 1.69 g, 24%) and endo (7b, 1.17 g, 17%) epimers along with several mixed exo/endo fractions (2.65 g, 38%).

7a. The exo-tosylhydrazone was prepared by separation of the exo/endo mixture as described above and obtained as a white solid. $^1$H NMR (400 MHz, CDCl$_3$) (spectrum complicated by conformers) δ 7.84 and 7.78 (d, J=8.3 Hz, 2H), 7.37 (br s, 1H), 7.32 (t, J=7.3 Hz, 2H), 6.47-6.36 (m, 2H), 4.67 and 4.55 (m, 1H), 3.49 and 3.36 (s, 3H), 3.09 and 2.99 (dd, J=9.8, 2.1 Hz and J=9.9, 1.9 Hz, 1H), 2.88 and 2.80 (dt, J=10.1, 2.4 Hz and J=9.8, 2.6 Hz, 1H), 2.70 (dd, J=5.1, 2.6 Hz, 1H), 2.51 and 2.45 (ddd, J=10.6, 4.4, 1.7 Hz, 1H), 2.44 (s, 3H), 2.39-2.04 (m, 3H), 1.40-1.24 (m, 1H), 1.11-0.99 (m, 3H); LR-MS calcd. for $C_{19}H_{26}N_3O_4S^+$ [M+H]$^+$ 392.16, found 391.90.

7b. The endo-tosylhydrazone was prepared by separation of the exo/endo mixture as described above and obtained as a white solid. $^1$H NMR (400 MHz, CDCl$_3$) (spectrum complicated by conformers) δ 7.79 (t, J=7.2 Hz, 2H), 7.52 (br t, J=16.9 Hz, 1H), 7.30 (d, J=8.1 Hz, 2H), 6.22-6.10 (m, 1H), 6.05-5.92 (m, 1H), 4.83 and 4.72 (d, J=4.1 Hz and 4.3 Hz, 1H), 3.68 and 3.65 (s, 3H), 3.32-3.18 (m, 1H), 3.01-2.86 (m, 2H), 2.73 (br s, 1H), 2.44 and 2.43 (s, 3H), 2.23-1.96 (m, 2H), 1.83-1.62 and 1.55-1.47 (m, 2H), 1.04-0.97 (m, 3H); LR-MS calcd. for $C_{19}H_{26}N_3O_4S^+$ [M+H]$^+$ 392.16, found 391.90.

exo-methyl 7-propyl-2-azabicyclo[2.2.2]oct-5-ene-2-carboxylate (2c). Exo-tosylhydrazone 7a (1.64 g, 4.19 mmol), sodium cyanoborohydride (1.05 g, 16.8 mmol), and p-toluenesulfonic acid monohydrate (67.0 mg, 0.352 mmol) were combined in anhydrous THF (17 mL), and the mixture was refluxed for 13 h. At this time an additional portion of p-TsOH.H$_2$O (17 mg, 0.088 mmol) was added, and reflux was continued for an additional 5 h. After cooling to room temperature, the reaction mixture was extracted with cyclohexane (3×20 mL). The combined organics were washed with H$_2$O (20 mL), sat. aq. NaHCO$_2$ (20 mL), and H$_2$O again (20 mL), dried over Na$_2$SO$_4$, and concentrated to yield a cloudy yellow oil. This was purified by column chromatography (7:1 hexanes:EtOAc) to yield exo-isoquinuclidine 2c as a thin, pale-yellow oil (460 mg, 52% yield). $^1$H NMR (400 MHz, CDCl$_3$) (spectrum complicated by conformers) δ 6.53-6.38 (m, 1H), 6.38-6.25 (m, 1H), 4.56 and 4.41 (d, J=6.1 Hz, 1H), 3.69 and 3.67 (s, 3H), 3.21 (td, J=10.0, 2.2 Hz, 1H), 2.97 (ddt, J=18.6, 10.0, 2.6 Hz, 1H), 2.72-2.59 (br m, 1H), 1.67-1.49 (m, 2H), 1.47-1.24 (m, 4H), 1.00 (dd, J=11.2, 2.8 Hz, 1H), 0.92-0.86 (m, 3H); $^{13}$C NMR (101 MHz, CDCl$_3$) (spectrum complicated by conformers). δ 156.2 and 155.8, 133.4 and 133.3, 132.9 and 132.8, 51.7, 49.2 and 48.8, 48.1 and 47.8, 38.1, 36.6 and 36.5, 30.5 and 30.3, 29.7 and 29.6, 20.3 and 20.2, 13.8; LR-MS calcd. for C$_{12}$H$_{20}$NO$_2$$^+$ [M+H]$^+$ 210.15, found 210.07.

endo-methyl 7-propyl-2-azabicyclo[2.2.2]oct-5-ene-2-carboxylate (2d). Sodium cyanoborohydride (264 mg, 4.20 mmol) and ZnCl$_2$ (286 mg, 2.10 mmol) were dissolved in anhydrous MeOH and this solution was added to a solution of endo-tosylhydrazone 7b in anhydrous MeOH (13 mL). After refluxing for 3.5 h the reaction was quenched with 1.0% aq. NaOH (70 mL) and extracted with cyclohexane (3×50 mL). The combined organics were washed with H$_2$O (50 mL) and brine (50 mL), dried over Na$_2$SO$_4$, and concentrated to yield a pale-yellow cloudy oil. This was purified by column chromatography (6:1 hexanes:EtOAc) to yield endo-isoquinuclidine 2d as a thin yellow oil (372 mg, 60% yield).

$^1$H NMR (400 MHz, CDCl$_3$) (spectrum complicated by conformers) δ 6.38 (dd; J=14.3, 6.9 Hz, 1H), 6.34-6.22 (m, 1H), 4.65-4.61 and 4.48-4.43 (br m, 1H), 3.69 and 3.66 (s, 3H), 3.24-3.16 (m, 1H), 2.94 (ddt, J=19.6, 10.1, 2.5 Hz, 1H), 2.69 (br s, 1H), 2.13-1.98 (m, 1H), 1.85-1.76 (m, 1H), 1.35-1.23 (m, 2H), 1.23-1.10 (m, 1H), 0.99-0.82 (m, 5H); $^{13}$C NMR (101 MHz, CDCl$_3$) (spectrum complicated by conformers). δ 155.5 and 155.1, 134.4 and 134.0, 130.6 and 130.0, 52.0 and 51.9, 49.5 and 49.0, 46.9 and 46.5, 38.6 and 38.3, 37.7, 31.1 and 30.8, 30.2, 19.72 and 19.66, 13.9; LR-MS calcd. for C$_{12}$H$_{20}$NO$_2$$^+$ [M+H]$^+$ 210.15, found 210.02.

exo/endo-methyl 7-benzoyl-2-azabicyclo[2.2.2]oct-5-ene-2-carboxylate (8). Amide 5 (2.00 g, 7.87 mmol) was dissolved in anhydrous THF (80 mL) and PhMgBr (15.7 mL of 3.0 M soln. in Et$_2$O, 47.2 mmol) was added at room temperature. After stirring for 15 min. the reaction was quenched with ice-cold 5% HCl in 6:1 EtOH:H$_2$O (160 mL), diluted with H$_2$O (250 mL), and extracted with CH$_2$Cl$_2$ (3×80 mL). The combined organics were washed with H$_2$O (2×100 mL), dried over Na$_2$SO$_4$, and concentrated to yield a yellow oil. This was purified by column chromatography (7:3 hexanes:EtOAc) to yield ketone 8 as an off-white waxy solid (1.91 g, 89%, 40:60 exo:endo determined by $^1$H NMR, 89% yield). $^1$H NMR (400 MHz, CDCl$_3$) (spectrum complicated by conformers). δ 8.02-7.85 (m, 2H), 7.61-7.51 (m, 1H), 7.51-7.41 (m, 2H), 6.60-6.24 (m, 2H), 5.20 and 5.03 (br s, 0.6H), 4.97 and 4.82 (d, J=6.0 Hz, 0.4H), 4.04-3.90 (m, 0.6H), 3.74, 3.73, 3.60, and 3.37 (s, 3H), 3.65-3.54 (m, 0.4H), 3.49-3.34 (m, 1H), 3.09-2.93 (m, 1H), 2.88 (br s, 1H), 2.28 (dd, J=23.0, 12.0 Hz, 0.4H), 2.10-1.75 (m, 1.2H), 1.61-1.49 (m, 0.4H); LR-MS calcd. for C$_{16}$H$_{18}$NO$_3$$^+$ [M+H]$^+$ 272.13, found 272.26.

exo/endo-methyl 7-(hydroxy(phenyl)methyl)-2-azabicyclo[2.2.2]oct-5-ene-2-carboxylate (9). Ketone 8 (1.67 g, 6.16 mmol) was dissolved in MeOH (50 mL) and the solution was chilled to 0° C. NaBH$_4$ (233 mg, 6.16 mmol) was then added and the solution was warmed to room temperature and stirred for 30 min. The volatiles were removed in vacuo to yield a white solid, which was partitioned between CH$_2$Cl$_2$ (25 mL) and H$_2$O (25 mL). After separating the organics, the aqueous layer was extracted with additional CH$_2$Cl$_2$ (25 mL). The combined organics were washed with H$_2$O (25 mL) and saturated aqueous NH$_4$Cl (2×25 mL), dried over Na$_2$SO$_4$, and concentrated to yield alcohol 9 as a white solid (1.63 g, 97%). $^1$H NMR (400 MHz, CDCl$_3$) (Due to the presence of conformers and 4 diastereomers, the $^1$H NMR spectrum is significantly complicated.) δ 7.42-7.23 (m, 5H), 6.56-6.20 (m, 2H), 5.25-4.92 (m, 0.74H), 4.34-4.01 (m, 0.76H), 3.95 (dd, J=10.4, 3.9 Hz, 0.41H), 3.86 (d, J=3.2 Hz, 0.23H), 3.77, 3.73, 3.68, 3.61, and 3.55 (s, 3H), 3.35-3.15 (m, 1H), 3.08-2.88 (m, 1H), 2.83 (br s, 0.24H), 2.65 (br s, 0.74H), 2.61-2.45 (m, 0.64H), 2.43 (br s, 0.09H), 2.06-1.96 (m, 0.38H), 1.96-1.66 (m, 1H), 1.56 (br s, 0.25H), 1.45-1.34 (m, 0.45H), 1.22 (t, J=12.1 Hz, 0.41H), 0.99-0.86 (m, 0.36H), 0.82-0.70 (m, 0.44H); LR-MS calcd. for C$_{16}$H$_{20}$NO$_3$$^+$ [M+H]$^+$ 274.14, found 274.06.

exo/endo-methyl 7-(iodo(phenyl)methyl)-2-azabicyclo[2.2.2]oct-5-ene-2-carboxylate (10). Alcohol 9 (137 mg, 0.50 mmol) was dissolved in anhydrous toluene (2.3 mL) and CH$_3$CN (1.1 mL), and the solution was cooled to 0° C. Triphenylphosphine (386 mg, 1.47 mmol), imidazole (202 mg, 2.96 mmol), and iodine (386 mg, 1.52 mmol) were then added and the mixture was allowed to warm to room temperature and stirred for 1 h. At this time the reaction was quenched with H$_2$O (5 mL) and extracted with CH$_2$Cl$_2$ (3×5 mL). The combined organics were washed with saturated aqueous Na$_2$S$_2$O$_3$ (5 mL) and brine (5 mL), dried over Na$_2$SO$_4$, and concentrated to yield an off-white solid. This was purified by column chromatography (6:4 hexanes:Et$_2$O) to yield iodide 10 as a pale-yellow oil (151 mg, 79% yield). $^1$H NMR (400 MHz, CDCl$_3$) (Due to the presence of conformers and 4 diastereomers, the $^1$H NMR spectrum is significantly complicated). δ 7.48-7.12 (m, 5H), 6.65-5.97 (m, 2H), 5.42-5.07 (m, 0.19H), 5.03-4.85 (m, 0.40H), 4.52-4.34 (m, 0.69H), 4.29-4.10 (m, 0.44H), 3.78, 3.74, 3.72, 3.68, 3.63, 3.59, and 3.41 (s, 3H), 3.36-3.05 (m, 1.41H), 3.04-2.67 (m, 2H), 2.64-2.41 (m, 0.61H), 2.04 (br s, 0.36H), 1.93 (br s, 0.36H), 1.77-1.57 (m, 0.27H), 1.50 (br d, J=11.5 Hz, 0.36H), 1.45-1.34 (m, 0.11H), 1.33-1.21 (m, 0.66H), 1.15 (br s, 0.04H), 0.97 (br d, J=6.6 Hz, 0.04H), 0.89 (br s, 0.13H), 0.80 (br d, J=9.3 Hz, 0.20H); LR-MS calcd. for C$_{16}$H$_{19}$INO$_2$$^+$ [M+H]$^+$ 384.04, found=384.17.

exo/endo-methyl 7-(((4-methylbenzoyl)oxy)(phenyl) methyl)-2-azabicyclo [2.2.2]oct-5-ene-2-carboxylate (11). Alcohol 9 (480 mg, 1.76 mmol) was dissolved in anhydorus CH$_2$Cl$_2$ (22 mL), and the solution was cooled to 0° C. Tetramethylethylenediamine (0.58 mL, 450 mg, 3.87 mmol) and p-toluoyl chloride (0.51 mL, 598 mg, 3.87 mmol) were then added, and the mixture was warmed to room temperature and stirred for 30 min. After quenching with saturated aqueous NaHCO$_3$ (20 mL), the organic layer was separated and the remaining aqueous layer was extracted with additional CH$_2$Cl$_2$ (2×20 mL). The combined organics were washed with saturated aqueous NaHCO$_3$ (20 mL) and brine (20 mL), dried over Na$_2$SO$_4$, and concentrated to yield an off-white oil. This was purified by column chromatography (3:1 hexanes:EtOAc) to yield ester 11 as a white solid (567 mg, 82). $^1$H NMR (400 MHz, CDCl$_3$) (Due to the presence of conformers and 4 diastereomers, the $^1$H NMR spectrum is significantly complicated). δ 8.03-7.87 (m, 2H), 7.51-7.18 (m, 7H), 6.60-6.22 (m, 2H), 5.83 (t, J=11.3 Hz, 0.02H), 5.70-5.58 (m 0.30H), 5.44 (d, J=10.0 Hz, 0.20H), 5.36-5.29 (m, 0.40H), 5.14-5.03 (m, 0.32H), 4.94-4.86 (m, 0.37H), 4.34 (br s, 0.09H), 4.15 (br s, 0.11H), 3.73, 3.71, 3.66, 3.63, 3.61, 3.58 and 3.34 (s, 3H), 3.40-3.33 (m, 0.43H), 3.33-3.19 (m, 0.68H), 3.08-2.78 (m, 1.87H), 2.72 (s, 0.78H), 2.42 and 2.40 (s, 3H), 2.34 (dd, J=11.0, 5.0 Hz, 0.30H), 1.94 (t, J=11.1 Hz, 0.20H), 1.79 (br s, 0.05H), 1.70 (br s, 0.21H), 1.58-1.37 (m, 0.70H), 1.37-1.23 (m, 0.36H), 1.15-1.01 (m, 0.33H), 0.99-0.89 (m, 0.50H); LR-MS calcd. for $C_{24}H_{26}NO_4^+$ [M+H]$^+$ 392.19, found 392.20.

exo-methyl 7-benzyl-2-azabicyclo[2.2.2]oct-5-ene-2-carboxylate (2e). Iodide 10 (474 mg, 1.24 mmol) and an excess of NaBH$_4$ (938 mg, 24.8 mmol) were dissolved in anhydrous DMPU (12 mL, freshly distilled from CaH$_2$) and stirred for 15 h at room temp. The reaction was quenched with H$_2$O (100 mL) and extracted with Et$_2$O (3×40 mL). The combined organics were washed with H$_2$O (3×25 mL) and brine (25 mL), dried over Na$_2$SO$_4$, and concentrated to yield a clear colorless oil (319 mg, mixture of exo/endo epimers, 9.5:1 reduction:elimination). The exo epimer was separated from this mixture by column chromatography (32 g silica gel, 8% to 14% EtOAc in hexanes in 1% steps, 32 mL for each step, 16 mL fractions) to yield exo-isoquinuclidine 2e as a nearly colorless oil (87 mg, 88:12 exo:endo, 27% yield). The endo-epimer could not be separated from a close eluting impurity of the styrene elimination product. $^1$H NMR (400 MHz, CDCl$_3$) (spectrum complicated by conformers, peaks for endo-epimer impurity not listed) δ 7.32-7.10 (m, 5H), 6.48-6.27 (m, 2H), 4.58 and 4.35 (d, J=6.1 Hz and J=5.8 Hz, 1H), 3.73 and 3.70 (s, 3H), 3.30 (ddd, J=9.7, 7.7, 2.1 Hz, 1H), 3.03 (ddt, J=19.1, 9.9, 2.6 Hz, 1H), 2.79-2.55 (m, 3H), 1.97-1.83 (m, 1H), 1.67-1.57 (m, 1H), 1.17-1.07 (m, 1H); $^{13}$C NMR (126 MHz, CDCl$_3$) (spectrum complicated by conformers). δ 157.0 and 156.6, 140.8 and 140.7, 133.90 and 133.86, 133.34 and 133.29, 129.3 and 129.2 (2C), 128.4 and 128.3 (2C), 126.1 and 126.0, 52.5 and 52.3, 49.3 and 49.1, 48.72 and 48.68, 41.1 and 40.8, 40.5, 31.0 and 30.8, 29.8 and 29.7; LR-MS calcd. for $C_{16}H_{20}NO_2^+$ [M+H]$^+$ 258.15, found 258.24.

endo-methyl 7-benzyl-2-azabicyclo[2.2.2]oct-5-ene-2-carboxylate (2f). SmI$_2$ solution (16.6 mL of 0.1 M in THF, 1.66 mmol) was brought to reflux. HMPA (1.15 mL, 1.19 g, 6.62 mmol) was then added followed by a solution of ester 11 (108 mg, 0.276 mmol) in anhydrous THF (2.4 mL, freshly distilled from Na/benzophenone ketyl), and the dark purple mixture was refluxed for 5 min. After removing from heat, the reaction was immediately quenched with saturated aqueous NH$_4$Cl (20 mL), and the resulting mixture was extracted with DCM (3×20 mL). The combined organics were washed with brine (2×20 mL), dried over Na$_2$SO$_4$, and concentrated to yield a cloudy white oil. This was purified by column chromatography (8:2 hexanes:EtOAc) to yield endo-isoquinuclidine 2f as a colorless oil (29 mg, 41%, pure endo-epimer). The correspronding exo-epimer is unstable under the reaction conditions and was not recovered from the reaction mixture. $^1$H NMR (400 MHz, CDCl$_3$) (spectrum complicated by conformers) δ 7.32-7.09 (m, 5H), 6.51-6.29 (m, 2H), 4.63 and 4.41 (d, J=5.4 and J=5.3 Hz, 1H), 3.65 and 3.64 (s, 3H), 3.20 (dd, J=15.7, 5.6 Hz, 1H), 2.94 (ddd, J=12.0, 10.1, 6.4 Hz, 1H), 2.72 (br s, 1H), 2.57-2.41 (m, 2H), 2.37-2.22 (m, 1H), 1.83-1.69 (m, 1H), 1.02 (ddd, J=12.8, 7.1, 3.0 Hz, 1H); $^{13}$C NMR (101 MHz, CDCl$_3$) (spectrum complicated by conformers). δ 155.9 and 155.6, 139.8 and 139.7, 135.0 and 134.6, 130.9 and 130.3 and 130.2, 129.0 and 128.9 (2C), 128.5 (2C), 126.2, 52.4 and 52.3, 49.4 and 49.1, 47.2 and 46.9, 41.7, 40.3 and 40.2, 31.3 and 31.1, 30.0 and 29.9; LR-MS calcd. for $C_{16}H_{20}NO_2^+$ [M+H]$^+$ 258.15, found 258.28.

EXAMPLE 5

Synthesis of 7-Substituted Isoquinuclidines
(Method B)

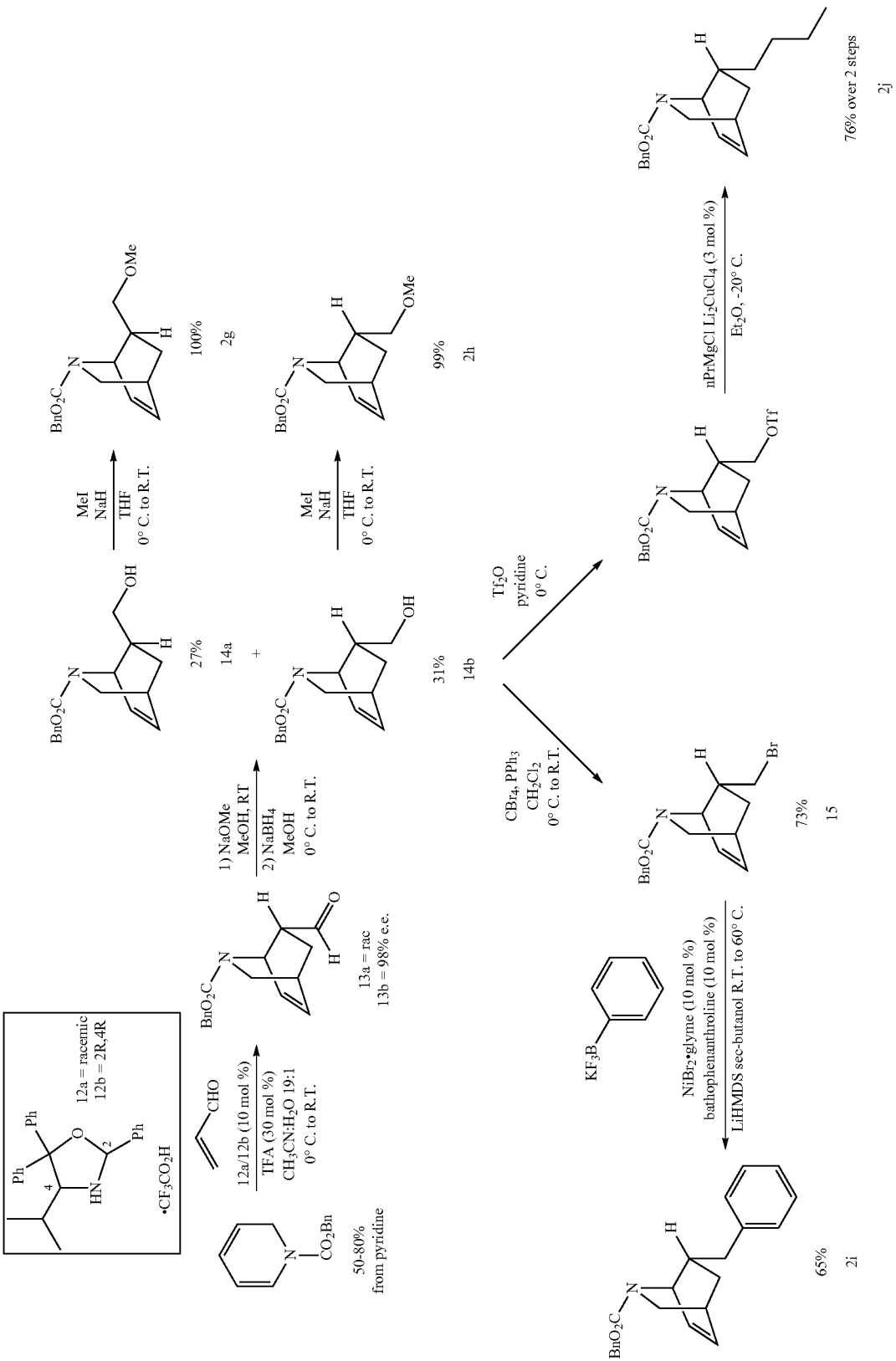

4-isopropyl-2,5,5-triphenyloxazolidine 2,2,2-trifluoroacetate (12a and 12b). Oxazolidine catalysts 12a and 12b were prepared according to the procedures described by Nakano et al. and obtained as white solids (Nakano, H. et al. 2010).

exo-benzyl 7-(hydroxymethyl)-2-azabicyclo[2.2.2]oct-5-ene-2-carboxylate (14a) and endo-benzyl 7-(hydroxymethyl)-2-azabicyclo[2.2.2]oct-5-ene-2-carboxylate (14b). To a $CH_3CN$ (57 mL) solution of catalyst 12 (273 mg, 0.60 mmol), cold water (3.0 mL), trifluoroacetic acid (0.14 mL, 1.8 mmol), and distilled acrolein (0.40 mL, 6.0 mmol) were added at 0° C., and the solution was stirred. After 1 min., N-(benzyloxycarbonyl)-1,2-dihydropyridine (2.58 g, 12.0 mmol) was added, and the solution was stirred at 0° C. for 24 h. The reaction was quenched with water (30 mL) and extracted with $Et_2O$ (3×30 mL). The combined organic extracts were washed with brine (30 mL), dried over $Na_2SO_4$, and concentrated under reduced pressure to give the crude endo-aldehyde 13 (1.82 g), which was used in the next reaction without further purification.

To a stirred solution of crude endo-aldehyde (1.82 g) in anhydrous MeOH (10 mL), NaOMe (1.0 g) was added, and the mixture was stirred at room temperature for 12 h. The reaction was quenched with water (30 mL) and extracted with EtOAc (3×30 mL). The combined organic extracts were washed with brine (20 mL), dried over $Na_2SO_4$, and concentrated under reduced pressure to give the crude exo/endo mixture of aldehyde 13 (1.71 g), which was used in the next reaction without further purification.

To a stirred solution of the crude exo/endo-aldehyde 13 (1.71 g) in ethanol (5.0 mL), $NaBH_4$ (122 mg, 3.2 mmol) was added, and the mixture was stirred at room temperature for 1 h. The solvent was evaporated under reduced pressure, and the residue was diluted with water (10 mL) and extracted with EtOAc (3×30 mL). The combined organic extracts were washed with brine (10 mL), dried over $Na_2SO_4$, and concentrated under reduced pressure. The epimers were separated by column chromatography (7:3 hexanes:EtOAc) to give 27% exo-alcohol 14a and 31% endo-alcohol 14b over three steps.

14a. Exo-alcohol 14a was prepared and separated as described above and obtained as a colorless oil (443 mg, 27%). $^1$H NMR (400 MHz, $CDCl_3$) (spectrum complicated by conformers) δ 7.38-7.30 (m, 5H), 6.47-6.42 (m, 2H), 5.22-5.07 (m, 2H), 4.87-4.68 (m, 1H), 3.69-3.57 (m, 1H), 3.27-3.17 (m, 2H), 3.04-3.00 (m, 1H), 2.72-2.65 (m, 1H), 1.95-1.79 (m, 1H), 1.57-1.49 (m, 1H), 0.92-0.80 (m, 1H) [OH not seen]; $^{13}$C NMR (101 MHz, $CDCl_3$) (spectrum complicated by conformers) δ 156.9, 136.7, 135.0 and 134.7, 132.2 and 132.1, 128.6 and 128.5, 127.9, 127.7, 67.1, 64.9 and 64.7, 48.5 and 48.3, 46.6 and 46.1, 41.2 and 40.8, 30.4 and 30.2, 25.7; LR-MS calcd. for $C_{16}H_{20}NO_3^+$ $[M+H]^+$ 274.14, found 274.28.

14b. Endo-alcohol 14b was prepared and separated as described above and obtained as a colorless oil (508 mg, 31%). $^1$H NMR (400 MHz, $CDCl_3$) (spectrum complicated by conformers) δ 7.35-7.27 (m, 5H), 6.42-6.28 (m, 2H), 5.19-5.09 (m, 2H), 4.90-4.83 (m, 1H), 3.30-3.24 (m, 2H), 3.20-3.14 (m, 1H), 3.03-2.99 (m, 1H), 2.74 (br s, 1H), 2.45-2.31 (m, 1H), 1.84-1.74 (m, 1H), 0.92-0.81 (m, 1H) [OH not seen]; $^{13}$C NMR (101 MHz, $CDCl_3$) (spectrum complicated by conformers) δ 155.2 and 154.8, 136.9 and 136.8, 134.9 and 134.6, 130.4 and 130.0, 128.4, 127.8, 127.6, 66.7, 65.5 and 65.4, 47.3 and 47.2, 46.9 and 46.8, 41.5, 30.8 and 30.5, 26.1; LR-MS calcd. for $C_{16}H_{20}NO_3^+$ $[M+H]^+$ 274.14, found 274.20.

endo-benzyl 7-(bromomethyl)-2-azabicyclo[2.2.2]oct-5-ene-2-carboxylate (15). To a stirred solution of endo-alcohol 14b (3.25 g, 12.0 mmol) in anhydrous $CH_2Cl_2$ (30 mL), carbon tetrabromide (4.78 g, 14.4 mmol) and triphenylphosphine (3.78 g, 14.4 mmol) were added in three portions at 0° C., and the mixture was stirred for 16 h at room temperature. The reaction mixture was then concentrated under reduced pressure and purified directly by column chromatography (8:2 hexanes:EtOAc) to provide pure endo-bromide 15 as a colorless oil (2.93 g, 73%); $^1$H NMR (400 MHz, $CDCl_3$) (spectrum complicated by conformers) δ 7.40-7.28 (m, 5H), 6.50-6.44 (m, 1H), 6.37-6.29 (m, 1H), 5.22-5.12 (m, 2H), 4.95-4.92 (m, 1H), 3.29 (d, J=10.0 Hz, 1H), 3.12-2.95 (m, 3H), 2.78 (br s, 1H), 2.62-2.48 (m, 1H), 1.92 (dtd, J=11.8, 9.2, 2.3 Hz, 1H), 0.99 (ddd, J=15.6, 7.1, 3.5 Hz, 1H); $^{13}$C NMR (100 MHz, $CDCl_3$) (spectrum complicated by conformers). δ 155.1 and 154.6, 136.9, 135.8 and 135.3, 129.9 and 129.3, 128.4, 127.9 and 127.8, 127.6, 66.8, 48.5 and 48.3, 46.8 and 46.5, 41.7 and 41.5, 36.0 and 35.9, 31.2 and 31.0, 30.0; LR-MS calcd. for $C_{16}H_{19}BrNO_2^+$ $[M+H]^+$ 336.06 and 338.06, found 335.77 and 337.77.

exo-benzyl 7-(methoxymethyl)-2-azabicyclo[2.2.2]oct-5-ene-2-carboxylate (2g). To a solution of exo-alcohol 14a (546 mg, 2.00 mmol) in anhydrous THF (10 mL) was added NaH (160 mg of 60% in mineral oil, 4.00 mmol), and the resulting mixture was cooled to 0° C. MeI (187 μL, 3.00 mmol) was then added and the mixture was allowed to warm to room temperature and stirred for 2 h. At this time, additional MeI (187 μL, 3.00 mmol) was added, and the mixture was stirred for a further 18 h. The reaction was then quenched with aqueous $NH_4Cl$ and extracted with $Et_2O$ (3×). The combined organics were washed with brine, dried over $Na_2SO_4$, and concentrated to provide the pure ether isoquinuclidine 2g as a yellow oil (575 mg, 100%). $^1$H NMR (400 MHz, $CDCl_3$) (spectrum complicated by conformers) δ 7.42-7.27 (m, 5H), 6.53-6.32 (m, 2H), 5.27-5.02 (m, 2H), 4.75 (d, J=6.0 Hz, 1H), 3.36-3.14 (m, 6H), 3.03 (ddd, J=10.0, 5.8, 2.8 Hz, 1H), 2.76-2.65 (m, 1H), 1.95-1.81 (m, 1H), 1.65-1.55 (m, 1H), 1.09-0.93 (m, 1H); $^{13}$C NMR (101 MHz, $CDCl_3$) (spectrum complicated by conformers) δ 155.9, 155.8, 137.2, 137.1, 134.2, 133.8, 133.4, 132.9, 128.5, 127.9, 127.8, 75.4, 74.9, 66.8, 66.7, 59.1, 58.9, 48.6, 48.3, 47.3, 47.1, 39.2, 39.1, 30.6, 30.3, 26.5, 26.2; LR-MS calcd. for $C_{17}H_{22}NO_3^+$ $[M+H]^+$ 288.16, found 288.65.

endo-benzyl 7-(methoxymethyl)-2-azabicyclo[2.2.2]oct-5-ene-2-carboxylate (2h). To a solution of endo-alcohol 14b (546 mg, 2.00 mmol) in anhydrous THF (10 mL) was added NaH (160 mg of 60% in mineral oil, 4.00 mmol), and the resulting mixture was cooled to 0° C. MeI (187 μL, 3.00 mmol) was then added and the mixture was allowed to warm to room temperature and stirred for 2 h. At this time, additional MeI (187 μL, 3.00 mmol) was added, and the mixture was stirred for a further 18 h. The reaction was then quenched with aqueous $NH_4Cl$ and extracted with $Et_2O$ (3×). The combined organics were washed with brine, dried over $Na_2SO_4$, and concentrated to provide the pure ether isoquinuclidine 2h as a yellow oil (570 mg, 99%). $^1$H NMR (400 MHz, $CDCl_3$) (spectrum complicated by conformers) δ 7.43-7.23 (m, 5H), 6.45-6.26 (m, 2H), 5.22-5.08 (m, 2H), 4.90-4.76 (m, 1H), 3.34-3.30 (m, 1H), 3.29 (d, J=3.6 Hz, 3H), 3.07-2.91 (m, 3H), 2.72 (s, 1H), 2.55-2.40 (m, 1H), 1.82-1.72 (m, 1H), 0.91-0.76 (m, 1H); $^{13}$C NMR (101 MHz, $CDCl_3$) (spectrum complicated by conformers) δ 155.0, 154.8, 137.0, 134.7, 134.3, 130.7, 130.0, 128.3, 127.72, 127.65, 75.6, 75.4, 66.5, 58.5, 47.3, 47.2, 46.9, 38.7, 38.5, 30.8, 30.5, 26.4, 26.2; LR-MS calcd. for $C_{17}H_{22}NO_3^+$ [M+H]$^+$ 288.16, found 288.65.

endo-benzyl 7-benzyl-2-azabicyclo[2.2.2]oct-5-ene-2-carboxylate (2i). Potassium phenyltrifluoroborate (139 mg, 0.75 mmol) and bathophenanthroline (24 mg, 0.072 mmol) were combined with LiHMDS (376 mg, 2.25 mmol), NiBr$_2$·glyme (23 mg, 0.075 mmol), and sec-butanol (1.5 ml) in a glovebox. The reaction was stirred at room temperature for 30 min. outside the glovebox followed by addition of bromide 15 (250 mg, 0.74 mmol). The reaction was then warmed to 60° C. and stirred for 21 h after which time it was cooled to room temperature and run through a short silica column with EtOAc (40 mL). The organics were concentrated to give a yellow oil, which was purified by column chromatography (6:1 hexanes:EtOAc) to give the pure product as a yellow oil (160.1 mg, 65%). $^1$H NMR (400 MHz, CDCl$_3$) (spectrum complicated by conformers). δ 7.46-7.11 (m, 10H), 6.59-6.30 (m, 2H), 5.24-4.95 (m, 2H), 4.77-4.47 (m, 1H), 3.30 (dt, J=10.6, 2.7 Hz, 1H), 3.17-2.99 (m, 1H), 2.83-2.67 (m, 1H), 2.62-2.11 (m, 3H), 1.96-1.72 (m, 1H), 1.06 (dq, J=12.8, 3.2 Hz, 1H); LR-MS calcd. for $C_{22}H_{24}NO_2^+$ [M+H]$^+$ 334.18, found 334.35.

endo-benzyl 7-butyl-2-azabicyclo[2.2.2]oct-5-ene-2-carboxylate (2j). A solution of trifluoromethanesulfonic anhydride (1M in CH$_2$Cl$_2$, 5.0 mL, 5.0 mmol) in anhydrous CH$_2$Cl$_2$ (10 mL) was added dropwise to a solution of endo-alcohol 14b (920 mg, 3.4 mmol) and pyridine (3.0 mL) in anhydrous CH$_2$Cl$_2$ (20 mL) at 0° C. over a period of 10 min. The resulting mixture was stirred for 2 h at 0° C. and then diluted with CH$_2$Cl$_2$ (30 mL), washed with 10% aqueous HCl and 5% aqueous NaHCO$_3$, and dried over Na$_2$SO$_4$. The solvent was removed under reduced pressure to afford essentially pure triflate product as a colorless oil (1.32 g), which was used in the next step without further purification.

To a solution of freshly prepared crude triflate (162 mg, 0.40 mmol) and Li$_2$CuCl$_4$ (0.12 mL; 0.012 mmol, 0.1 M in THF) in anhydrous Et$_2$O (2.0 mL) was added nPrMgCl (0.60 mL, 1.2 mmol, 2.0 M in Et$_2$O) at −20° C., and the reaction mixture was stirred for 6 h. The reaction was quenched with H$_2$O (2 mL), warmed to room temperature, and then acidified with 2N HCl (5 mL). The organic layer was separated, and the aqueous layer was extracted with CH$_2$Cl$_2$ (3×10 mL). The combined organic layers were washed with water and brine, dried over Na$_2$SO$_4$, and concentrated to afford the crude product. This material was purified by column chromatography (9:1 hexanes:EtOAc) to provide pure endo-isoquinuclidine 2j as a colorless oil (95 mg, 76% over 2 steps). $^1$H NMR (400 MHz, CDCl$_3$) (spectrum complicated by conformers) δ 7.43-7.26 (m, 5H), 6.43-6.23 (m, 2H), 5.19-5.09 (m, 2H), 4.69-4.53 (m, 1H), 3.25 (dd, J=10.2, 2.1 Hz, 1H), 2.99 (dt, J=10.1, 2.6 Hz, 1H), 2.68 (br s, 1H), 2.09-1.99 (m, 1H), 1.87-1.77 (m, 1H), 1.30-1.12 (m, 5H), 0.99-0.84 (m, 5H); $^{13}$C NMR (101 MHz, CDCl$_3$) (spectrum complicated by conformers) δ 155.2 and 154.8, 137.2, 134.8 and 134.3, 130.9 and 130.2, 128.5, 127.83 and 127.75, 127.7, 66.6, 49.8 and 49.4, 47.2 and 46.8, 39.0 and 38.9, 35.4 and 35.3, 31.3 and 31.1, 30.5, 29.1, 22.8 and 22.7, 14.1; LR-MS calcd. for $C_{19}H_{26}NO_2^+$ [M+H]$^+$ 300.20, found 299.90.

EXAMPLE 6

Synthesis of 7-Unsubstituted and 7-Phenyl Isoquinuclidines

Scheme 4. Synthesis of 7-unsubstituted and 7-phenyl isoquinuclidines

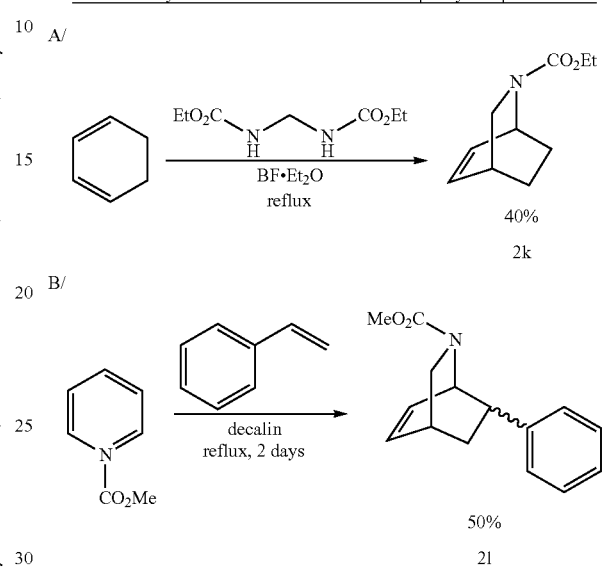

ethyl 2-azabicyclo[2.2.2]oct-5-ene-2-carboxylate (2k). Unsubstituted isoquinuclidine 2k was prepared according to literature procedure (Borne, R. F. et al. 1973) and obtained as an oil (3.77 g, 40%).

exo/endo-methyl 7-phenyl-2-azabicyclo[2.2.2]oct-5-ene-2-carboxylate (2l). Isoquinuclidine 21 was prepared according to literature procedure (Krow, G. R. et al. 2007) and obtained as a mixture of endo and exo isomers (colorless oil, 2.86 g, 50%).

EXAMPLE 7

Synthesis of Heteroarene Fragments

Scheme 5. Unsubstituted and Monosubstituted Bromoethylbenzofurans

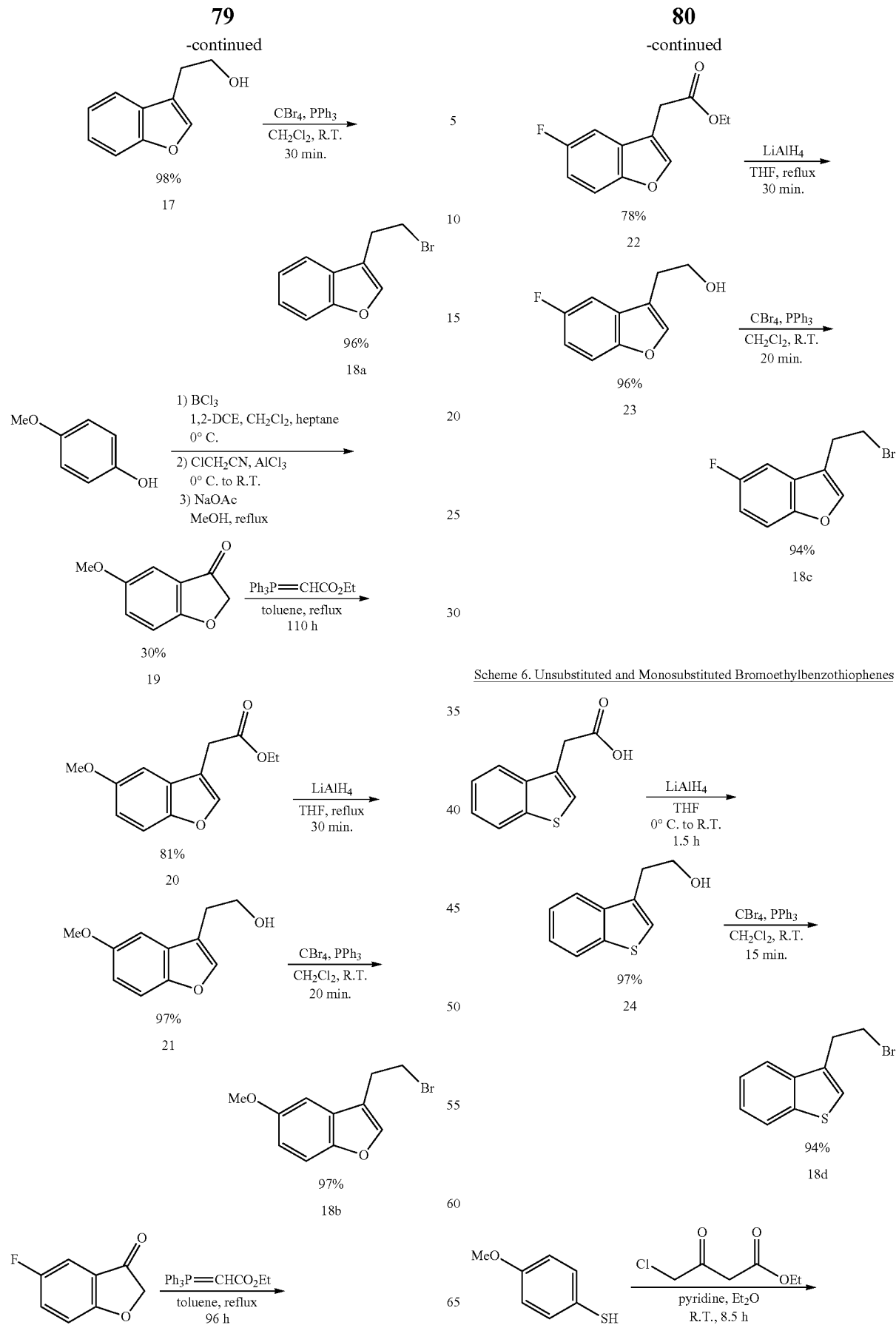

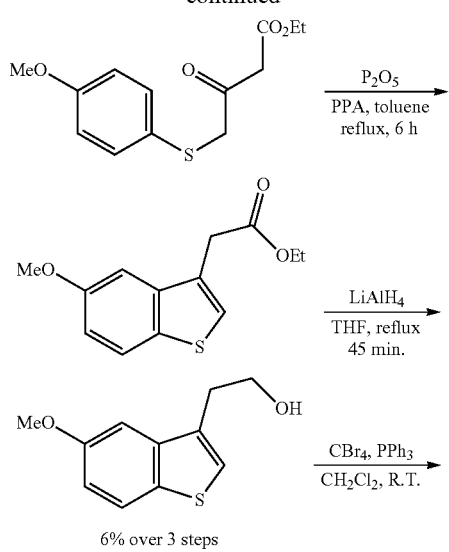

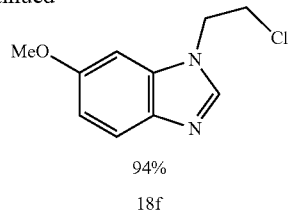

94%

18f

Scheme 8. Disubstituted Benzofurans

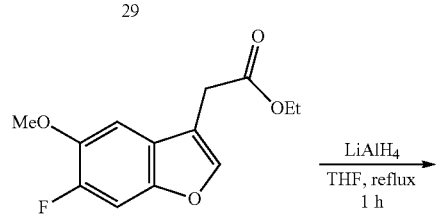

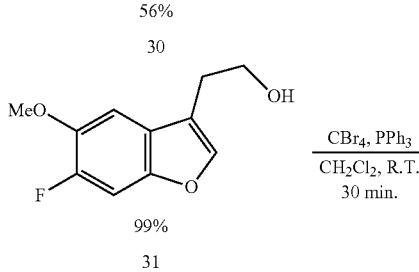

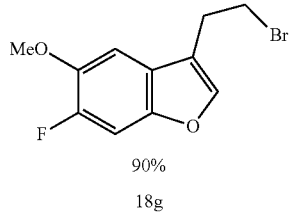

90%

18g

Scheme 7. Benzimidazoles

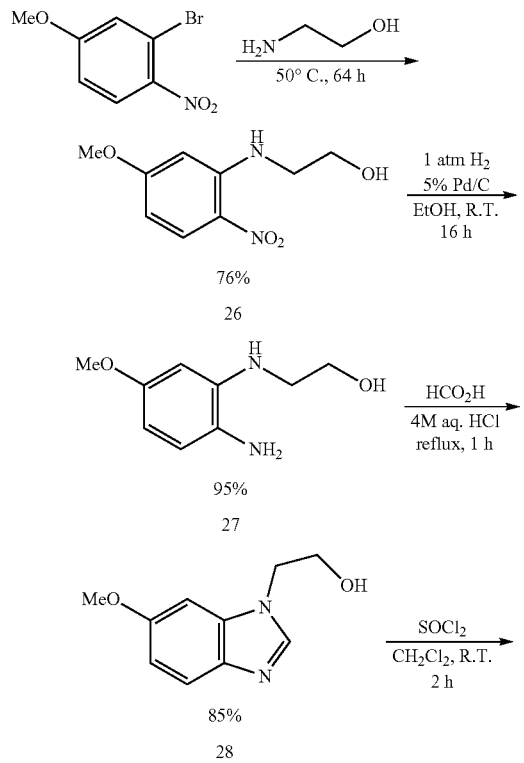

ethyl 2-(benzofuran-3-yl)acetate (16). Compound 16 was prepared by a slight modification of the literature procedure (Kozikowski, A. P. et al. 2007). A solution of benzofuran-3(2H)-one (5.00 g, 37.3 mmol) and (carbethoxymethylene)triphenylphosphorane (14.28 g, 41.0 mmol) in anhydrous toluene (125 mL) was refluxed for 87 h and then concentrated in vacuo. On standing, copious crystals formed in the dark-brown liquid. The mixture was diluted with 10:1 hexanes:EtOAc, and the crystalline mass crushed thoroughly. The supernatant was then decanted, leaving behind as much of the solids as possible. The residual crystalline solids were washed 3× with 10:1 hexanes:EtOAc, removing and saving the supernatant each time. The combined washes were then purified directly by column chromatography (10:1 hexanes:EtOAc, large fractions collected) to yield the pure ester 16 as an orange oil (6.30 g, 83%). Spectral and physical properties were in agreement with those previously reported (Mejia-Oneto, J. M. & Padwa, A. 2004).

2-(benzofuran-3-yl)ethanol (17). A solution of ester 16 (6.21 g, 30.4 mmol) in anhydrous THF (25 mL) was added dropwise to a suspension of LiAlH$_4$ (3.00 g, 79.0 mmol) in anhydrous THF (80 mL) over 10 min., and the resulting mixture was then refluxed for 1 h. After cooling to room temperature the reaction was quenched by the successive addition of H$_2$O (3 mL), 15% aqueous NaOH (3 mL), and H$_2$O again (9 mL). The resulting mixture was stirred vigorously until the aluminum salts were white and loose and then filtered, washing the filter cake with Et$_2$O (2×30 mL, then 2×50 mL). The combined filtrate and washings were concentrated to yield the pure alcohol 17 as a yellow oil (4.81 g, 98%). Spectral and physical properties were in agreement with those previously reported (Pearson, J. R. & Porter, Q. N. 1991).

3-(2-bromoethyl)benzofuran (18a). To a solution of alcohol 17 (4.76 g, 29.35 mmol) and carbon tetrabromide (14.60 g, 44.03 mmol) in anhydrous CH$_2$Cl$_2$ (60 mL) at room temperature was carefully added triphenylphosphine (11.55 g, 44.03 mmol), and the resulting dark orange-brown mixture was left to stir for 30 min. At this time the reaction mixture was filtered through a silica plug, washing the plug with additional CH$_2$Cl$_2$ (150 mL). The filtrate was concentrated to afford a yellow oil that was re-dissolved in CH$_2$Cl$_2$ (50 mL) and washed through a second silica plug, again washing the plug with additional CH$_2$Cl$_2$ (150 mL). The yellow oil obtained on concentration of the filtrate was then purified by column chromatography (hexanes, 2 column volumes→20:1 hexanes:Et$_2$O, 3 column volumes) to yield pure bromide 18a as a pale-yellow oil (6.35 g, 96%). Spectral and physical properties were in agreement with those previously reported (Pearson, J. R. & Porter, Q. N. 1991).

5-methoxybenzofuran-3(2H)-one (19). Benzofuranone 19 was prepared from 4-methoxyphenol according to literature procedure (Hammond, M. L. et al. 1990) and obtained as orange-tan crystals (2.49 g, 30%).

ethyl 2-(5-methoxybenzofuran-3-yl)acetate (20). A solution of benzofuranone 19 (2.46 g, 15.0 mmol) and (carbethoxymethylene) triphenylphosphorane (5.75 g, 16.5 mmol) in anhydrous toluene (50 mL) was refluxed for 110 h and then concentrated in vacuo. The resulting oily brown solid was triturated with 9:1 hexanes:EtOAc (50 mL) and filtered, and the remaining solids were washed with additional portions of 9:1 hexanes:EtOAc (2×50 mL). The combined filtrates were concentrated to give an orange oil (3.88 g). This material was purified by column chromatography (1:1 hexanes:CH$_2$Cl$_2$) to yield ester 20 as a thin orange oil (2.83 g, 81%). Spectral and physical properties were in agreement with those previously reported (Chan, J. H-T. et al. 1975).

2-(5-methoxybenzofuran-3-yl)ethanol (21). To a suspension of LiAlH$_4$ (1.18 g, 30.97 mmol) in anhydrous THF (30 mL) at room temperature was added a solution of ester 20 (2.79 g, 11.91 mmol) in anhydrous THF (10 mL) over 10 min., and the mixture was refluxed for 30 min. After cooling to room temperature the reaction was quenched by the successive addition of H$_2$O (1.2 mL), 15% aqueous NaOH (1.2 mL), and H$_2$O again (3.6 mL). The resulting mixture was stirred vigorously until the aluminum salts were white and loose and then filtered, washing the filter cake with Et$_2$O (3×30 mL). The combined filtrate and washings were concentrated to yield the pure alcohol 21 as a yellow oil (2.22 g, 97%). Spectral and physical properties were in agreement with those previously reported (Tomaszewski, Z. et al. 1992).

3-(2-bromoethyl)-5-methoxybenzofuran (18b). To a solution of alcohol 21 (2.18 g, 11.34 mmol) and carbon tetrabromide (5.64 g, 17.01 mmol) in anhydrous CH$_2$Cl$_2$ (23 mL) at room temperature was carefully added triphenylphosphine (4.46 g, 17.01 mmol) and the resulting dark orange-brown mixture was left to stir for 20 min. At this time the reaction mixture was filtered through a silica plug, washing the plug with additional CH$_2$Cl$_2$ (175 mL), and the filtrate was concentrated to afford a yellow oil. This material was purified by column chromatography (hexanes, 2 column volumes→20:1 hexanes:Et$_2$O, 2 column volumes→10:1 hexanes:Et$_2$O, 2 column volumes) to yield pure bromide 18b as a pale-yellow oil that slowly crystallized to a white solid (2.81 g, 97%). $^1$H NMR (500 MHz, CDCl$_3$) δ 7.51 (s, 1H), 7.37 (d, J=8.9 Hz, 1H), 6.97 (d, J=2.5 Hz, 1H), 6.91 (dd, J=8.9, 2.6 Hz, 1H), 3.86 (s, 3H), 3.64 (t, J=7.4 Hz, 2H), 3.23 (td, J=7.4, 0.7 Hz, 2H); $^{13}$C NMR (126 MHz, CDCl$_3$) δ 156.1, 150.4, 143.1, 128.1, 117.8, 113.2, 112.3, 101.9, 56.2, 31.3, 27.7; LR-MS calcd. for C$_{10}$H$_{10}$BrO$^+$ [M+H]$^+$ 255.00 and 257.00, found 255.29 and 257.29.

ethyl 2-(5-fluorobenzofuran-3-yl)acetate (22). A solution of 5-fluorobenzofuran-3(2H)-one (990 mg, 6.51 mmol) and (carbethoxymethylene) triphenylphosphorane (2.49 g, 7.16 mmol) in anhydrous toluene (22 mL) was refluxed for 96 h and then concentrated in vacuo. The resulting brown solid was triturated with 9:1 hexanes:EtOAc (25 mL) and filtered, and the remaining solids were washed with additional portions of 9:1 hexanes:EtOAc (4×15 mL). The combined filtrates were concentrated to give an orange oil (1.70 g). This material was purified by column chromatography (8:2 hexanes:CH$_2$Cl$_2$, 4 column volumes→7:3 hexanes:CH$_2$Cl$_2$, 3 column volumes) to yield ester 22 as a thin red-orange oil (1.12 g, 78%). $^1$H NMR (500 MHz, CDCl$_3$) (spectrum complicated by F—H coupling) δ 7.66 (s, 1H), 7.40 (dd, J=8.9, 4.1 Hz, 1H), 7.23 (dd, J=8.5, 2.6 Hz, 1H), 7.02 (td, J=9.0, 2.6 Hz, 1H), 4.20 (q, J=7.1 Hz, 2H), 3.65 (s, 2H), 1.28 (t, J=7.1 Hz, 3H); $^{13}$C NMR (126 MHz, CDCl$_3$) (spectrum complicated by F—C coupling) δ 170.5, 160.3 and 158.4, 151.6, 144.7, 128.7 and 128.6, 113.7 and 113.6, 112.5 and 112.4, 112.3, 105.7 and 105.5, 61.4, 29.9, 14.3; LR-MS calcd. for C$_{12}$H$_{12}$FO$_3^+$ [M+H]$^+$ 223.08, found 223.13.

2-(5-fluorobenzofuran-3-yl)ethanol (23). To a suspension of LiAlH$_4$ (483 mg, 12.74 mmol) in anhydrous THF (12 mL) at room temperature was added a solution of ester 22 (1.09 g, 4.90 mmol) in anhydrous THF (4.0 mL) over 10 min., and the mixture was refluxed for 30 min. After cooling to room temperature the reaction was quenched by the successive addition of H$_2$O (0.50 mL), 15% aqueous NaOH (0.50 mL), and H$_2$O again (1.5 mL). The resulting mixture was stirred vigorously until the aluminum salts were white and loose, diluted with Et$_2$O (20 mL), and then filtered, washing the filter cake with Et$_2$O (3×10 mL). The combined filtrate and washings were concentrated to yield the pure alcohol 23 as a pale-yellow oil (848 mg, 96%). $^1$H NMR (400 MHz, CDCl$_3$) (spectrum complicated by F—H coupling) δ 7.55 (s, 1H), 7.39 (dd, J=8.9, 4.1 Hz, 1H), 7.22 (dd, J=8.5, 2.6 Hz, 1H), 7.01 (td, J=9.0, 2.6 Hz, 1H), 3.91 (t, J=6.2 Hz, 2H), 2.90 (td, J=6.3, 0.9 Hz, 2H), 1.63 (br s, 1H); $^{13}$C NMR (101 MHz, CDCl$_3$) (spectrum complicated by F—C coupling) δ 160.4 and 158.1, 151.7, 144.1, 129.0 and 128.9, 117.4 and 117.3, 112.4, 112.3 and 112.1, 105.5 and 105.2, 61.8, 27.1; LR-MS calcd. for $C_{10}H_{10}FO_2^+$ [M+H]$^+$ 181.07, found 181.13.

3-(2-bromoethyl)-5-fluorobenzofuran (18c). To a solution of alcohol 23 (823 mg, 4.57 mmol) and carbon tetrabromide (2.28 g, 6.86 mmol) in anhydrous $CH_2Cl_2$ (9.0 mL) at room temperature was carefully added triphenylphosphine (1.80 g, 6.86 mmol), and the resulting dark orange-brown mixture was left to stir for 20 min. At this time the reaction mixture was filtered through a silica plug, washing the plug with additional $CH_2Cl_2$ (200 mL), and the filtrate was concentrated to afford a yellow oil. This material was purified by column chromatography (hexanes, 2 column volumes→20:1 hexanes:Et$_2$O, 2 column volumes→10:1 hexanes:Et$_2$O, 1 column volume) to yield pure bromide 18c as a thin, pale-yellow oil (1.05 g, 94%). $^1$H NMR (500 MHz, CDCl$_3$) (spectrum complicated by F—H coupling) δ 7.58 (s, 1H), 7.41 (dd, J=8.9, 4.1 Hz, 1H), 7.19 (dd, J=8.4, 2.6 Hz, 1H), 7.03 (td, J=9.0, 2.6 Hz, 1H), 3.63 (t, J=7.2 Hz, 2H), 3.23 (t, J=7.2 Hz, 2H); $^{13}$C NMR (126 MHz, CDCl$_3$) (spectrum complicated by F—C coupling) δ 160.3 and 158.4, 151.6, 144.1, 128.5 and 128.4, 117.98 and 117.95, 112.53 and 112.50, 112.5 and 112.3, 105.1, 104.9, 31.1, 27.6; LR-MS calcd. for $C_{10}H_8BrFO^+$ [M]$^+$ 241.97 and 243.97, found 242.01 and 244.00.

2-(benzo[b]thiophen-3-yl)ethanol (24). Alcohol 24 was prepared via LiAlH$_4$ reduction of benzo[b]thiophene-3-acetic acid as previously described (Hatzenbuhler, N. T. et al. 2005). The crude product was obtained as an orange oil of sufficient purity for the next step (895 mg, 97%). Spectral and physical properties were in agreement with those previously reported (Campaigne, E. et al. 1968).

3-(2-bromoethyl)benzo[b]thiophene (18d). To a solution of alcohol 24 (895 mg, 5.02 mmol) and carbon tetrabromide (2.50 g, 7.53 mmol) in anhydrous $CH_2Cl_2$ (10 mL) at room temperature was carefully added triphenylphosphine (1.98 g, 7.53 mmol), and the resulting dark red-brown mixture was stirred for 15 min. The reaction mixture was then concentrated and purified directly by column chromatography (6:1 hexanes:EtOAc) to yield pure bromide 18d as an orange oil after thorough drying under high vacuum to remove bromoform impurity (1.14 g, 94%). Spectral and physical properties were in agreement with those previously reported (Martins, A. & Lautens, M. 2008).

2-(5-methoxybenzo[b]thiophen-3-yl)ethanol (25). To a solution of 4-methoxythiophenol (3.94 mL, 32.0 mmol) and anhydrous pyridine (10.44 mL, 128.0 mmol) in anhydrous Et$_2$O (65 mL) was added ethyl 4-chloroacetoacetate (4.36 mL, 32.0 mmol) at 0° C., and the resulting mixture was allowed to warm to room temperature and stirred for 6.5 h. The reaction was then quenched with H$_2$O (100 mL) and diluted with additional Et$_2$O (50 mL). The organic layer was separated, and the residual aqueous extracted with additional Et$_2$O (100 mL). The combined organics were washed with 5% aqueous HCl (100 mL) and H$_2$O (100 mL), dried over Na$_2$SO$_4$, and concentrated to give an orange oil. This material was purified by column chromatography (9:1 hexanes:EtOAc, 2 column volumes→7:3 hexanes:EtOAc, 1.5 column volumes) to provide the thioether product as an impure yellow oil (6.13 g) that was used in the next step without further purification.

A mixture of polyphosphoric acid (60 g), P$_2$O$_5$ (1.4 g), and celite (40 g) in toluene (200 mL) was refluxed for 45 min. A solution of the crude thioether from the previous step (6.03 g) in toluene (20 mL) was then added, and reflux was continued for 6 h. At this time, the reaction was cooled to room temperature and filtered, washing the filter cake and undissolved solids first with toluene and then with Et$_2$O. The combined filtrate and washings were washed with concentrated aqueous K$_2$CO$_3$ (100 mL) and H$_2$O (100 mL), dried over Na$_2$SO$_4$, and concentrated to yield an orange oil. This material was purified by column chromatography (9:1 hexanes:CH$_2$Cl$_2$, 4 column volumes→7:3 hexanes:CH$_2$Cl$_2$, 3 column volumes→4:6 hexanes:CH$_2$Cl$_2$, 4 column volumes) to provide the impure benzothiophenyl ester as a yellow-brown oil (1.09 g) that was used in the next step without further purification.

To a suspension of LiAlH$_4$ (421 mg, 11.10 mmol) in anhydrous THF (10.5 mL) at room temperature was added a solution of the crude benzothiophenyl ester (1.07 g) in anhydrous THF (3.5 mL) over 10 min., and the mixture was refluxed for 45 min. After cooling to room temperature the reaction was quenched by the successive addition of H$_2$O (0.42 mL), 15% aqueous NaOH (0.42 mL), and H$_2$O again (1.26 mL). The resulting mixture was stirred vigorously until the aluminum salts were white and loose and then filtered, washing the filter cake with Et$_2$O (3×15 mL). The combined filtrate and washings were concentrated to yield a yellow-orange oil. This material was purified by repeated column chromatography (column 1 and 2 same: 8:2 hexanes:EtOAc, 2 column volumes→7:3 hexanes:EtOAc, 2 column volumes→6:4 hexanes:EtOAc, 2 column volumes) to provide the pure alcohol 25 as a yellow oil (359 mg, 6% over 3 steps). $^1$H NMR (400 MHz, CDCl$_3$) δ 7.73 (d, J=8.8 Hz, 1H), 7.22 (d, J=0.4 Hz, 1H), 7.20 (d, J=2.4 Hz, 1H), 7.02 (dd, J=8.8, 2.5 Hz, 1H), 3.97 (d, J=3.4 Hz, 2H), 3.89 (s, 3H), 3.09 (td, J=6.5, 0.8 Hz, 2H), 1.56 (br s, 1H); $^{13}$C NMR (101 MHz, CDCl$_3$) δ 157.6, 140.1, 133.0, 132.7, 124.3, 123.7, 114.5, 104.3, 62.0, 55.8, 32.1; LR-MS calcd. for $C_{11}H_{13}O_2S^+$ [M+H]$^+$ 209.06, found 209.39.

3-(2-bromethyl)-5-methoxybenzo[b]thiophene (18e). To a solution of alcohol 25 (346 mg, 1.66 mmol) and carbon tetrabromide (826 mg, 2.49 mmol) in anhydrous $CH_2Cl_2$ (3.4 mL) at room temperature was carefully added triphenylphosphine (653 mg, 2.49 mmol), and the resulting yellow-orange solution was left to stir for 20 min. At this time, the reaction mixture was purified directly by column chromatography (hexanes, 2 column volumes→20:1 hexanes:Et$_2$O, 2 column volumes→10:1 hexanes:Et$_2$O, 1 column volume) to yield pure bromide 18e as a nearly colorless oil that slowly crystallized to a white solid (430 mg, 96%). $^1$H NMR (400 MHz, CDCl$_3$) δ 7.73 (d, J=8.8 Hz, 1H), 7.25 (s, 1H), 7.15 (d, J=2.4 Hz, 1H), 7.03 (dd, J=8.8, 2.4 Hz, 1H), 3.90 (s, 3H), 3.68 (t, J=7.6 Hz, 2H), 3.38 (dd, J=7.9, 7.2 Hz, 2H); $^{13}$C NMR (101 MHz, CDCl$_3$) δ 157.7, 139.6, 133.1, 132.9, 124.6, 123.8, 114.6, 104.0, 55.8, 32.5, 31.0; LR-MS calcd. for $C_{11}H_{12}BrOS^+$ [M+H]$^+$ 270.98 and 272.98, found 271.30 and 273.30.

2-((5-methoxy-2-nitrophenyl)amino)ethanol (26). Aminoalcohol 26 was prepared according to literature procedure (Bolli, M. et al. 2012) and obtained as a yellow crystalline solid (3.06 g, 76%).

2-((2-amino-5-methoxyphenyl)amino)ethanol (27). Aniline 27 was prepared from aminoalcohol 26 according to literature procedure (Bolli, M. et al. 2012) and obtained as a purple-brown solid (2.47 g, 95%).

2-(6-methoxy-1H-benzo[d]imidazol-1-yl)ethanol (28). A mixture of aniline 27 (2.45 g, 13.44 mmol), formic acid (1.03 mL, 26.88 mmol), and 4M aqueous HCl (90 mL) was refluxed for 1 h. The reaction was then cooled in ice, basified with saturated NH$_4$OH, and extracted with CH$_2$Cl$_2$ (4×100 mL). The combined organics were washed with brine (100 mL), dried over Na$_2$SO$_4$, and concentrated to provide benzimidazole alcohol 28 as a brownish-purple solid (2.19 g, 85%). $^1$H NMR (500 MHz, CDCl$_3$) δ 7.56 (s, 1H), 7.27 (d, J=8.8 Hz, 1H), 6.75 (d, J=2.3 Hz, 1H), 6.71 (dd, J=8.8, 2.4 Hz, 1H), 5.11 (br s, 1H), 4.17 (t, J=5.1 Hz, 2H), 4.00 (d, J=5.1 Hz, 2H), 3.83 (s, 3H); $^{13}$C NMR (126 MHz, CDCl$_3$) δ 156.8, 142.7, 137.5, 134.1, 120.1, 111.5, 93.3, 60.4, 56.0, 48.0; LR-MS calcd. for C$_{10}$H$_{13}$N$_2$O$_2$$^+$ [M+H]$^+$ 193.10, found 193.24.

1-(2-chloroethyl)-6-methoxy-1H-benzo[d]imidazole (18f). To a mixture of benzimidazole alcohol 28 (346 mg, 1.80 mmol) in anhydrous CH$_2$Cl$_2$ (2.5 mL) was added SOCl$_2$ (131 µL, 1.80 mmol) dropwise over 2 min. at room temperature. After stirring for 2 h, the reaction was quenched with saturated aqueous NaHCO$_3$ (20 mL) and extracted with CH$_2$Cl$_2$ (3×10 mL). The combined organics were washed with H$_2$O (10 mL), dried over Na$_2$SO$_4$, and concentrated to provide benzimidazole chloride 18f as a tan solid (355 mg, 94%). $^1$H NMR (400 MHz, CDCl$_3$) δ 7.87 (s, 1H), 7.70 (d, J=8.8 Hz, 1H), 6.94 (dd, J=8.8, 2.4 Hz, 1H), 6.82 (d, J=2.3 Hz, 1H), 4.46 (t, J=6.2 Hz, 2H), 3.88 (s, 3H), 3.84 (t, J=6.2 Hz, 2H); $^{13}$C NMR (101 MHz, CDCl$_3$) δ 157.2, 142.6, 138.4, 134.2, 121.3, 111.7, 93.1, 56.1, 46.7, 42.1; LR-MS calcd. for C$_{10}$H$_{12}$ClN$_2$O$^+$ [M+H]$^+$ 211.06, found 211.06.

6-fluoro-5-methoxybenzofuran-3(2H)-one (29). To a solution of BCl$_3$ (1M in CH$_2$Cl$_2$, 41.6 mmol, 41.6 mL) at 0° C. was added a solution of 3-fluoro-4-methoxyphenol (4.93 g, 34.69 mmol) in anhydrous 1,2-DCE (17 mL) slowly over 20 min. Chloroacetonitrile (2.63 mL, 41.6 mmol) was then added over 2 min. followed by AlCl$_3$ (2.31 g, 17.4 mmol) in three equal portions, and the resulting yellow-orange mixture was allowed to warm to room temperature and stirred for 14 h. The reaction was then quenched with ice (35 mL) and 10% aqueous HCl (35 mL), and the resulting mixture was stirred for 20 min. At this time, the organic layer was separated and the aqueous phase extracted with additional CH$_2$Cl$_2$ (2×50 mL, 25 mL). The combined organics were washed with brine (50 mL), dried over Na$_2$SO$_4$, filtered, and concentrated to provide the crude intermediate α-chloroacetophenone as a yellow solid (6.54 g, $^1$H NMR indicated 74 mass % product, 26 mass % starting material). This material (6.51 g) was combined with sodium acetate (8.53 g, 104 mmol) in anhydrous MeOH (35 mL), and the mixture was refluxed for 45 min. The reaction was then cooled to room temperature and filtered, washing the filter cake with MeOH (2×15 mL). The combined filtrate and washings were concentrated to ~½ the volume and diluted with 5% aqueous NaCl (85 mL). An attempt was made to collect the resulting solids by filtration, but they were very clumpy and clogging of the filter occurred. Therefore, the combined liquids (filtrate and supernatant) were extracted with Et$_2$O (2×40 mL), and these extracts were combined with the residual solids and concentrated. The resulting residue was taken up in CH$_2$Cl$_2$ (75 mL) and the solution was washed with brine (20 mL), dried over Na$_2$SO$_4$, and concentrated to give a dark-brown oil (2.83 g). This material was dissolved in a minimal amount of Et$_2$O and cooled to −78° C., causing powdery crystals to form, which were collected by filtration and washed once at the filter with −78° C. Et$_2$O. These solids were dried to provide the pure benzofuranone 29 as a yellowish-brown powder (555 mg, 9% over 2 steps). $^1$H NMR (400 MHz, CDCl$_3$) (spectrum complicated by F—H coupling) δ 7.16 (d, J=8.5 Hz, 1H), 6.89 (d, J=10.5 Hz, 1H), 4.63 (s, 2H), 3.88 (s, 3H); $^{13}$C NMR (101 MHz, CDCl$_3$) (spectrum complicated by F—C coupling) δ 198.6, 169.6, 161.0 and 158.4, 144.7, 116.4, 105.82 and 105.77, 102.2 and 102.0, 75.7, 56.8; LR-MS calcd. for C$_9$H$_8$FO$_3$$^+$ [M+H]$^+$ 183.04, found 183.21.

ethyl 2-(6-fluoro-5-methoxybenzofuran-3-yl)acetate (30). A solution of benzofuranone 29 (543 mg, 2.98 mmol) and (carbethoxymethylene) triphenylphosphorane (1.14 g, 3.28 mmol) in anhydrous toluene (10 mL) was refluxed for 74 h and then concentrated in vacuo. The resulting dark-brown solid was triturated with 9:1 hexanes:EtOAc (20 mL) and filtered, and the remaining solids were washed with additional portions of 9:1 hexanes:EtOAc (3×10 mL). The combined filtrates were concentrated to give a yellow-orange oil (673 mg). This material was purified by column chromatography (1:1 hexanes:CH$_2$Cl$_2$, 3 column volumes→4:6 hexanes:CH$_2$Cl$_2$, 2 column volumes→3:7 hexanes:CH$_2$Cl$_2$, 3 column volumes→CH$_2$Cl$_2$, 2 column volumes) to yield ester 30 as a yellow oil (423 mg, 56%). $^1$H NMR (500 MHz, CDCl$_3$) (spectrum complicated by F—H coupling) δ 7.59 (s, 1H), 7.24 (d, J=10.6 Hz, 1H), 7.08 (d, J=8.2 Hz, 1H), 4.19 (q, J=7.1 Hz, 2H), 3.93 (s, 3H), 3.66 (d, J=0.9 Hz, 2H), 1.28 (t, J=7.1 Hz, 4H); $^{13}$C NMR (126 MHz, CDCl$_3$) (spectrum complicated by F—C coupling) δ 170.7, 152.5 and 150.5, 148.8 and 148.7, 145.3 and 145.2, 143.7 and 143.6, 123.1, 113.4, 103.07 and 103.05, 100.3 and 100.1, 61.3, 57.0, 30.1, 14.4; LR-MS calcd. for C$_{13}$H$_{14}$FO$_4$$^+$ [M+H]$^+$ 253.09, found 253.01.

2-(6-fluoro-5-methoxybenzofuran-3-yl)ethanol (31). A solution of ester 30 (414 mg, 1.64 mmol) in anhydrous THF (1.5 mL) was added dropwise to a suspension of LiAlH$_4$ (162 mg, 4.26 mmol) in anhydrous THF (4.0 mL) over 2 min., and the resulting mixture was then refluxed for 1 h. After cooling to room temperature, the reaction was quenched by the successive addition of H$_2$O (0.16 mL), 15% aqueous NaOH (0.16 mL), and H$_2$O again (0.48 mL). The resulting mixture was stirred vigorously until the aluminum salts were white and loose and then filtered, washing the filter cake with Et$_2$O (3×5 mL). The combined filtrate and washings were concentrated to yield the pure alcohol 31 as a yellow-orange oil (343 mg, 99%). $^1$H NMR (500 MHz, CDCl$_3$) (spectrum complicated by F—H coupling) δ 7.49 (s, 1H), 7.24 (d, J=10.7 Hz, 1H), 7.06 (d, J=8.2 Hz, 1H), 3.93 (s, 3H), 3.92 (t, J=6.4 Hz, 2H), 2.91 (td, J=6.4, 0.8 Hz, 2H), 1.61 (br s, 1H); $^{13}$C NMR (126 MHz, CDCl$_3$) (spectrum complicated by F—C coupling) δ 152.4 and 150.5, 148.9 and 148.8, 145.2 and 145.1, 143.0 and 142.9, 123.44 and 123.42, 117.08 and 117.07, 102.90 and 102.88, 100.4 and 100.2, 62.0, 57.1, 27.2; LR-MS calcd. for C$_{11}$H$_{12}$FO$_3$$^+$ [M+H]$^+$ 211.08, found 211.07.

3-(2-bromoethyl)-6-fluoro-5-methoxybenzofuran (18g). To a solution of alcohol 31 (332 mg, 1.58 mmol) and carbon tetrabromide (787 mg, 2.37 mmol) in anhydrous CH$_2$Cl$_2$ (3.2 mL) at room temperature was carefully added triphenylphosphine (622 mg, 2.37 mmol), and the resulting mixture was left to stir for 30 min. At this time, the reaction mixture was purified directly by column chromatography (hexanes, 2 column volumes→20:1 hexanes:Et$_2$O, 2 column volumes→10:1 hexanes:Et$_2$O, 3 column volumes) to yield pure bromide 18g as an off-white crystalline solid (389 mg, 90%). $^1$H NMR (500 MHz, CDCl$_3$) (spectrum complicated by F—H coupling) δ 7.51 (s, 1H), 7.25 (d, J=10.5 Hz, 1H), 7.02 (d, J=8.1 Hz, 1H), 3.94 (s, 3H), 3.63 (t, J=7.3 Hz, 2H), 3.23 (td, J=7.3, 0.8 Hz, 2H); $^{13}$C NMR (126 MHz, CDCl$_3$) (spectrum complicated by F—C coupling) δ 152.50 and 150.6, 148.8 and 148.7, 145.3 and 145.2, 142.92 and 142.89, 122.9, 117.8, 102.52 and 102.50, 100.5 and 100.3, 57.2, 31.2, 27.6; LR-MS calcd. for C$_{11}$H$_{11}$BrFO$_2$$^+$ [M+H]$^+$ 272.99 and 274.99, found 272.83 and 274.83.

EXAMPLE 8
Synthesis of N-Arylalkylisoquinuclidines by Alkylation
Scheme 9. N-Arylalkylisoquinuclidines by Alkylation
A/
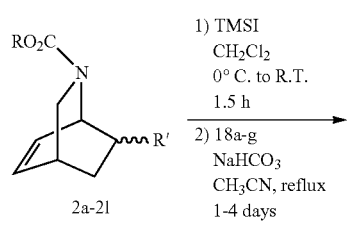
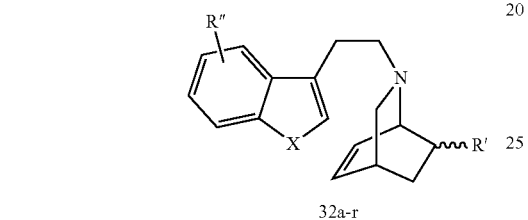
32a-r
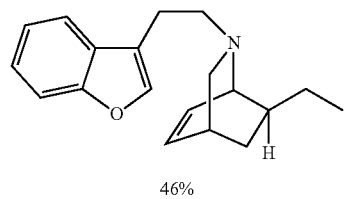
32a
46%
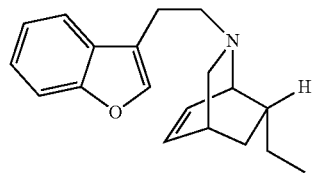
32b
60%
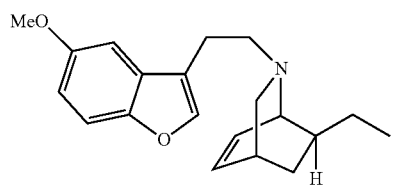
32c
74%
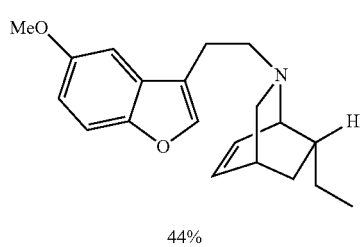
32d
44%
-continued
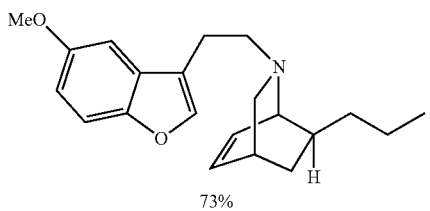
32e
73%
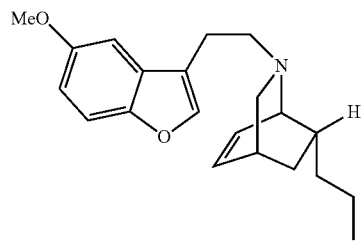
32f
62%
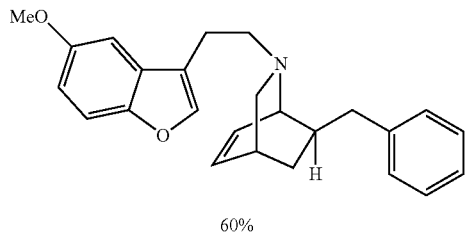
32g
60%
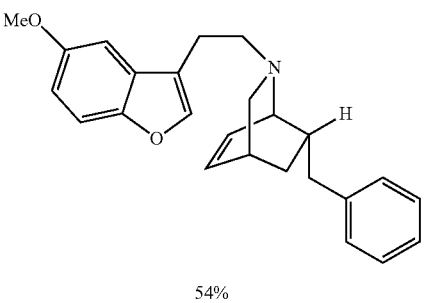
32h
54%
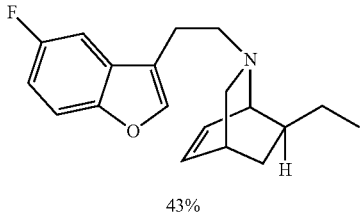
32i
43%
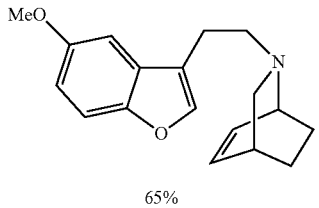
32j
65%

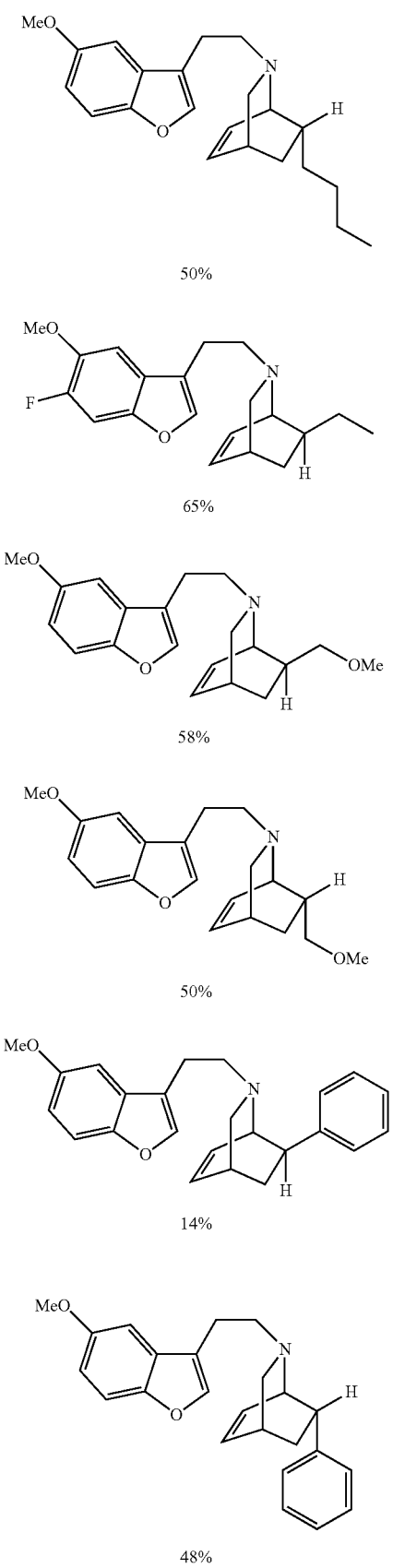

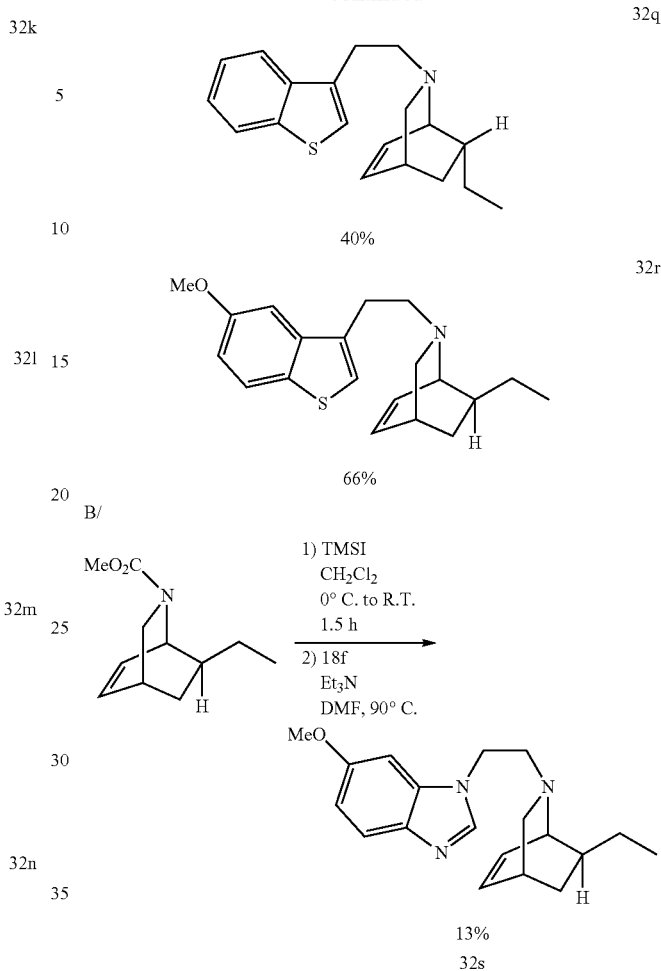

General Procedure for Preparation of N-arylalkylisoquinuclidines (32a-r). To a solution of a carbamate protected isoquinuclidine 2a-1 (1 equivalent) in anhydrous $CH_2Cl_2$ (0.125 M, based on 2) at 0° C. was added iodotrimethylsilane (4 equivalents), and the resulting mixture was stirred for 10 min. at 0° C. and then at room temperature until TLC indicated that no 2 remained (typically ~1 h). The reaction mixture was then quenched with MeOH (3.0 mL per mmol of 2) concentrated to yield the deprotected isoquinuclidine hydroiodide salt in quantitative yield (for benzyl carbamate protected isoquinuclidines, the resulting salt was washed several times with hexanes to remove the benzyl iodide byproduct). To this material was added the appropriate bromoalkylheteroarene 18 (1 equivalent) and $NaHCO_3$ (4 equivalents) followed by anhydrous $CH_3CN$ (0.208 M, based on 2), and the resulting mixture was refluxed until TLC indicated the disappearance of the bromide (typically >24 h). The reaction was then diluted with $H_2O$, made strongly basic with aqueous NaOH, and extracted with $CHCl_3$ (3×). The combined organics were washed with $H_2O$, dried over $Na_2SO_4$, and concentrated to provide the crude product, which was purified by column chromatography with an appropriate solvent mixture (as described below for each compound).

exo-2-(2-(benzofuran-3-yl)ethyl)-7-ethyl-2-azabicyclo[2.2.2]oct-5-ene (32a). The product 32a was purified by column chromatography (19:1 hexanes:EtOAc) and obtained as an orange-brown oil (940 mg, 46%). $^1$H NMR (400 MHz, CDCl$_3$) δ 7.54 (d, J=7.3 Hz, 1H), 7.49 (s, 1H), 7.47-7.41 (m, 1H), 7.30-7.25 (m, 1H), 7.22 (td, J=7.4, 1.1 Hz, 1H), 6.32 (ddd, J=12.0, 10.7, 6.9 Hz, 2H), 3.22 (d, J=5.2 Hz, 1H), 3.09 (dd, J=9.1, 2.1 Hz, 1H), 2.87-2.66 (m, 3H), 2.57-2.48 (m, 1H), 2.44 (br s, 1H), 1.94 (dt, J=9.0, 2.4 Hz, 1H), 1.64-1.42 (m, 3H), 1.35-1.24 (m, 1H), 0.95-0.90 (m, 1H), 0.87 (t, J=7.4 Hz, 3H); $^{13}$C NMR (126 MHz, CDCl$_3$) δ 155.3, 141.7, 133.1, 132.8, 128.6, 124.1, 122.2, 119.7, 119.1, 111.5, 57.9, 56.3, 56.2, 41.3, 31.8, 29.9, 27.4, 23.0, 12.6; HRMS (FAB+) m/z: [M+H]$^+$ Calcd for C$_{19}$H$_{24}$NO$^+$ 282.1853; found 282.1862.

endo-2-(2-(benzofuran-3-yl)ethyl)-7-ethyl-2-azabicyclo [2.2.2]oct-5-ene (32b). The product 32b was purified by column chromatography (15:1 hexanes:EtOAc+2% Et$_3$N, 3 column volumes→9:1 hexanes:EtOAc+2% Et$_3$N, 3 column volumes) and obtained as a pale-yellow oil (422 mg, 60%). $^1$H NMR (500 MHz, CDCl$_3$) δ 7.55 (d, J=7.3 Hz, 1H), 7.45 (s, 1H), 7.45 (d, J=5.8 Hz, 1H), 7.30-7.25 (m, 1H), 7.25-7.20 (m, 1H), 6.39 (t, J=7.3 Hz, 1H), 6.17-6.11 (m, 1H), 3.41-3.34 (m, 1H), 3.03 (dd, J=9.6, 1.8 Hz, 1H), 2.91-2.74 (m, 3H), 2.59-2.53 (m, 1H), 2.53-2.47 (m, 1H), 2.07 (dt, J=9.6, 2.7 Hz, 1H), 2.05-1.98 (m, 1H), 1.78 (ddd, J=12.1, 9.2, 2.8 Hz, 1H), 1.23-1.13 (m, 1H), 1.06-0.96 (m, 1H), 0.86 (t, J=7.4 Hz, 3H), 0.82-0.76 (m, 1H); $^{13}$C NMR (75 MHz, CDCl$_3$) δ 155.3, 141.7, 133.7, 130.2, 128.5, 124.2, 122.3, 119.8, 118.9, 111.5, 57.9, 57.4, 54.5, 40.9, 31.6, 30.7, 28.8, 23.2, 11.8; HRMS (FAB+) m/z: [M+H]$^+$ Calcd for C$_{19}$H$_{24}$NO$^+$ 282.1853; found 282.1864.

exo-7-ethyl-2-(2-(5-methoxybenzofuran-3-yl)ethyl)-2-azabicyclo [2.2.2] oct-5-ene (32c). The product 32c was purified by column chromatography (20:1 hexanes:Et$_2$O, 3 column volumes→20:1 hexanes:Et$_2$O+2% Et$_3$N, 5 column volumes) and obtained as a pale-yellow oil (288 mg, 74%). $^1$H NMR (400 MHz, CDCl$_3$) δ 7.46 (s, 1H), 7.33 (d, J=8.9 Hz, 1H), 6.98 (d, J=2.5 Hz, 1H), 6.87 (dd, J=8.9, 2.6 Hz, 1H), 6.38-6.27 (m, 2H), 3.86 (s, 3H), 3.23 (dd, J=3.4, 1.8 Hz, 1H), 3.09 (dd, J=9.1, 2.2 Hz, 1H), 2.85-2.63 (m, 3H), 2.57-2.47 (m, 1H), 2.44 (dd, J=4.0, 2.1 Hz, 1H), 1.94 (dt, J=9.1, 2.5 Hz, 1H), 1.64-1.42 (m, 3H), 1.35-1.25 (m, 1H), 0.95-0.90 (m, 1H), 0.88 (t, J=7.4 Hz, 3H); $^{13}$C NMR (101 MHz, CDCl$_3$) δ 155.8, 150.3, 142.6, 133.1, 132.8, 129.2, 119.2, 112.6, 111.9, 102.5, 57.8, 56.3, 56.3, 56.2, 41.3, 31.8, 29.9, 27.40, 23.1, 12.6; LR-MS calcd. for C$_{20}$H$_{26}$NO$_2^+$ [M+H]$^+$ 312.20, found 312.59.

endo-7-ethyl-2-(2-(5-methoxybenzofuran-3-yl)ethyl)-2-azabicyclo[2.2.2] oct-5-ene (32d). The product 32d was purified by repeated column chromatography (column 1=9:1 hexanes:EtOAc, 2 column volumes→9:1 hexanes:EtOAc+2% Et$_3$N, 6 column volumes; column 2=9:1 hexanes:EtOAc+2% Et$_3$N) and obtained as a pale-yellow oil (103 mg, 44%). $^1$H NMR (500 MHz, CDCl$_3$) δ 7.42 (s, 1H), 7.33 (d, J=8.9 Hz, 1H), 7.00 (d, J=2.5 Hz, 1H), 6.88 (dd, J=8.9, 2.6 Hz, 1H), 6.38 (t, J=7.2 Hz, 1H), 6.17-6.11 (m, 1H), 3.85 (s, 3H), 3.40-3.35 (m, 1H), 3.02 (dd, J=9.6, 1.7 Hz, 1H), 2.88-2.70 (m, 3H), 2.57-2.48 (m, 2H), 2.07 (dt, J=9.6, 2.7 Hz, 1H), 2.04-1.98 (m, 1H), 1.78 (ddd, J=12.1, 9.2, 2.8 Hz, 1H), 1.23-1.13 (m, 1H), 1.00 (tt, J=14.8, 7.4 Hz, 1H), 0.85 (t, J=7.4 Hz, 3H), 0.82-0.75 (m, 1H); $^{13}$C NMR (126 MHz, CDCl$_3$) δ 155.8, 150.3, 142.4, 133.7, 130.2, 129.0, 118.9, 112.7, 111.9, 102.4, 57.8, 57.4, 56.1, 54.5, 40.9, 31.6, 30.7, 28.8, 23.2, 11.8; LR-MS calcd. for C$_{20}$H$_{26}$NO$_2^+$ [M+H]$^+$ 312.20, found 312.63.

exo-2-(2-(5-methoxybenzofuran-3-yl)ethyl)-7-propyl-2-azabicyclo[2.2.2] oct-5-ene (32e). The product 32c was purified by column chromatography (20:1 hexanes:Et$_2$O, 3 column volumes→20:1 hexanes:Et$_2$O+2% Et$_3$N, 5 column volumes) and obtained as a pale-yellow oil (288 mg, 74%). $^1$H NMR (500 MHz, CDCl$_3$) δ 7.46 (s, 1H), 7.33 (d, J=8.9 Hz, 1H), 6.98 (d, J=2.5 Hz, 1H), 6.87 (dd, J=8.9, 2.6 Hz, 1H), 6.36-6.27 (m, 2H), 3.86 (s, 3H), 3.19 (d, J=5.2 Hz, 1H), 3.09 (dd, J=9.1, 2.2 Hz, 1H), 2.84-2.63 (m, 3H), 2.55-2.47 (m, 1H), 2.44 (dd, J=3.8, 2.0 Hz, 1H), 1.93 (dt, J=9.1, 2.4 Hz, 1H), 1.57-1.36 (m, 4H), 1.33-1.24 (m, 2H), 0.92 (ddd, J=11.8, 4.3, 2.1 Hz, 1H), 0.88 (t, J=7.3 Hz, 3H); $^{13}$C NMR (126 MHz, CDCl$_3$) δ 155.7, 150.2, 142.6, 133.0, 132.8, 129.2, 119.2, 112.5, 111.9, 102.4, 57.8, 56.7, 56.2, 56.1, 39.1, 37.0, 31.7, 29.9, 23.0, 21.2, 14.5; LR-MS calcd. for C$_{21}$H$_{28}$NO$_2^+$ [M+H]$^+$ 326.21, found 326.62.

endo-2-(2-(5-methoxybenzofuran-3-yl)ethyl)-7-propyl-2-azabicyclo [2.2.2]oct-5-ene (32f). The product 32f was purified by column chromatography (12.5:1 hexanes: EtOAc+2% Et$_3$N) and obtained as a yellow oil (151 mg, 62%). $^1$H NMR (500 MHz, CDCl$_3$) δ 7.41 (s, 1H), 7.33 (d, J=8.9 Hz, 1H), 6.99 (d, J=2.6 Hz, 1H), 6.87 (dd, J=8.9, 2.6 Hz, 1H), 6.38 (t, J=7.3 Hz, 1H), 6.14 (dd, J=7.5, 5.9 Hz, 1H), 3.85 (s, 3H), 3.34 (ddd, J=5.0, 2.5, 1.3 Hz, 1H), 3.02 (dd, J=9.6, 1.9 Hz, 1H), 2.88-2.70 (m, 3H), 2.57-2.48 (m, 2H), 2.16-2.08 (m, 1H), 2.06 (dt, J=9.6, 2.7 Hz, 1H), 1.77 (ddd, J=12.1, 9.2, 2.8 Hz, 1H), 1.36-1.21 (m, 2H), 1.15 (ddt, J=13.0, 9.5, 6.4 Hz, 1H), 1.00-0.91 (m, 1H), 0.87 (t, J=7.3 Hz, 3H), 0.83-0.75 (m, 1H); $^{13}$C NMR (126 MHz, CDCl$_3$) δ 155.8, 150.3, 142.4, 133.7, 130.3, 129.0, 118.9, 112.7, 111.9, 102.4, 57.8, 57.6, 56.1, 54.4, 38.6, 38.4, 31.6, 30.8, 23.2, 20.2, 14.4; LR-MS calcd. for C$_{21}$H$_{28}$NO$_2^+$ [M+H]$^+$ 326.21, found 326.60.

exo-7-benzyl-2-(2-(5-methoxybenzofuran-3-yl)ethyl)-2-azabicyclo[2.2.2] oct-5-ene (32g). The product 32g was purified by column chromatography (20:1 hexanes:Et$_2$O, 4 column volumes→20:1 hexanes:Et$_2$O+2% Et$_3$N, 4 column volumes) and obtained as a pale-yellow oil (41.9 mg, 60%). $^1$H NMR (500 MHz, CDCl$_3$) δ 7.47 (s, 1H), 7.36 (d, J=8.9 Hz, 1H), 7.19-7.10 (m, 3H), 7.01 (dd, J=6.5, 2.0 Hz, 3H), 6.91 (dd, J=8.9, 2.6 Hz, 1H), 6.34 (t, J=7.2 Hz, 1H), 6.22-6.17 (m, 1H), 3.88 (s, 3H), 3.20 (dd, J=9.0, 2.3 Hz, 1H), 3.00 (d, J=5.5 Hz, 1H), 2.84 (dd, J=13.1, 9.5 Hz, 1H), 2.81-2.68 (m, 4H), 2.54-2.47 (m, 2H), 1.99 (dt, J=9.0, 2.5 Hz, 1H), 1.74-1.66 (m, 1H), 1.51 (ddd, J=10.8, 6.2, 3.1 Hz, 1H), 1.03 (ddd, J=12.3, 4.9, 2.1 Hz, 1H); $^{13}$C NMR (126 MHz, CDCl$_3$) δ 155.8, 150.3, 142.6, 142.1, 133.2, 132.6, 129.2, 129.1, 128.2, 125.6, 119.2, 112.7, 112.0, 102.4, 57.9, 56.18, 56.15, 55.5, 41.2, 40.0, 31.7, 29.9, 23.0; HRMS (FAB+) m/z: [M+H]$^+$ Calcd for C$_{25}$H$_{28}$NO$_2^+$ 374.2115, found 374.2111.

endo-7-benzyl-2-(2-(5-methoxybenzofuran-3-yl)ethyl)-2-azabicyclo [2.2.2]oct-5-ene (32h). The product 32h was purified by column chromatography (15:1 hexanes:EtOAc+2% Et$_3$N) and obtained as a pale-yellow oil (95.8 mg, 54%). $^1$H NMR (400 MHz, CDCl$_3$) δ 7.41 (d, J=1.1 Hz, 1H), 7.38 (d, J=8.9 Hz, 1H), 7.34-7.31 (m, 2H), 7.26-7.21 (m, 3H), 7.02 (d, J=2.6 Hz, 1H), 6.93 (dd, J=8.9, 2.6 Hz, 1H), 6.53 (ddd, J=7.9, 6.4, 1.4 Hz, 1H), 6.28 (ddd, J=8.2, 5.4, 1.4 Hz, 1H), 3.90 (s, 3H), 3.32 (ddd, J=5.3, 2.7, 1.4 Hz, 1H), 3.10 (dd, J=9.6, 2.1 Hz, 1H), 2.89-2.81 (m, 1H), 2.80-2.73 (m, 2H), 2.62-2.54 (m, 3H), 2.45 (dd, J=8.1, 6.7 Hz, 2H), 2.12 (d, J=9.5 Hz, 1H), 1.83 (ddd, J=12.2, 9.1, 2.8 Hz, 1H), 0.98-0.93 (m, 1H); $^{13}$C NMR (101 MHz, CDCl$_3$) δ 156.1, 150.6, 142.7, 140.9, 134.4, 130.2, 129.4, 129.2, 128.7, 126.3, 119.1, 113.0, 112.2, 102.8, 58.0, 57.1, 56.5, 54.7, 42.4, 40.6, 31.9, 30.7, 23.3; LR-MS calcd. for C$_{25}$H$_{28}$NO$_2^+$ [M+H]$^+$ 374.21, found 374.07.

exo-7-ethyl-2-(2-(5-fluorobenzofuran-3-yl)ethyl)-2-azabicyclo[2.2.2] oct-5-ene (32i). The product 32i was purified by column chromatography (20:1 hexanes:Et$_2$O, 2 column volumes→20:1 hexanes:Et$_2$O+2% Et$_3$N, 4 column volumes) and obtained as a pale-yellow oil (38.8 mg, 43%). $^1$H NMR (400 MHz, CDCl$_3$) (spectrum complicated by F—H coupling) δ 7.52 (s, 1H), 7.36 (dd, J=8.9, 4.1 Hz, 1H), 7.18 (dd, J=8.6, 2.6 Hz, 1H), 6.98 (td, J=9.0, 2.6 Hz, 1H), 6.38-6.27 (m, 2H), 3.20 (dt, J=5.2, 1.7 Hz, 1H), 3.07 (dd, J=9.1, 2.3 Hz, 1H), 2.83-2.61 (m, 3H), 2.54-2.47 (m, 1H), 2.47-2.42 (m, 1H), 1.93 (dt, J=9.1, 2.6 Hz, 1H), 1.58-1.43 (m, 3H), 1.34-1.26 (m, 1H), 0.91 (ddd, J=12.2, 4.9, 2.2 Hz, 1H), 0.86 (t, J=7.4 Hz, 3H); $^{13}$C NMR (101 MHz, CDCl$_3$) (spectrum complicated by F—C coupling) δ 160.3 and 158.0, 151.5, 143.6, 133.1, 132.8, 129.6, 119.5, 112.1 and 112.0, 111.9 and 111.6, 105.4 and 105.2, 57.7, 56.4, 56.2, 41.3, 31.8, 29.9, 27.4, 23.0, 12.6; LR-MS calcd. for C$_{19}$H$_{23}$FNO$^+$ [M+H]$^+$ 300.18, found 300.26.

2-(2-(5-methoxybenzofuran-3-yl)ethyl)-2-azabicyclo[2.2.2]oct-5-ene (32j). The product 32j was purified by column chromatography (9:1 hexanes:EtOAc+2% Et$_3$N, 2 column volumes→8:2 hexanes:EtOAc+2% Et$_3$N, 4 column volumes) and obtained as a yellow oil (185 mg, 65%). $^1$H NMR (500 MHz, CDCl$_3$) δ 7.41 (s, 1H), 7.33 (d, J=8.9 Hz, 1H), 6.99 (d, J=2.5 Hz, 1H), 6.88 (dd, J=8.9, 2.6 Hz, 1H), 6.40 (t, J=7.0 Hz, 1H), 6.27 (ddd, J=8.0, 5.5, 1.0 Hz, 1H), 3.85 (s, 3H), 3.46 (d, J=1.7 Hz, 1H), 3.09 (dd, J=9.6, 2.0 Hz, 1H), 2.85-2.70 (m, 3H), 2.57-2.46 (m, 2H), 2.09 (dt, J=9.6, 2.7 Hz, 1H), 2.01 (ddt, J=12.6, 9.4, 3.4 Hz, 1H), 1.62-1.54 (m, 1H), 1.33 (tdd, J=12.0, 3.7, 2.7 Hz, 1H), 1.29-1.20 (m, 1H); $^{13}$C NMR (126 MHz, CDCl$_3$) δ 155.8, 150.3, 142.4, 133.4, 131.9, 129.0, 118.9, 112.7, 111.9, 102.4, 58.1, 56.1, 55.7, 52.9, 30.9, 26.9, 23.1, 22.2; LR-MS calcd. for C$_{18}$H$_{22}$NO$_2^+$ [M+H]$^+$ 284.16, found 284.54.

endo-7-butyl-2-(2-(5-methoxybenzofuran-3-yl)ethyl)-2-azabicyclo[2.2.2] oct-5-ene (32k). The product 32k was purified by column chromatography (12.5:1 hexanes:EtOAc, 2 column volumes→12.5:1 hexanes:EtOAc+2% Et$_3$N, 3 column volumes→9:1 hexanes:EtOAc+2% Et$_3$N, 4 column volumes) followed by preparative TLC (9:1 hexanes:EtOAc+2% Et$_3$N) and obtained as a yellow oil (67.3 mg, 50%). $^1$H NMR (500 MHz, CDCl$_3$) δ 7.41 (s, 1H), 7.33 (d, J=8.9 Hz, 1H), 7.00 (d, J=2.6 Hz, 1H), 6.87 (dd, J=8.9, 2.6 Hz, 1H), 6.38 (t, J=7.2 Hz, 1H), 6.17-6.12 (m, 1H), 3.85 (s, 3H), 3.35 (dd, J=3.8, 1.4 Hz, 1H), 3.02 (dd, J=9.6, 1.8 Hz, 1H), 2.88-2.70 (m, 3H), 2.57-2.46 (m, 2H), 2.14-2.03 (m, 2H), 1.77 (ddd, J=12.1, 9.2, 2.8 Hz, 1H), 1.31-1.12 (m, 5H), 1.01-0.92 (m, 1H), 0.87 (t, J=6.9 Hz, 3H), 0.82-0.76 (m, 1H); $^{13}$C NMR (126 MHz, CDCl$_3$) δ 155.8, 150.3, 142.4, 133.7, 130.3, 129.0, 118.9, 112.7, 111.9, 102.5, 57.8, 57.6, 56.1, 54.5, 38.9, 35.9, 31.6, 30.9, 29.4, 23.2, 23.0, 14.2; LR-MS calcd. for C$_{22}$H$_{30}$NO$_2^+$ [M+H]$^+$ 340.23, found 340.07.

exo-7-ethyl-2-(2-(6-fluoro-5-methoxybenzofuran-3-yl)ethyl)-2-azabicyclo[2.2.2]oct-5-ene (32l). The product 32l was purified by column chromatography (20:1 hexanes:Et$_2$O, 3 column volumes→20:1 hexanes:Et$_2$O+2% Et$_3$N, 3 column volumes→10:1 hexanes:Et$_2$O+2% Et$_3$N, 2 column volumes) and obtained as a pale-yellow oil (64.5 mg, 65%). $^1$H NMR (500 MHz, CDCl$_3$) (spectrum complicated by F—H coupling). δ 7.46 (s, 1H), 7.21 (d, J=10.7 Hz, 1H), 7.02 (d, J=8.3 Hz, 1H), 6.37-6.32 (m, 1H), 6.32-6.27 (m, 1H), 3.94 (s, 3H), 3.22 (dt, J=5.2, 1.6 Hz, 1H), 3.08 (dd, J=9.1, 2.3 Hz, 1H), 2.83-2.62 (m, 3H), 2.54-2.48 (m, 1H), 2.45 (dd, J=3.9, 2.2 Hz, 1H), 1.93 (dt, J=9.1, 2.6 Hz, 1H), 1.59-1.44 (m, 3H), 1.34-1.26 (m, 1H), 0.91 (ddd, J=12.2, 4.8, 2.1 Hz, 1H), 0.87 (t, J=7.4 Hz, 3H); $^{13}$C NMR (126 MHz, CDCl$_3$) (spectrum complicated by F—C coupling). δ 152.2 and 150.3, 148.6 and 148.5, 144.9 and 144.8, 142.5 and 142.4, 133.1, 132.7, 123.9, 119.2, 103.04 and 103.02, 100.1 and 100.0, 57.79, 57.19, 56.37, 56.24, 41.30, 31.75, 29.88, 27.41, 22.98, 12.61; LR-MS calcd. for C$_{20}$H$_{25}$FNO$_2^+$ [M+H]$^+$ 330.19, found 329.99.

exo-2-(2-(5-methoxybenzofuran-3-yl)ethyl)-7-(methoxymethyl)-2-azabicyclo[2.2.2]oct-5-ene (32m). The product 32m was purified by column chromatography (15:1 hexanes:EtOAc, 2 column volumes→15:1 hexanes:EtOAc+2% Et$_3$N) and obtained as a light-brown oil (76.1 mg, 58%). $^1$H NMR (400 MHz, CDCl$_3$) δ 7.46 (d, J=1.2 Hz, 1H), 7.33 (d, J=8.9 Hz, 1H), 6.97 (d, J=2.6 Hz, 1H), 6.87 (dd, J=8.9, 2.6 Hz, 1H), 6.38 (ddd, J=8.0, 6.4, 1.5 Hz, 1H), 6.30 (ddd, J=8.1, 5.4, 1.4 Hz, 1H), 3.86 (s, 3H), 3.54 (t, J=9.0 Hz, 1H), 3.43 (dt, J=5.4, 1.8 Hz, 1H), 3.33 (dd, J=8.8, 5.7 Hz, 1H), 3.27 (s, 3H), 3.06 (dd, J=9.1, 2.4 Hz, 1H), 2.87-2.79 (m, 1H), 2.78-2.63 (m, 2H), 2.53 (ddd, J=11.2, 6.4, 2.6 Hz, 1H), 2.47 (ddd, J=6.3, 4.6, 3.0 Hz, 1H), 1.93 (dt, J=9.1, 2.6 Hz, 1H), 1.74 (ddd, J=5.5, 3.4, 2.0 Hz, 1H), 1.46-1.37 (m, 1H), 0.84 (ddd, J=12.4, 5.2, 2.2 Hz, 1H). $^{13}$C NMR (101 MHz, CDCl$_3$) δ 155.8, 150.3, 142.7, 133.6, 132.2, 129.2, 119.2, 112.6, 111.8, 102.5, 75.4, 58.8, 57.5, 56.2, 56.1, 53.8, 39.5, 31.4, 26.3, 22.9; LR-MS calcd. for C$_{20}$H$_{26}$NO$_3^+$ [M+H]$^+$ 328.19, found 328.42.

endo-2-(2-(5-methoxybenzofuran-3-yl)ethyl)-7-(methoxymethyl)-2-azabicyclo[2.2.2]oct-5-ene (32n). The product 32n was purified by column chromatography (5:1 hexanes:EtOAc with 2% triethylamine) and obtained as a light-brown oil (173.1 mg, 50%). $^1$H NMR (400 MHz, CDCl$_3$) δ 7.42 (d, J=1.1 Hz, 1H), 7.32 (d, J=8.9 Hz, 1H), 6.99 (d, J=2.6 Hz, 1H), 6.87 (dd, J=8.9, 2.6 Hz, 1H), 6.41 (ddd, J=8.1, 6.5, 1.4 Hz, 1H), 6.21-6.14 (m, 1H), 3.85 (s, 3H), 3.57 (ddd, J=5.4, 2.9, 1.5 Hz, 1H), 3.30 (s, 3H), 3.07 (dd, J=9.5, 2.1 Hz, 1H), 3.01-2.97 (m, 2H), 2.89-2.72 (m, 3H), 2.59-2.49 (m, 3H), 2.07 (dt, J=9.6, 2.7 Hz, 1H), 1.72 (ddd, J=12.3, 9.5, 2.8 Hz, 1H), 0.66 (ddt, J=12.5, 4.7, 2.8 Hz, 1H); $^{13}$C NMR (101 MHz, CDCl$_3$) δ 156.1, 150.6, 142.7, 134.2, 130.2, 129.3, 119.1, 113.1, 112.2, 102.7, 76.5, 59.0, 58.0, 56.4, 54.9, 54.9, 39.0, 31.4, 26.9, 23.4; LR-MS calcd. for C$_{20}$H$_{26}$NO$_3^+$ [M+H]$^+$ 328.19, found 327.79.

exo-2-(2-(5-methoxybenzofuran-3-yl)ethyl)-7-phenyl-2-azabicyclo [2.2.2] oct-5-ene (32o). The product 32o was obtained as a mixture with the endo-epimer 32p from isoquinuclidine 21. It was separated by column chromatography (20:1 hexanes:Et$_2$O, 3 column volumes→20:1 hexanes:Et$_2$O+2% Et$_3$N, 3 column volumes→8:2 hexanes:Et$_2$O+2% Et$_3$N, 5 column volumes→1:1 hexanes:Et$_2$O+2% Et$_3$N, 1 column volume) and obtained as a nearly colorless oil (30.7 mg, 14%). $^1$H NMR (500 MHz, CDCl$_3$) δ 7.43-7.39 (m, 2H), 7.34 (d, J=8.8 Hz, 1H), 7.29-7.24 (m, 2H), 7.24-7.17 (m, 2H), 6.91 (d, J=2.5 Hz, 1H), 6.88 (dd, J=8.8, 2.6 Hz, 1H), 6.48-6.43 (m, 2H), 3.84 (s, 3H), 3.34 (dt, J=4.4, 2.0 Hz, 1H), 3.32 (dd, J=9.0, 2.4 Hz, 1H), 2.82-2.57 (m, 5H), 2.53 (ddd, J=11.4, 8.1, 5.0 Hz, 1H), 2.09 (dt, J=9.0, 2.5 Hz, 1H), 1.81-1.73 (m, 1H), 1.55 (ddd, J=12.7, 5.9, 2.0 Hz, 1H); $^{13}$C NMR (126 MHz, CDCl$_3$) δ 155.7, 150.2, 145.0, 142.8, 132.9, 132.9, 129.1, 128.7, 127.9, 126.0, 118.8, 112.5, 111.8, 102.3, 59.1, 57.7, 56.3, 56.1, 45.7, 31.9, 29.5, 22.7; LR-MS calcd. for C$_{24}$H$_{26}$NO$_2^+$ [M+H]$^+$ 360.20, found 359.92.

endo-2-(2-(5-methoxybenzofuran-3-yl)ethyl)-7-phenyl-2-azabicyclo [2.2.2]oct-5-ene (32p). The product 32p was obtained as a mixture with the exo-epimer 32o from isoquinuclidine 21. It was separated by column chromatography (20:1 hexanes:Et$_2$O, 3 column volumes→20:1 hexanes:Et$_2$O+2% Et$_3$N, 3 column volumes→8:2 hexanes:Et$_2$O+2% Et$_3$N, 5 column volumes→1:1 hexanes:Et$_2$O+2% Et$_3$N, 1 column volume) and obtained as a yellow oil (103 mg, 48%). $^1$H NMR (500 MHz, CDCl$_3$) δ 7.44 (s, 1H), 7.34 (d, J=8.9 Hz, 1H), 7.28-7.22 (m, 2H), 7.21-7.15 (m, 3H), 7.00

(d, J=2.6 Hz, 1H), 6.89 (dd, J=8.9, 2.6 Hz, 1H), 6.59 (t, J=7.4 Hz, 1H), 6.19 (ddd, J=8.0, 5.3, 1.0 Hz, 1H), 3.86 (s, 3H), 3.54-3.51 (m, 1H), 3.50-3.46 (m, 1H), 3.13 (dd, J=9.7, 1.7 Hz, 1H), 2.91-2.75 (m, 3H), 2.71 (dd, J=3.6, 1.5 Hz, 1H), 2.63-2.56 (m, 1H), 2.18 (dt, J=9.7, 2.7 Hz, 1H), 2.13 (ddd, J=12.7, 9.7, 2.8 Hz, 1H), 1.56 (ddt, J=12.7, 5.4, 2.7 Hz, 1H); $^{13}$C NMR (126 MHz, CDCl$_3$) δ 155.9, 150.3, 145.4, 142.4, 134.3, 130.7, 129.0, 128.4, 128.2, 126.2, 118.8, 112.8, 112.0, 102.4, 59.2, 57.5, 56.2, 54.2, 44.5, 32.4, 31.9, 23.2; LR-MS calcd. for $C_{24}H_{26}NO_2^+$ [M+H]$^+$ 360.20, found 359.94.

endo-2-(2-(benzo[b]thiophen-3-yl)ethyl)-7-ethyl-2-azabicyclo[2.2.2] oct-5-ene (32q). The product 32q was purified by column chromatography (9:1 hexanes:EtOAc, 3 column volumes→9:1 hexanes:EtOAc+2% Et$_3$N, 3 column volumes) and obtained as a yellow oil (150 mg, 40%). $^1$H NMR (500 MHz, CDCl$_3$) δ 7.84 (d, J=7.8 Hz, 1H), 7.77 (d, J=7.7 Hz, 1H), 7.41-7.36 (m, 1H), 7.36-7.30 (m, 1H), 7.13 (s, 1H), 6.40 (t, J=7.2 Hz, 1H), 6.17-6.12 (m, 1H), 3.44-3.39 (m, 1H), 3.08-2.97 (m, 3H), 2.97-2.88 (m, 1H), 2.66-2.57 (m, 1H), 2.55-2.49 (m, 1H), 2.11 (dt, J=9.7, 2.7 Hz, 1H), 2.09-2.01 (m, 1H), 1.80 (ddd, J=12.1, 9.2, 2.8 Hz, 1H), 1.24-1.14 (m, 1H), 1.07-0.96 (m, 1H), 0.86 (t, J=7.4 Hz, 3H), 0.83-0.77 (m, 1H); $^{13}$C NMR (101 MHz, CDCl$_3$) δ 140.5, 139.2, 135.1, 133.8, 130.2, 124.2, 124.0, 123.0, 121.8, 121.7, 58.0, 57.5, 54.4, 40.6, 31.6, 30.7, 28.8, 27.9, 11.7; HRMS (FAB+) m/z: [M+H]$^+$ Calcd for $C_{19}H_{24}NS^+$ 298.1624; found 298.1625.

exo-7-ethyl-2-(2-(5-methoxybenzo[b]thiophen-3-yl)ethyl)-2-azabicyclo [2.2.2]oct-5-ene (32r). The product 32r was purified by column chromatography (20:1 hexanes:Et$_2$O, 3 column volumes→20:1 hexanes:Et$_2$O+2% Et$_3$N, 3 column volumes→10:1 hexanes:Et$_2$O+2% Et$_3$N, 3 column volumes) and obtained as a pale-yellow oil (108 mg, 66%). $^1$H NMR (400 MHz, CDCl$_3$) δ 7.72-7.67 (m, 1H), 7.18 (s, 2H), 7.02-6.96 (m, 1H), 6.38-6.27 (m, 2H), 3.90 (s, 3H), 3.24 (d, J=3.9 Hz, 1H), 3.11 (d, J=8.7 Hz, 1H), 2.96-2.78 (m, 3H), 2.62-2.51 (m, 1H), 2.45 (br s, 1H), 1.96 (d, J=9.0 Hz, 1H), 1.63-1.42 (m, 3H), 1.36-1.27 (m, 1H), 0.96-0.91 (m, 1H), 0.88 (t, J=7.4 Hz, 3H); $^{13C}$ NMR (101 MHz, CDCl$_3$) δ 157.5, 140.5, 135.1, 133.1, 132.8, 123.5, 122.9, 114.1, 104.5, 58.0, 56.4, 56.3, 55.8, 41.3, 31.8, 29.9, 27.9, 27.3, 12.6; LR-MS calcd. for $C_{20}H_{26}NOS^+$ [M+H]$^+$ 328.17, found 328.45.

exo-7-ethyl-2-(2-(6-methoxy-1H-benzo[d]imidazol-1-yl)ethyl)-2-azabicyclo[2.2.2]oct-5-ene (32s). To a solution of isoquinuclidine 2a (97.6 mg, 0.500 mmol) in anhydrous CH$_2$Cl$_2$ (4.0 mL) at 0° C. was added iodotrimethylsilane (285 μL, 2.00 mmol), and the orange solution was allowed to warm to room temperature and stirred for 1 h. The reaction was then quenched with MeOH (1.5 mL) and concentrated to provide the isoquinuclidine HI salt as an orange-brown solid. This material was dissolved in anhydrous DMF (1.9 mL), chloride 18f (105 mg, 0.500 mmol) and triethylamine (209 μL, 1.50 mmol) were added, and the reaction was heated to 70° C. for 12 h. At this time additional triethylamine (209 μL, 1.50 mmol) was added and the temperature was raised to 90° C. for an additional 33 h (still incomplete conversion). The reaction was then diluted with H$_2$O (10 mL), made strongly basic with NaOH, and extracted with Et$_2$O (3×10 mL). The combined organics were washed with H$_2$O (10 mL) and brine (10 mL), dried over Na$_2$SO$_4$, and concentrated to give an orange-brown oil. This material was purified by column chromatography (1:1 hexanes:EtOAc+2% Et$_3$N) followed by preparative TLC (9:1 CH$_2$Cl$_2$:Et$_2$O) to provide the pure product 32s as a yellow oil (19.6 mg, 13%). $^1$H NMR (400 MHz, CDCl$_3$) δ 7.88 (s, 1H), 7.66 (d, J=8.8 Hz, 1H), 6.89 (dd, J=8.8, 2.4 Hz, 1H), 6.80 (d, J=2.4 Hz, 1H), 6.36-6.29 (m, 1H), 6.29-6.23 (m, 1H), 4.06 (dd, J=6.8, 5.4 Hz, 2H), 3.87 (s, 3H), 3.07-3.00 (m, 2H), 3.00-2.91 (m, 1H), 2.56 (dt, J=12.8, 5.3 Hz, 1H), 2.44 (dd, J=3.9, 2.3 Hz, 1H), 1.87 (dt, J=9.0, 2.6 Hz, 1H), 1.48-1.32 (m, 3H), 1.29-1.19 (m, 1H), 0.86 (ddd, J=12.2, 4.6, 2.2 Hz, 1H), 0.74 (t, J=7.4 Hz, 3H); $^{13}$C NMR (101 MHz, CDCl$_3$) δ 156.7, 143.1, 138.4, 134.6, 133.3, 132.5, 120.8, 111.0, 93.4, 58.2, 57.4, 56.5, 56.0, 44.1, 41.0, 31.6, 29.7, 27.4, 12.5; LR-MS calcd. for $C_{19}H_{26}N_3O^+$ [M+H]$^+$ 312.21, found 312.01.

EXAMPLE 9

Synthesis of N-Arylalkylisoquinuclidines by Reduction

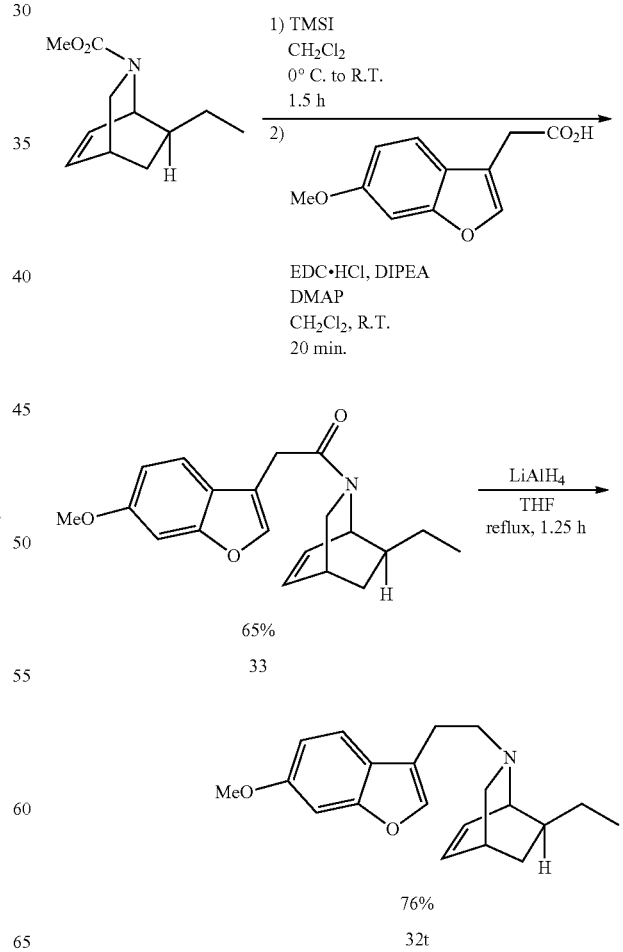

Scheme 10. N-Arylalkylisoquinuclidines by Reduction exo-1-(7-ethyl-2-azabicyclo[2.2.2]oct-5-en-2-yl)-2-(6-methoxy-benzofuran-3-yl)ethanone (33). To a solution of isoquinuclidine 2a (146 mg, 0.750 mmol) in anhydrous CH$_2$Cl$_2$ (6.0 mL) at 0° C. was added iodotrimethylsilane (427 µL, 3.00 mmol), and the orange solution was allowed to warm to room temperature and stirred for 1 h. The reaction was then quenched with MeOH (2.3 mL) and concentrated to provide the isoquinuclidine HI salt as an orange-brown solid. To this material was added 2-(6-methoxy-1-benzofuran-3-yl)acetic acid (155 mg, 0.750 mmol), N-(3-dimethylaminopropyl)-N'-ethylcarbodiimide hydrochloride (151 mg, 0.787 mmol), 4-(dimethylamino)pyridine (9.2 mg, 0.075 mmol), and iPr$_2$NEt (157 µL, 0.900 mmol) followed by anhydrous CH$_2$Cl$_2$ (10.5 mL), and the resulting solution was stirred for 20 min. at room temperature. The reaction was then quenched with H$_2$O (20 mL) and diluted with CH$_2$Cl$_2$ (10 mL). The organic layer was separated and washed with 1% aqueous NaOH (2×10 mL), 2% aqueous HCl (2×10 mL), and H$_2$O (10 mL), dried over Na$_2$SO$_4$, and concentrated to give a yellow oil. This material was washed through a short silica column with 1:1 hexanes:EtOAc, and the eluate concentrated to provide pure amide 33 as a nearly colorless oil (155 mg, 65%). $^1$H NMR (500 MHz, CDCl$_3$) (some partial integrals due to conformers) δ 7.48-7.41 (m, 2H), 7.00-6.98 (m, 1H), 6.89-6.84 (m, 1H), 6.47 (ddd, J=7.8, 6.3, 1.4 Hz, 0.6H), 6.34 (td, J=6.6, 1.1 Hz, 1H), 6.26 (ddd, J=7.8, 6.1, 1.4 Hz, 0.4H), 5.15 (d, J=6.2 Hz, 0.6H), 4.25 (d, J=6.1 Hz, 0.4H), 3.84 (d from conformers, 3H), 3.78-3.51 (m, 2H), 3.37 (dd, J=9.2, 2.2 Hz, 0.6H), 3.29 (dd, J=11.7, 2.0 Hz, 0.4H), 3.17-3.10 (m, 1H), 2.77-2.68 (m, 1H), 1.69-1.63 (m, 1H), 1.53-1.44 (m, 1H), 1.44-1.22 (m, 2H), 1.06 (ddd, J=12.6, 4.5, 2.2 Hz, 0.4H), 0.97 (ddd, J=12.8, 4.5, 2.3 Hz, 0.6H), 0.93 (t, J=7.3 Hz, 3H); $^{13}$C NMR (126 MHz, CDCl$_3$) (spectrum complicated by conformers) δ 167.0, 158.3, 156.4, 141.7, 141.6, 134.6, 134.0, 133.5, 132.5, 121.4, 121.3, 120.2, 120.0, 114.5, 113.9, 111.8, 111.7, 96.14, 96.10, 55.9, 52.7, 49.5, 48.3, 46.9, 41.0, 40.5, 31.3, 30.6, 30.4, 30.2, 29.77, 29.75, 27.8, 27.7, 12.5, 12.3; LR-MS calcd. for C$_{20}$H$_{24}$NO$_3^+$ [M+H]$^+$ 326.18, found 326.61.

exo-7-ethyl-2-(2-(6-methoxybenzofuran-3-yl)ethyl)-2-azabicyclo [2.2.2]oct-5-ene (32t). To a solution of amide 33 (144 mg, 0.442 mmol) in anhydrous THF (4.5 mL) at room temperature was carefully added LiAlH$_4$ (36.9 mg, 0.972 mmol), and the resulting mixture was refluxed for 1.25 h. After cooling to room temperature, the reaction was quenched by the successive addition of H$_2$O (37 µL), 15% aqueous NaOH (37 µL), and H$_2$O again (111 µL). The resulting mixture was diluted with Et$_2$O (10 mL) and stirred vigorously until the aluminum salts were white and loose and then filtered, washing the filter cake with Et$_2$O.

The combined filtrate and washings were concentrated to yield the crude product. This material was purified by column chromatography (20:1 hexanes:EtOAc+2% Et$_3$N) to provide the pure product 32t as a pale yellow-green oil (104 mg, 76%). $^1$H NMR (400 MHz, CDCl$_3$) δ 7.40-7.37 (m, 2H), 6.99 (d, J=2.2 Hz, 1H), 6.86 (dd, J=8.5, 2.2 Hz, 1H), 6.37-6.26 (m, 2H), 3.85 (s, 3H), 3.22 (dt, J=5.2, 1.8 Hz, 1H), 3.08 (dd, J=9.1, 2.3 Hz, 1H), 2.83-2.62 (m, 3H), 2.55-2.47 (m, 1H), 2.44 (ddd, J=7.8, 4.9, 3.0 Hz, 1H), 1.93 (dt, J=9.1, 2.6 Hz, 1H), 1.61-1.43 (m, 3H), 1.34-1.27 (m, 1H), 0.95-0.90 (m, 1H), 0.88 (t, J=7.4 Hz, 3H); $^{13}$C NMR (101 MHz, CDCl$_3$) δ 158.0, 156.2, 140.8, 133.1, 132.8, 122.1, 119.8, 119.0, 111.3, 96.2, 58.0, 56.3, 56.2, 55.9, 41.4, 31.8, 29.9, 27.4, 23.1, 12.6; LR-MS calcd. for C$_{20}$H$_{26}$NO$_2^+$ [M+H]$^+$ 312.20, found 312.56.

EXAMPLE 10

Synthesis of Heteroarylazepines by Ni(0) Cyclization

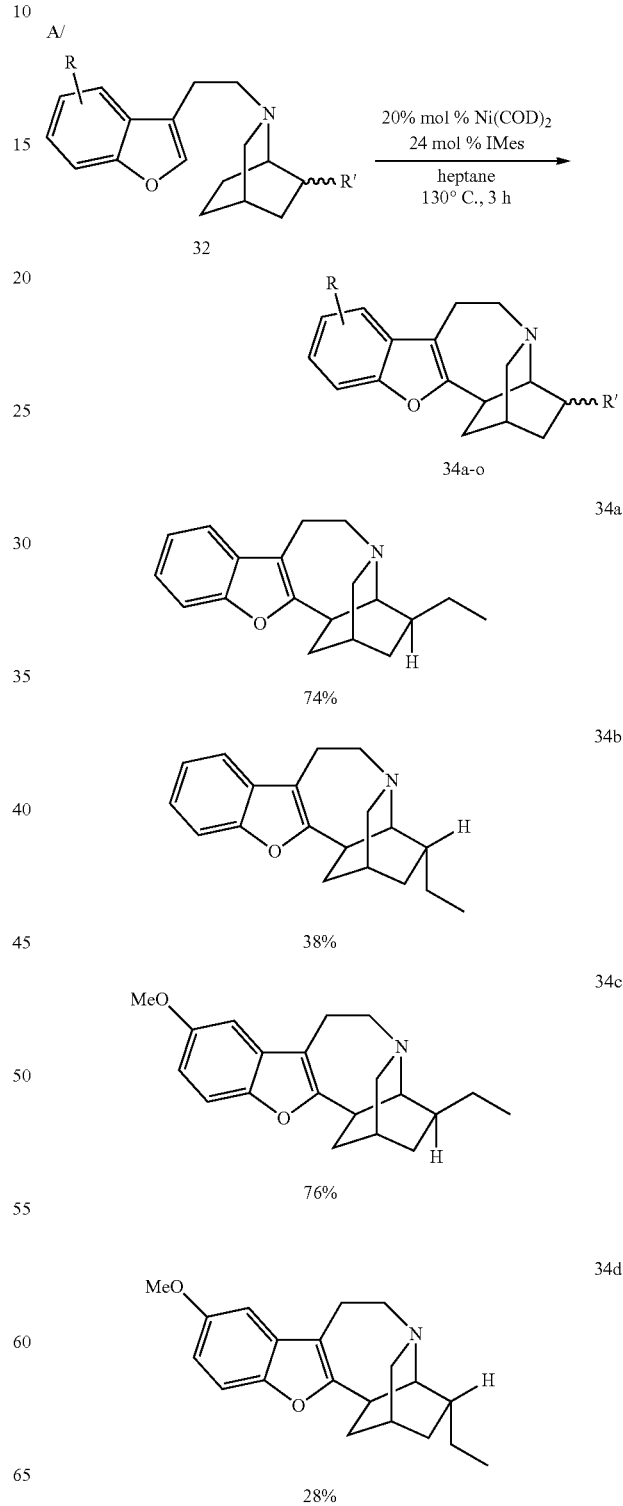

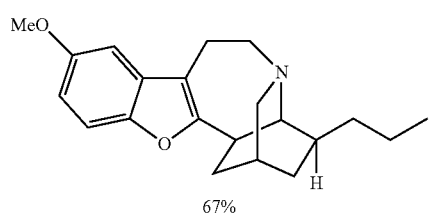
34e
67%
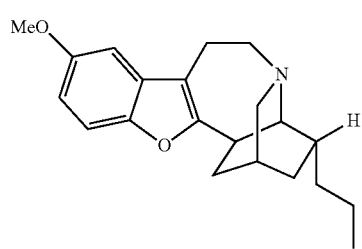
34f
36%
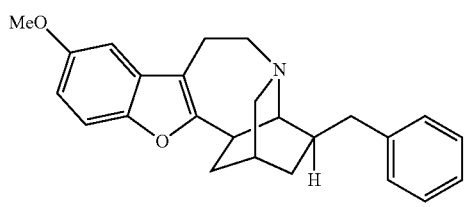
34g
62%
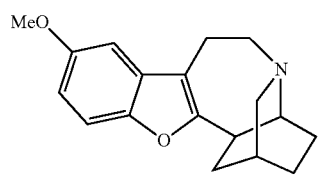
34h
71%
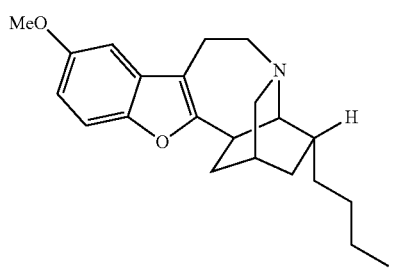
34i
41%
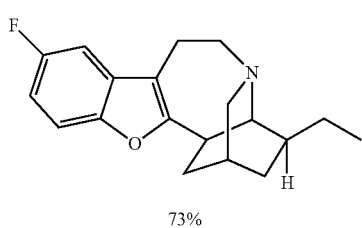
34j
73%
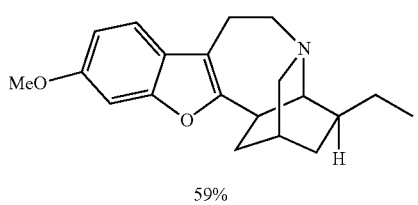
34k
59%
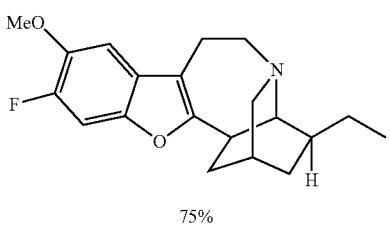
34l
75%
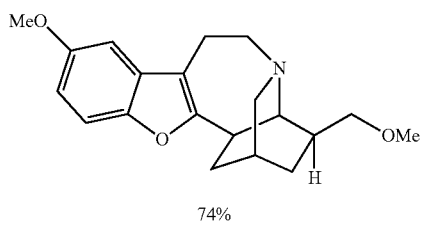
34m
74%
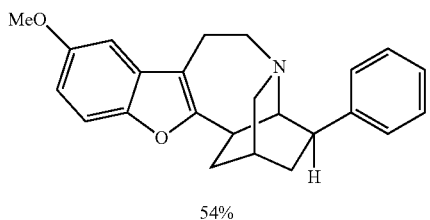
34n
54%
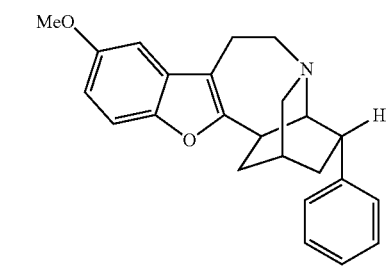
34o
<10%
B/
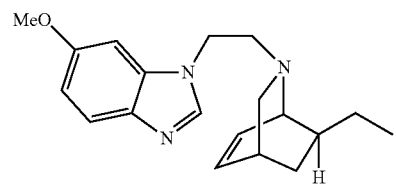
32s
$\xrightarrow{\substack{20\% \text{ mol }\% \\ \text{Ni(COD)}_2 \\ 24 \text{ mol }\% \\ \text{IMes} \\ \text{heptane} \\ 130°\text{ C.}, 3\text{ h}}}$

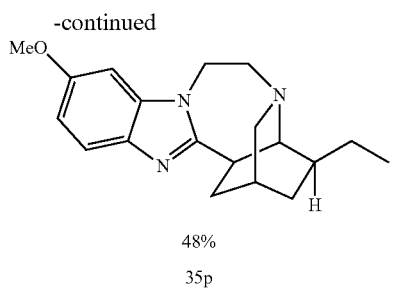

48%

35p

General Procedure for Preparation of Heteroarylazepines by Ni(0) C—H Insertion (34a-p). In a glovebox, a vial was charged with Ni(COD)$_2$ (0.20 equivalents) and 1,3-bis(2,4,6-trimethylphenyl)-1,3-dihydro-2H-imidazol-2-ylidene (IMes, 0.24 equivalents) followed by anhydrous heptane (0.100 M based on Ni((COD)$_2$), and the resulting black solution was stirred at room temperature for 15 min. To this mixture was then added a solution of the N-arylalkylisoquinuclidine substrate 32 (1 equivalent) in anhydorus heptane (0.333 M based on 32), and the reaction vessel was sealed, removed from the glovebox, and heated at 130° C. for 3 h. After cooling to room temperature the reaction mixture was purified directly by a combination of column chromatography and/or preparative TLC as described below for each substrate. (*Note: For substrates that are insoluble in heptane, the catalyst solution is instead added into the heterogeneous mixture of the substrate and heptane.)

Heteroarylazepine 34a. The crude reaction mixture was purified directly by column chromatography (40:1 hexanes: EtOAc+2% Et$_3$N) to yield several fractions as pale-yellow oils. The central fractions provided pure product 34a (20.3 mg), while the early (96.1 mg) and later (26.1 mg) fractions were contaminated with co-eluting impurities. The later fractions were purified on a second chromatography column (hexanes+4% Et$_3$N) to provide a colorless oil (14.2 mg). This material was combined with the early fractions from the first column and the whole was purified by preparative TLC (80:1 hexanes:EtOAc+2% Et$_3$N) to provide a second portion of pure product 34a as a nearly colorless oil (83.8 mg). Overall yield of pure product was 104 mg (74%). $^1$H NMR (500 MHz, CDCl$_3$) δ 7.43-7.39 (m, 1H), 7.39-7.35 (m, 1H), 7.24-7.18 (m, 2H), 3.47-3.39 (m, 1H), 3.28-3.13 (m, 3H), 3.02-2.92 (m, 2H), 2.82 (s, 1H), 2.54 (d, J=15.7 Hz, 1H), 2.05 (t, J=12.4 Hz, 1H), 1.90-1.77 (m, 2H), 1.66 (ddd, J=13.3, 6.4, 3.1 Hz, 1H), 1.62-1.43 (m, 3H), 1.25-1.17 (m, 1H), 0.92 (t, J=7.2 Hz, 3H); $^{13}$C NMR (126 MHz, CDCl$_3$) δ 160.0, 153.7, 130.9, 123.3, 122.1, 118.7, 111.6, 110.6, 57.3, 53.3, 49.7, 41.5, 41.1, 33.0, 32.3, 27.5, 26.5, 19.5, 11.9; HRMS (FAB+) m/z: [M]$^+$ Calcd for C$_{19}$H$_{23}$NO$^+$ 281.1775; found 281.1772.

Heteroarylazepine 34b. The crude reaction mixture was purified directly by column chromatography (9:1 hexanes: EtOAc+2% Et$_3$N) to yield an orange-brown oil contaminated with a co-eluting impurity. This material was further purified by preparative TLC (Et$_2$O+1% Et$_3$N) to provide the pure product 34b as a pale-yellow oil (53.3 mg, 38%). $^1$H NMR (500 MHz, CDCl$_3$) δ 7.43-7.39 (m, 1H), 7.38-7.34 (m, 1H), 7.24-7.18 (m, 2H), 3.44 (ddd, J=13.8, 4.7, 2.3 Hz, 1H), 3.38-3.29 (m, 2H), 3.25 (ddd, J=17.0, 12.3, 4.7 Hz, 1H), 3.12-3.02 (m, 2H), 2.88 (s, 1H), 2.57-2.49 (m, 1H), 2.09-1.94 (m, 3H), 1.92-1.85 (m, 1H), 1.62 (ddd, J=13.3, 6.0, 3.7 Hz, 1H), 1.47-1.34 (m, 2H), 1.18-1.09 (m, 1H), 0.95 (t, J=7.4 Hz, 3H); $^{13}$C NMR (126 MHz, CDCl$_3$) δ 160.7, 153.4, 130.7, 123.3, 122.2, 118.6, 112.1, 110.7, 56.5, 53.5, 49.1, 41.9, 34.3, 34.1, 31.6, 28.5, 26.4, 18.9, 12.3; HRMS (FAB+) m/z: [M+H]$^+$ Calcd for C$_{19}$H$_{24}$NO$^+$ 282.1853; found 282.1859.

Heteroarylazepine 34c. The crude reaction mixture was purified directly by column chromatography (30:1 hexanes: EtOAc+1% Et$_3$N) to yield the crude product as a pale-yellow oil. This material was further purified by preparative TLC (30:1 hexanes:EtOAc+1% Et$_3$N) to provide the pure product 34c as a pale-brown oil (118 mg, 76%). $^1$H NMR (500 MHz, CDCl$_3$) δ 7.24 (d, J=8.8 Hz, 1H), 6.86 (d, J=2.5 Hz, 1H), 6.81 (dd, J=8.8, 2.6 Hz, 1H), 3.85 (s, 3H), 3.46-3.36 (m, 1H), 3.25-3.11 (m, 3H), 3.02-2.91 (m, 2H), 2.80 (s, 1H), 2.52-2.42 (m, 1H), 2.08-1.99 (m, 1H), 1.88-1.76 (m, 2H), 1.64 (ddd, J=13.1, 6.4, 3.2 Hz, 1H), 1.59-1.42 (m, 3H), 1.24-1.16 (m, 1H), 0.91 (t, J=7.1 Hz, 3H); $^{13}$C NMR (126 MHz, CDCl$_3$) δ 161.1, 155.8, 148.6, 131.4, 111.8, 111.4, 111.0, 101.9, 57.2, 56.2, 53.3, 49.8, 41.5, 41.2, 33.1, 32.3, 27.5, 26.5, 19.5, 11.9; LR-MS calcd. for C$_{20}$H$_{26}$NO$_2$$^+$ [M+H]$^+$ 312.20, found 312.52.

Heteroarylazepine 34d. The crude reaction mixture was purified directly by column chromatography (9:1 hexanes: EtOAc+2% Et$_3$N, 4 column volumes→8:2 hexanes:EtOAc+ 2% Et$_3$N, 3 column volumes) to yield the crude product as a yellow-orange oil. This material was further purified by preparative TLC (Et$_2$O+1% Et$_3$N) to provide the pure product 34d as a nearly colorless oil that slowly crystallized to a white solid (27.0 mg, 28%). $^1$H NMR (400 MHz, CDCl$_3$) δ 7.24 (d, J=8.8 Hz, 1H), 6.87 (d, J=2.5 Hz, 1H), 6.80 (dd, J=8.8, 2.6 Hz, 1H), 3.85 (s, 3H), 3.43 (ddd, J=13.6, 4.6, 2.2 Hz, 1H), 3.36-3.17 (m, 3H), 3.11-3.02 (m, 2H), 2.86 (s, 1H), 2.46 (dt, J=16.4, 2.9 Hz, 1H), 2.08-1.91 (m, 3H), 1.91-1.85 (m, 1H), 1.65-1.57 (m, 1H), 1.45-1.33 (m, 2H), 1.17-1.07 (m, 1H), 0.93 (t, J=7.4 Hz, 3H); $^{13}$C NMR (101 MHz, CDCl$_3$) δ 161.7, 155.9, 148.4, 131.3, 112.3, 111.5, 111.1, 101.8, 56.5, 56.2, 53.5, 49.1, 42.0, 34.5, 34.2, 31.7, 28.5, 26.4, 19.0, 12.3; LR-MS calcd. for C$_{20}$H$_{26}$NO$_2$$^+$ [M+H]$^+$ 312.20, found 312.63.

Heteroarylazepine 34e. The crude reaction mixture was purified directly by column chromatography (30:1 hexanes: EtOAc+1% Et$_3$N) to yield the crude product as a pale-yellow oil. This material was further purified by preparative TLC (20:1 hexanes:EtOAc+2% Et$_3$N) to provide the pure product 34e as a nearly colorless oil that slowly crystallized to a white solid (82.6 mg, 67%). $^1$H NMR (500 MHz, CDCl$_3$) δ 7.24 (d, J=8.8 Hz, 1H), 6.86 (d, J=2.5 Hz, 1H), 6.80 (dd, J=8.8, 2.6 Hz, 1H), 3.85 (s, 3H), 3.47-3.37 (m, 1H), 3.24-3.11 (m, 3H), 3.00-2.91 (m, 2H), 2.76 (s, 1H), 2.52-2.43 (m, 1H), 2.08-1.99 (m, 1H), 1.87-1.82 (m, 1H), 1.82-1.75 (m, 1H), 1.69-1.59 (m, 2H), 1.55-1.38 (m, 2H), 1.37-1.28 (m, 2H), 1.23-1.17 (m, 1H), 0.92 (t, J=7.3 Hz, 3H); $^{13}$C NMR (126 MHz, CDCl$_3$) δ 161.0, 155.8, 148.6, 131.4, 111.8, 111.4, 111.0, 101.8, 57.8, 56.2, 53.3, 49.7, 41.2, 39.3, 37.1, 33.0, 32.4, 26.5, 20.4, 19.5, 14.5; LR-MS calcd. for C$_{21}$H$_{28}$NO$_2$$^+$ [M+H]$^+$ 326.21, found 326.59.

Heteroarylazepine 34f. The crude reaction mixture was purified directly by column chromatography (9:1 hexanes: EtOAc+2% Et$_3$N, 3 column volumes→8:2 hexanes:EtOAc+ 2% Et$_3$N, 3 column volumes) to yield the crude product as a yellow-brown oil. This material was further purified by preparative TLC (Et$_2$O+1% Et$_3$N) to provide the pure product 34f as a nearly colorless oil that slowly crystallized to a white solid (46.3 mg, 36%). $^1$H NMR (500 MHz, CDCl$_3$) δ 7.24 (d, J=8.8 Hz, 1H), 6.86 (d, J=2.5 Hz, 1H), 6.80 (dd, J=8.8, 2.6 Hz, 1H), 3.85 (s, 3H), 3.42 (ddd, J=13.9, 4.6, 2.2 Hz, 1H), 3.36-3.26 (m, 2H), 3.22 (ddd, J=17.0, 12.3, 4.7 Hz, 1H), 3.10-3.01 (m, 2H), 2.83 (dd, J=2.9, 2.0 Hz, 1H), 2.49-2.42 (m, 1H), 2.11-2.00 (m, 2H), 2.00-1.93 (m, 1H), 1.90-1.85 (m, 1H), 1.61 (ddd, J=13.3, 6.7, 3.5 Hz, 1H), 1.42-1.27 (m, 4H), 1.16-1.08 (m, 1H), 0.93 (t, J=5.1 Hz, 3H); $^{13}$C NMR (126 MHz, CDCl$_3$) δ 161.7, 155.8, 148.3, 131.3, 112.3, 111.5, 111.1, 101.7, 56.8, 56.1, 53.5, 49.1, 39.6, 38.0, 34.5, 34.1, 31.8, 26.8, 20.8, 19.0, 14.4; LR-MS calcd. for C$_{21}$H$_{28}$NO$_2^+$ [M+H]$^+$ 326.21, found 326.66.

Heteroarylazepine 34g. The crude reaction mixture was purified directly by column chromatography (30:1 hexanes:EtOAc+1% Et$_3$N) to yield the crude product as a yellow-orange oil. This material was further purified by preparative TLC (30:1 hexanes:EtOAc+2% Et$_3$N) to provide the pure product 34g as a nearly colorless glass (26.0 mg, 62%). $^1$H NMR (500 MHz, CDCl$_3$) δ 7.26 (t, J=7.4 Hz, 2H), 7.22-7.18 (m, 3H), 7.16 (t, J=7.2 Hz, 1H), 6.85 (d, J=2.5 Hz, 1H), 6.79 (dd, J=8.8, 2.6 Hz, 1H), 3.84 (s, 3H), 3.52-3.42 (m, 1H), 3.26-3.12 (m, 2H), 3.08-3.00 (m, 3H), 2.86 (dd, J=13.3, 9.2 Hz, 1H), 2.75 (dd, J=13.3, 6.0 Hz, 1H), 2.70 (s, 1H), 2.52-2.42 (m, 1H), 2.07-1.93 (m, 2H), 1.88 (s, 1H), 1.86-1.78 (m, 1H), 1.64 (ddd, J=13.3, 6.3, 3.2 Hz, 1H), 1.31 (ddt, J=12.6, 6.5, 2.3 Hz, 1H); $^{13}$C NMR (126 MHz, CDCl$_3$) δ 160.9, 155.8, 148.5, 141.64, 131.4, 129.3, 128.3, 125.8, 111.8, 111.4, 110.9, 101.9, 56.2, 55.7, 53.1, 49.8, 41.5, 40.9, 40.7, 33.1, 32.5, 26.6, 19.5; LR-MS calcd. for C$_{25}$H$_{28}$NO$_2^+$ [M+H]$^+$ 374.21, found 374.70.

Heteroarylazepine 34h. The crude reaction mixture was purified directly by column chromatography (8:2 hexanes:EtOAc+2% Et$_3$N, 3 column volumes→7:3 hexanes:EtOAc+2% Et$_3$N, 3 column volumes) to yield the pure product 34h as a brown oil that slowly crystallized to a pale-brown solid (101 mg, 71%). $^1$H NMR (500 MHz, CDCl$_3$) δ 7.24 (d, J=8.8 Hz, 1H), 6.86 (d, J=2.5 Hz, 1H), 6.80 (dd, J=8.8, 2.6 Hz, 1H), 3.84 (s, 3H), 3.43-3.38 (m, 1H), 3.31-3.16 (m, 3H), 3.11-3.04 (m, 2H), 3.04-3.00 (m, 1H), 2.51-2.44 (m, 1H), 2.15-2.07 (m, 1H), 2.06-1.99 (m, 1H), 1.88 (s, 1H), 1.81-1.73 (m, 1H), 1.73-1.60 (m, 3H); $^{13}$C NMR (126 MHz, CDCl$_3$) δ 161.1, 155.8, 148.5, 131.3, 111.9, 111.5, 111.0, 101.8, 56.2, 53.3, 53.2, 49.7, 39.9, 33.7, 29.4, 25.6, 23.9, 19.0; LR-MS calcd. for C$_{18}$H$_{22}$NO$_2^+$ [M+H]$^+$ 284.16, found 284.51.

Heteroarylazepine 34i. The crude reaction mixture was purified directly by column chromatography (9:1 hexanes:EtOAc+2% Et$_3$N, 3 column volumes→8:2 hexanes:EtOAc+2% Et$_3$N, 4 column volumes→7:3 hexanes:EtOAc+2% Et$_3$N, 3 column volumes) to yield the crude product as a yellow oil. This material was further purified by preparative TLC (Et$_2$O+1% Et$_3$N) to provide the pure product 34i as a nearly colorless oil (27.5 mg, 41%). $^1$H NMR (500 MHz, CDCl$_3$) δ 7.24 (d, J=8.8 Hz, 1H), 6.86 (d, J=2.5 Hz, 1H), 6.80 (dd, J=8.8, 2.6 Hz, 1H), 3.85 (s, 3H), 3.42 (ddd, J=13.9, 4.6, 2.2 Hz, 1H), 3.36-3.26 (m, 2H), 3.22 (ddd, J=16.9, 12.3, 4.7 Hz, 1H), 3.10-3.02 (m, 2H), 2.85-2.81 (m, 1H), 2.49-2.42 (m, 1H), 2.07-1.93 (m, 3H), 1.90-1.85 (m, 1H), 1.61 (ddd, J=13.4, 6.7, 3.5 Hz, 1H), 1.41-1.24 (m, 6H), 1.15-1.08 (m, 1H), 0.90 (t, J=6.8 Hz, 3H); $^{13}$C NMR (126 MHz, CDCl$_3$) δ 161.7, 155.9, 148.4, 131.3, 112.3, 111.5, 111.1, 101.8, 56.8, 56.2, 53.5, 49.1, 39.9, 35.5, 34.5, 34.1, 31.9, 30.0, 26.4, 23.0, 19.0, 14.2; LR-MS calcd. for C$_{22}$H$_{30}$NO$_2^+$ [M+H]$^+$ 340.23, found 340.42.

Heteroarylazepine 34j. The crude reaction mixture was purified directly by column chromatography (80:1 hexanes:EtOAc+2% Et$_3$N) to yield the crude product as a pale-yellow oil. This material was further purified by preparative TLC (80:1 hexanes:EtOAc+2% Et$_3$N) to provide the pure product 34j as a very pale-pink oil that slowly crystallized to a white solid (22.7 mg, 73%). $^1$H NMR (400 MHz, CDCl$_3$) (spectrum complicated by F—H coupling) δ 7.26 (dd, J=8.7, 4.2 Hz, 1H), 7.04 (dd, J=8.7, 2.6 Hz, 1H), 6.90 (td, J=9.1, 2.6 Hz, 1H), 3.46-3.35 (m, 1H), 3.25-3.10 (m, 3H), 2.99-2.91 (m, 2H), 2.80 (d, J=1.6 Hz, 1H), 2.49-2.38 (m, 1H), 2.09-1.99 (m, 1H), 1.89-1.75 (m, 2H), 1.67-1.60 (m, 1H), 1.60-1.39 (m, 1H), 1.23-1.15 (m, 1H), 0.91 (t, J=7.2 Hz, 3H); $^{13}$C NMR (101 MHz, CDCl$_3$) (spectrum complicated by F—C coupling) δ 162.0, 160.4 and 158.0, 149.8, 131.8 and 131.7, 112.04 and 112.01, 111.1 and 111.0, 110.7 and 110.5, 104.6 and 104.3, 57.2, 53.2, 49.7, 41.5, 41.2, 33.0, 32.2, 27.5, 26.5, 19.4, 11.9; LR-MS calcd. for C$_{19}$H$_{23}$FNO$^+$ [M+H]$^+$ 300.18, found 300.37.

Heteroarylazepine 34k. The crude reaction mixture was purified directly by column chromatography (30:1 hexanes:EtOAc+1% Et$_3$N) to yield the crude product as a yellow oil. This material was further purified by preparative TLC (30:1 hexanes:EtOAc+1% Et$_3$N) to provide the pure product 34k as a nearly colorless oil (54.7 mg, 59%). $^1$H NMR (500 MHz, CDCl$_3$) δ 7.25 (d, J=8.5 Hz, 1H), 6.93 (d, J=2.2 Hz, 1H), 6.83 (dd, J=8.5, 2.2 Hz, 1H), 3.84 (s, 3H), 3.44-3.36 (m, 1H), 3.23-3.11 (m, 3H), 2.97 (d, J=8.9 Hz, 1H), 2.93 (dt, J=8.9, 3.2 Hz, 1H), 2.79 (d, J=1.8 Hz, 1H), 2.53-2.44 (m, 1H), 2.02 (tt, J=11.6, 2.3 Hz, 1H), 1.87-1.75 (m, 2H), 1.66-1.61 (m, 1H), 1.59-1.42 (m, 3H), 1.19 (ddt, J=12.7, 6.6, 2.3 Hz, 1H), 0.91 (t, J=7.2 Hz, 3H); $^{13}$C NMR (126 MHz, CDCl$_3$) δ 159.1, 157.5, 154.6, 124.3, 118.8, 113.3, 110.6, 95.8, 57.4, 55.9, 53.3, 49.6, 41.5, 41.0, 33.1, 32.3, 27.5, 26.6, 19.5, 11.9; LR-MS calcd. for C$_{20}$H$_{26}$NO$_2^+$ [M+H]$^+$ 312.20, found 312.57

Heteroarylazepine 34l. The crude reaction mixture was purified directly by column chromatography (20:1 hexanes:EtOAc+2% Et$_3$N) to yield the pure product 34l as a yellow oil that slowly crystallized to a pale-yellow solid (42.0 mg, 75%). $^1$H NMR (500 MHz, CDCl$_3$) (spectrum complicated by F—H coupling) δ 7.12 (d, J=10.7 Hz, 1H), 6.90 (d, J=8.2 Hz, 1H), 3.92 (s, 3H), 3.45-3.36 (m, 1H), 3.24-3.11 (m, 3H), 2.99-2.91 (m, 2H), 2.78 (d, J=1.4 Hz, 1H), 2.49-2.40 (m, 1H), 2.06-1.98 (m, 1H), 1.88-1.75 (m, 2H), 1.62 (ddd, J=13.2, 6.4, 3.1 Hz, 1H), 1.59-1.42 (m, 3H), 1.19 (ddt, J=12.7, 6.4, 2.3 Hz, 1H), 0.90 (t, J=7.2 Hz, 3H); $^{13}$C NMR (126 MHz, CDCl$_3$) (spectrum complicated by F—C coupling) δ 160.93 and 160.90, 151.7 and 149.7, 147.0 and 146.9, 144.6 and 144.5, 126.1 and 126.0, 111.57 and 111.56, 102.46 and 102.45, 99.5 and 99.3, 57.24, 57.20, 53.2, 49.7, 41.5, 41.1, 33.1, 32.3, 27.5, 26.5, 19.5, 11.9; LR-MS calcd. for C$_{20}$H$_{25}$FNO$_2^+$ [M+H]$^+$ 330.19, found 329.98.

Heteroarylazepine 34m. The crude reaction mixture was purified directly by column chromatography (20:1 hexanes:EtOAc+2% Et$_3$N) to yield the pure product 34m as a beige oil (27.1 mg, 55%). A few fractions contaminated with a co-eluting spot were further purified by preparative TLC using the same solvent system to yield additional product (9.3 mg, 19%). $^1$H NMR (400 MHz, CDCl$_3$) δ 7.28-7.21 (m, 1H), 6.87 (d, J=2.6 Hz, 1H), 6.81 (dd, J=8.8, 2.6 Hz, 1H), 3.85 (s, 3H), 3.57 (t, J=8.9 Hz, 1H), 3.42-3.38 (m, 2H), 3.37 (s, 3H), 3.31 (dd, J=9.0, 5.5 Hz, 1H), 3.24-3.14 (m, 3H), 3.00 (dt, J=11.6, 1.9 Hz, 2H), 2.96-2.89 (m, 1H), 2.55-2.44 (m, 1H), 2.13-1.96 (m, 2H), 1.88 (dq, J=4.1, 2.0 Hz, 1H), 1.79-1.62 (m, 2H), 1.18-1.08 (m, 1H); $^{13}$C NMR (101 MHz, CDCl$_3$) δ 160.7, 155.7, 148.6, 131.4, 111.7, 111.4, 110.9, 101.8, 75.2, 58.9, 56.1, 54.4, 52.9, 49.5, 40.5, 39.4, 33.2, 28.3, 26.1, 19.5; LR-MS calcd. for C$_{20}$H$_{26}$NO$_3^+$ [M+H]$^+$ 328.19, found 327.79.

Heteroarylazepine 34n. The crude reaction mixture was purified directly by column chromatography (30:1 hexanes:EtOAc+1% Et$_3$N) to yield the crude product as a nearly colorless oil. This material was further purified by repeated preparative TLC (TLC 1=30:1 hexanes:EtOAc+1% Et$_3$N; TLC 2=20:1 hexanes:EtOAc+2% Et$_3$N) to provide the pure product 34n as a nearly colorless oil (14.5 mg, 54%). $^1$H NMR (500 MHz, CDCl$_3$) δ 7.46 (d, J=7.3 Hz, 2H), 7.32 (t, J=7.6 Hz, 2H), 7.26 (d, J=8.8 Hz, 1H), 7.22 (t, J=7.3 Hz, 1H), 6.87 (d, J=2.5 Hz, 1H), 6.82 (dd, J=8.8, 2.5 Hz, 1H), 3.85 (s, 3H), 3.44-3.36 (m, 2H), 3.26-3.16 (m, 1H), 3.15-3.07 (m, 4H), 2.92 (dd, J=10.2, 8.1 Hz, 1H), 2.55-2.48 (m, 1H), 2.21-2.08 (m, 2H), 2.02 (d, J=1.7 Hz, 1H), 1.84-1.74 (m, 2H); $^{13}$C NMR (126 MHz, CDCl$_3$) δ 160.2, 155.8, 148.7, 146.8, 131.4, 128.2, 128.0, 126.1, 111.8, 111.6, 111.0, 102.0, 58.8, 56.2, 52.6, 49.6, 45.1, 41.5, 33.8, 32.6, 26.7, 19.7; LR-MS calcd. for $C_{24}H_{26}NO_2^+$ [M+H]$^+$ 360.20, found 359.58.

Heteroarylazepine 34o. The crude reaction mixture was purified directly by column chromatography (7:3 hexanes:EtOAc+2% Et$_3$N, 4 column volumes→1:1 hexanes:EtOAc+2% Et$_3$N, 5 column volumes) to yield the crude product 34o as a yellow oil (11.9 mg, <10%) that was used in the next step without further purification. LR-MS calcd. for $C_{24}H_{26}NO_2^+$ [M+H]$^+$ 360.20, found 359.87.

Heteroarylazepine 34p. The crude reaction mixture was purified directly by column chromatography (1:1 CH$_2$Cl$_2$:Et$_2$O, 4 column volumes→1:1 CH$_2$Cl$_2$:Et$_2$O+2% Et$_3$N, 3 column volumes) to yield the pure produce 34p as a pale reddish-brown glass (9.3 mg, 48%). $^1$H NMR (500 mz, CDCl$_3$) δ 7.53 (d, J=8.7 Hz, 1H), 6.84 (dd, J=8.7, 2.3 Hz, 1H), 6.74 (d, J=2.1 Hz, 1H), 4.59-4.50 (m, 1H), 3.93 (d, J=14.8 Hz, 1H), 3.86 (s, 3H), 3.41-3.33 (m, 1H), 3.33-3.18 (m, 2H), 3.13 (d, J=10.9 Hz, 1H), 3.04 (dt, J=10.7, 2.7 Hz, 1H), 2.89 (d, J=2.4 Hz, 1H), 2.23-2.14 (m, 1H), 1.94 (s, 1H), 1.91-1.82 (m, 1H), 1.80-1.69 (m, 2H), 1.60-1.50 (m, 1H), 1.47-1.36 (m, 1H), 1.27-1.20 (m, 1H), 0.87 (t, J=7.4 Hz, 3H); $^{13}$C NMR (126 MHz, CDCl$_3$) δ 158.8, 156.4, 137.2, 136.8, 119.7, 110.5, 93.2, 56.1, 55.1, 54.7, 51.0, 42.2, 41.9, 40.6, 31.5, 30.8, 28.9, 26.5, 12.1. HRMS (FAB+) m/z: [M+H]$^+$ Calcd for $C_{19}H_{26}N_3O^+$ 312.2070; found 312.2048.

EXAMPLE 11

Synthesis of Heteroarylazepines by Pd(II) Mediated Cyclization

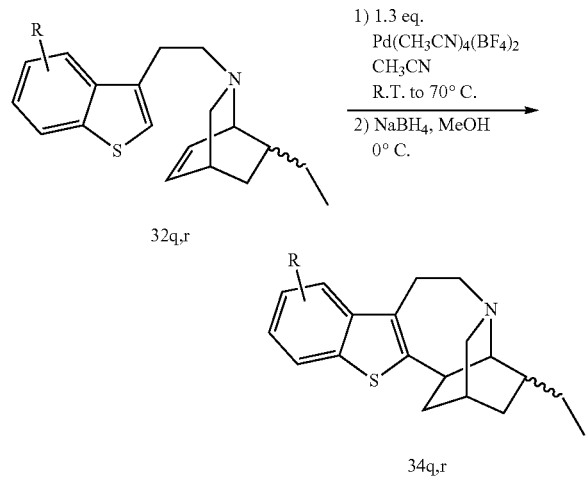

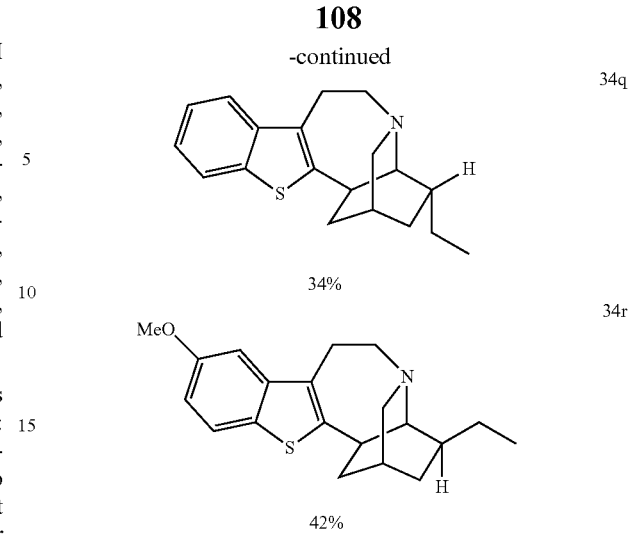

General Procedure for Preparation of Heteroarylazepines by Pd(II) Mediated Cyclization (34q-r). In a glovebox, a Schlenk flask was charged with Pd(CH$_3$CN)$_4$(BF$_4$)$_2$ (1.3 equivalents). It was then sealed and removed from the glovebox and anhydrous CH$_3$CN (0.0929 M, based on Pd(CH$_3$CN)$_4$(BF$_4$)$_2$) was added to form a yellow solution. To this solution was added a solution of the substrate 32 (1 equivalent) in anhydrous CH$_3$CN (0.0278 M based on 32) resulting in a color change (yellow to orange). The reaction mixture was stirred for 2 h at room temperature and then warmed to 70° C. and stirred for a further 16 h. At this time, the reaction was cooled to 0° C., and anhydrous MeOH (0.111 M, based on 32) was added followed by NaBH$_4$ (3.2 equivalents), causing the immediate precipitation of palladium black. The resulting black mixture was stirred for 20 min. at 0° C., then diluted with Et$_2$O, filtered through celite, and the filter cake washed with additional Et$_2$O (4×). The combined filtrate and washings were concentrated to afford the crude product. This material was purified by column chromatography or preparative TLC with an appropriate solvent mixture (as described below for each compound).

Heteroarylazepine 34q. The product 34q was purified by column chromatography (9:1 hexanes:EtOAc+2% Et$_3$N, 4 column volumes→8:2 hexanes:EtOAc+2% Et$_3$N, 2 column volumes) and obtained as a pale-yellow oil (6.0 mg, 34%). $^1$H NMR (500 MHz, CDCl$_3$) δ 7.74 (d, J=7.9 Hz, 1H), 7.62 (d, J=8.1 Hz, 1H), 7.35 (t, J=7.6 Hz, 1H), 7.26 (t, J=7.6 Hz, 1H), 3.46-3.30 (m, 3H), 3.28-3.18 (m, 1H), 3.18-3.09 (m, 2H), 2.92 (s, 1H), 2.82 (d, J=14.7 Hz, 1H), 2.13 (t, J=12.5 Hz, 1H), 2.02-1.90 (m, 3H), 1.75 (dd, J=13.4, 6.6 Hz, 1H), 1.46-1.36 (m, 2H), 1.11-1.00 (m, 1H), 0.94 (t, J=7.4 Hz, 3H); $^{13}$C NMR (126 MHz, CDCl$_3$) δ 145.3, 141.6, 138.2, 131.0, 124.0, 123.5, 122.2, 120.9, 57.7, 54.6, 50.7, 42.2, 35.6, 35.2, 31.6, 28.0, 26.5, 23.5, 12.2; HRMS (FAB+) m/z: [M+H]$^+$ Calcd for $C_{19}H_{24}NS^+$ 298.1624; found 298.1620.

Heteroarylazepine 34r. The product 34r was purified by preparative TLC (20:1 hexanes:EtOAc+2% Et$_3$N) and obtained as a colorless oil that slowly crystallized to a white solid (41.7 mg, 42%). $^1$H NMR (500 MHz, CDCl$_3$) δ 7.59 (d, J=8.7 Hz, 1H), 7.07 (d, J=2.4 Hz, 1H), 6.91 (dd, J=8.7, 2.4 Hz, 1H), 3.87 (s, 3H), 3.41 (ddd, J=16.3, 12.6, 3.8 Hz, 1H), 3.32 (dt, J=14.5, 3.3 Hz, 1H), 3.22-3.13 (m, 1H), 3.10 (dt, J=9.8, 2.4 Hz, 1H), 3.04 (dt, J=9.9, 2.5 Hz, 1H), 2.97-2.92 (m, 1H), 2.91 (s, 1H), 2.71 (dt, J=16.3, 2.8 Hz, 1H), 2.14 (tt, J=11.9, 3.0 Hz, 1H), 1.89 (dt, J=5.4, 2.7 Hz, 1H), 1.80 (ddt, J=13.1, 10.5, 2.6 Hz, 1H), 1.73 (ddt, J=13.3, 5.6, 2.7 Hz, 1H), 1.65-1.50 (m, 3H), 1.48-1.38 (m, 1H), 1.20 (ddd, J=13.1, 7.1, 3.0 Hz, 1H), 0.90 (t, J=7.3 Hz, 3H); $^{13}$C N (126 MHz, CDCl$_3$) δ 157.6, 147.3, 143.0, 130.6, 129.8, 122.8, 113.0, 104.0, 57.4, 55.7, 54.2, 50.8, 42.6, 42.2, 35.2, 31.8, 28.6, 26.9, 24.1, 12.2; LR-MS calcd. for C$_{20}$H$_{26}$NOS$^+$ [M+H]$^+$ 328.17, found 328.50.
EXAMPLE 12
Synthesis of Hydroxyheteroarylazepines by Demethylation
Scheme 13. Demethylation
A/
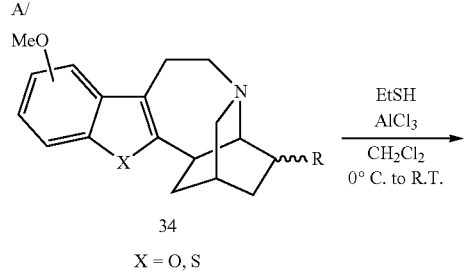
34
X = O, S
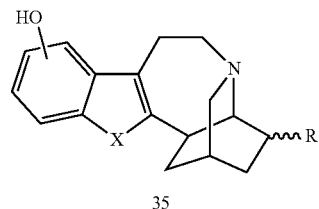
35
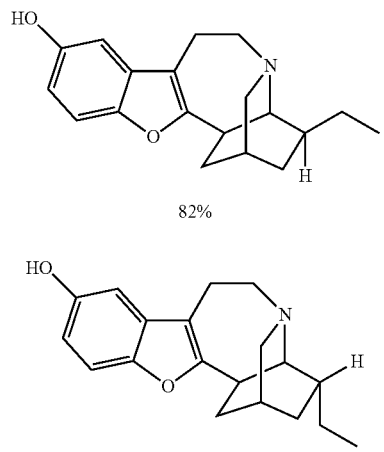
35a
82%
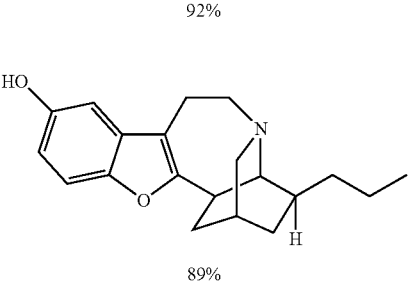
35b
92%
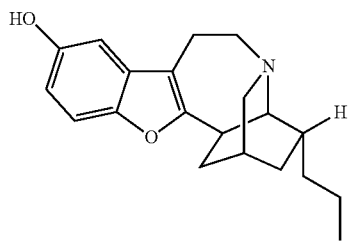
35c
89%
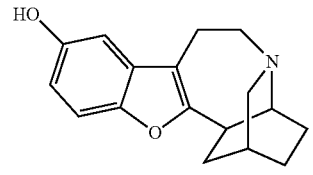
35d
78%
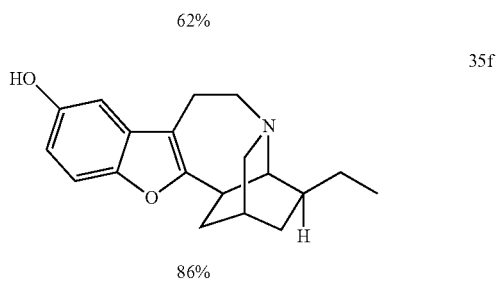
35e
62%
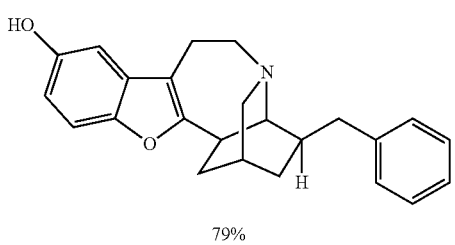
35f
86%
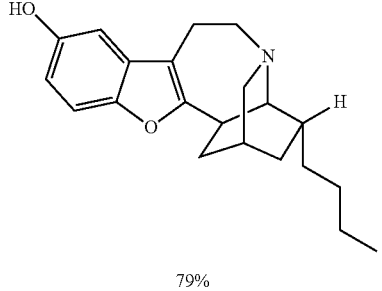
35g
79%
35h
79%
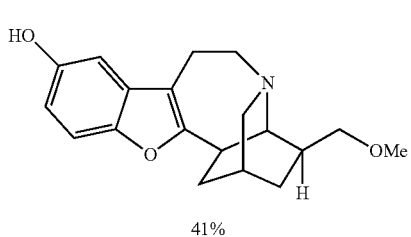
35i
41%

General Procedure for Preparation of Hydroxyheteroarylazepines by Demethylation (35a-o). To a solution of the methoxyheteroarylazepine 34 (1 equivalent) in dry dichloromethane (0.125 M, based on 34) at 0° C. was added aluminum chloride (6 equivalents) followed by ethanethiol (18 equivalents), and the resulting mixture was allowed to warm to room temperature and stirred until TLC indicated the complete consumption of starting material (typically <1.5 h). The reaction was then quenched with saturated aqueous $NaHCO_2$ (100 mL per mmol of 34) and extracted with $CH_2Cl_2$ (4×-6×, until no further extraction by TLC). The combined organic layers were dried over $Na_2SO_4$ and concentrated to provide the crude product. This material was purified by column chromatography with an appropriate solvent mixture as described below for each substrate.

Hydroxyheteroarylazepine 35a. The product 35a was purified by column chromatography (1:1 hexanes:EtOAc) and obtained as a white foamy solid (24.3 mg, 82%). $^1$H NMR (500 MHz, $CDCl_3$) δ 7.19 (d, J=8.6 Hz, 1H), 6.80 (d, J=2.5 Hz, 1H), 6.70 (dd, J=8.6, 2.5 Hz, 1H), 4.71 (br s, 1H), 3.44-3.34 (m, 1H), 3.20-3.10 (m, 3H), 2.99-2.91 (m, 2H), 2.81 (s, 1H), 2.48-2.37 (m, 1H), 2.08-2.00 (m, 1H), 1.88-1.77 (m, 2H), 1.64 (ddd, J=13.2, 6.3, 3.1 Hz, 1H), 1.59-1.43 (m, 3H), 1.21 (ddd, J=10.5, 4.8, 2.2 Hz, 1H), 0.91 (t, J=7.1 Hz, 3H); $^{13}$C NMR (126 MHz, $CDCl_3$) δ 161.1, 151.4, 148.6, 131.8, 111.64, 111.55, 110.9, 104.2, 57.3, 53.3, 49.6, 41.6, 41.1, 33.0, 32.2, 27.5, 26.4, 19.4, 12.0; LR-MS calcd. for $C_{19}H_{24}NO_2^+$ $[M+H]^+$ 298.18, found 298.51.

Hydroxyheteroarylazepine 35b. The product 35b was purified by column chromatography (20:1 $CH_2Cl_2$:MeOH, 4 column volumes→20:1 acetone:MeOH, 4 column volumes) and obtained as a white foamy solid (13.7 mg, 92%). $^1$H NMR (500 MHz, $CDCl_3$) δ 7.19 (d, J=8.7 Hz, 1H), 6.79 (d, J=2.4 Hz, 1H), 6.71 (dd, J=8.7, 2.5 Hz, 1H), 5.62 (br s, 1H), 3.40 (ddd, J=14.2, 4.6, 2.4 Hz, 1H), 3.34-3.26 (m, 2H), 3.20-3.08 (m, 2H), 3.02 (d, J=9.8 Hz, 1H), 2.91 (s, 1H), 2.43 (dt, J=16.6, 2.9 Hz, 1H), 2.08-1.95 (m, 3H), 1.90 (s, 1H), 1.65-1.58 (m, 1H), 1.44-1.33 (m, 2H), 1.15-1.09 (m, 1H), 0.92 (t, J=7.3 Hz, 3H); $^{13}$C NMR (126 MHz, $CDCl_3$) δ 161.5, 152.1, 148.2, 131.4, 112.11, 112.07, 111.0, 104.2, 56.5, 53.6, 49.0, 41.2, 34.0, 33.9, 31.4, 28.4, 26.1, 18.8, 12.3; LR-MS calcd. for $C_{19}H_{24}NO_2^+$ $[M+H]^+$ 298.18, found 298.56.

Hydroxyheteroarylazepine 35c. The product 35c was purified by column chromatography (7:3 hexanes:EtOAc) and obtained as a very pale-pink foamy solid (27.8 mg, 89%). $^1$H NMR (500 MHz, $CDCl_3$) δ 7.19 (d, J=8.6 Hz, 1H), 6.80 (d, J=2.5 Hz, 1H), 6.70 (dd, J=8.6, 2.6 Hz, 1H), 4.63 (br s, 1H), 3.45-3.34 (m, 1H), 3.20-3.10 (m, 3H), 2.99-2.91 (m, 2H), 2.77 (s, 1H), 2.48-2.37 (m, 1H), 2.03 (dd, J=13.3, 11.9 Hz, 1H), 1.85 (s, 1H), 1.83-1.75 (m, 1H), 1.69-1.60 (m, 2H), 1.55-1.38 (m, 2H), 1.37-1.28 (m, 2H), 1.24-1.17 (m, 1H), 0.91 (t, J=7.3 Hz, 3H); $^{13}$C NMR (126 MHz, $CDCl_3$) δ 161.1, 151.4, 148.6, 131.8, 111.58, 111.53, 110.9, 104.2, 57.8, 53.3, 49.6, 41.1, 39.3, 37.1, 32.9, 32.3, 26.4, 20.4, 19.4, 14.5; LR-MS calcd. for $C_{20}H_{26}NO_2^+$ [M+H]$^+$ 312.20, found 312.56.

Hydroxyheteroarylazepine 35d. The product 35d was purified by column chromatography (20:1 CH$_2$Cl$_2$:MeOH, 4 column volumes→20:1 acetone:MeOH, 4 column volumes) and obtained as a white foamy solid (24.3 mg, 78%). $^1$H NMR (500 MHz, CDCl$_3$) δ 7.19 (d, J=8.7 Hz, 1H), 6.79 (d, J=2.5 Hz, 1H), 6.71 (dd, J=8.7, 2.5 Hz, 1H), 5.44 (br s, 1H), 3.39 (ddd, J=14.1, 4.6, 2.5 Hz, 1H), 3.34-3.26 (m, 2H), 3.20-3.07 (m, 2H), 3.02 (d, J=9.8 Hz, 1H), 2.88 (dd, J=2.7, 1.9 Hz, 1H), 2.43 (dt, J=16.6, 3.0 Hz, 1H), 2.18-2.11 (m, 1H), 2.09-2.02 (m, 1H), 1.99 (ddd, J=13.6, 5.7, 2.9 Hz, 1H), 1.92-1.87 (m, 1H), 1.62 (ddd, J=13.2, 6.7, 3.3 Hz, 1H), 1.40-1.25 (m, 4H), 1.16-1.08 (m, 1H), 0.94-0.87 (m, 3H); $^{13}$C NMR (126 MHz, CDCl$_3$) δ 161.5, 152.2, 148.2, 131.4, 112.2, 112.1, 111.0, 104.3, 56.8, 53.7, 49.0, 39.0, 37.9, 34.0, 34.0, 31.7, 26.2, 20.8, 18.8, 14.4; LR-MS calcd. for $C_{20}H_{26}NO_2^+$ [M+H]$^+$ 312.20, found 312.59.

Hydroxyheteroarylazepine 35e. The poorly soluble crude product was triturated with a small quantity of MeOH and the supernatant carefully removed by pipet. This washing procedure was repeated once more and the resulting solids were dried in vacuo to provide the pure product 35e as a white solid (16.7 mg, 62%). $^1$H NMR (500 MHz, CDCl$_3$+ several drops MeOD) δ 7.05 (d, J=8.7 Hz, 1H), 6.69 (d, J=2.2 Hz, 1H), 6.61 (dd, J=8.7, 2.4 Hz, 1H), 3.82 (br s, 2H), 3.28-3.19 (m, 1H), 3.14-2.98 (m, 3H), 2.96-2.86 (m, 3H), 2.38 (d, J=16.6 Hz, 1H), 2.07-1.88 (m, 2H), 1.78 (s, 1H), 1.69-1.51 (m, 4H); $^{13}$C NMR (126 MHz, CDCl$_3$+several drops MeOD) δ 160.2, 152.3, 147.9, 131.1, 111.7, 111.3, 110.6, 103.6, 53.1, 52.9, 49.1, 39.1, 33.2, 28.4, 25.0, 23.3, 18.4; LR-MS calcd. for $C_{17}H_{20}NO_2^+$ [M+H]$^+$ 270.15, found 270.51.

Hydroxyheteroarylazepine 35f. The product 35f was purified by column chromatography (1:1 hexanes:EtOAc) and obtained as a pale-gray solid (25.7 mg, 86%). $^1$H NMR (400 MHz, CDCl$_3$) δ 7.20 (d, J=8.3 Hz, 1H), 6.86 (d, J=2.1 Hz, 1H), 6.73 (dd, J=8.3, 2.2 Hz, 1H), 4.84 (br s, 1H), 3.46-3.34 (m, 1H), 3.22-3.10 (m, 3H), 2.99-2.90 (m, 2H), 2.81 (d, J=2.0 Hz, 1H), 2.55-2.41 (m, 1H), 2.02 (t, J=12.3 Hz, 1H), 1.90-1.76 (m, 2H), 1.63 (ddd, J=13.2, 6.3, 2.9 Hz, 1H), 1.59-1.43 (m, 3H), 1.25-1.17 (m, 1H), 0.90 (t, J=7.1 Hz, 3H); $^{13}$C NMR (101 MHz, CDCl$_3$) δ 158.8, 154.5, 153.3, 124.3, 118.9, 111.3, 111.1, 98.1, 57.6, 53.3, 49.4, 41.5, 40.9, 33.0, 32.1, 27.3, 26.4, 19.4, 12.0; LR-MS calcd. for $C_{19}H_{24}NO_2^+$ [M+H]$^+$ 298.18, found 298.59.

Hydroxyheteroarylazepine 35g. The product 35g was purified by column chromatography (7:3 hexanes:EtOAc) and obtained as a white foamy solid (14.2 mg, 79%). $^1$H NMR (400 MHz, CDCl$_3$) δ 7.29-7.24 (m, 2H), 7.22-7.14 (m, 4H), 6.78 (d, J=2.5 Hz, 1H), 6.68 (dd, J=8.6, 2.6 Hz, 1H), 4.83 (br s, 1H), 3.52-3.38 (m, 1H), 3.23-3.10 (m, 2H), 3.07-2.98 (m, 3H), 2.86 (dd, J=13.3, 9.1 Hz, 1H), 2.78-2.67 (m, 2H), 2.48-2.35 (m, 1H), 2.06-1.92 (m, 2H), 1.88 (s, 1H), 1.86-1.77 (m, 1H), 1.63 (ddd, J=13.2, 6.4, 3.2 Hz, 1H), 1.36-1.28 (m, 1H); $^{13}$C NMR (101 MHz, CDCl$_3$) δ 161.0, 151.3, 148.5, 141.6, 131.7, 129.3, 128.3, 125.8, 111.6, 111.5, 110.9, 104.1, 55.7, 53.0, 49.7, 41.5, 40.8, 40.6, 33.0, 32.4, 26.5, 19.4; LR-MS calcd. for $C_{24}H_{26}NO_2^+$ [M+H]$^+$ 360.20, found 360.69.

Hydroxyheteroarylazepine 35h. The product 35h was purified by column chromatography (20:1 CH$_2$Cl$_2$:MeOH, 4 column volumes→20:1 acetone:MeOH, 6 column volumes) and obtained as a white foamy solid (15.4 mg, 79%). $^1$H NMR (400 MHz, CDCl$_3$) δ 7.19 (d, J=8.7 Hz, 1H), 6.80 (d, J=2.5 Hz, 1H), 6.72 (dd, J=8.7, 2.5 Hz, 1H), 5.73 (br s, 1H), 3.41 (ddd, J=14.1, 4.8, 2.7 Hz, 1H), 3.37-3.27 (m, 2H), 3.21-3.09 (m, 2H), 3.02 (d, J=9.9 Hz, 1H), 2.91 (s, 1H), 2.46 (dt, J=16.6, 2.9 Hz, 1H), 2.20-2.10 (m, 1H), 2.10-1.95 (m, 2H), 1.91 (s, 1H), 1.62 (ddd, J=13.1, 6.6, 3.3 Hz, 1H), 1.42-1.21 (m, 6H), 1.17-1.09 (m, 1H), 0.88 (t, J=6.7 Hz, 3H); $^{13}$C NMR (101 MHz, CDCl$_3$) δ 161.3, 152.1, 148.2, 131.4, 112.2, 112.1, 111.0, 104.2, 56.9, 53.8, 49.1, 39.0, 35.3, 33.9, 33.7, 31.6, 29.9, 26.1, 23.0, 18.8, 14.2; LR-MS calcd. for $C_{21}H_{28}NO_2^+$ [M+H]$^+$ 326.21, found 326.34.

Hydroxyheteroarylazepines 35i and 35j. The crude product was purified by column chromatography (1:2 hexanes: EtOAc) to give both the ether (35i) and alcohol (35j) analogs.

35i. Ether 35i was prepared and separated as described above and obtained as a beige oil (10.3 mg, 41%). $^1$H NMR (400 MHz, CDCl$_3$) δ 7.17 (d, J=8.6 Hz, 1H), 6.76 (d, J=2.5 Hz, 1H), 6.71 (dd, J=8.6, 2.6 Hz, 1H), 4.00 (br s, 1H), 3.61 (t, J=9.2 Hz, 1H), 3.39 (s, 3H), 3.38-3.28 (m, 2H), 3.16-3.07 (m, 2H), 3.04 (dd, J=11.4, 2.8 Hz, 1H), 2.99 (t, J=1.7 Hz, 1H), 2.92 (d, J=2.1 Hz, 2H), 2.43-2.35 (m, 1H), 2.03-1.96 (m, 2H), 1.85 (dp, J=4.2, 2.2 Hz, 1H), 1.71 (ddd, J=14.1, 10.4, 4.1 Hz, 1H), 1.62 (dq, J=10.2, 3.3 Hz, 1H), 1.15-1.07 (m, 1H); $^{13}$C NMR (101 MHz, CDCl$_3$) δ 160.4, 151.6, 148.5, 131.5, 111.8, 111.2, 110.9, 104.2, 75.0, 58.9, 54.4, 53.0, 49.4, 40.1, 39.3, 32.9, 28.0, 25.9, 19.4; LR-MS calcd. for $C_{19}H_{24}NO_3^+$ [M+H]$^+$ 314.18, found 314.47.

35j. Alcohol 35j was prepared and separated as described above and obtained as a white solid (3.2 mg, 13%). $^1$H NMR (500 MHz, Methanol-d4) δ 7.12 (d, J=8.6 Hz, 1H), 6.77 (d, J=2.5 Hz, 1H), 6.67 (dd, J=8.7, 2.5 Hz, 1H), 3.69 (d, J=5.4 Hz, 2H), 3.39-3.34 (m, 1H), 3.22 (d, J=3.5 Hz, 1H), 3.19 (s, 1H), 3.17 (d, J=2.8 Hz, 1H), 3.13 (t, J=1.9 Hz, 1H), 3.09-3.05 (m, 1H), 2.95 (d, J=9.4 Hz, 1H), 2.54-2.49 (m, 1H), 2.15-2.07 (m, 1H), 1.95-1.88 (m, 2H), 1.80 (ddd, J=12.9, 4.1, 2.1 Hz, 1H), 1.69-1.62 (m, 1H), 1.41 (ddt, J=12.9, 6.8, 2.4 Hz, 1H), 1.29 (s, 1H); $^{13}$C NMR (126 MHz, Methanol-d4) δ 161.2, 153.9, 149.5, 132.6, 112.8, 112.3, 111.4, 104.6, 66.3, 57.2, 53.7, 50.2, 41.25, 41.22, 33.9, 28.4, 27.4, 19.9; LR-MS calcd. for $C_{18}H_{22}NO_3^+$ [M+H]$^+$ 300.16, found 300.44.

Hydroxyheteroarylazepine 35k. The product 35k was purified by column chromatography (7:3 hexanes:EtOAc, 2 column volumes→1:1 hexanes:EtOAc, 4 column volumes) and obtained as a white foamy solid (19.6 mg, 62%). $^1$H NMR (500 MHz, CDCl$_3$) (spectrum complicated by F—H coupling) δ 7.11 (d, J=10.2 Hz, 1H), 6.94 (d, J=8.6 Hz, 1H), 4.24 (br s, 1H), 3.44-3.33 (m, 1H), 3.21-3.09 (m, 3H), 2.98-2.91 (m, 2H), 2.79 (d, J=1.5 Hz, 1H), 2.46-2.37 (m, 1H), 2.02 (t, J=12.4 Hz, 1H), 1.85 (s, 1H), 1.79 (ddd, J=8.1, 6.8, 3.5 Hz, 1H), 1.62 (ddd, J=13.2, 6.4, 3.1 Hz, 1H), 1.58-1.41 (m, 3H), 1.19 (ddt, J=12.7, 6.4, 2.2 Hz, 1H), 0.90 (t, J=7.2 Hz, 3H); $^{13}$C NMR (126 MHz, CDCl$_3$) (spectrum complicated by F—C coupling) δ 161.13 and 161.09, 150.1 and 148.2, 146.8 and 146.7, 140.10 and 140.0, 126.9, 111.4, 105.20 and 105.19, 98.5 and 98.3, 57.3, 53.2, 49.6, 41.5, 41.1, 33.0, 32.2, 27.4, 26.5, 19.4, 11.9; LR-MS calcd. for $C_{19}H_{23}FNO_2^+$ [M+H]$^+$ 316.17, found 315.99.

Hydroxyheteroarylazepine 35l. The product 35l was purified by column chromatography (8:2 hexanes:EtOAc, 2 column volumes→7:3 hexanes:EtOAc, 4 column volumes) and obtained as a white foamy solid (7.8 mg, 68%). $^1$H NMR (400 MHz, CDCl$_3$) δ 7.45 (d, J=7.3 Hz, 2H), 7.31 (t, J=7.5 Hz, 2H), 7.24-7.19 (m, 2H), 6.80 (d, J=2.5 Hz, 1H), 6.71 (dd, J=8.6, 2.6 Hz, 1H), 4.61 (br s, 1H), 3.43-3.34 (m, 2H), 3.23-3.04 (m, 5H), 2.95-2.88 (m, 1H), 2.49-2.41 (m, 1H), 2.20-2.07 (m, 2H), 2.04-1.99 (m, 1H), 1.84-1.73 (m, 2H); $^{13}$C NMR (101 MHz, CDCl$_3$) δ 160.4, 151.3, 148.8, 146.7, 131.8, 128.2, 127.9, 126.1, 111.7, 110.9, 104.2, 58.8, 52.6, 49.6, 45.1, 41.5, 33.7, 32.5, 26.7, 19.6; LR-MS calcd. for $C_{23}H_{24}NO_2^+$ [M+H]$^+$ 346.18, found 345.81.

Hydroxyheteroarylazepine 35m. The product 35m was purified by column chromatography (20:1 acetone:MeOH) and obtained as an off-white foamy solid (2.0 mg, <50%, 2% over 2 steps from 32p). $^1$H NMR (500 MHz, CDCl$_3$) δ 7.38-7.33 (m, 4H), 7.25-7.20 (m, 1H), 7.11 (d, J=8.7 Hz, 1H), 6.79 (d, J=2.5 Hz, 1H), 6.67 (dd, J=8.7, 2.5 Hz, 1H), 3.59 (br s, 1H), 3.48 (ddd, J=14.3, 4.8, 2.5 Hz, 1H), 3.44-3.35 (m, 1H), 3.27-3.06 (m, 5H), 2.45 (d, J=16.6 Hz, 1H), 2.28-2.14 (m, 2H), 2.12 (s, 1H), 2.08-2.02 (m, 1H), 1.69 (ddd, J=13.5, 7.3, 3.2 Hz, 1H); LR-MS calcd. for $C_{23}H_{24}NO_2^+$ [M+H]$^+$ 346.18, found 345.60.

Hydroxyheteroarylazepine 35n. The product 35n was purified by column chromatography (7:3 hexanes:EtOAc, 2 column volumes→1:1 hexanes:EtOAc, 4 column volumes→EtOAc, 4 column volumes) and obtained as a white foamy solid (18.3 mg, 58%). $^1$H NMR (500 MHz, CDCl$_3$) δ 7.55 (d, J=8.5 Hz, 1H), 7.02 (d, J=2.3 Hz, 1H), 6.82 (dd, J=8.5, 2.4 Hz, 1H), 4.81 (br s, 1H), 3.38-3.25 (m, 2H), 3.15 (dd, J=19.1, 7.8 Hz, 1H), 3.10-3.03 (m, 2H), 2.98-2.92 (m, 2H), 2.67-2.59 (m, 1H), 2.18-2.10 (m, 1H), 1.93-1.88 (m, 1H), 1.81 (dd, J=12.8, 10.6 Hz, 1H), 1.72 (ddt, J=11.2, 5.5, 2.6 Hz, 1H), 1.65-1.52 (m, 2H), 1.51-1.40 (m, 1H), 1.24-1.18 (m, 1H), 0.90 (t, J=7.2 Hz, 3H); $^{13}$C NMR (126 MHz, CDCl$_3$) δ 153.5, 147.3, 143.2, 130.4, 129.4, 122.9, 113.3, 106.7, 57.6, 54.2, 50.8, 42.5, 42.3, 35.1, 31.7, 28.5, 26.7, 23.9, 12.2; LR-MS calcd. for $C_{19}H_{24}NOS^+$ [M+H]$^+$ 314.16, found 314.43.

Hydroxyheteroarylazepine 35o. The product 35o was purified by column chromatography (EtOAc, 2 column volumes→9:1 EtOAc:acetone, 2 column volumes→8:2 EtOAc:acetone, 2 column volumes) and obtained as a white foamy solid (4.8 mg, 64%). $^1$H NMR (400 MHz, CDCl$_3$) δ 7.41 (dd, J=8.0, 1.1 Hz, 1H), 6.81-6.76 (m, 2H), 4.50 (ddd, J=14.0, 11.1, 2.5 Hz, 1H), 3.85 (dd, J=12.7, 2.1 Hz, 1H), 3.38 (dd, J=11.9, 7.5 Hz, 1H), 3.30-3.15 (m, 2H), 3.11 (d, J=11.0 Hz, 1H), 3.01 (d, J=10.7 Hz, 1H), 2.86 (d, J=2.5 Hz, 1H), 2.21-2.11 (m, 1H), 1.92 (s, 1H), 1.87-1.65 (m, 3H), 1.60-1.46 (m, 1H), 1.45-1.33 (m, 1H), 1.24-1.17 (m, 1H), 0.85 (t, J=7.3 Hz, 3H); $^{13}$C NMR (101 MHz, CDCl$_3$) δ 158.4, 153.7, 137.3, 135.3, 119.2, 111.8, 95.5, 55.0, 54.7, 51.0, 41.8, 40.7, 31.4, 30.7, 28.9, 26.5, 12.1; LR-MS calcd. for $C_{13}H_{24}N_3O^+$ [M+H]$^+$ 298.19, found 298.01.

EXAMPLE 13

Opioid Receptor Activity

DNA Transfection. Human KOR, MOR, or DOR cDNA was transfected alongside Gα$_{oB}$ with RLuc8 inserted at position 91 (Gα$_{oB}$-RLuc8), Gβ$_1$ (β$_1$), and Gγ$_2$ fused to the full-length mVenus at its N terminus (mVenus-γ2) into HEK-293T cells (5×10$^6$ cells/plate) in 10-cm dishes using PEI (Polysciences Inc.; Warrington, Pa.) in a 1:1 ratio diluted in Opti-MEM (Life Technologies Corp.; Grand Island, N.Y.) to assay for G protein activation as described previously (Rives, M.-L. et al. 2012; Negri, A. et al. 2013). Cells were maintained in the Dulbecco's Modified Eagle Medium (high glucose #11965; Life Technologies) supplemented with 10% FBS (Premium Select, Atlanta Biologicals; Atlanta, Ga.) and 100 U/mL penicillin and 100 μg/mL streptomycin (#15140, Life Technologies). After 24 hours the media was changed, and the experiment was performed 24 hours later (48 hours after transfection).

BRET Functional Assays. Transfected cells were dissociated and resuspended in phosphate-buffered saline (PBS). Approximately 200,000 cells/well were added to a black-framed, white well 96-well plate (#60050; Perkin Elmer; Waltham, Mass.). The microplate was centrifuged and the cells were resuspended in PBS. Then 5 μM of the luciferase substrate coelenterazine H was added to each well for 5 minutes. Following coelenterazine H addition, ligands were added and the BRET signal was measured at 5 minutes on a PHERAstar FS plate reader. Quantification of the BRET signal required calculating the ratio of the light emitted by the energy acceptor, mVenus (510-540 nm), over the light emitted by the energy donor, RLuc8 (485 nm). This drug-induced BRET signal was normalized using the E$_{max}$ of U-50,488 (KOR), DAMGO (MOR), or DPDPE (DOR) as the 100% maximal response for G protein activation. Dose response curves were fit using three-parameter logistics equation in GraphPad Prism 6.

The following compounds activated human KOR, DOR and/or MOR. Accordingly, the compounds listed in Table 3 are agonists of KOR, DOR and/or MOR.

TABLE 3

EC$_{50}$ at indicated opioid receptor.

| Compound | Structure | Human KOR | Human MOR | Human DOR |
|---|---|---|---|---|
| 34a | 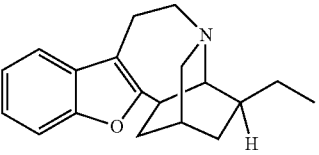 [SMILES: CCC1CC2CC3c4oc5ccccc5c4CCN(C2)C13] | >10 μM | — | — |
| 34b | 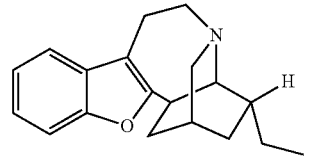 [SMILES: CCC1CC2CC3c4oc5ccccc5c4CCN(C2)C13] | >10 μM | — | — |

TABLE 3-continued

| Compound | Structure | Human KOR | Human MOR | Human DOR |
|---|---|---|---|---|
| 34c | 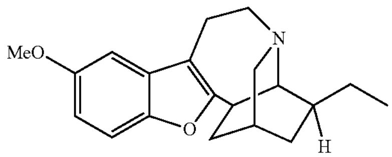 [SMILES: CCC1CC2CC3c4oc5ccc(OC)cc5c4CCN(C2)C13] | >10 μM | >10 μM | — |
| 34d | 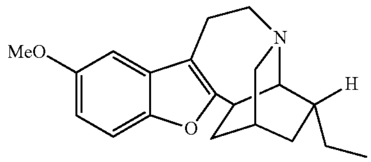 [SMILES: CCC1CC2CC3c4oc5ccc(OC)cc5c4CCN(C2)C13] | >10 μM | — | — |
| 34e | 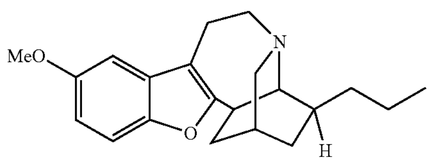 [SMILES: CCCC1CC2CC3c4oc5ccc(OC)cc5c4CCN(C2)C13] | — | >10 μM | — |
| 34f | 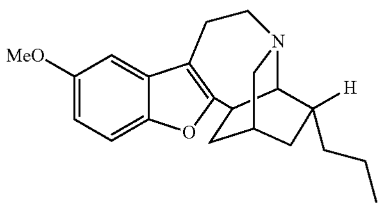 [SMILES: CCCC1CC2CC3c4oc5ccc(OC)cc5c4CCN(C2)C13] | >10 μM | — | — |
| 34h | 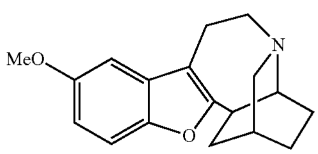 [SMILES: COc1ccc2oc3c(c2c1)CCN1CC2CCC1C3C2] | >10 μM | — | — |
| 34i | 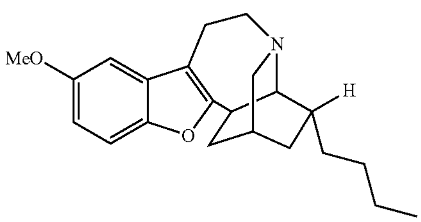 [SMILES: CCCCC1CC2CC3c4oc5ccc(OC)cc5c4CCN(C2)C13] | >10 μM | >10 μM | — |
| 34j | 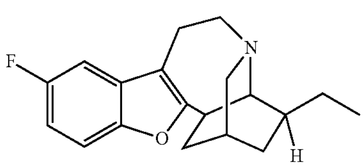 [SMILES: CCC1CC2CC3c4oc5ccc(F)cc5c4CCN(C2)C13] | >10 μM | >10 μM | — |
| 34k | 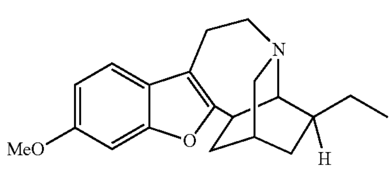 [SMILES: CCC1CC2CC3c4oc5cc(OC)ccc5c4CCN(C2)C13] | <10 μM | <10 μM | >10 μM |

TABLE 3-continued

EC$_{50}$ at indicated opioid receptor.

| Compound | Structure | Human KOR | Human MOR | Human DOR |
|---|---|---|---|---|
| 34l | 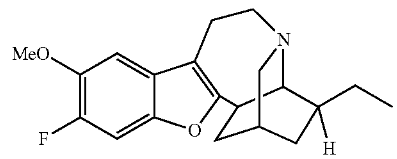 [SMILES: CCC1CC2CC3c4oc5cc(F)c(OC)cc5c4CCN(C2)C13] | >10 μM | — | — |
| 34m | 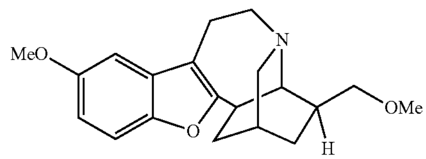 [SMILES: COCC1CC2CC3c4oc5ccc(OC)cc5c4CCN(C2)C13] | >10 μM | >10 μM | >10 μM |
| 34n | 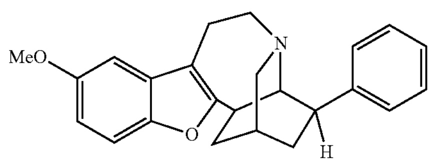 [SMILES: COc1ccc2oc3c(c2c1)CCN1CC2CC(c4ccccc4)C1C3C2] | >10 μM | — | — |
| 34q | 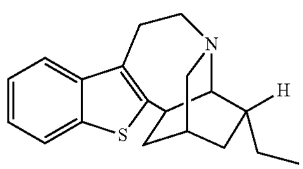 [SMILES: CCC1CC2CC3c4sc5ccccc5c4CCN(C2)C13] | >10 μM | — | — |
| 34r | 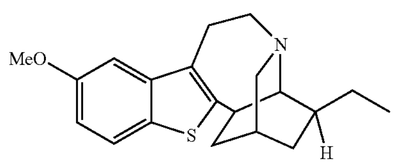 [SMILES: CCC1CC2CC3c4sc5ccc(OC)cc5c4CCN(C2)C13] | >10 μM | >10 μM | — |
| 35a | 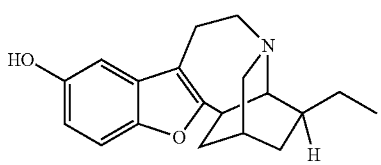 [SMILES: CCC1CC2CC3c4oc5ccc(O)cc5c4CCN(C2)C13] | <10 μM | <10 μM | <10 μM |
| 35b | 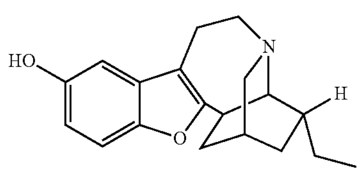 [SMILES: CCC1CC2CC3c4oc5ccc(O)cc5c4CCN(C2)C13] | <10 μM | <10 μM | <10 μM |
| 35c | 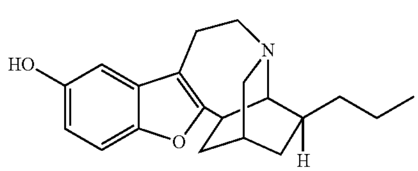 [SMILES: CCCC1CC2CC3c4oc5ccc(O)cc5c4CCN(C2)C13] | <10 μM | <10 μM | <10 μM |
| 35d | 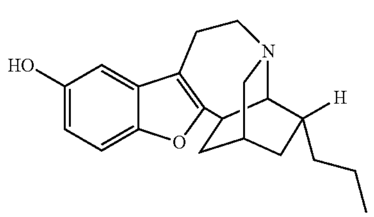 [SMILES: CCCC1CC2CC3c4oc5ccc(O)cc5c4CCN(C2)C13] | <10 μM | <10 μM | <10 μM |

TABLE 3-continued

EC$_{50}$ at indicated opioid receptor.

| Compound | Structure | Human KOR | Human MOR | Human DOR |
|---|---|---|---|---|
| 35e | 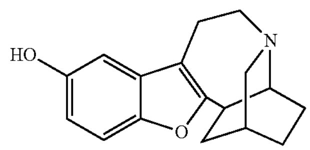 [SMILES: Oc1ccc2oc3c(c2c1)CCN1CC2CCC1C3C2] | <10 μM | <10 μM | — |
| 35f | 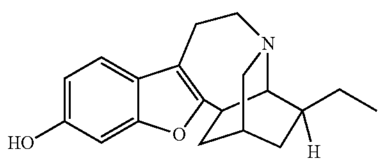 [SMILES: CCC1CC2CC3c4oc5cc(O)ccc5c4CCN(C2)C13] | <10 μM | <10 μM | >10 μM |
| 35g | 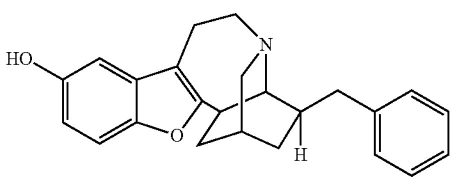 [SMILES: Oc1ccc2oc3c(c2c1)CCN1CC2CC(Cc4ccccc4)C1C3C2] | <10 μM | <10 μM | <10 μM |
| 35h | 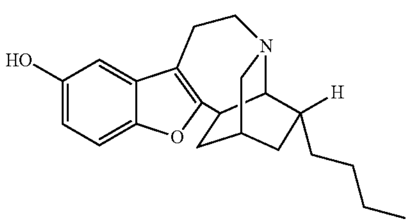 [SMILES: CCCCC1CC2CC3c4oc5ccc(O)cc5c4CCN(C2)C13] | <10 μM | <10 μM | <10 μM |
| 35i | 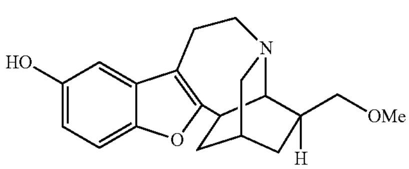 [SMILES: COCC1CC2CC3c4oc5ccc(O)cc5c4CCN(C2)C13] | <10 μM | <10 μM | <10 μM |
| 35j | 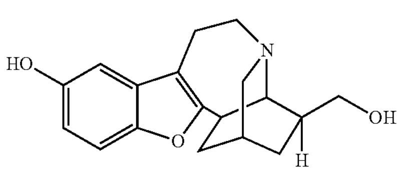 [SMILES: OCC1CC2CC3c4oc5ccc(O)cc5c4CCN(C2)C13] | <10 μM | <10 μM | <10 μM |
| 35k | 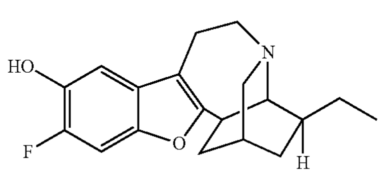 [SMILES: CCC1CC2CC3c4oc5cc(F)c(O)cc5c4CCN(C2)C13] | <10 μM | <10 μM | <10 μM |
| 35l | 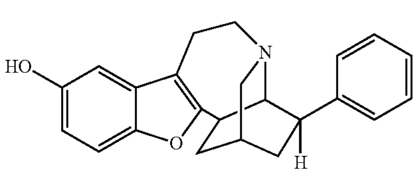 [SMILES: Oc1ccc2oc3c(c2c1)CCN1CC2CC(c4ccccc4)C1C3C2] | >10 μM | >10 μM | >10 μM |

TABLE 3-continued

EC$_{50}$ at indicated opioid receptor.

| Compound | Structure | Human KOR | Human MOR | Human DOR |
|---|---|---|---|---|
| 35m | 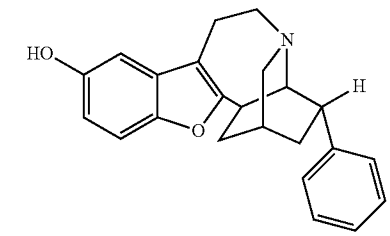 [SMILES: Oc1ccc2oc3c(c2c1)CCN1CC2CC(c4ccccc4)C1C3C2] | — | <10 μM | <10 μM |
| 35n | 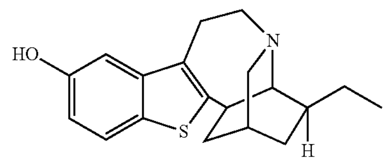 [SMILES: CCC1CC2CC3c4sc5ccc(O)cc5c4CCN(C2)C13] | <10 μM | <10 μM | — |
| 35o | 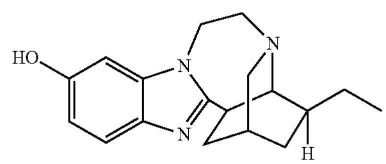 [SMILES: CCC1CC2CC3c4nc5ccc(O)cc5n4CCN(C2)C13] | >10 μM | — | — |

(— = inactive as an agonist at 100 μM)

EXAMPLE 14

Activity of Compound 35d

Figure 2:
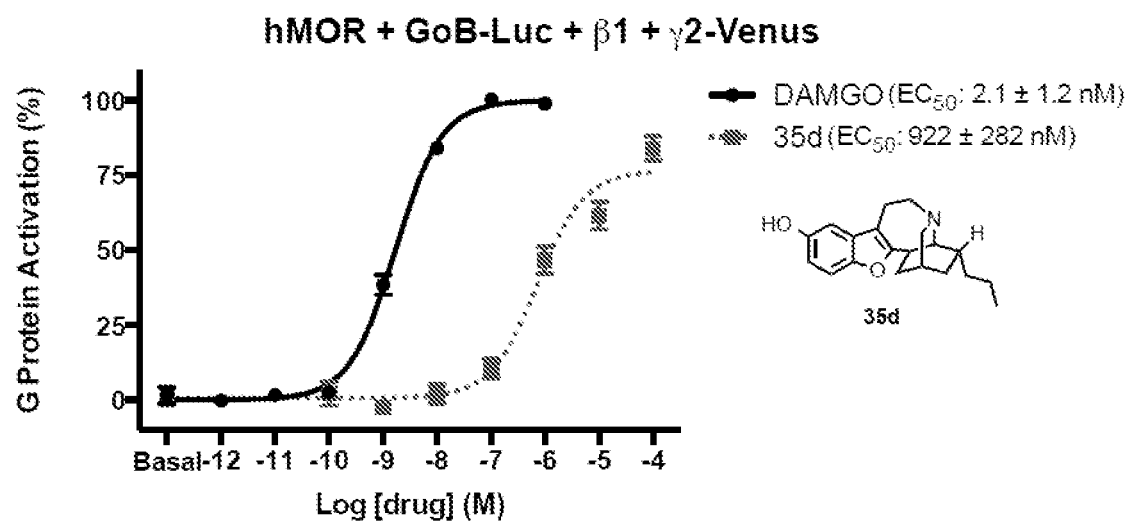
FIG. 2: Human MOR was co-expressed with $G\alpha_{oB}$-RLuc8, $\beta_1$, and mVenus-$\gamma_2$. The induced BRET signal by either 35d (EC$_{50}$: 922±282 nM) or control agonist DAMGO (EC$_{50}$: 2.1±1.2 nM) was measured at 5 minutes. Data represent mean±SEM of 2 independent experiments.
Figure 3:
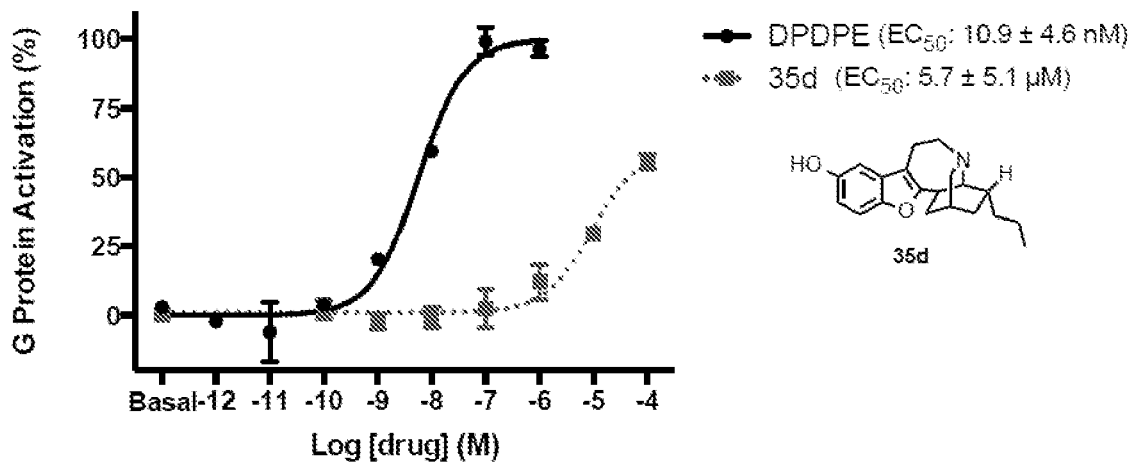
FIG. 3: Human DOR was co-expressed with $G\alpha_{oB}$-RLuc8, $\beta_1$, and mVenus-$\gamma_2$. The induced BRET signal by either 35d (EC$_{50}$: 5.7±5.1 µM) or control agonist DPDPE (EC$_{50}$: 10.9±4.6 nM) was measured at 5 minutes. Data represent mean±SEM of 2 independent experiments.
Figure 4:
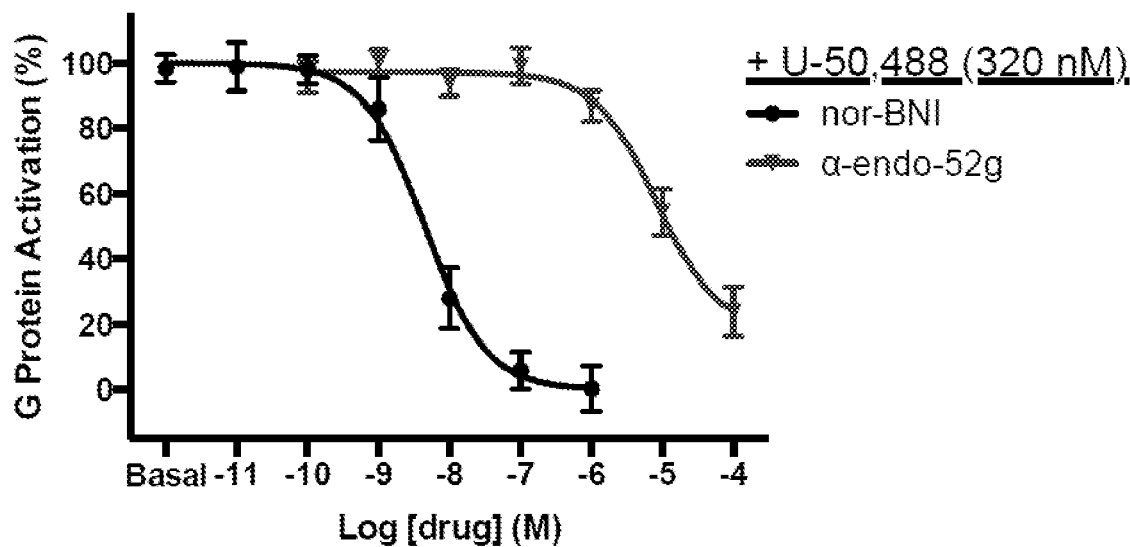
FIG. 4: Human KOR was co-expressed with Gα$_{oB}$-RLuc8, β$_1$, and mVenus-γ$_2$. The induced BRET signal by reference agonist U-50,488 (320 nM) was inhibited by α-endo-52g (IC$_{50}$: 8.2±0.5 μM) or reference antagonist nor-BNI (IC$_{50}$: 6.0±4.2 nM) at 30 minutes. Data represent mean±SEM of 2 independent experiments.
Figure 5:
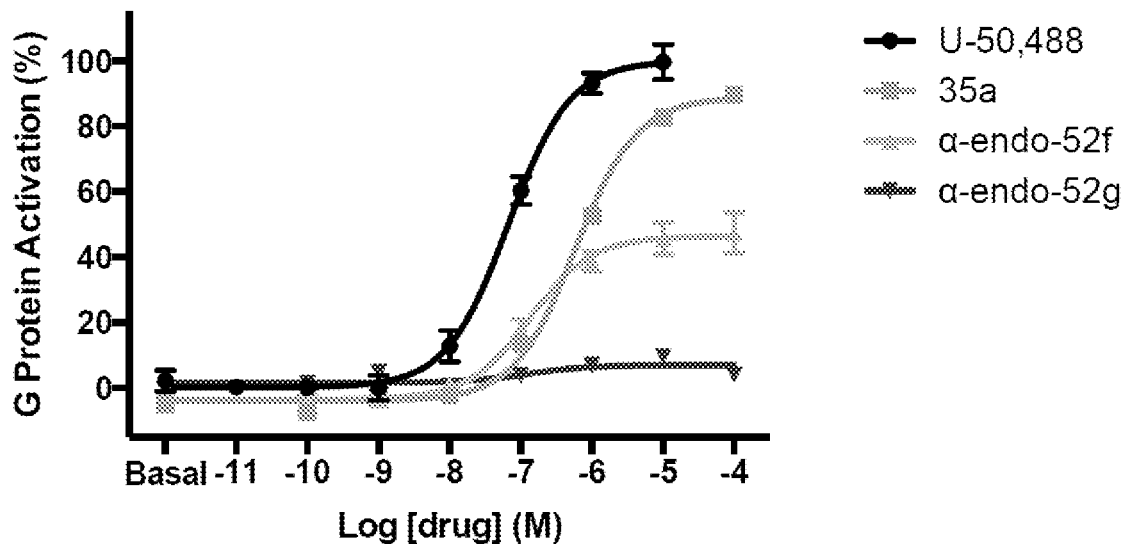
FIG. 5: Human KOR was co-expressed with Gα$_{oB}$-RLuc8, β$_1$, and mVenus-γ$_2$. The induced BRET signal by either 35a (0.66±0.13 μM), α-endo-52f (EC$_{50}$: 0.12±0.014 μM), α-endo-52g (not active as agonist), or control agonist U-50,488 (EC$_{50}$: 64.0±0.7 nM) was measured at 5 minutes. Data represent mean±SEM of 2 independent experiments.
Figure 6:
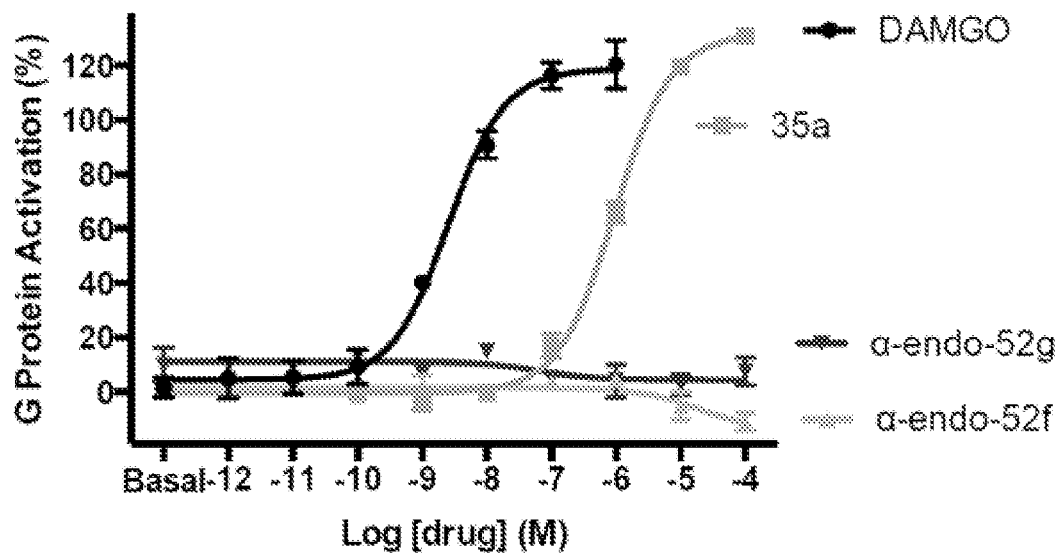
FIG. 6: Human MOR was co-expressed with Gα$_{oB}$-RLuc8, β$_1$, and mVenus-γ$_2$. The induced BRET signal by either 35a (0.98±0.14 μM), α-endo-52f (not active as agonist), α-endo-52g (not active as agonist), or control agonist DAMGO (EC$_{50}$: 2.1±1.2 nM) was measured at 5 minutes. Data represent mean±SEM of 2 independent experiments.
Figure 7:
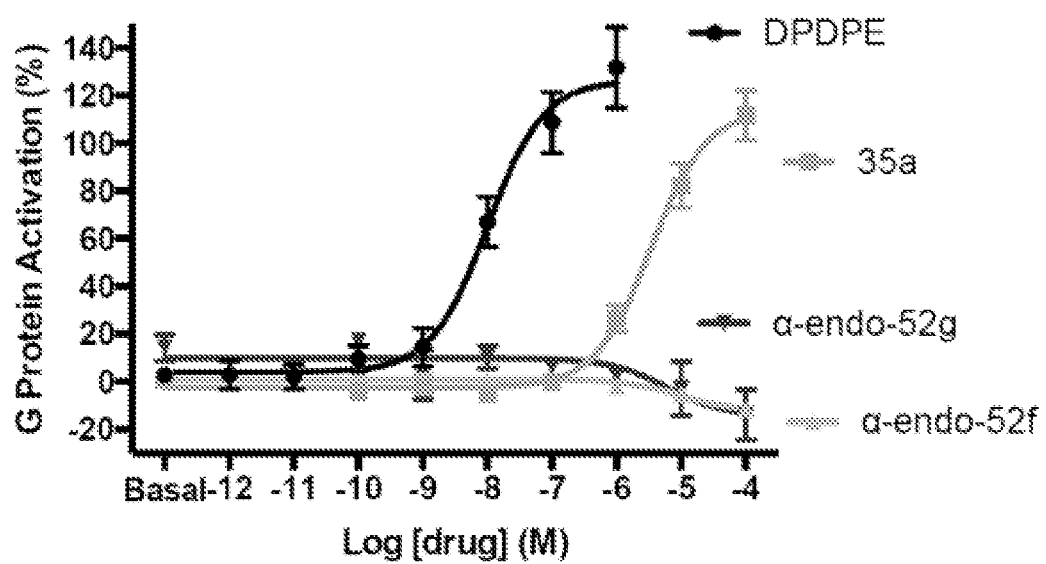
FIG. 7: Human DOR was co-expressed with Gα$_{oB}$-RLuc8, β$_1$, and mVenus-γ$_2$. The induced BRET signal by either 35a (4.5±1.2 μM), α-endo-52f (not active as agonist), α-endo-52g (not active as agonist), or control agonist DPDPE (EC$_{50}$: 10.9±4.6 nM) was measured at 5 minutes. Data represent mean±SEM of 2 independent experiments.

FIGS. 1-3 demonstrate the agonist activity and potency of compound 35d at KOR, MOR, and DOR. Compounds of Table 3 activate KOR, MOR, and/or DOR in an analogous manner.

EXAMPLE 15

Synthesis of Additional Benzofuran Compounds

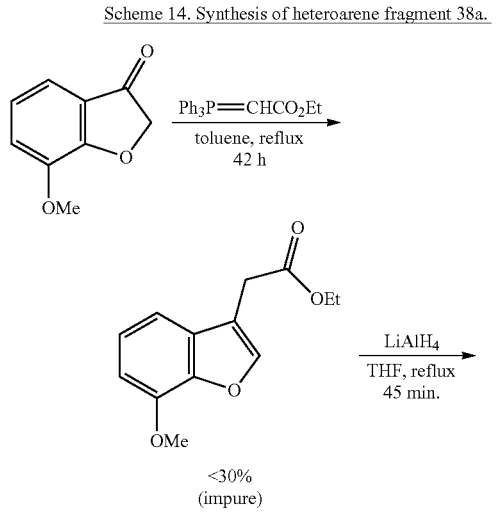

Scheme 14. Synthesis of heteroarene fragment 38a.

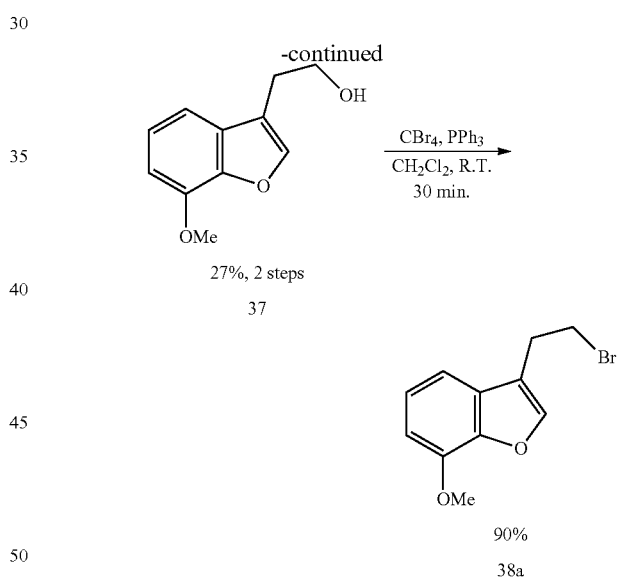

Ethyl 2-(7-methoxybenzofuran-3-yl)acetate (36). A solution of the 7-methoxybenzofuran-3(2H)-one (commercially obtained) (1 equivalent) and (carbethoxymethylene)triphenylphosphorane (1.1 equivalent) in anhydrous toluene (0.30 M, based on benzofuranone) was refluxed until TLC indicated the consumption of starting material and then concentrated in vacuo. The resulting material was triturated with 9:1 hexanes:EtOAc (~7 mL per mmol substrate) and filtered, and the remaining solids were washed with additional portions of 9:1 hexanes:EtOAc (3×~3 mL per mmol substrate). The combined filtrates were concentrated to give the crude product, which was purified by column chromatography (9:1 hexanes:EtOAc) to provide a pale-yellow oil still containing impurities (423 mg, <30%). $^1$H NMR (500 MHz, CDCl$_3$) (Peak list excludes impurity peaks) δ 7.64 (s, 1H), 7.20-7.14 (m, 2H), 6.82 (dd, J=7.0, 1.8 Hz, 1H), 4.19 (q, J=7.1 Hz, 2H), 4.01 (s, 3H), 3.68 (d, J=1.0 Hz, 2H), 1.27 (t, J=7.1 Hz, 4H); LR-MS calcd. for $C_{13}H_{15}O_4^+$ [M+H]$^+$ 235.10, found 235.25.

2-(7-Methoxybenzofuran-3-yl)ethanol (37). To a suspension of LiAlH$_4$ (2.6 equivalents) in anhydrous THF (1.03 M, based on LiAlH$_4$) at room temperature was carefully added a solution of the ester 36 (1 equivalent) in anhydrous THF (1.2 M, based on 36), and the mixture was refluxed until TLC indicated the complete consumption of starting material. After cooling to room temperature, the reaction was quenched by the successive addition of H$_2$O (1 mL per gram LiAlH$_4$), 15% aqueous NaOH (1 mL per gram LiAlH$_4$), and H$_2$O again (3 mL per gram LiAlH$_4$). The resulting mixture was stirred vigorously until the aluminum salts were white and loose and then filtered, washing the filter cake with Et$_2$O (3×). The combined filtrate and washings were concentrated to yield the product directly as a pale-yellow oil (304 mg, 27% over 2 steps from benzofuranone). $^1$H NMR (500 MHz, CDCl$_3$) δ 7.52 (s, 1H), 7.20-7.14 (m, 2H), 6.82 (dd, J=6.3, 2.6 Hz, 1H), 4.01 (s, 3H), 3.92 (t, J=6.2 Hz, 2H), 2.94 (td, J=6.4, 0.8 Hz, 2H), 1.54 (br s, 1H); $^{13}$C NMR (126 MHz, CDCl$_3$) δ 145.8, 144.9, 142.4, 129.9, 123.4, 117.3, 112.0, 106.7, 61.9, 56.2, 27.3; LR-MS calcd. for $C_{11}H_{13}O_3^+$ [M+H]$^+$ 193.09, found 193.20.

3-(2-Bromoethyl)-7-methoxybenzofuran (38a). To a solution of the alcohol 37 (1 equivalent) and carbon tetrabromide (1.5 equivalents) in anhydrous CH$_2$Cl$_2$ (0.5 M, based on 37) at room temperature was carefully added triphenylphosphine (1.5 equivalents) and the resulting dark orange-brown mixture was left to stir until TLC indicated the complete consumption of starting material. The reaction mixture was then purified directly by column chromatography (hexanes, 2 column volumes→20:1 hexanes:Et$_2$O, 2 column volumes→10:1 hexanes:Et$_2$O, 2 column volumes) to provide a pale-yellow oil (347 mg, 90%). $^1$H NMR (500 MHz, CDCl$_3$) δ 7.54 (s, 1H), 7.19 (t, J=7.8 Hz, 1H), 7.13 (dd, J=7.8, 1.0 Hz, 1H), 6.83 (d, J=7.8 Hz, 1H), 4.01 (s, 3H), 3.64 (t, J=7.4 Hz, 2H), 3.25 (td, J=7.4, 0.8 Hz, 2H); $^{13}$C NMR (126 MHz, CDCl$_3$) δ 145.8, 144.8, 142.3, 129.3, 123.6, 118.0, 111.6, 106.8, 56.2, 31.3, 27.8; LR-MS calcd. for $C_{11}H_{12}BrO_2^+$ [M+H]$^+$ 255.00 and 257.00, found 255.49 and 257.49.

Scheme 15. Synthesis of heteroarene fragment 38b.

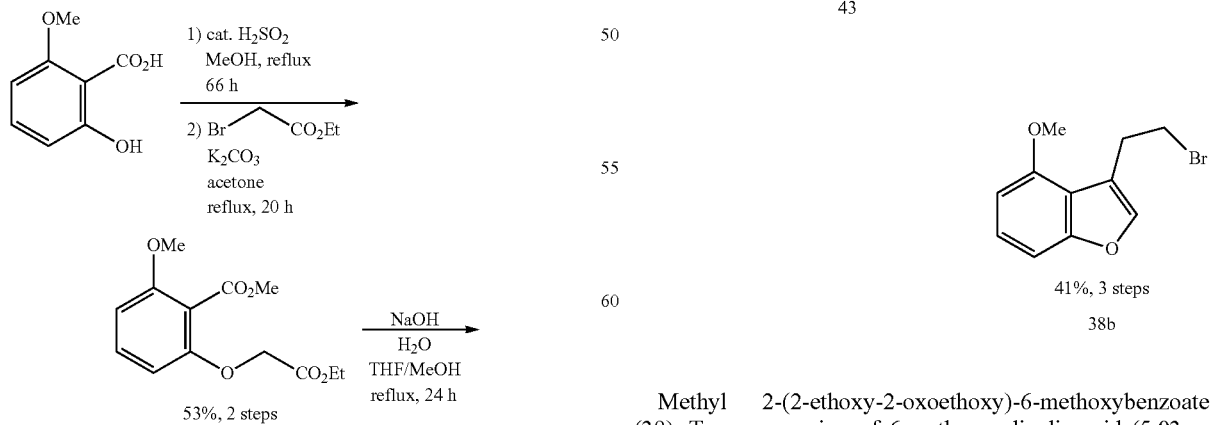

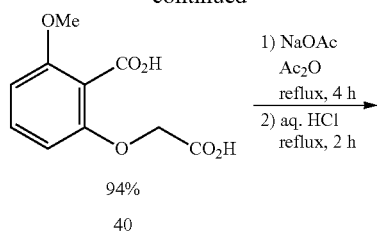

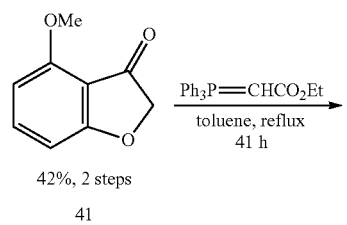

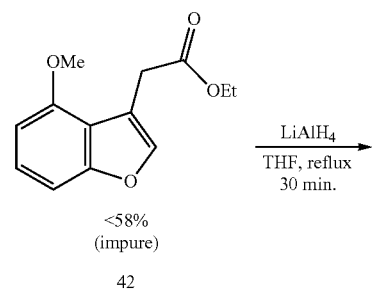

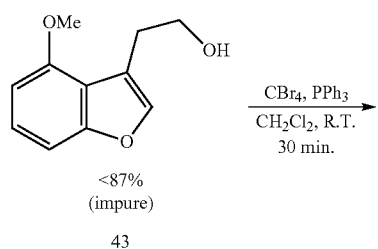

Methyl 2-(2-ethoxy-2-oxoethoxy)-6-methoxybenzoate (39). To a suspension of 6-methoxysalicylic acid (5.03 g, 29.90 mmol) in anhydrous MeOH (37 mL) was added H$_2$SO$_4$ (0.75 mL), and the mixture was refluxed for 66 h, adding additional H$_2$SO$_4$ at 38 h (incomplete conversion). The reaction was then concentrated to provide a mixture of an off-white solid and a pale-orange oil. This material was dissolved in CH$_2$Cl$_2$ (75 mL) and washed with water (50 mL), saturated aqueous NaHCO$_3$ (2×50 mL), and water again (50 mL), dried over Na$_2$SO$_4$, and concentrated to provide the intermediate ester as a pale-orange oil, which slowly crystallized to give a waxy, pale-tan solid containing impurities (4.27 g, <78%, ~11 mol % impurity by NMR).

This impure methyl ester (4.19 g) was mixed with K$_2$CO$_3$ (11.44 g, 82.80 mmol), anhydrous acetone (115 mL) and ethyl bromoacetate (2.55 mL, 3.84 g, 23.00 mmol) were added, and the mixture was refluxed for 20 h. The reaction was then cooled to room temperature and filtered, washing the filter cake with additional acetone, and the filtrate was concentrated to give an orange oil. This material was dissolved in CH$_2$Cl$_2$ (75 mL), washed with water (2×50 mL), saturated aqueous Na$_2$SO$_4$ (50 mL), and brine (50 mL), dried over Na$_2$SO$_4$, and concentrated to provide an orange oil (5.23 g). This crude product was purified by column chromatography (8:2 hexanes:EtOAc, 2 column volumes→7:3 hexanes:EtOAc, 4 column volumes) to provide the pure diester 39 as a nearly colorless oil (4.17 g, 53% over 2 steps). $^1$H NMR (400 MHz, CDCl$_3$) δ 7.26 (t, J=8.4 Hz, 1H), 6.60 (d, J=8.3 Hz, 1H), 6.44 (d, J=8.2 Hz, 1H), 4.62 (s, 2H), 4.24 (q, J=7.1 Hz, 2H), 3.92 (s, 3H), 3.82 (s, 3H), 1.27 (t, J=7.1 Hz, 3H); $^{13}$C NMR (101 MHz, CDCl$_3$) δ 168.5, 166.7, 157.7, 155.9, 131.2, 114.1, 105.3, 105.1, 66.4, 61.5, 56.2, 52.6, 14.3; LR-MS calcd. for C$_{13}$H$_{17}$O$_6^+$ [M+H]$^+$ 269.10, found 268.96.

2-(Carboxymethoxy)-6-methoxybenzoic acid (40). To a solution of diester 39 (4.15 g, 15.47 mmol) in THF (46 mL) and MeOH (46 mL) was added 5M aqueous NaOH (31 mL) and the mixture was refluxed for 24 h. It was then cooled to room temperature and concentrated in vacuo until most of the THF and MeOH had been removed. The thick, pinkish-white slurry was diluted with water (200 mL) (solids dissolve), filtered, and acidified with saturated aqueous HCl. The mixture was then extracted with CH$_2$Cl$_2$ (50 mL) and EtOAc (5×50 mL) (difficult to extract due to high aqueous solubility) and the combined organics were dried over Na$_2$SO$_4$ and concentrated to yield dicarboxylic acid 40 as a tan crystalline solid. (3.30 g, 94%). $^1$H NMR (400 MHz, DMSO-d$_6$) δ 12.84 (br s, 2H), 7.27 (t, J=8.4 Hz, 1H), 6.70 (d, J=8.4 Hz, 1H), 6.54 (d, J=8.4 Hz, 1H), 4.67 (s, 2H), 3.76 (s, 3H); $^{13}$C NMR (101 MHz, DMSO-d$_6$) δ 169.9, 166.4, 156.3, 154.7, 130.2, 114.6, 104.9, 104.6, 65.1, 55.8; LR-MS calcd. for C$_{10}$H$_{11}$O$_6^+$ [M+H]$^+$ 227.06, found 226.89.

4-Methoxybenzofuran-3(2H)-one (41). A mixture of dicarboxylic acid 40 (3.30 g, 14.59 mmol) and sodium acetate (2.92 g, 35.57 mmol) in acetic anhydride (29 mL) was refluxed for 4 h. The reaction was then cooled to room temperature, poured into ice water (150 mL), and the resulting mixture was stirred for 20 min. It was then extracted with CH$_2$Cl$_2$ (100 mL) and the organic layer was dried over Na$_2$SO$_4$ and concentrated to give a dark-brown oil (3.06 g, difficult to remove residual Ac$_2$O). To this material was added 1M aqueous HCl (30 mL), and the mixture was refluxed for 2 h, cooled to room temperature, and extracted with CH$_2$Cl$_2$ (3×30 mL). The combined organics were washed with water (30 mL), dried over Na$_2$SO$_4$, and concentrated to provide a dark-red solid (2.31 g). This material was triturated with boiling Et$_2$O and then cooled to 0° C. and the solids collected by filtration, washing 3× with ice-cold Et$_2$O. The product 41 was thus obtained as a pale, reddish-brown solid containing minor impurities (1.01 g, 42% over 2 steps). $^1$H NMR (500 MHz, CDCl$_3$) δ 7.52 (t, J=8.3 Hz, 1H), 6.68 (d, J=8.3 Hz, 1H), 6.47 (d, J=8.2 Hz, 1H), 4.60 (s, 2H), 3.96 (s, 3H); $^{13}$C NMR (126 MHz, CDCl$_3$) δ 197.4, 175.4, 158.4, 139.6, 110.7, 105.6, 103.3, 74.9, 56.3; LR-MS calcd. for C$_9$H$_9$O$_3^+$ [M+H]$^+$ 165.06, found 164.97.

Ethyl 2-(4-methoxybenzofuran-3-yl)acetate (42). A solution of 41 (1 equivalent) and (carbethoxymethylene)triphenylphosphorane (1.1 equivalent) in anhydrous toluene (0.30 M, based on benzofuranone) was refluxed until TLC indicated the consumption of starting material and then concentrated in vacuo. The resulting material was triturated with 9:1 hexanes:EtOAc (~7 mL per mmol substrate) and filtered, and the remaining solids were washed with additional portions of 9:1 hexanes:EtOAc (3×~3 mL per mmol substrate). The combined filtrates were concentrated to give the crude product 42, which was purified by column chromatography (9:1 hexanes:EtOAc) to provide a pale-yellow oil still containing minor impurities (409 mg, <58%). $^1$H NMR (500 MHz, CDCl$_3$) δ 7.49 (s, 1H), 7.19 (t, J=8.1 Hz, 1H), 7.08 (d, J=8.3 Hz, 1H), 6.62 (d, J=8.0 Hz, 1H), 4.20 (q, J=7.1 Hz, 2H), 3.87 (s, 3H), 3.84 (s, 2H), 1.27 (t, J=7.1 Hz, 3H); $^{13}$C NMR (126 MHz, CDCl$_3$) δ 171.5, 156.7, 154.8, 141.6, 125.3, 117.5, 113.3, 104.9, 103.2, 60.9, 55.5, 30.9, 14.4; LR-MS calcd. for C$_{13}$H$_{15}$O$_4^+$ [M+H]$^+$ 235.10, found 234.98.

2-(4-Methoxybenzofuran-3-yl)ethanol (43). To a suspension of LiAlH$_4$ (2.6 equivalents) in anhydrous THF (1.03 M, based on LiAlH$_4$) at room temperature was carefully added a solution of the ester 42 (1 equivalent) in anhydrous THF (1.2 M, based on 42), and the mixture was refluxed until TLC indicated the complete consumption of starting material. After cooling to room temperature, the reaction was quenched by the successive addition of H$_2$O (1 mL per gram LiAlH$_4$), 15% aqueous NaOH (1 mL per gram LiAlH$_4$), and H$_2$O again (3 mL per gram LiAlH$_4$). The resulting mixture was stirred vigorously until the aluminum salts were white and loose and then filtered, washing the filter cake with Et$_2$O (3×). The product 43 was obtained as a pale-yellow oil containing minor impurities (286 mg, <87%). $^1$H NMR (400 MHz, CDCl$_3$) δ 7.38 (s, 1H), 7.20 (t, J=8.1 Hz, 1H), 7.10 (dd, J=8.3, 0.6 Hz, 1H), 6.65 (d, J=7.9 Hz, 1H), 3.95-3.89 (br m, 2H), 3.92 (s, 3H), 3.05 (td, J=6.2, 0.8 Hz, 2H), 1.77 (br s, 1H); $^{13}$C NMR (101 MHz, CDCl$_3$) δ 157.2, 154.7, 141.2, 128.6, 125.2, 117.0, 105.1, 103.2, 62.9, 55.6, 28.4; LR-MS calcd. for C$_{11}$H$_{13}$O$_3^+$ [M+H]$^+$ 193.09, found 192.97.

3-(2-Bromoethyl)-4-methoxybenzofuran (38b). To a solution of the alcohol 43 (1 equivalent) and carbon tetrabromide (1.5 equivalents) in anhydrous CH$_2$Cl$_2$ (0.5 M, based on 43) at room temperature was carefully added triphenylphosphine (1.5 equivalents) and the resulting dark orange-brown mixture was left to stir until TLC indicated the complete consumption of starting material. The reaction mixture was then purified directly by column chromatography (hexanes, 2 column volumes→20:1 hexanes:Et$_2$O, 2 column volumes→10:1 hexanes:Et$_2$O, 2 column volumes) to provide a pale-yellow oil that slowly solidified to large, vitreous pale-yellow crystals (313 mg, <85%, 41% over 3 steps from 41). Note: The product was found to be unstable at room temperature. $^1$H NMR (500 MHz, CDCl$_3$) δ 7.39 (s, 1H), 7.21 (t, J=8.1 Hz, 1H), 7.10 (d, J=8.2 Hz, 1H), 6.65 (d, J=8.0 Hz, 1H), 3.93 (s, 3H), 3.69 (t, J=7.3 Hz, 2H), 3.31 (t, J=7.3 Hz, 2H); $^{13}$C NMR (126 MHz, CDCl$_3$) δ 157.0, 154.6, 141.2, 125.3, 117.7, 117.1, 105.0, 103.1, 55.6, 32.9, 29.0.

Scheme 16. Synthesis of heteroarene fragment 38c.

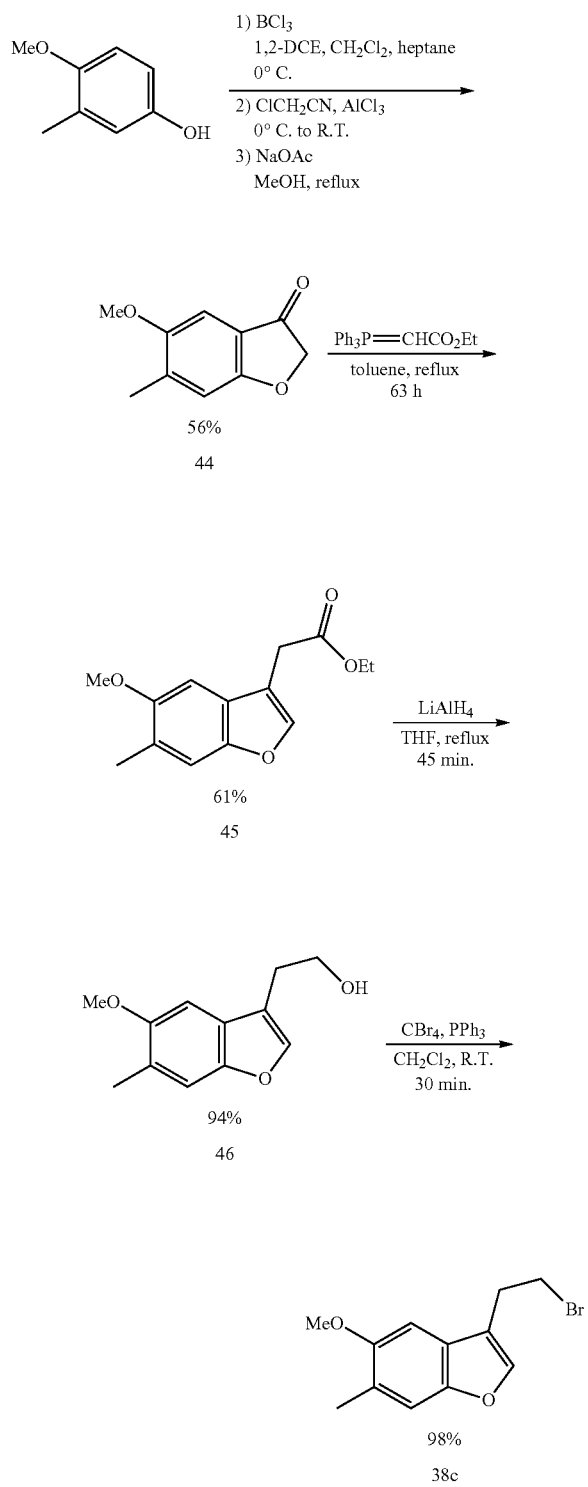

5-Methoxy-6-methylbenzofuran-3(2H)-one (44). To a solution of BCl₃ (1M in CH₂Cl₂, 8.69 mL, 8.69 mmol) at 0° C. was added a solution of 4-methoxy-3-methylphenol (1.00 g, 7.24 mmol) in anhydrous 1,2-dichloroethane (3.6 mL) slowly over 20 min. Chloroacetonitrile (549 μL, 8.69 mmol) was then added over 2 min., followed by AlCl₃ (483 mg, 3.62 mmol) in three equal portions, and the resulting orange mixture was allowed to warm to room temperature and stirred for 15 h. The reaction was then quenched with ice (7 mL) and 10% aqueous HCl (7 mL), diluted with CH₂Cl₂ (10 mL), stirred for 20 min., and then extracted with CH₂Cl₂ (4×10 mL, 3×20 mL, emulsion=difficult extraction). The combined organics were washed with brine (20 mL), dried over Na₂SO₄, and concentrated to provide a yellow solid (1.20 g). This material was purified by column chromatography (9:1 hexanes:EtOAc) to provide the pure intermediate α-chloroacetophenone as very pale-yellow plates (999 mg, 64%).

This material (974 mg, 4.54 mmol) was combined with sodium acetate (1.12 g, 13.62 mmol) in anhydrous MeOH (4.5 mL), and the mixture was refluxed for 50 min. The reaction was then cooled to room temperature and filtered, washing the filter cake with MeOH (2×5 mL). The collected solids (0.80 g, mixture of product and NaOAc) were partitioned between CH₂Cl₂ (20 mL) and water (20 mL) and the organic layer was separated, dried over Na₂SO₄, and concentrated to provide pure product 44 as powdery, off-white crystals (649 mg). The combined filtrate and washings were concentrated and the residue was partitioned between CH₂Cl₂ (25 mL) and water (25 mL). The organic layer was separated, dried over Na₂SO₄ and concentrated to give an orange residue, which was recrystallized from methanol to provide additional pure product 44 as yellow-orange needles (58.5 mg). Total yield of benzofuranone 44 was 708 mg (88%, 56% over 2 steps). $^1$H NMR (500 MHz, CDCl₃) δ 6.96 (s, 1H), 6.94 (s, 1H), 4.60 (s, 2H), 3.82 (s, 3H), 2.30 (s, 3H); $^{13}$C NMR (126 MHz, CDCl₃) δ 199.91, 169.64, 153.78, 140.71, 118.89, 115.12, 101.77, 75.42, 55.90, 18.17; LR-MS calcd. for $C_{10}H_{11}O_3^+$ [M+H]⁺ 179.07, found 179.17.

Ethyl 2-(5-methoxy-6-methylbenzofuran-3-yl)acetate (45). A solution of 44 (1 equivalent) and (carbethoxymethylene)triphenylphosphorane (1.1 equivalent) in anhydrous toluene (0.30 M, based on benzofuranone) was refluxed until TLC indicated the consumption of starting material and then concentrated in vacuo. The resulting material was triturated with 9:1 hexanes:EtOAc (~7 mL per mmol substrate) and filtered, and the remaining solids were washed with additional portions of 9:1 hexanes:EtOAc (3×~3 mL per mmol substrate). The combined filtrates were concentrated to give the crude product 45, which was purified by column chromatography (1:1 hexanes:CH₂Cl₂, 2 column volumes→4:6 hexanes:CH₂Cl₂, 2 column volumes→3:7 hexanes:CH₂Cl₂, 2 column volumes CH₂Cl₂, 2 column volumes) to provide a yellow oil (542 mg, 61%). $^1$H NMR (500 MHz, CDCl₃) δ 7.53 (s, 1H), 7.25 (s, 1H), 6.93 (s, 1H), 4.19 (q, J=7.1 Hz, 2H), 3.88 (s, 3H), 3.66 (d, J=0.9 Hz, 2H), 2.31 (s, 3H), 1.27 (t, J=7.1 Hz, 30H); $^{13}$C NMR (126 MHz, CDCl₃) δ 171.0, 154.5, 150.0, 142.6, 125.7, 124.9, 113.3, 113.0, 99.8, 61.2, 56.0, 30.2, 17.2, 14.4; LR-MS calcd. for $C_{14}H_{17}O_4^+$ [M+H]⁺ 249.11, found 248.84.

2-(5-Methoxy-6-methylbenzofuran-3-yl)ethanol (46). To a suspension of LiAlH₄ (2.6 equivalents) in anhydrous THF (1.03 M, based on LiAlH₄) at room temperature was carefully added a solution of the ester 45 (1 equivalent) in anhydrous THF (1.2 M, based on 45), and the mixture was refluxed until TLC indicated the complete consumption of starting material. After cooling to room temperature, the reaction was quenched by the successive addition of H₂O (1 mL per gram LiAlH₄), 15% aqueous NaOH (1 mL per gram LiAlH₄), and H₂O again (3 mL per gram LiAlH₄). The resulting mixture was stirred vigorously until the aluminum salts were white and loose and then filtered, washing the filter cake with Et$_2$O (3×). The product 46 was obtained as a pale-yellow oil (416 mg, 94%). $^1$H NMR (500 MHz, CDCl$_3$) δ 7.42 (s, 1H), 7.25 (s, 1H), 6.92 (s, 1H), 3.95-3.89 (br m, 2H), 3.88 (s, 3H), 2.92 (td, J=6.4, 0.8 Hz, 2H), 2.32 (s, 3H), 1.54 (br s, 1H); $^{13}$C NMR (126 MHz, CDCl$_3$) δ 154.5, 150.2, 142.0, 126.0, 124.8, 116.9, 113.1, 99.7, 62.1, 56.0, 27.4, 17.1; LR-MS calcd. for C$_{12}$H$_{15}$O$_3^+$ [M+H]$^+$ 207.10, found 207.23.

3-(2-Bromoethyl)-5-methoxy-6-methylbenzofuran (38c). To a solution of the alcohol 46 (1 equivalent) and carbon tetrabromide (1.5 equivalents) in anhydrous CH$_2$Cl$_2$ (0.5 M, based on 46) at room temperature was carefully added triphenylphosphine (1.5 equivalents) and the resulting dark orange-brown mixture was left to stir until TLC indicated the complete consumption of starting material. The reaction mixture was then purified directly by column chromatography (hexanes, 2 column volumes→20:1 hexanes:Et$_2$O, 2 column volumes→10:1 hexanes:Et$_2$O, 2 column volumes) to provide a pale-yellow oil that slowly crystallized to a pale-yellow solid (517 mg, 98%). $^1$H NMR (500 MHz, CDCl$_3$) δ 7.44 (s, 1H), 7.26 (s, 1H), 6.87 (s, 1H), 3.89 (s, 3H), 3.64 (t, J=7.5 Hz, 2H), 3.23 (t, J=7.5 Hz, 2H), 2.32 (s, 3H); $^{13}$C NMR (126 MHz, CDCl$_3$) δ 154.6, 150.0, 141.9, 125.4, 124.9, 117.7, 113.2, 99.2, 56.0, 31.5, 27.9, 17.2.

Scheme 17. Synthesis of heteroarene fragment 48b.

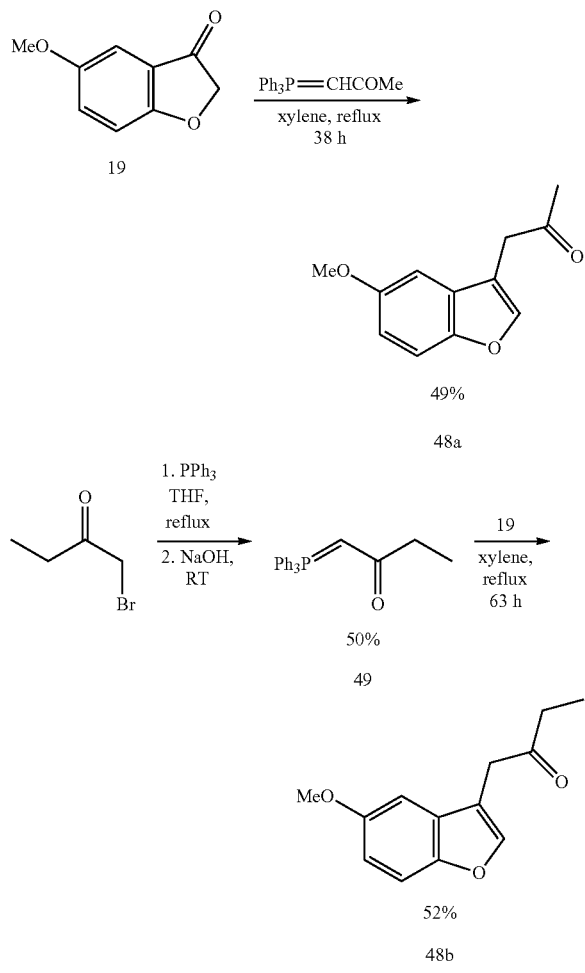

1-(5-Methoxybenzofuran-3-yl)propan-2-one (48a). A dark-red mixture of benzofuranone 19 (246 mg, 1.50 mmol) and 1-(triphenylphosphoranylidene)-2-propanone (860 mg, 2.70 mmol) in anhydrous xylene (12 mL) was refluxed for 38 h and then concentrated to provide a reddish-brown, sticky solid (1.23 g). This material was triturated with 8:2 hexanes:EtOAc (10 mL) and the mixture was filtered. The trituration/filtration procedure was repeated with two additional portions of solvent, and the combined filtrates were concentrated to provide a dark-orange oil (505 mg). This crude product was purified by column chromatography (10% EtOAc in hexanes, 4 column volumes→15% EtOAc in hexanes, 4 column volumes→20% EtOAc in hexanes, 2 column volumes) to provide ketone 48a as a dark-orange oil that slowly crystallized to a waxy orange solid (150 mg, 49%). $^1$H NMR (500 MHz, CDCl$_3$) δ 7.59 (s, 1H), 7.39-7.35 (m, 1H), 6.93-6.89 (m, 2H), 3.84 (s, 3H), 3.73 (s, 2H), 2.22 (s, 3H); $^{13}$C NMR (126 MHz, CDCl$_3$) δ 205.4, 156.2, 150.3, 143.9, 128.3, 113.5, 113.5, 112.2, 102.0, 56.1, 39.1, 29.2; LR-MS calcd. for C$_{12}$H$_{13}$O$_3^+$ [M+H]$^+$ 205.09, found 205.33.

1-(Triphenylphosphanylidene)butan-2-one (49). To a solution of 1-bromo-2-butanone (4.75 g, 31.46 mmol) in anhydrous THF (200 mL) was added triphenylphosphine (8.25 g, 31.46 mmol), and the mixture was refluxed for 4 h. The product was collected by filtration, washed with diethyl ether (3×75 mL), and dried to provide a white powder (8.62 g). This material was dissolved in CH$_2$Cl$_2$ (100 mL), water (64 mL) and 2M aqueous NaOH (32 mL) were added, and the resulting biphasic mixture was left to stir for 20 h at room temperature. The product was extracted with CH$_2$Cl$_2$ (3×100 mL), and the combined organics were washed with brine (50 mL), dried over Na$_2$SO$_4$, and concentrated in vacuo to yield compound 49 as fine, slightly yellow crystals (5.20 g, 50%). $^1$H NMR (400 MHz, CDCl$_3$) δ 7.69-7.61 (m, 6H), 7.57-7.50 (m, 3H), 7.48-7.41 (m, 6H), 3.72 and 3.66 (br s, J=25.1 Hz, 1H), 2.33 (qd, J=7.6, 1.3 Hz, 2H), 1.17 (t, J=7.6 Hz, 3H); $^{13}$C NMR (101 MHz, CDCl$_3$) δ 195.2, 133.2 and 133.1, 131.99 and 131.96, 128.98 and 128.95, 128.1 and 127.2, 50.4 and 49.4, 34.8 and 34.7, 11.7.

1-(5-Methoxybenzofuran-3-yl)butan-2-one (48b). A mixture of 49 (2.39 g, 7.2 mmol) and 19 (0.66 g, 4.0 mmol) in anhydrous m-xylene (32 mmol) was refluxed for 63 h. The reaction mixture was then cooled to room temperature and concentrated in vacuo to yield a red-brown sticky solid with chunks. This material was triturated with 8:2 hexanes: EtOAc and filtered. This procedure was repeated twice, and the combined filtrates were concentrated to give an orange oil. The crude material was purified by column chromatography (9:1 CH$_2$Cl$_2$:hexanes, 3 column volumes→CH$_2$Cl$_2$, 1.5 column volumes) to provide the product as a yellow oil (0.44 g, 52%). $^1$H NMR (500 MHz, CDCl$_3$) δ 7.59 (s, 1H), 7.37 (dd, J=8.3, 1.1 Hz, 1H), 6.92-6.89 (m, 2H), 3.85 (s, 3H), 3.72 (s, 2H), 2.54 (q, J=7.3 Hz, 2H), 1.07 (t, J=7.3 Hz, 3H); $^{13}$C NMR (126 MHz, CDCl$_3$) δ 208.1, 156.1, 150.3, 143.9, 128.4, 113.6, 113.4, 112.2, 102.1, 56.1, 37.9, 35.2, 7.9.

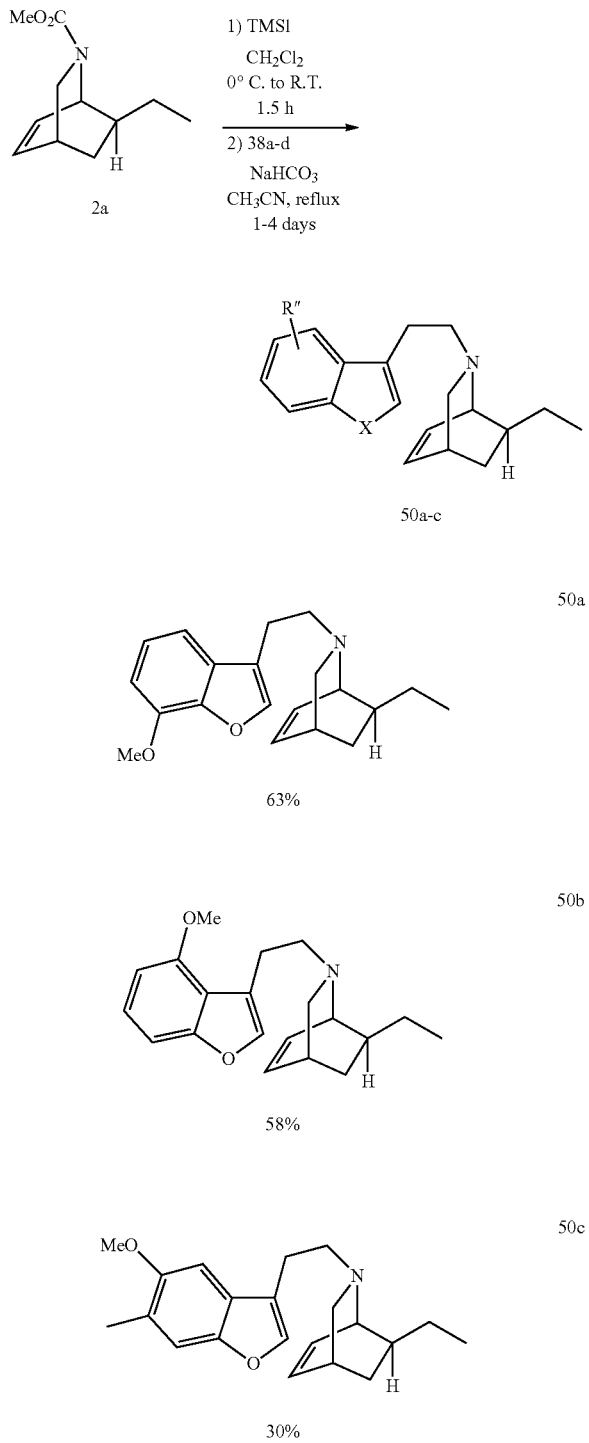

Scheme 18. Synthesis of intermediates 50a-c.

General Procedure for Preparation of N-heteroarylethyl-isoquinuclidines (50) by Alkylation. To a solution of carbamate protected isoquinuclidine 2a (1 equivalent) in anhydrous $CH_2Cl_2$ (0.125 M, based on 2) at 0° C. was added iodotrimethylsilane (4 equivalents), and the resulting mixture was stirred for 10 min. at 0° C. and then at room temperature until TLC indicated that no 2 remained (typically ~1 h). The reaction mixture was then quenched with MeOH (3.0 mL per mmol of 2) and concentrated to yield the deprotected isoquinuclidine hydroiodide salt in quantitative yield. To this material was added bromoethylheteroarene 38 (1 equivalent) and $NaHCO_3$ (4 equivalents), followed by anhydrous $CH_3CN$ (0.208 M, based on 2), and the resulting mixture was refluxed until TLC indicated the disappearance of the bromide (typically >24 h). The reaction was then diluted with water, made strongly basic with aqueous NaOH, and extracted with $CHCl_3$ (3×). The combined organics were washed with water, dried over $Na_2SO_4$, and concentrated to provide the crude product, which was purified by column chromatography with an appropriate solvent mixture (as described below for each compound).

exo-7-Ethyl-2-(2-(7-methoxybenzofuran-3-yl)ethyl)-2-azabicyclo[2.2.2] oct-5-ene (50a). The product 50a was prepared according to the general procedure and purified by column chromatography (20:1 hexanes:$Et_2O$, 3 column volumes→20:1 hexanes:$Et_2O$+2% $Et_3N$, 3 column volumes→10:1 hexanes:$Et_2O$+2% $Et_3N$, 3 column volumes) to provide a pale-yellow oil (59.1 mg, 63%). $^1$H NMR (400 MHz, $CDCl_3$) δ 7.50 (s, 1H), 7.17-7.11 (m, 2H), 6.82-6.76 (m, 1H), 6.37-6.27 (m, 2H), 4.00 (s, 3H), 3.22 (dt, J=5.1, 1.8 Hz, 1H), 3.07 (dd, J=9.1, 2.3 Hz, 1H), 2.85-2.63 (m, 3H), 2.52 (ddd, J=12.5, 8.9, 5.0 Hz, 1H), 2.46-2.40 (m, 1H), 1.93 (dt, J=9.1, 2.6 Hz, 1H), 1.63-1.42 (m, 3H), 1.34-1.24 (m, 1H), 0.94-0.89 (m, 1H), 0.87 (t, J=7.4 Hz, 3H); $^{13}$C NMR (101 MHz, $CDCl_3$) δ 145.7, 144.5, 141.8, 133.0, 132.8, 130.4, 123.0, 119.4, 112.1, 106.3, 57.8, 56.3, 56.21, 56.17, 41.3, 31.8, 29.9, 27.4, 23.1, 12.6; LR-MS calcd. for $C_{20}H_{26}NO_2^+$ [M+H]$^+$ 312.20, found 312.26.

exo-7-Ethyl-2-(2-(4-methoxybenzofuran-3-yl)ethyl)-2-azabicyclo[2.2.2] oct-5-ene (50b). The product 50b was prepared according to the general procedure and purified by column chromatography (20:1 hexanes:$Et_2O$, 3 column volumes→20:1 hexanes:$Et_2O$+2% $Et_3N$, 3 column volumes→10:1 hexanes:$Et_2O$+2% $Et_3N$, 3 column volumes) to provide a pale-yellow oil (53.9 mg, 58%). $^1$H NMR (400 MHz, $CDCl_3$) δ 7.35 (s, 1H), 7.16 (t, J=8.1 Hz, 1H), 7.06 (dd, J=8.3, 0.6 Hz, 1H), 6.61 (d, J=7.9 Hz, 1H), 6.37-6.27 (m, 2H), 3.91 (s, 3H), 3.24 (dt, J=4.9, 1.8 Hz, 1H), 3.07 (dd, J=9.1, 2.3 Hz, 1H), 2.95-2.75 (m, 3H), 2.53-2.40 (m, 2H), 1.97 (dt, J=9.0, 2.6 Hz, 1H), 1.65-1.43 (m, 3H), 1.34-1.25 (m, 1H), 0.95-0.89 (m, 1H), 0.88 (t, J=7.4 Hz, 3H); $^{13}$C NMR (101 MHz, $CDCl_3$) δ 156.8, 155.0, 140.4, 133.0, 132.9, 124.7, 119.3, 118.1, 104.8, 102.9, 58.8, 56.1 (2C), 55.5, 41.4, 31.8, 30.0, 27.3, 24.3, 12.6; LR-MS calcd. for $C_{20}H_{26}NO_2^+$ [M+H]$^+$ 312.20, found 312.35.

exo-7-Ethyl-2-(2-(5-methoxy-6-methylbenzofuran-3-yl)ethyl)-2-azabicyclo[2.2.2]oct-5-ene (50c). The product 50c was prepared according to the general procedure and purified by column chromatography (20:1 hexanes:$Et_2O$, 2 column volumes→20:1 hexanes:$Et_2O$+2% $Et_3N$, 6 column volumes) to provide a pale-yellow oil (29.4 mg, 30%). $^1$H NMR (500 MHz, $CDCl_3$) δ 7.40 (s, 1H), 7.22 (s, 1H), 6.89 (s, 1H), 6.38-6.28 (m, 2H), 3.89 (s, 3H), 3.24 (dd, J=3.6, 1.7 Hz, 1H), 3.09 (dd, J=9.1, 2.2 Hz, 1H), 2.84-2.64 (m, 3H), 2.52 (ddd, J=10.7, 8.3, 5.2 Hz, 1H), 2.47-2.42 (m, 1H), 2.32 (s, 3H), 1.94 (dt, J=9.1, 2.5 Hz, 1H), 1.63-1.45 (m, 3H), 1.35-1.27 (m, 1H), 0.95-0.91 (m, 1H), 0.89 (t, J=7.4 Hz, 3H); $^{13}$C NMR (126 MHz, $CDCl_3$) δ 154.2, 149.9, 141.4, 133.1, 132.8, 126.5, 124.2, 119.1, 112.9, 99.8, 57.9, 56.27, 56.25, 56.0, 41.3, 31.8, 29.9, 27.4, 23.1, 17.1, 12.6.

Scheme 19. Preparation of N-benzofuranylethylisoquinuclidines (50e-f) by Reductive Amination

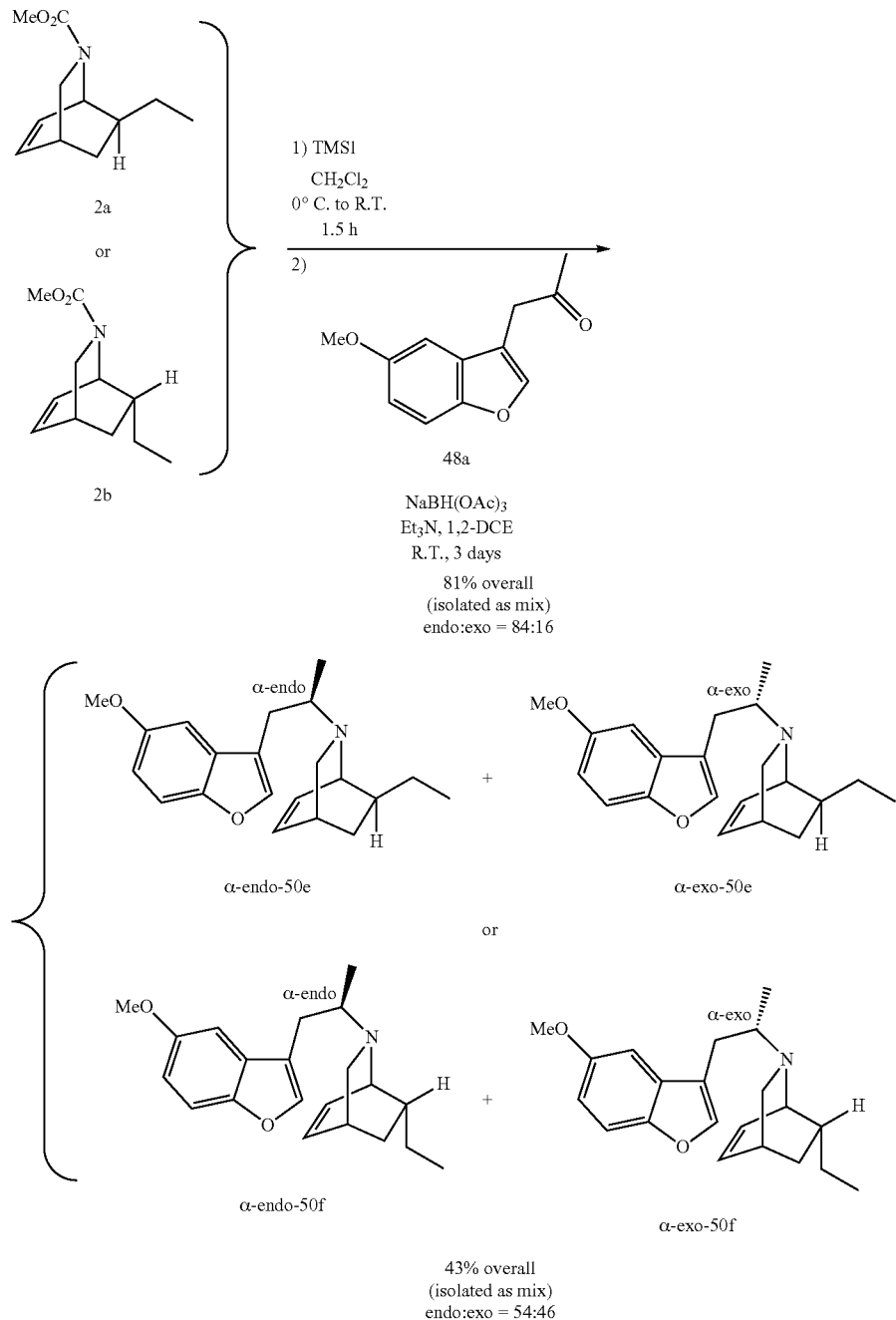

exo-7-Ethyl-2-(α-endo-1-(5-methoxybenzofuran-3-yl) propan-2-yl)-2-azabicyclo[2.2.2]oct-5-ene and exo-7-ethyl-2-(α-exo-1-(5-methoxybenzofuran-3-yl) propan-2-yl)-2-azabicyclo[2.2.2]oct-5-ene (α-endo-50e and α-exo-50e). To a solution of isoquinuclidine 2a (97.6 mg, 0.500 mmol) in anhydrous $CH_2Cl_2$ (4.0 mL) at 0° C. was added iodotrimethylsilane (285 μL, 2.00 mmol), and the orange solution was allowed to warm to room temperature and stirred for 1.5 h. The reaction was then quenched with MeOH (1.5 mL) and concentrated to provide the isoquinuclidine hydroiodide salt as an orange-brown solid. This material was dissolved in anhydrous 1,2-dichloroethane (3.0 mL), $Et_3N$ (139 μL, 1.00 mmol), ketone 48a (102 mg, 0.500 mmol), and $NaBH(OAc)_3$ (212 mg, 1.00 mmol) were added, and the pale-orange mixture was stirred at room temperature for 66 h. At this time, the reaction was diluted with water (25 mL), basified with concentrated aqueous NaOH, and extracted with $CH_2Cl_2$ (3×10 mL). The combined organics were washed with water (10 mL), dried over $Na_2SO_4$, and concentrated to provide a red-brown oil (163 mg). This material was purified by column chromatography (20:1 hexanes: $Et_2O$+2% $Et_3N$) to provide a mixture of the two diastereomers α-endo-50e and α-exo-50e as a yellow-orange oil (132 mg, 81%, 84:16 α-endo:α-exo). $^1$H NMR (500 MHz, CDCl$_3$) (Partial integrals due to 84:16 mixture of two diastereomers) δ 7.44 (s, 1H), 7.34 (d, J=8.9 Hz, 1H), 6.98 (d, J=2.6 Hz, 0.84H), 6.96 (d, J=2.6 Hz, 0.16H), 6.88 (dd, J=8.9, 2.6 Hz, 1H), 6.37-6.24 (m, 2H), 3.863 (s, 2.52H), 3.858 (s, 0.48H) 3.33 (dt, J=4.0, 2.2 Hz, 0.84H), 3.18 (d, J=5.5 Hz, 0.16H), 3.09 (dd, J=8.5, 2.5 Hz, 0.84H), 3.00-2.95 (m, 0.16H), 2.92 (dd, J=8.3, 2.6 Hz, 0.16H), 2.85 (dd, J=14.6, 5.7 Hz, 0.16H), 2.77 (dd, J=14.4, 4.2 Hz, 0.84H), 2.75-2.66 (m, 0.84H), 2.50 (dd, J=14.6, 8.5 Hz, 0.84H), 2.46 (br d, J=1.9 Hz, 1H), 2.35 (dt, J=8.4, 2.3 Hz, 0.16H), 2.31 (dd, J=14.5, 8.3 Hz, 0.16H), 2.23 (dt, J=8.5, 2.4 Hz, 0.84H), 1.62-1.41 (m, 3H), 1.33-1.26 (m, 1H), 0.98-0.86 (m, 6.52H), 0.82 (t, J=7.4 Hz, 0.48H); $^{13}$C NMR (126 MHz, CDCl$_3$) (Additional peaks due to 84:16 mixture of two diastereomers) δ 155.7, 150.3, 143.1, 142.9, 134.4, 133.6, 132.2, 131.8, 129.5, 129.3, 119.0, 118.7, 112.5, 112.4, 111.9, 111.8, 102.8, 102.5, 58.6, 57.9, 56.2, 56.1, 54.6, 53.3, 51.3, 50.8, 42.6, 42.0, 31.93, 31.86, 30.2, 30.1, 29.6, 29.3, 27.1, 26.8, 18.1, 17.6, 12.6, 12.5; LR-MS calcd. for $C_{21}H_{28}NO_2^+$ [M+H]$^+$ 326.21, found 326.61.

endo-7-Ethyl-2-(α-endo-1-(5-methoxybenzofuran-3-yl)propan-2-yl)-2-azabicyclo[2.2.2]oct-5-ene and endo-7-ethyl-2-(α-exo-1-(5-methoxybenzofuran-3-yl)propan-2-yl)-2-azabicyclo[2.2.2]oct-5-ene (α-endo-50f and α-exo-50f). To a solution of isoquinuclidine 2b (195 mg, 1.00 mmol) in anhydrous CH$_2$Cl$_2$ (8.0 mL) at 0° C. was added iodotrimethylsilane (569 μL, 4.00 mmol), and the orange solution was allowed to warm to room temperature and stirred for 1.5 h. The reaction was then quenched with MeOH (3.0 mL) and concentrated to provide the isoquinuclidine hydroiodide salt as an orange-brown solid. To this material (insoluble) was added anhydrous 1,2-dichloroethane (6.0 mL), Et$_3$N (279 μL, 2.00 mmol), ketone 48a (204 mg, 1.00 mmol), and NaBH(OAc)$_3$ (424 mg, 2.00 mmol), and the resulting pale-orange mixture was stirred at room temperature for 34 h. At this time, additional NaBH(OAc)$_3$ (212 mg, 1.00 mmol) was added and the reaction was stirred for an additional 51 h. the reaction was then diluted with water (25 mL), basified with concentrated aqueous NaOH, and extracted with CH$_2$Cl$_2$ (3×10 mL). The combined organics were washed with water (10 mL), dried over Na$_2$SO$_4$, and concentrated to provide a dark-brown oil (323 mg). This material was purified by repeated column chromatography (Column 1: 7:3 hexanes: EtOAc, 4 column volumes→7:3 hexanes:EtOAc+2% Et$_3$N, 4 column volumes; Column 2: 9:1 hexanes:EtOAc+2% Et$_3$N) to provide a mixture of the two diastereomers α-endo-50f and α-exo-50f as a yellow oil (139 mg, 43%, 54:46 α-endo:α-exo). $^1$H NMR (500 MHz, CDCl$_3$) (Partial integrals due to 54:46 mixture of two diastereomers) δ 7.50 (s, 0.46H), 7.43 (s, 0.54H), 7.35-7.32 (m, 1H), 6.98 (d, J=2.6 Hz, 0.54H), 6.97 (d, J=2.6 Hz, 0.46H), 6.90-6.86 (m, 1H), 6.39-6.33 (m, 1H), 6.22-6.18 (m, 0.46H), 6.11 (ddd, J=7.9, 5.4, 1.0 Hz, 0.54H), 3.86 (s, 1.38H), 3.85 (s, 1.62H), 3.55-3.50 (m, 0.54H), 3.49 (ddd, J=5.4, 2.8, 1.4 Hz, 0.46H), 3.10 (dd, J=9.4, 2.0 Hz, 0.54H), 2.97-2.83 (m, 2H), 2.68-2.59 (m, 0.54H), 2.55-2.46 (m, 1.46H), 2.45-2.36 (m, 0.92H), 2.24 (dt, J=9.4, 2.6 Hz, 0.54H), 2.04-1.93 (m, 1H), 1.84-1.78 (m, 1H), 1.24-1.10 (m, 1H), 1.06-0.94 (m, 1H), 1.01 (d, J=6.3 Hz, 1.62H), 0.96 (d, J=6.4 Hz, 1.38H), 0.87-0.78 (m, 4H); $^{13}$C NMR (126 MHz, CDCl$_3$) (Additional peaks due to 54:46 mixture of two diastereomers) δ 155.8, 150.3, 143.1, 133.2, 131.2, 130.3, 129.4, 118.6, 112.50, 112.46, 111.9, 102.9, 102.6, 59.3, 58.3, 56.1, 53.7, 53.5, 52.7, 51.0, 42.0, 41.6, 31.8, 31.0, 31.0, 29.7, 29.5, 28.84, 28.75, 18.5, 18.1, 11.78, 11.76.

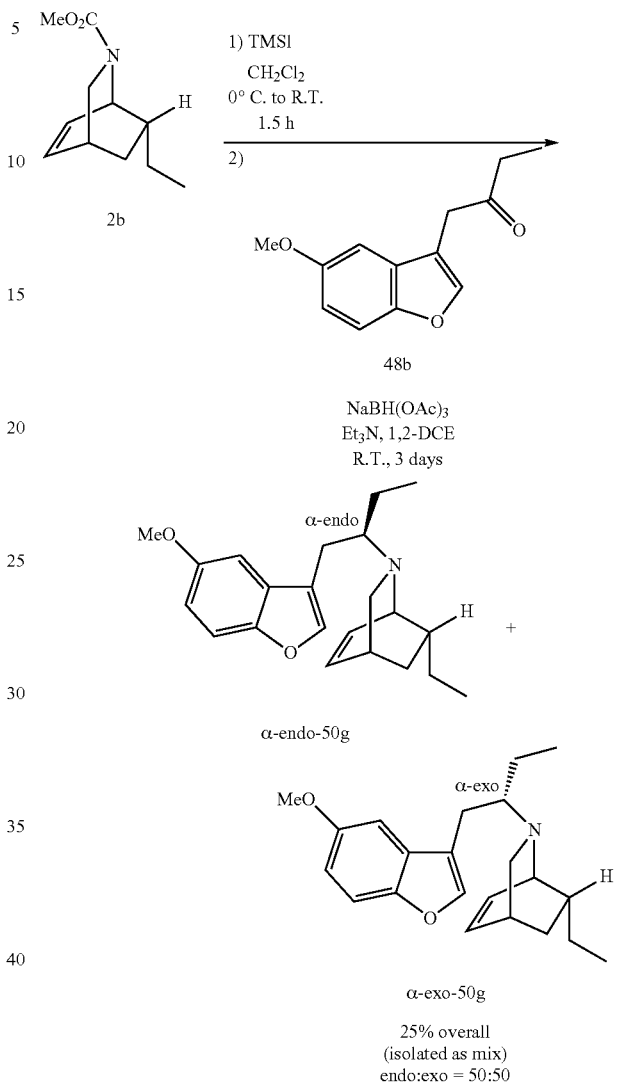

Scheme 20. Preparation of N-benzofuranylethylisoquinuclidines (50g) by Reductive Amination endo-7-Ethyl-2-(α-endo-1-(5-methoxybenzofuran-3-yl)butan-2-yl)-2-azabicyclo[2.2.2]oct-5-ene and endo-7-ethyl-2-(α-exo-1-(5-methoxybenzofuran-3-yl)butan-2-yl)-2-azabicyclo[2.2.2]oct-5-ene (α-endo-50g and α-exo-50g). To a solution of isoquinuclidine 2b (391 mg, 2.00 mmol) in anhydrous CH$_2$Cl$_2$ (16.0 mL) at 0° C. was added iodotrimethylsilane (1.14 mL, 8.00 mmol), and the orange solution was allowed to warm to room temperature and stirred for 1.5 h. The reaction was then quenched with MeOH (6.0 mL) and concentrated to provide the isoquinuclidine hydroiodide salt as an orange-brown solid. This material was dissolved in dry 1,2-dichloroethane (6.0 mL), ketone 48b (218 mg, 1.00 mmol), triethylamine (0.279 mL, 4.00 mmol), and sodium triacetoxyborohydride (424 mg, 2.00 mmol) were added, and the reaction mixture was left to stir at room temperature. After 52 h, TLC indicated slow conversion and presence of a significant amount of starting material. Acetic acid (0.286 mL, 5.00 mmol) was added and the reaction was stirred for an additional 50 h. The mixture was then diluted with water (50 mL), basified with concentrated aqueous NaOH, and extracted with CH$_2$Cl$_2$ (3×20 mL). The combined organics were washed with water (20 mL), dried over Na$_2$SO$_4$, and concentrated in vacuo. The resulting crude product was purified by column chromatography (7:3 hexanes:EtOAc, 4 column volumes→7:3 hexanes:EtOAc+2% Et$_3$N, 4 column volumes) to provide a mixture of the two diastereomers α-endo-50g and α-exo-50g as a pale-yellow oil (84 mg, 25%, ~1:1 α-endo:α-exo). $^1$H NMR (400 MHz, CDCl$_3$) (Partial integrals due to ~1:1 mixture of two diastereomers) δ 7.50 (s, 0.5H), 7.44 (s, 0.5H), 7.35 (s, 0.5H), 7.33 (s, 0.5H), 6.99 (d, J=7.9, 0.5H), 6.98 (d, J=7.8, 0.5H), 6.882 (d, J=8.9, 0.5H), 6.875 (d, J=8.8, 0.5H), 6.37-6.29 (m, 1H), 6.21-6.10 (m, 1H), 3.86 (s, 3H), 3.38 (s, 1H), 3.03-2.94 (m, 1H), 2.84-2.78 (m, 0.5H), 2.73-2.57 (m, 2H), 2.54-2.48 (m, 1H), 2.44-2.35 (m, 1H), 2.33-2.24 (m, 0.5H), 2.03-1.94 (m, 1H), 1.84-1.75 (m, 1H), 1.47-1.35 (m, 2H), 1.20-1.09 (m, 1H), 1.02-0.76 (m, 8H). $^{13}$C NMR (101 MHz, CDCl$_3$) (Additional peaks due to ~1:1 mixture of two diastereomers) δ 155.7, 143.1, 143.0, 133.0, 132.8, 131.3, 131.0, 112.3, 111.8, 102.8, 102.6, 64.6, 64.4, 56.12, 56.09, 53.9, 52.0, 51.2, 42.9, 42.8, 32.0, 30.83, 30.79, 28.7, 28.6, 25.9, 25.5, 24.5, 24.3, 11.8, 11.3, 10.7.

Scheme 21. Synthesis of Heteroarylazepines by Ni(0) Cyclization

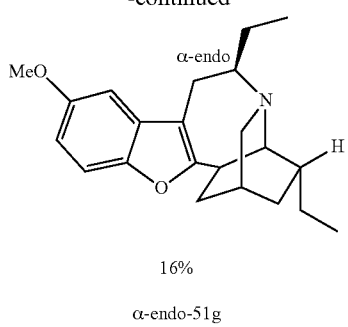

16%

α-endo-51g

General Procedure for Preparation of Hetereoarylazepines by Ni(0)-catalyzed Cyclization (51). In a glovebox, a vial was charged with Ni(COD)$_2$ (0.20 equivalents) and 1,3-bis (2,4,6-trimethylphenyl)-1,3-dihydro-2H-imidazol-2-ylidene (IMes, 0.24 equivalents) followed by anhydrous heptane (0.100 M, based on Ni(COD)$_2$), and the resulting black solution was stirred at room temperature for 15 min. To this mixture was then added a solution of the N-benzofuranyl-ethylisoquinuclidine substrate 50 (1 equivalent) in anhydrous heptane (0.333 M, based on 50), and the reaction vessel was sealed, removed from the glovebox, and heated at 130° C. for 3 h. After cooling to room temperature, the reaction mixture was purified directly by a combination of column chromatography and/or preparative TLC as described below for each substrate. (Note: For substrates that are insoluble in heptane, the catalyst solution is instead added into the heterogeneous mixture of the substrate and heptane.)

Heteroarylazepine (51a). Prepared according to the general procedure. The crude reaction mixture was purified directly by column chromatography (30:1 hexanes:EtOAc+ 1% Et$_3$N) to yield the crude product as a pale-green oil. This material was further purified by preparative TLC (20:1 hexanes:EtOAc+2% Et$_3$N) to provide the pure product 51a as a nearly colorless oil (33.7 mg, 68%). $^1$H NMR (500 MHz, CDCl$_3$) δ 7.12 (t, J=7.8 Hz, 1H), 7.01 (d, J=7.7 Hz, 1H), 6.75 (d, J=7.9 Hz, 1H), 4.00 (s, 3H), 3.41 (dd, J=14.7, 4.3 Hz, 1H), 3.27-3.11 (m, 3H), 2.98 (d, J=9.0 Hz, 1H), 2.93 (dt, J=8.9, 3.0 Hz, 1H), 2.79 (s, 1H), 2.50 (dd, J=17.3, 3.0 Hz, 1H), 2.08-1.99 (m, 1H), 1.87-1.75 (m, 2H), 1.65 (dd, J=13.3, 3.1 Hz, 1H), 1.58-1.41 (m, 3H), 1.22-1.14 (m, 1H), 0.90 (t, J=7.1 Hz, 3H); $^{13}$C NMR (126 MHz, CDCl$_3$) δ 160.2, 144.9, 142.6, 132.5, 122.8, 112.1, 111.2, 105.5, 57.4, 56.1, 53.3, 49.7, 41.5, 41.0, 33.2, 32.2, 27.5, 26.5, 19.5, 11.9; LR-MS calcd. for C$_{20}$H$_{26}$NO$_2^+$ [M+H]$^+$ 312.20, found 312.03.

Heteroarylazepine (51b). Prepared according to the general procedure. The crude reaction mixture was purified directly by column chromatography (30:1 hexanes:EtOAc+ 1% Et$_3$N) to yield the crude product as a pale-yellow oil. This material was further purified by preparative TLC (20:1 hexanes:EtOAc+2% Et$_3$N) to provide the pure product 51b as a cloudy, very pale-green oil (29.4 mg, 63%). $^1$H NMR (500 MHz, CDCl$_3$) δ 7.10 (t, J=8.1 Hz, 1H), 6.98 (d, J=8.2 Hz, 1H), 6.59 (d, J=8.0 Hz, 1H), 3.88 (s, 3H), 3.39-3.29 (m, 2H), 3.19-3.03 (m, 3H), 2.98 (d, J=9.1 Hz, 1H), 2.93 (dt, J=9.1, 3.0 Hz, 1H), 2.79 (s, 1H), 2.08-1.99 (m, 1H), 1.87-1.75 (m, 2H), 1.64 (ddd, J=13.3, 6.3, 3.2 Hz, 1H), 1.58-1.50 (m, 2H), 1.50-1.42 (m, 1H), 1.22-1.16 (m, 1H), 0.91 (t, J=7.1 Hz, 3H); $^{13}$C NMR (126 MHz, CDCl$_3$) δ 158.6, 155.1, 154.9, 123.9, 119.7, 112.2, 104.2, 103.1, 57.0, 55.5, 53.9, 49.8, 41.5, 41.2, 33.3, 32.3, 27.6, 26.5, 20.7, 12.0; LR-MS calcd. for C$_{20}$H$_{26}$NO$_2^+$ [M+H]$^+$ 312.20, found 312.38.

Heteroarylazepine (51c). Prepared according to the general procedure. The crude reaction mixture was purified directly by column chromatography (20:1 hexanes:EtOAc+ 2% Et$_3$N) to yield the crude product as a pale-yellow oil. This material was further purified by preparative TLC (20:1 hexanes:EtOAc+2% Et$_3$N) to provide the pure product 51c as a very pale-brown oil (20.1 mg, 70%). $^1$H NMR (500 MHz, CDCl$_3$) δ 7.13 (s, 1H), 6.78 (s, 1H), 3.86 (s, 3H), 3.46-3.34 (m, 1H), 3.25-3.09 (m, 3H), 2.98 (d, J=9.0 Hz, 1H), 2.93 (dt, J=8.9, 3.1 Hz, 1H), 2.79 (s, 1H), 2.55-2.41 (m, 1H), 2.30 (s, 3H), 2.06-1.97 (m, 1H), 1.86-1.75 (m, 2H), 1.62 (ddd, J=13.2, 6.3, 3.1 Hz, 1H), 1.56-1.42 (m, 3H), 1.22-1.15 (m, 1H), 0.90 (t, J=7.2 Hz, 3H); $^{13}$C NMR (126 MHz, CDCl$_3$) δ 159.7, 154.2, 148.2, 128.8, 123.0, 112.2, 111.7, 99.4, 57.3, 56.1, 53.4, 49.7, 41.5, 41.1, 33.1, 32.3, 27.5, 26.5, 19.6, 17.0, 11.9; LR-MS calcd. for C$_{21}$H$_{28}$NO$_2^+$ [M+H]$^+$ 326.21, found 326.52.

Heteroarylazepine (α-endo-51e). The product α-endo-51e was prepared according to the general procedure, starting from the mixed diastereomers 50e, and obtained as a mixture with the α-exo-epimer, α-exo-51e. It was separated by column chromatography (40:1 hexanes:EtOAc+1% Et$_3$N, 3 column volumes→20:1 hexanes:EtOAc+2% Et$_3$N, 2 column volumes) to provide a very pale-brown oil (72.4 mg, 64%, 76% based on quantity of α-endo in starting material). $^1$H NMR (500 MHz, CDCl$_3$) δ 7.23 (d, J=8.8 Hz, 1H), 6.86 (d, J=2.6 Hz, 1H), 6.80 (dd, J=8.8, 2.6 Hz, 1H), 3.85 (s, 3H), 3.30-3.22 (m, 1H), 3.12 (dt, J=11.5, 2.5 Hz, 1H), 2.98-2.88 (m, 2H), 2.83 (d, J=8.7 Hz, 1H), 2.77 (d, J=1.8 Hz, 1H), 2.54 (dd, J=16.7, 4.1 Hz, 1H), 2.02 (tt, J=7.5, 2.2 Hz, 1H), 1.86-1.81 (br m, 1H), 1.81-1.74 (m, 1H), 1.62 (ddd, J=13.3, 6.5, 3.0 Hz, 1H), 1.59-1.44 (m, 3H), 1.23 (d, J=6.7 Hz, 3H), 1.20-1.13 (m, 1H), 0.90 (t, J=7.1 Hz, 3H); $^{13}$C NMR (126 MHz, CDCl$_3$) δ 161.0, 155.8, 148.4, 131.5, 111.5, 110.92, 110.86, 101.8, 58.7, 58.3, 56.15, 46.2, 41.4, 40.8, 33.8, 32.7, 27.5, 26.5, 26.3, 21.5, 11.9; LR-MS calcd. for C$_{21}$H$_{28}$NO$_2^+$ [M+H]$^+$ 326.21, found 326.64.

Heteroarylazepine (α-exo-51e). The product α-exo-51e was prepared according to the general procedure, starting from the mixed diastereomers 50e, and obtained as a mixture with the α-endo-epimer, α-endo-51e. It was separated by column chromatography (40:1 hexanes:EtOAc+1% Et$_3$N, 3 column volumes→20:1 hexanes:EtOAc+2% Et$_3$N, 2 column volumes) followed by preparative TLC (20:1 hexanes: EtOAc+2% Et$_3$N) to provide a very pale-yellow oil containing minor impurities (6.7 mg, 6%, 38% based on quantity of α-exo in starting material). $^1$H NMR (500 MHz, CDCl$_3$) δ 7.25 (d, J=8.5 Hz, 1H), 6.86 (d, J=2.5 Hz, 1H), 6.79 (dd, J=8.8, 2.6 Hz, 1H), 3.85 (s, 3H), 3.21-3.15 (m, 2H), 3.15-3.11 (m, 1H), 3.09 (dt, J=8.7, 3.1 Hz, 1H), 3.03 (dd, J=16.0, 5.5 Hz, 1H), 2.87 (dt, J=8.6, 1.7 Hz, 1H), 2.53 (ddd, J=16.0, 7.2, 0.9 Hz, 1H), 2.03-1.96 (m, 1H), 1.85-1.74 (m, 3H), 1.60-1.50 (m, 2H), 1.49-1.41 (m, 1H), 1.21-1.14 (m, 1H), 1.17 (d, J=6.7 Hz, 3H), 0.92 (t, J=7.2 Hz, 3H); $^{13}$C NMR (126 MHz, CDCl$_3$) δ 160.1, 155.8, 149.0, 131.2, 111.2, 111.0, 110.6, 101.7, 56.7, 56.2, 55.4, 47.1, 40.8, 40.4, 32.6, 32.4, 27.52, 27.45, 26.3, 22.1, 11.9; LR-MS calcd. for C$_{21}$H$_{28}$NO$_2^+$ [M+H]$^+$ 326.21, found 326.67.

Heteroarylazepine (α-endo-51f). The product α-endo-51f was prepared according to the general procedure, starting from the mixed diastereomers 50f, and obtained as a mixture with the α-exo-epimer, α-exo-51f. It was separated by column chromatography (30:1 hexanes:EtOAc+2% Et$_3$N, 4 column volumes→9:1 hexanes:EtOAc+2% Et$_3$N, 4 column volumes→7:3 hexanes:EtOAc+2% Et$_3$N, 1 column volume)

followed by preparative TLC (9:1 hexanes:EtOAc+2% Et₃N) to provide a yellow oil (58.9 mg, 44%, 81% based on quantity of α-endo in starting material). ¹H NMR (500 MHz, CDCl₃) δ 7.23 (d, J=8.8 Hz, 1H), 6.87 (d, J=2.5 Hz, 1H), 6.80 (dd, J=8.8, 2.6 Hz, 1H), 3.85 (s, 3H), 3.46-3.37 (m, 1H), 3.26 (ddd, J=11.7, 3.6, 1.9 Hz, 1H), 3.04-2.96 (m, 2H), 2.93 (d, J=9.2 Hz, 1H), 2.83 (s, 1H), 2.49 (dd, J=16.6, 3.6 Hz, 1H), 2.06-1.92 (m, 3H), 1.86 (s, 1H), 1.62-1.55 (m, 1H), 1.44-1.30 (m, 2H), 1.27 (d, J=6.7 Hz, 3H), 1.15-1.07 (m, 1H), 0.93 (t, J=7.4 Hz, 3H); ¹³C NMR (126 MHz, CDCl₃) δ 161.8, 155.8, 148.2, 131.4, 111.5, 111.3, 111.0, 101.7, 58.7, 57.7, 56.1, 45.6, 42.4, 35.0, 34.4, 32.1, 28.6, 26.5, 25.6, 21.9, 12.3; LR-MS calcd. for $C_{21}H_{28}NO_2^+$ [M+H]⁺ 326.21, found 326.06.

Heteroarylazepine (α-exo-51f). The product α-exo-51f was prepared according to the general procedure, starting from the mixed diastereomers 50f, and obtained as a mixture with the α-endo-epimer, α-endo-51f. It was separated by column chromatography (30:1 hexanes:EtOAc+2% Et₃N, 4 column volumes→9:1 hexanes:EtOAc+2% Et₃N, 4 column volumes→7:3 hexanes:EtOAc+2% Et₃N, 1 column volume) followed by preparative TLC (9:1 hexanes:EtOAc+2% Et₃N) to provide a yellow oil containing significant impurities, which was used in the next step without further purification (25.7 mg, <19%, <41% based on quantity of α-exo in starting material). ¹H NMR (500 MHz, CDCl₃) (peak list excludes impurity peaks) δ 7.25 (d, J=8.8 Hz, 1H), 6.86 (d, J=2.5 Hz, 1H), 6.80 (dd, J=8.8, 2.5 Hz, 1H), 3.85 (s, 3H), 3.27 (dt, J=10.2, 2.2 Hz, 1H), 3.25-3.15 (m, 3H), 3.00 (dd, J=16.2, 3.8 Hz, 1H), 2.87-2.82 (m, 1H), 2.56 (dd, J=16.2, 7.2 Hz, 1H), 2.07 (ddd, J=14.3, 5.8, 2.9 Hz, 1H), 2.00-1.87 (m, 2H), 1.86-1.80 (m, 1H), 1.67-1.59 (m, 1H), 1.46-1.31 (m, 2H), 1.24 (d, J=6.6 Hz, 3H), 1.11-1.06 (m, 1H), 0.94 (t, J=7.4 Hz, 3H); LR-MS calcd. for $C_{21}H_{28}NO_2^+$ [M+H]⁺ 326.21, found 326.30.

Heteroarylazepine (α-endo-51g). The product α-endo-51g was prepared according to the general procedure, starting from the mixed diastereomers 50g, and obtained as a single isomer, α-endo-51g, and purified by preparative TLC (30:1 Hexanes:EtOAc with 2% Et₃N) yielding a dark-orange, glassy oil (13.6 mg, 16%). ¹H NMR (400 MHz, CDCl₃) δ 7.23 (d, J=8.7 Hz, 1H), 6.87 (d, J=2.6 Hz, 1H), 6.79 (dd, J=8.8, 2.6 Hz, 1H), 3.85 (s, 3H), 3.28 (dt, J=11.5, 2.9 Hz, 1H), 3.10-2.99 (m, 1H), 2.97-2.88 (m, 1H), 2.87 (s, 2H), 2.77 (t, J=2.6 Hz, 1H), 2.50 (dd, J=16.3, 3.4 Hz, 1H), 2.07-1.90 (m, 3H), 1.84 (s, 1H), 1.61-1.54 (m, 2H), 1.50-1.32 (m, 3H), 1.15-1.07 (m, 1H), 1.00 (t, J=7.3 Hz, 3H), 0.93 (t, J=7.3 Hz, 3H). ¹³C NMR (101 MHz, CDCl₃) δ 161.7, 155.8, 151.8, 148.2, 131.6, 111.4, 110.9, 101.8, 64.8, 57.8, 56.2, 45.3, 42.2, 34.87, 34.80, 32.2, 28.6, 27.8, 26.6, 24.5, 12.4, 11.7.

Scheme 22. Demethylation of methoxyheteroarylazepines

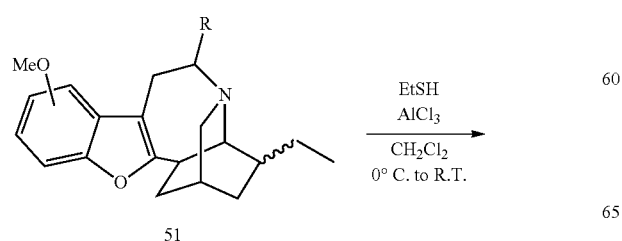

51

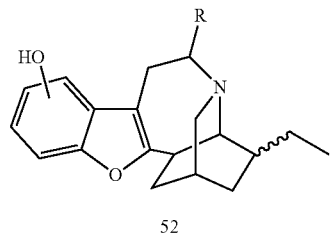

52

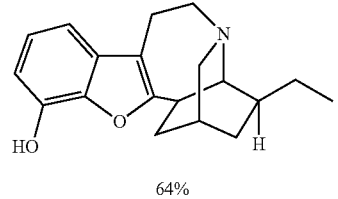

52a

64%

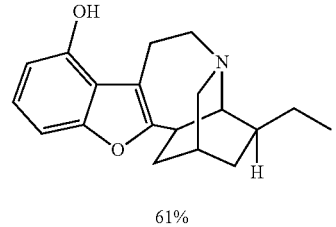

52b

61%

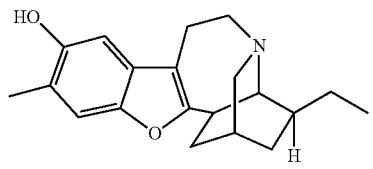

52c

68%

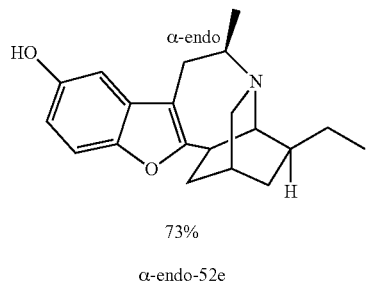

73%

α-endo-52e

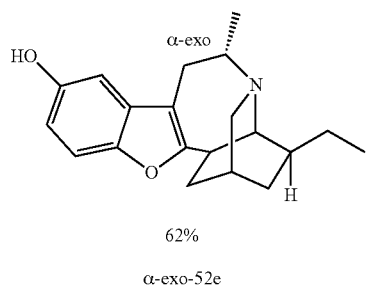

62%

α-exo-52e

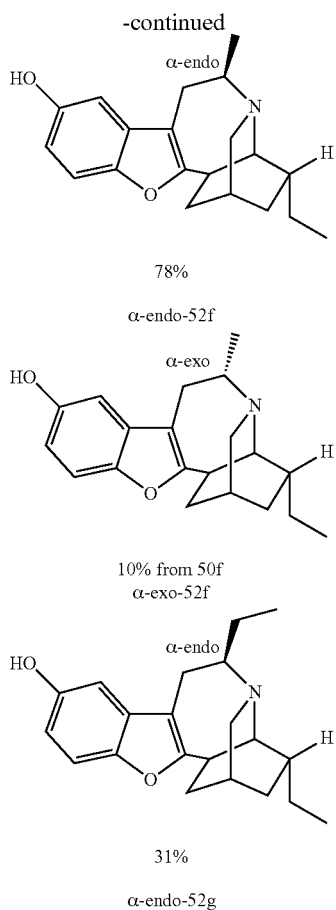

78%
α-endo-52f

10% from 50f
α-exo-52f

31%
α-endo-52g

General Procedure for Preparation of Hydroxyheteroarylazepinesby Demethylation (52). To a solution of the methoxyheteroarylazepine 51 (1 equivalent) in dry dichloromethane (0.125 M, based on 51) at 0° C. was added aluminum chloride (6 equivalents) followed by ethanethiol (18 equivalents), and the resulting mixture was allowed to warm to room temperature and stirred until TLC indicated the complete consumption of starting material (typically <1.5 h). The reaction was then quenched with saturated aqueous NaHCO$_3$ (100 mL per mmol of 51) and extracted with CH$_2$Cl$_2$ (4×-6×, until no further extraction by TLC). The combined organic layers were dried over Na$_2$SO$_4$ and concentrated to provide the crude product. This material was purified by column chromatography with an appropriate solvent mixture as described below for each substrate.

Hydroxyheteroarylazepine (52a). The product 52a was prepared according to the general procedure and purified by column chromatography (7:3 hexanes:EtOAc, 2 column volumes→1:1 hexanes:EtOAc, 3 column volumes) to provide an off-white, foamy solid (14.2 mg, 64%). $^1$H NMR (500 MHz, CDCl$_3$) δ 7.06 (t, J=7.8 Hz, 1H), 6.96 (dd, J=7.7, 1.0 Hz, 1H), 6.75 (dd, J=7.8, 1.0 Hz, 1H), 5.53 (br s, 1H), 3.46-3.37 (m, 1H), 3.25-3.13 (m, 3H), 3.00-2.94 (m, 2H), 2.82 (d, J=1.6 Hz, 1H), 2.55-2.46 (m, 1H), 2.07-1.99 (m, 1H), 1.86 (s, 1H), 1.84-1.77 (m, 1H), 1.65 (ddd, J=13.2, 6.5, 3.1 Hz, 1H), 1.59-1.45 (m, 3H), 1.25-1.19 (m, 1H), 0.91 (t, J=7.2 Hz, 3H); $^{13}$C NMR (126 MHz, CDCl$_3$) δ 160.1, 141.8, 140.6, 132.6, 123.1, 112.5, 111.0, 109.9, 57.4, 53.3, 49.6, 41.6, 41.0, 33.1, 32.2, 27.5, 26.4, 19.6, 11.9; LR-MS calcd. for C$_{19}$H$_{24}$NO$_2{}^+$ [M+H]$^+$ 298.18, found 298.15.

Hydroxyheteroarylazepine (52b). The product 52b was prepared according to the general procedure and purified by column chromatography (1:1 hexanes:EtOAc, 4 column volumes→EtOAc, 2 column volumes) to provide a white, foamy solid (9.1 mg, 61%). $^1$H NMR (400 MHz, CDCl$_3$) δ 7.00 (t, J=7.6 Hz, 1H), 6.95 (d, J=7.6 Hz, 1H), 6.47 (d, J=7.5 Hz, 1H), 5.12 (br s, 1H), 3.45-3.32 (m, 2H), 3.23-3.12 (m, 2H), 3.07-2.91 (m, 3H), 2.81 (s, 1H), 2.09-1.98 (m, 1H), 1.88-1.75 (m, 2H), 1.64 (ddd, J=13.2, 6.3, 3.2 Hz, 1H), 1.60-1.42 (m, 3H), 1.24-1.15 (m, 1H), 0.91 (t, J=7.1 Hz, 3H); $^{13}$C NMR (101 MHz, CDCl$_3$) δ 155.7, 150.5, 123.9, 118.9, 111.6, 108.0, 104.0, 57.2, 53.8, 49.7, 41.5, 41.2, 33.2, 32.3, 27.5, 26.4, 20.8, 12.0; LR-MS calcd. for C$_{19}$H$_{24}$NO$_2{}^+$ [M+H]$^+$ 298.18, found 298.32.

Hydroxyheteroarylazepine (52c). The product 52c was prepared according to the general procedure and purified by column chromatography (1:1 hexanes:EtOAc, 2 column volumes→EtOAc, 3 column volumes) to provide a white, foamy solid (9.7 mg, 68%). $^1$H NMR (400 MHz, CDCl$_3$) δ 7.10 (s, 1H), 6.75 (s, 1H), 4.61 (br s, 1H), 3.45-3.32 (m, 1H), 3.21-3.07 (m, 3H), 3.00-2.89 (m, 2H), 2.79 (d, J=1.6 Hz, 1H), 2.50-2.35 (m, 1H), 2.33 (s, 3H), 2.07-1.96 (m, 1H), 1.87-1.75 (m, 2H), 1.62 (ddd, J=13.3, 6.4, 3.1 Hz, 1H), 1.58-1.41 (m, 3H), 1.23-1.14 (m, 1H), 0.90 (t, J=7.2 Hz, 3H); $^{13}$C NMR (101 MHz, CDCl$_3$) δ 160.2, 149.7, 148.7, 129.5, 120.2, 112.0, 111.3, 103.7, 57.3, 53.3, 49.7, 41.5, 41.1, 33.1, 32.3, 27.5, 26.5, 19.6, 16.6, 11.9; LR-MS calcd. for C$_{20}$H$_{26}$NO$_2{}^+$ [M+H]$^+$ 312.20, found 312.48.

Hydroxyheteroarylazepine (α-endo-52e). The product α-endo-52e was prepared according to the general procedure and purified by column chromatography (8:2 hexanes:EtOAc) to provide a white, foamy solid (22.6 mg, 73%). $^1$H NMR (400 MHz, CDCl$_3$) δ 7.19 (d, J=8.6 Hz, 1H), 6.81 (d, J=2.5 Hz, 1H), 6.70 (dd, J=8.6, 2.6 Hz, 1H), 4.64 (br s, 1H), 3.30-3.18 (m, 1H), 3.11 (dt, J=11.5, 2.6 Hz, 1H), 2.96-2.86 (m, 2H), 2.82 (d, J=8.7 Hz, 1H), 2.77 (d, J=2.1 Hz, 1H), 2.48 (dd, J=16.8, 4.1 Hz, 1H), 2.02 (ddd, J=13.6, 4.5, 2.3 Hz, 1H), 1.87-1.71 (m, 2H), 1.62 (ddd, J=13.2, 6.6, 2.9 Hz, 1H), 1.58-1.43 (m, 3H), 1.22 (d, J=6.7 Hz, 3H), 1.20-1.13 (m, 1H), 0.90 (t, J=7.2 Hz, 3H); $^{13}$C NMR (101 MHz, CDCl$_3$) δ 161.3, 151.2, 148.5, 131.9, 111.4, 110.9, 110.7, 104.2, 58.7, 58.3, 46.2, 41.4, 40.8, 33.7, 32.7, 27.5, 26.5, 26.3, 21.4, 11.9; LR-MS calcd. for C$_{20}$H$_{26}$NO$_2{}^+$ [M+H]$^+$ 312.20, found 312.49.

Hydroxyheteroarylazepine (α-exo-52e). The product α-exo-52e was prepared according to the general procedure and purified by column chromatography (6:4 hexanes:EtOAc, 4 column volumes→1:1 hexanes:EtOAc, 2 column volumes) to provide a yellow glass (3.9 mg, 62%). $^1$H NMR (400 MHz, CDCl$_3$) δ 7.20 (d, J=8.6 Hz, 1H), 6.80 (d, J=2.5 Hz, 1H), 6.69 (dd, J=8.6, 2.6 Hz, 1H), 4.52 (br s, 1H), 3.20-3.06 (m, 4H), 2.99 (dd, J=16.0, 5.5 Hz, 1H), 2.86 (d, J=8.8 Hz, 1H), 2.49 (ddd, J=16.0, 7.2, 1.0 Hz, 1H), 2.04-1.95 (m, 1H), 1.85-1.73 (m, 3H), 1.61-1.40 (m, 3H), 1.20-1.12 (m, 1H), 1.15 (d, J=6.7 Hz, 3H), 0.92 (t, J=7.2 Hz, 3H); $^{13}$C NMR (101 MHz, CDCl$_3$) 160.4, 151.2, 149.1, 131.7, 111.2, 111.0, 110.4, 104.0, 56.6, 55.4, 47.1, 40.8, 40.4, 32.6, 32.4, 27.5, 27.5, 26.3, 22.1, 11.9; LR-MS calcd. for C$_{20}$H$_{26}$NO$_2{}^+$ [M+H]$^+$ 312.20, found 312.47.

Hydroxyheteroarylazepine (α-endo-52f). The product α-endo-52f was prepared according to the general procedure and purified by column chromatography (20:1 CH$_2$Cl$_2$:MeOH, 2 column volumes→20:1 acetone:MeOH, 3 column volumes) to provide a white, foamy solid (24.4 mg, 78%). $^1$H NMR (500 MHz, CDCl$_3$) δ 7.18 (d, J=8.6 Hz, 1H), 6.81 (d, J=2.5 Hz, 1H), 6.71 (dd, J=8.6, 2.4 Hz, 1H), 5.63 (br s, 1H), 3.44 (br s, 1H), 3.26 (dd, J=11.8, 2.0 Hz, 1H), 3.04 (br s, 1H), 2.99-2.86 (m, 3H), 2.45 (dd, J=16.7, 2.5 Hz, 1H), 2.15-1.96 (m, 3H), 1.89 (br s, 1H), 1.58 (ddd, J=13.3, 6.4, 3.5 Hz, 1H), 1.43-1.31 (m, 2H), 1.28 (d, J=7.8 Hz, 3H), 1.11 (d, J=13.2 Hz, 1H), 0.91 (t, J=7.4 Hz, 3H); $^{13}$C NMR (126 MHz, CDCl$_3$) δ 161.5, 151.7, 148.2, 131.6, 111.8, 111.0, 110.9, 104.1, 59.0, 57.8, 45.6, 41.5, 34.7, 33.8, 31.8, 28.5, 26.2, 25.6, 21.4, 12.2; LR-MS calcd. for $C_{20}H_{26}NO_2^+$ [M+H]$^+$ 312.20, found 312.16.

Hydroxyheteroarylazepine (α-exo-52f). The product α-exo-52f was prepared according to the general procedure and purified by column chromatography (20:1 acetone: MeOH) to provide a white, foamy solid (12.4 mg, 10% over 2 steps from 50f). $^1$H NMR (500 MHz, CDCl$_3$) δ 7.20 (d, J=8.7 Hz, 1H), 6.81 (d, J=2.5 Hz, 1H), 6.71 (dd, J=8.7, 2.5 Hz, 1H), 5.36 (br s, 1H), 3.32 (d, J=8.5 Hz, 1H), 3.28-3.17 (m, 3H), 2.95 (dd, J=16.4, 3.6 Hz, 1H), 2.86 (d, J=10.5 Hz, 1H), 2.56 (dd, J=16.3, 6.9 Hz, 1H), 2.09 (t, J=12.3 Hz, 1H), 2.03-1.90 (m, 2H), 1.86 (br s, 1H), 1.67-1.59 (m, 1H), 1.44-1.30 (m, 2H), 1.26 (d, J=5.7 Hz, 3H), 1.12-1.03 (m, 1H), 0.92 (t, J=7.4 Hz, 3H); $^{13}$C NMR (126 MHz, CDCl$_3$) δ 160.8, 151.8, 148.7, 131.3, 111.9, 111.8, 111.1, 104.1, 60.6, 54.6, 50.2, 41.0, 33.5, 32.8, 31.6, 27.9, 26.4, 25.9, 21.3, 12.1; LR-MS calcd. for $C_{20}H_{26}NO_2^+$ [M+H]$^+$ 312.20, found 312.18.

Hydroxyheteroarylazepine (α-endo-52g). The product α-endo-52g was prepared according to the general procedure and purified by preparative TLC (20:1 CH$_2$Cl$_2$:MeOH, silica washed with 10:1 acetone:MeOH) to provide a pale-brown glass (2.0 mg, 31%). $^1$H NMR (500 MHz, CDCl$_3$) δ 7.18 (d, J=8.6 Hz, 1H), 6.82 (d, J=2.5 Hz, 1H), 6.69 (d, J=7.4 Hz, 1H), 4.67 (br s, 1H), 3.26 (d, J=11.7 Hz, 1H), 3.02 (s, 1H), 2.95-2.80 (m, 3H), 2.76 (s, 1H), 2.45 (d, J=16.3 Hz, 1H), 2.04-1.87 (m, 3H), 1.84 (s, 1H), 1.58 (d, J=13.4 Hz, 2H), 1.48-1.31 (m, 3H), 1.10 (d, J=12.0 Hz, 1H), 0.99 (t, J=7.2 Hz, 3H), 0.93 (t, J=7.3 Hz, 3H). LR-MS calcd. for $C_{21}H_{28}NO_2^+$ [M+H]$^+$ 326.21, found 326.63.

EXAMPLE 16

Biological Data of Additional Benzofuran Compounds

The following compounds activate or inhibit human KOR, DOR and/or MOR. Accordingly, the compounds listed in Table 4 are agonists or antagonists of KOR, DOR and/or MOR. α-endo-52g is a KOR antagonist and has no agonist activity. α-endo-52f is a selective KOR agonist. In contrast, compound 35a is a full agonist at all three receptors (FIGS. 4-7).

TABLE 4

EC$_{50}$ at indicated opioid receptor. Data represent mean EC$_{50}$ ± SEM of at least two independent trials, E$_{max}$ in parentheses. For some compounds inactive as agonists, IC$_{50}$ for inhibition of a reference agonist is provided, indicating antagonist activity.

| Compound | Structure | Human KOR | Human MOR | Human DOR |
|---|---|---|---|---|
| 52a | 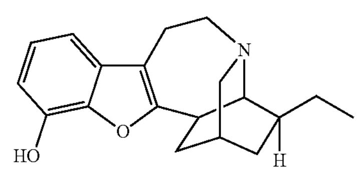 [SMILES: CCC1CC2CC3c4oc5c(O)cccc5c4CCN(C2)C13] | >10 μM | — | — |
| 52b | 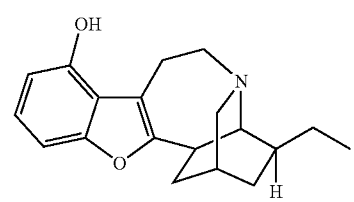 [SMILES: CCC1CC2CC3c4oc5cccc(O)c5c4CCN(C2)C13] | — | >10 μM | — |
| 52c | 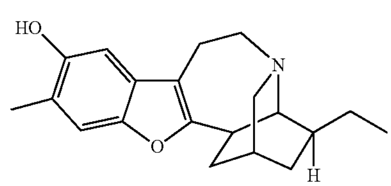 [SMILES: CCC1CC2CC3c4oc5cc(C)c(O)cc5c4CCN(C2)C13] | >10 μM | >10 μM | >10 μM |
| α-endo-52e | 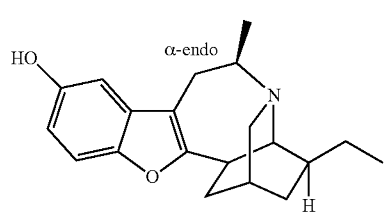 [SMILES: CCC1CC2CC3c4oc5ccc(O)cc5c4C[C@@H](C)N(C2)C13] | 2.4 μM ± 0.19 (26%) | 29 μM ± 30 (24%) | — |

TABLE 4-continued

EC$_{50}$ at indicated opioid receptor. Data represent mean EC$_{50}$ ± SEM of at least two independent trials, E$_{max}$ in parentheses. For some compounds inactive as agonists, IC$_{50}$ for inhibition of a reference agonist is provided, indicating antagonist activity.

| Compound | Structure | Human KOR | Human MOR | Human DOR |
|---|---|---|---|---|
| α-exo-52e | α-exo | 0.44 μM ± 0.059 (88%) | 0.40 μM ± 0.056 (98%) | 4.2 μM ± 0.67 (98%) |
| α-endo-52f | α-endo | 0.12 μM ± 0.014 (47%) | — | — |
| α-exo-52f | α-exo | 0.14 μM ± 0.006 (72%) | 0.48 μM ± 0.20 (50%) | — |
| α-endo-52g | α-endo | — (IC$_{50}$ 8.2 μM ± 0.5) | — | — |

(— = inactive as an agonist at 100 μM)

EXAMPLE 17

Preparation of Additional Heteroarylazepines 59 and 60

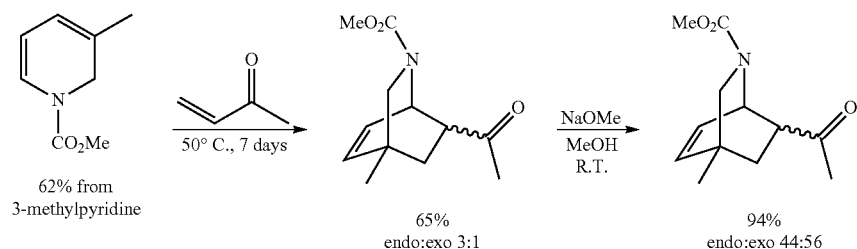

Scheme 23. Synthesis of Substituted Isoquinuclidines.

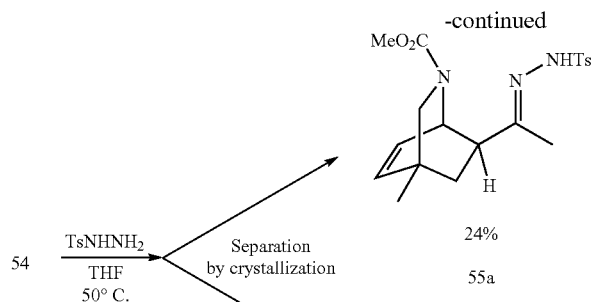

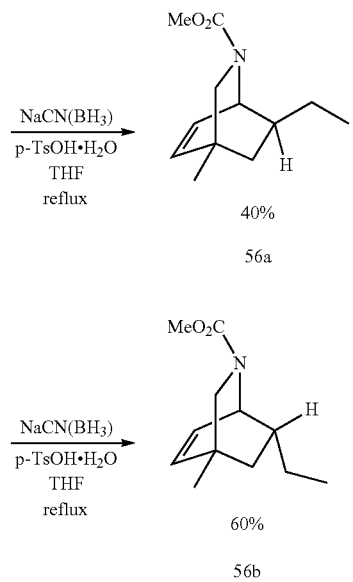

B/

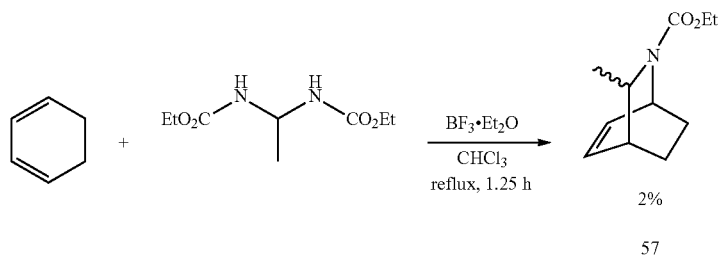

exo/endo-Methyl 7-acetyl-4-methyl-2-azabicyclo[2.2.2]oct-5-ene-2-carboxylate (54, synthesis and epimerization). Isoquinuclidine 53 was prepared following the procedure described by Krow et al. (2007). yielding a mixture of endo and exo isomers 53 in a ratio of 3:1 (65% yield). To a solution of 53 (17.29 g, 77.44 mmol) in MeOH (296 mL) was added NaOMe (12.56 g, 232.5 mmol) and the resulting solution was left to stir at room temperature. After 1 h, NMR indicated an endo:exo ratio of 44:56, so the reaction was diluted with H$_2$O (102 mL), and the MeOH was evaporated in vacuo. The remaining aqueous layer was extracted with DCM (4×50 mL), and the combined organics were washed with H$_2$O (2×100 mL) and brine (105 mL), dried over Na$_2$SO$_4$, and concentrated to yield 54 as a yellow oil (16.19 g, 94%), which was used in the next step without further purification.

exo-Methyl 4-methyl-7-(1-(2-tosylhydrazono)ethyl)-2-azabicyclo [2.2.2]oct-5-ene-2-carboxylate (55a) and endo-methyl 4-methyl-7-(1-(2-tosylhydrazono)ethyl)-2-azabicyclo[2.2.2]oct-5-ene-2-carboxylate (55b). A mixture of exo/endo-isoquinuclidines 54 (16.19 g, 72.5 mmol) and p-toluenesulfonhydrazide (13.5 g, 72.5 mmol) in anhydrous THF (59 mL) was heated at 50° C. for 23 h after which time a white precipitate had formed. The reaction mixture was cooled to room temperature, and the white precipitate was collected by filtration and washed 3× with ice-cold MeOH to provide the pure endo-tosylhydrazone 55b as a fine white powder (9.62 g, 34%). The filtrate and washings were combined and concentrated to a tan solid, which was recrystallized from MeOH to obtain the pure exo-tosylhydrazone 55a as yellow plates (6.89 g, 24%).

exo-Methyl 7-ethyl-4-methyl-2-azabicyclo[2.2.2]oct-5-ene-2-carboxylate (56a). A mixture of exo-tosylhydrazone 55a (3.50 g, 8.94 mmol), sodium cyanoborohydride (2.25 g, 35.76 mmol), and p-toluenesulfonic acid (143 mg, 0.751 mmol) in anhydrous THF (36 mL) was refluxed. After 42 h, additional p-toluenesulfonic acid was added (144 mg, 0.757 mmol) and the mixture was refluxed for an additional 4 h. At this time, the reaction was cooled to room temperature, diluted with H$_2$O (24 mL), and extracted with cyclohexane (3×12 mL). The combined organics were washed with H$_2$O (24 mL), saturated aqueous NaHCO$_3$ (24 mL), and H$_2$O (6 mL), dried over Na$_2$SO$_4$, and concentrated to provide a yellow oil. This was washed through a short silica column with 9:1 hexanes:EtOAc, and the eluate was concentrated to yield the pure exo-isoquinuclidine 56a as a thin, nearly colorless oil (745 mg, 40%). $^1$H NMR (500 MHz, CDCl$_3$) (spectrum complicated by conformers) δ 6.43 and 6.38 (dd, J=8.0, 6.2 Hz, 1H), 6.04 (t, J=9.2 Hz, 1H), 4.58 and 4.43 (d, J=6.1 Hz, 1H), 3.68 and 3.66 (s, 3H), 2.97 (t, J=10.1 Hz, 1H), 2.81 and 2.76 (dd, J=10.1, 2.7 Hz, 1H), 1.63 (s, 1H), 1.53-1.29 (m, 3H), 1.15 and 1.13 (s, 3H), 0.98-0.88 (m, 3H), 0.87-0.81 (m, 1H).

endo-Methyl 7-ethyl-4-methyl-2-azabicyclo[2.2.2]oct-5-ene-2-carboxylate (56b). A mixture of endo-tosylhydrazone 55b (3.50 g, 8.94 mmol), sodium cyanoborohydride (2.25 g, 35.76 mmol), and p-toluenesulfonic acid (143 mg, 0.751 mmol) in anhydrous THF (36 mL) was refluxed for 39 h. The reaction was cooled to room temperature, diluted with H₂O (24 mL), and extracted with cyclohexane (3×12 mL). The combined organics were washed with H₂O (24 mL), saturated aqueous NaHCO₃ (24 mL), and H₂O (6 mL), dried over Na₂SO₄, and concentrated to provide a yellow oil. This was purified by column chromatography (9:1 hexanes:EtOAc) to yield the pure endo-isoquinuclidine 56b as a thin, slightly yellow oil (1.08 g, 60%). ¹H NMR (400 MHz, CDCl₃) (spectrum complicated by conformers) δ 6.27 and 6.21 (dd, J=8.1, 6.0 Hz, 1H), 6.08 (dd, J=8.0, 5.6 Hz, 1H), 4.67-4.60 and 4.50-4.43 (m, 1H), 3.69 and 3.66 (s, 1H), 2.99 (t, J=9.4 Hz, 1H), 2.78 and 2.73 (dd, J=10.1, 3.1 Hz, 1H), 2.03-1.89 (m, 1H), 1.67-1.58 (m, 1H), 1.16 and 1.15 (s, 3H), 0.85 (t, J=7.3 Hz, 3H), 0.81 and 0.77 (dd, J=4.6, 3.2 Hz, 1H).

exo/endo-Ethyl 3-methyl-2-azabicyclo[2.2.2]oct-5-ene-2-carboxylate (57). To a refluxing solution of diethyl ethane-1,1-diyldicarbamate (3.70 g, 18.11 mmol) and BF₃·Et₂O (569 μL, 643 mg, 4.53 mmol) in anhydrous CHCl₃ (100 mL) was added 1,3-cyclohexadiene (1.98 mL, 1.67 g, 20.83 mmol) dropwise over ~3 min. and the orange solution was left to reflux for 1.25 h (eventually turns dark-brown) (Krow et al. 2007). The reaction mixture was then cooled to room temperature, washed with water (30 mL), saturated aqueous NaHCO₃ (30 mL), and water again (30 mL), dried over Na₂SO₄, and concentrated to provide an orange oil (2.72 g). The product 57 was separated from this mixture by column chromatography (9:1 hexanes:EtOAc) and obtained as a pale-yellow oil consisting of mixed exo and endo isomers (70.1 mg, 2%, exo:endo=~85:15). ¹H NMR (500 MHz, CDCl₃) (spectrum complicated by conformers and mixed isomers) δ 6.50-6.15 (m, 2H), 4.74 and 4.60 (s, 1H), 4.23-3.96 (m, 2H), 3.73-3.67 and 3.63-3.57 (m, 0.15H), 3.28 (s, 0.85H), 2.55 (s, 0.15H), 2.42 (s, 0.85H), 1.95-1.83 (m, 2H), 1.43-1.33 (m, 1H), 1.30 (s, 3H), 1.27-1.21 (m, 3H), 1.17-1.08 (m, 1H).

Synthesis of N-Heteroarylalkylisoquinuclidines

Scheme 24. Synthesis of N-heteroarylalkylisoquinuclidines by alkylation or reductive amination.

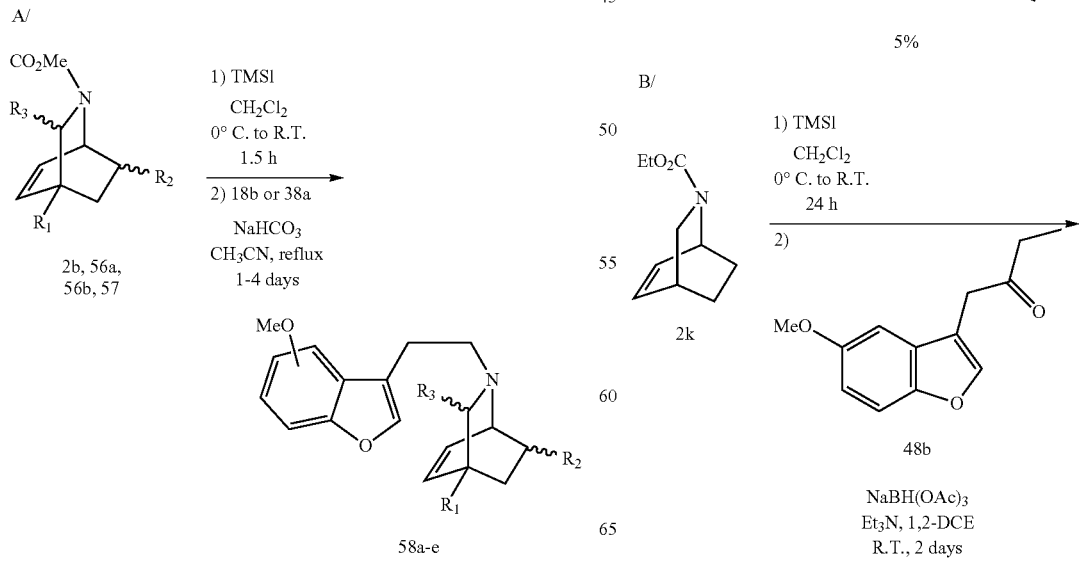

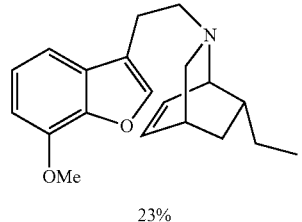

58a

23%

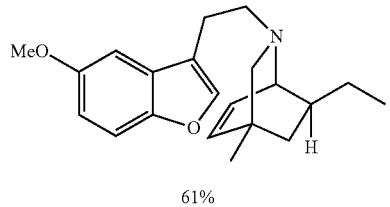

58b

61%

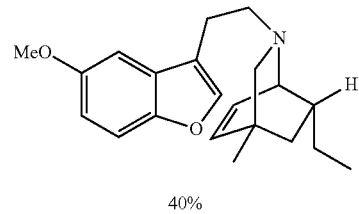

58c

40%

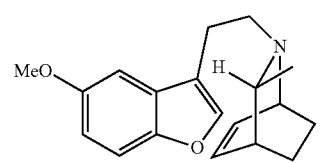

58d

51%

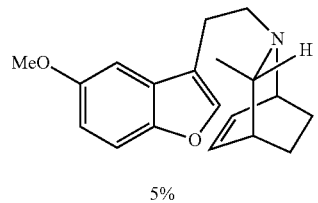

58e

5%

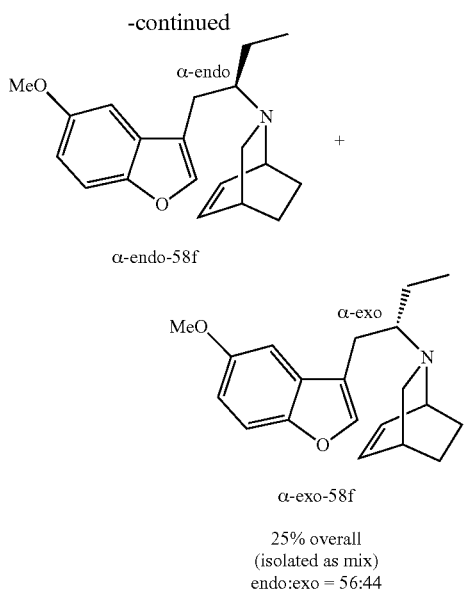

α-endo-58f

α-exo-58f

25% overall
(isolated as mix)
endo:exo = 56:44

Preparation of N-benzofuranylethylisoquinualidines (58) by Alkylation

General Procedure for Preparation of N-benzofuranyl-ethyl-isoquinuclidines (58) by Alkylation. To a solution of carbamate protected isoquinuclidine 2, 56, or 57 (1 equivalent) in anhydrous $CH_2Cl_2$ (0.125 M, based on the isoquinuclidine) at 0° C. was added iodotrimethylsilane (4 equivalents), and the resulting mixture was stirred for 10 min. at 0° C. and then at room temperature until TLC indicated that no protected isoquinuclidine remained (typically ~1 h for methyl carbamates and overnight for ethyl carbamates). The reaction mixture was then quenched with MeOH (3.0 mL per mmol of isoquinuclidine) and concentrated to yield the deprotected isoquinuclidine hydroiodide salt in quantitative yield. To this material was added bromoethylbenzofuran 18 or 38 (1 equivalent) and $NaHCO_3$ (4 equivalents), followed by anhydrous $CH_3CN$ (0.208 M, based on the isoquinuclidine), and the resulting mixture was refluxed until TLC indicated the disappearance of the bromide (typically >24 h). The reaction was then diluted with water, made strongly basic with aqueous NaOH, and extracted with $CHCl_3$ (3×). The combined organics were washed with water, dried over $Na_2SO_4$, and concentrated to provide the crude product, which was purified by column chromatography or preparative TLC with an appropriate solvent mixture (as described below for each compound).

endo-7-Ethyl-2-(2-(7-methoxybenzofuran-3-yl)ethyl)-2-azabicyclo [2.2.2]oct-5-ene (58a). The product 58a was prepared according to the general procedure and purified by column chromatography (15:1 hexanes:$Et_2O$, 3 column volumes→15:1 hexanes:$Et_2O$+2% $Et_3N$, 3 column volume→10:1 hexanes:$Et_2O$+2% $Et_3N$, 3 column volumes) to provide a pale-yellow oil (36.2 mg, 23%). $^1H$ NMR (400 MHz, $CDCl_3$) δ 7.45 (d, J=1.1 Hz, 1H), 7.15 (dd, J=4.5, 0.7 Hz, 2H), 6.79 (m, 1H), 6.38 (ddd, J=8.0, 6.3, 1.3 Hz, 1H), 6.16-6.10 (m, 1H), 4.00 (s, 3H), 3.36 (ddd, J=5.4, 2.8, 1.4 Hz, 1H), 3.02 (dd, J=9.6, 2.0 Hz, 1H), 2.90-2.74 (m, 3H), 2.58-2.54 (m, 1H), 2.52-2.46 (m, 1H), 2.06 (dt, J=9.6, 2.7 Hz, 1H), 2.00 (ddt, J=11.6, 4.5, 2.5 Hz, 1H), 1.78 (ddd, J=12.1, 9.2, 2.8 Hz, 1H), 1.17 (dt, J=13.3, 7.3 Hz, 1H), 1.06-0.95 (m, 1H), 0.88-0.82 (m, 3H), 0.78 (ddt, J=12.3, 4.7, 2.8 Hz, 1H); $^{13}C$ NMR (101 MHz, $CDCl_3$) δ 146.0, 141.9, 134.0, 130.8, 130.5, 123.4, 119.8, 119.6, 112.5, 106.8, 58.2, 57.7, 56.6, 54.8, 41.2, 31.9, 31.1, 29.2, 23.6, 12.1; LR-MS calcd. for $C_{20}H_{26}NO_2^+$ [M+H]$^+$ 312.20, found 312.23.

exo-7-Ethyl-2-(2-(5-methoxybenzofuran-3-yl)ethyl)-4-methyl-2-azabicyclo[2.2.2]oct-5-ene (58b). The product 58b was prepared according to the general procedure and purified by column chromatography (20:1 hexanes:$Et_2O$+2% $Et_3N$) to provide a brown oil (199.5 mg, 61%). $^1H$ NMR (400 MHz, $CDCl_3$) δ 7.48 (s, 1H), 7.35 (d, J=8.9 Hz, 1H), 7.00 (d, J=2.6 Hz, 1H), 6.89 (dd, J=8.9, 2.6 Hz, 1H), 6.28 (dd, J=8.1, 5.4 Hz, 1H), 6.09 (d, J=8.1, 1.2 Hz, 1H), 3.87 (s, 3H), 3.23 (d, J=5.4, 1.6 Hz, 1H), 2.89-2.64 (m, 4H), 2.53 (ddd, J=10.3, 7.9, 5.1 Hz, 1H), 1.77 (dd, J=9.0, 2.7 Hz, 1H), 1.65-1.47 (m, 2H), 1.41-1.26 (m, 3H), 1.08 (s, 3H), 0.89 (t, J=7.4 Hz, 3H), 0.78 (dd, 1H); $^{13}C$ NMR (101 MHz, $CDCl_3$) δ 155.7, 150.2, 142.6, 137.9, 131.7, 129.1, 119.1, 112.5, 111.8, 102.4, 62.9, 57.6, 56.8, 56.1, 41.7, 37.8, 35.3, 27.5, 23.3, 23.0, 12.6.

endo-7-Ethyl-2-(2-(5-methoxybenzofuran-3-yl)ethyl)-4-methyl-2-azabicyclo[2.2.2]oct-5-ene (58c). The product 58c was prepared according to the general procedure and purified by column chromatography (6:4 hexanes:$Et_2O$+2% $Et_3N$) to provide a brown oil (131.5 mg, 40%). $^1H$ NMR (500 MHz, $CDCl_3$) δ 7.34 (d, J=0.5 Hz, 1H), 7.32 (d, J=0.5 Hz, 1H), 7.00 (d, J=2.6 Hz, 1H), 6.88 (dd, J=8.9, 2.6 Hz, 1H), 6.11 (d, J=3.4 Hz, 2H), 3.85 (s, 3H), 3.38-3.32 (m, 1H), 2.88-2.70 (m, 4H), 2.57-2.49 (m, 1H), 2.04 (dddd, J=14.2, 11.7, 6.7, 2.7 Hz, 1H), 1.87 (dd, J=9.5, 3.1 Hz, 1H), 1.59 (dd, J=12.2, 9.2 Hz, 1H), 1.23-1.12 (m, 1H), 1.09 (s, 3H), 1.04-0.95 (m, 1H), 0.85 (t, J=7.4 Hz, 3H), 0.71-0.65 (m, 1H); $^{13}C$ NMR (126 MHz, $CDCl_3$) δ 155.8, 150.3, 142.4, 138.4, 129.2, 129.0, 119.0, 112.7, 111.9, 102.5, 61.3, 57.9, 57.7, 56.2, 41.3, 38.6, 35.3, 28.6, 23.3, 23.2, 11.7.

exo-2-(2-(5-Methoxybenzofuran-3-yl)ethyl)-3-methyl-2-azabicyclo [2.2.2]oct-5-ene (58d). The product 58d was prepared according to the general procedure and obtained as a mixture with the minor diastereomer 58e. It was separated by preparative TLC (9:1 hexanes:EtOAc+2% $Et_3N$) and obtained as a viscous, pale-yellow oil (52.2 mg, 51%). $^1H$ NMR (400 MHz, $CDCl_3$) δ 7.45 (s, 1H), 7.33 (d, J=8.9 Hz, 1H), 6.99 (d, J=2.6 Hz, 1H), 6.88 (dd, J=8.9, 2.6 Hz, 1H), 6.54-6.47 (m, 1H), 6.20 (ddd, J=8.0, 5.2, 0.8 Hz, 1H), 3.85 (s, 3H), 3.48-3.40 (m, 1H), 2.86-2.65 (m, 3H), 2.57-2.44 (m, 1H), 2.25 (dd, J=5.4, 2.5 Hz, 1H), 2.11 (q, J=6.5 Hz, 1H), 1.94-1.75 (m, 2H), 1.33 (tt, J=11.6, 3.0 Hz, 1H), 1.18 (d, J=6.5 Hz, 3H), 1.08-0.97 (m, 1H); $^{13}C$ NMR (101 MHz, $CDCl_3$) δ 155.8, 150.2, 142.5, 135.4, 130.3, 129.0, 118.9, 112.7, 111.9, 102.3, 58.6, 57.2, 56.1, 52.8, 36.0, 27.2, 23.4, 20.7, 16.2.

endo-2-(2-(5-Methoxybenzofuran-3-yl)ethyl)-3-methyl-2-azabicyclo [2.2.2]oct-5-ene (58e). The product 58e was prepared according to the general procedure and obtained as a mixture with the major diastereomer 58d. It was separated by preparative TLC (9:1 hexanes:EtOAc+2% $Et_3N$) and obtained as a viscous, pale-yellow oil (5.5 mg, 5%). $^1H$ NMR (400 MHz, $CDCl_3$) δ 7.45 (s, 1H), 7.37-7.32 (m, 1H), 7.01 (d, J=2.6 Hz, 1H), 6.89 (dd, J=8.9, 2.5 Hz, 1H), 6.55 (ddd, J=7.9, 6.5, 1.3 Hz, 1H), 6.26 (t, J=7.3 Hz, 1H), 3.85 (s, 3H), 3.50-3.42 (m, 1H), 2.94-2.76 (m, 4H), 2.43-2.33 (m, 2H), 2.11-2.00 (m, 1H), 1.59-1.49 (m, 1H), 1.42-1.30 (m, 1H), 1.14-1.03 (m, 1H), 1.01 (d, J=6.3 Hz, 3H); $^{13}C$ NMR (101 MHz, $CDCl_3$) δ 155.8, 150.3, 142.4, 135.6, 132.2, 128.9, 118.9, 112.9, 112.0, 102.3, 60.6, 56.1, 55.0, 52.0, 36.6, 24.7, 24.3, 24.0, 18.1.

Preparation of N-benzofuranylethylisoquinuclidines (58) by Reductive Amination

α-endo-1-(5-Methoxybenzofuran-3-yl)butan-2-yl)-2-azabicyclo [2.2.2]oct-5-ene (α-endo-58f) and α-exo-1-(5-methoxybenzofuran-3-yl)butan-2-yl)-2-azabicyclo[2.2.2]oct-5-ene (α-exo-58f). To a solution of isoquinuclidine 2k (362 mg, 2.00 mmol) in anhydrous $CH_2Cl_2$ (16.0 mL) at 0° C. was added iodotrimethylsilane (1.14 mL, 8.00 mmol), and the orange solution was allowed to warm to room temperature and stirred for 24 h. The reaction was then quenched with MeOH (6.0 mL) and concentrated to provide the isoquinuclidine HI salt as an oily, crystalline orange solid. This material was washed with a small portion of hexanes, removing the supernatant by pipet, leaving a pale-orange, crystalline solid (oily component removed). To this material was added anhydrous 1,2-dichloroethane (6.0 mL), $Et_3N$ (558 μL, 4.00 mmol), ketone 48b (218 mg, 1.00 mmol), and $NaBH(OAc)_3$ (424 mg, 2.00 mmol), and the resulting orange mixture was stirred at room temperature for 40 h. The reaction was then diluted with water (25 mL), basified with concentrated aqueous NaOH, and extracted with $CH_2Cl_2$ (3×10 mL). The combined organics were washed with water (10 mL), dried over $Na_2SO_4$, and concentrated to provide a dark-brown oil (315 mg). This material was purified by repeated column chromatography (Column 1: 20:1 hexanes:EtOAc+2% $Et_3N$, 4 column volumes→9:1 hexanes:EtOAc+2% $Et_3N$, 2 column volumes; Column 2: 7:3 hexanes:EtOAc, 2 column volumes→7:3 hexanes:EtOAc+2% $Et_3N$, 4 column volumes) to provide a mixture of the two diastereomers α-endo-58f and α-exo-58f as a viscous, pale-yellow oil (79.4 mg, 25%, 56:44 α-endo:α-exo). $^1H$ NMR (500 MHz, $CDCl_3$) (partial integrals due to 56:44 mixture of two diastereomers) δ 7.50 (s, 0.44H), 7.44 (s, 0.56H), 7.35 (s, 0.44H), 7.33 (s, 0.56H), 6.99 (d, J=10.6 Hz, 0.44H), 6.98 (d, J=10.6 Hz, 0.56H), 6.89 (d, J=8.9 Hz, 0.56H), 6.88 (d, J=8.9 Hz, 0.44H), 6.37-6.32 (m, 1H), 6.32-6.26 (m, 1H), 3.86 (s, 3H), 3.50-3.43 (m, 1H), 3.08-3.02 (m, 1H), 2.80 (dd, J=14.9, 4.6 Hz, 0.44H), 2.73-2.52 (m, 3H), 2.43-2.35 (m, 1H), 2.30 (dt, J=8.7, 2.1 Hz, 0.56H), 2.00-1.90 (m, 1H), 1.64-1.56 (m, 1H), 1.46-1.34 (m, 2H), 1.34-1.21 (m, 2H), 0.94-0.85 (m, 3H); $^{13}C$ NMR (126 MHz, $CDCl_3$) (Additional peaks due to 56:44 mixture of two diastereomers) δ 155.7, 150.3, 150.2, 143.1, 133.1, 132.8, 132.6, 132.4, 129.43, 129.36, 118.9, 118.8, 112.32, 112.30, 111.8, 102.8, 102.6, 64.7, 64.5, 56.1, 53.2, 52.4, 49.6, 47.8, 31.34, 31.32, 28.93, 28.88, 25.7, 25.4, 24.4, 24.2, 22.33, 22.30, 11.3, 10.7.

Synthesis of Heteroarylazepines by Ni(0) Cyclization

Scheme 25. Synthesis of heteroarylazepines by Ni (0) cyclization

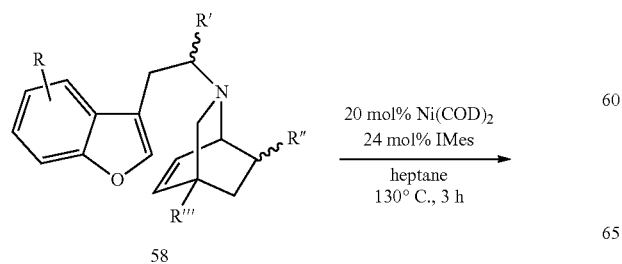

58

20 mol% $Ni(COD)_2$
24 mol% IMes
heptane
130° C., 3 h

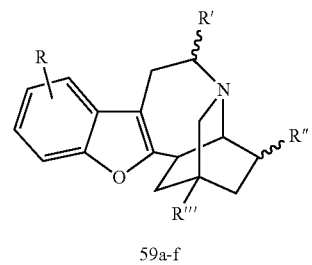

59a-f

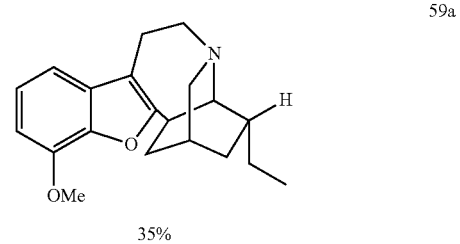

59a
35%

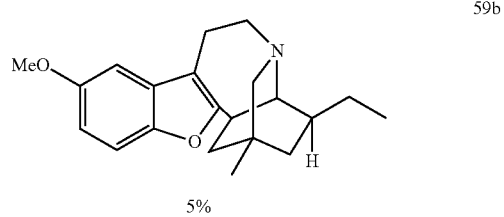

59b
5%

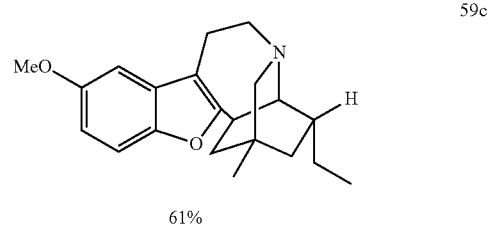

59c
61%

59d

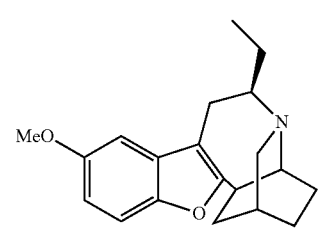

20%

α-endo-59f
45%

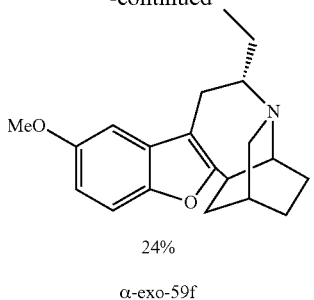

24%

α-exo-59f

General Procedure for Preparation of Oxaibogamine Analogs by Ni(0)-catalyzed cyclization (59). In a glovebox, a vial was charged with Ni(COD)$_2$ (0.20 equivalents) and 1,3-bis(2,4,6-trimethylphenyl)-1,3-dihydro-2H-imidazol-2-ylidene (IMes, 0.24 equivalents) followed by anhydrous heptane (0.100 M, based on Ni((COD)$_2$), and the resulting black solution was stirred at room temperature for 15 min. To this mixture was then added a solution of the N-benzofuranylethyliso-quinuclidine substrate 58 (1 equivalent) in anhydrous heptane (0.333 M, based on 58), and the reaction vessel was sealed, removed from the glovebox, and heated at 130° C. for 3 h. After cooling to room temperature, the reaction mixture was purified directly by a combination of column chromatography and/or preparative TLC as described below for each substrate. (Note: For substrates that are insoluble in heptane, the catalyst solution is instead added into the heterogeneous mixture of the substrate and heptane.)

Heteroarylazepine (59a). Prepared according to the general procedure. The crude reaction mixture was purified directly by column chromatography (15:1 hexanes:EtOAc+1% Et$_3$N) to yield the crude product as a pale yellow oil. This material was further purified by preparative TLC (10:1 hexanes:EtOAc+2% Et$_3$N) to provide the pure product 59a as a nearly colorless oil (12.7 mg, 35%). $^1$H NMR (500 MHz, CDCl$_3$) δ 7.13 (t, J=7.8 Hz, 1H), 7.02 (dd, J=7.8, 1.0 Hz, 1H), 6.74 (dd, J=7.9, 1.0 Hz, 1H), 4.00 (s, 3H), 3.42 (m, 2H), 3.36-3.21 (m, 2H), 3.10-3.04 (m, 2H), 2.86 (q, J=2.8, 2.2 Hz, 1H), 2.51-2.46 (m, 1H), 2.03 (ddt, J=14.0, 11.6, 2.5 Hz, 1H), 1.99-1.94 (m, 2H), 1.87 (dq, J=5.8, 2.5 Hz, 1H), 1.64-1.59 (m, 1H), 1.37 (m, 2H), 1.13-1.09 (m, 1H), 0.92 (t, J=7.4 Hz, 3H); $^{13}$C NMR (126 MHz, CDCl$_3$) δ 161.2, 145.2, 142.6, 132.6, 123.2, 112.9, 111.4, 105.7, 56.8, 56.3, 53.8, 49.3, 42.2, 34.5, 31.9, 28.7, 26.6, 19.3, 14.5, 12.6; LR-MS calcd. for C$_{20}$H$_{26}$NO$_2^+$ [M+H]$^+$ 312.20, found 312.03.

Heteroarylazepine (59b). Prepared according to the general procedure. The crude reaction mixture was purified directly by column chromatography (10:1 hexanes:EtOAc+2% Et$_3$N) followed by preparative TLC (10:1 hexanes:EtOAc+2% Et$_3$N) to yield the pure product 59b as a pale-yellow oil (8.9 mg, 5%). $^1$H NMR (500 MHz, CDCl$_3$) δ 7.24 (d, J=8.7 Hz, 1H), 6.86 (d, J=2.5 Hz, 1H), 6.80 (dd, J=8.8, 2.6 Hz, 1H), 3.84 (s, 3H), 3.43-3.36 (m, 1H), 3.22-3.16 (m, 2H), 3.14 (dt, J=11.5, 2.7 Hz, 1H), 2.82 (s, 1H), 2.75 (dd, J=8.9, 2.4 Hz, 1H), 2.65 (dd, J=8.9, 3.3 Hz, 1H), 2.50-2.45 (m, 1H), 1.98-1.87 (m, 1H), 1.63-1.42 (m, 4H), 1.37 (dt, J=13.2, 3.1 Hz, 1H), 1.09-0.99 (m, 1H), 0.90 (t, J=7.1 Hz, 3H), 0.82 (s, 3H); $^{13}$C NMR (126 MHz, CDCl$_3$) δ 160.9, 155.8, 148.6, 131.4, 111.8, 111.5, 111.0, 101.9, 57.6, 56.2, 56.0, 52.9, 41.1, 40.7, 40.1, 39.6, 30.2, 27.6, 25.9, 20.0, 12.0.

Heteroarylazepine (59c). Prepared according to the general procedure. The crude reaction mixture was purified directly by column chromatography (20:1 hexanes:EtOAc+2% Et$_3$N, 8 column volumes→10:1 hexanes:EtOAc+2% Et$_3$N, 8 column volumes) to yield the pure product 59c as a viscous, dark-brown oil (74.9 mg, 61%). $^1$H NMR (500 MHz, CDCl$_3$) δ 7.24 (d, J=8.8 Hz, 1H), 6.86 (d, J=2.6 Hz, 1H), 6.80 (dd, J=8.8, 2.6 Hz, 1H), 3.84 (s, 3H), 3.44-3.37 (m, 1H), 3.37-3.17 (m, 3H), 2.90-2.86 (m, 1H), 2.84-2.76 (m, 2H), 2.50-2.44 (m, 1H), 2.00-1.92 (m, 1H), 1.91-1.84 (m, 1H), 1.82-1.74 (m, 1H), 1.42-1.31 (m, 3H), 0.92 (t, J=7.3 Hz, 4H), 0.83 (s, 3H); $^{13}$C NMR (126 MHz, CDCl$_3$) δ 161.5, 155.8, 148.4, 131.3, 112.3, 111.5, 111.0, 101.8, 56.8, 56.2, 55.2, 53.0, 41.4, 40.9, 39.0, 34.2, 30.0, 28.5, 26.0, 19.0, 12.3.

Heteroarylazepine (59d). Prepared according to the general procedure. The crude reaction mixture was purified directly by column chromatography (9:1 hexanes:EtOAc+2% Et$_3$N) to yield the crude product as a pale-yellow oil. This material was further purified by preparative TLC (9:1 hexanes:EtOAc+2% Et$_3$N) to provide the pure product 59d as a viscous, nearly-colorless oil (10.3 mg, 20%). $^1$H NMR (500 MHz, CDCl$_3$) δ 7.24 (d, J=8.8 Hz, 1H), 6.85 (d, J=2.5 Hz, 1H), 6.80 (dd, J=8.8, 2.5 Hz, 1H), 3.84 (s, 3H), 3.57-3.47 (m, 1H), 3.23-3.09 (m, 4H), 3.03 (s, 1H), 2.52-2.42 (m, 1H), 2.21-2.12 (m, 1H), 1.97-1.87 (m, 2H), 1.75-1.69 (m, 1H), 1.63-1.54 (m, 2H), 1.48-1.37 (m, 1H), 1.14 (d, J=6.2 Hz, 3H); $^{13}$C NMR (126 MHz, CDCl$_3$) δ 161.19, 155.83, 148.52, 131.33, 111.87, 111.47, 111.04, 101.79, 56.17, 54.60, 52.02, 51.17, 39.31, 35.76, 31.00, 29.20, 19.18, 18.88, 18.55.

Heteroarylazepine (α-endo-59f). The product α-endo-59f was prepared according to the general procedure, starting from the mixed diastereomers 58f, and obtained as a mixture with the α-exo-epimer, α-exo-59f. It was separated by column chromatography (40:1 hexanes:EtOAc+1% Et$_3$N, 3 column volumes→40:1 hexanes:EtOAc+2% Et$_3$N, 2 column volumes→20:1 hexanes:EtOAc+2% Et$_3$N, 3 column volumes) followed by preparative TLC (20:1 hexanes:EtOAc+2% Et$_3$N) to provide a viscous, colorless oil (35.2 mg, 45%, 81% based on quantity of α-endo in starting material). $^1$H NMR (500 MHz, CDCl$_3$) δ 7.24 (d, J=8.8 Hz, 1H), 6.87 (d, J=2.5 Hz, 1H), 6.80 (dd, J=8.8, 2.5 Hz, 1H), 3.85 (s, 3H), 3.21-3.14 (m, 1H), 3.03-2.96 (m, 1H), 2.96-2.84 (m, 4H), 2.52 (dd, J=16.4, 3.6 Hz, 1H), 2.09 (t, J=12.4 Hz, 1H), 2.05-1.95 (m, 1H), 1.84 (s, 1H), 1.77-1.53 (m, 5H), 1.50-1.40 (m, 1H), 1.00 (t, J=7.3 Hz, 3H); $^{13}$H NMR (126 MHz, CDCl$_3$) δ 161.1, 155.8, 148.4, 131.5, 111.4, 110.93, 110.91, 101.8, 64.6, 56.2, 54.5, 46.1, 40.0, 34.4, 29.6, 27.7, 25.74, 24.6, 24.5, 11.7.

Heteroarylazepine (α-exo-59f). The product α-exo-59f was prepared according to the general procedure, starting from the mixed diastereomers 58f, and obtained as a mixture with the α-endo-epimer, α-endo-59f. It was separated by column chromatography (40:1 hexanes:EtOAc+1% Et$_3$N, 3 column volumes→40:1 hexanes:EtOAc+2% Et$_3$N, 2 column volumes→20:1 hexanes:EtOAc+2% Et$_3$N, 3 column volumes) followed by preparative TLC (20:1 hexanes:EtOAc+2% Et$_3$N) to provide a viscous, pale-yellow oil (18.4 mg, 24%, 54% based on quantity of α-exo in starting material). $^1$H NMR (500 MHz, CDCl$_3$) δ 7.25 (d, J=8.6 Hz, 1H), 6.87 (d, J=2.4 Hz, 1H), 6.79 (dd, J=8.8, 2.4 Hz, 1H), 3.85 (s, 3H), 3.34 (d, J=2.0 Hz, 1H), 3.27-3.22 (m, 1H), 3.19 (d, J=11.0 Hz, 1H), 3.01-2.91 (m, 2H), 2.84-2.77 (m, 1H), 2.59 (dd, J=16.0, 7.7 Hz, 1H), 2.13-2.04 (m, 1H), 1.98-1.90 (m, 1H), 1.86-1.68 (m, 4H), 1.65-1.57 (m, 1H), 1.57-1.49 (m, 2H), 0.98 (t, J=7.3 Hz, 3H); $^{13}$C NMR (126 MHz, CDCl$_3$) δ 160.3, 155.8, 148.9, 131.2, 111.2, 111.12, 111.06, 101.7, 65.0, 56.4, 56.2, 44.7, 39.0, 33.0, 29.4, 28.9, 26.6, 24.3, 23.8, 11.6.

Synthesis of Heteroarylazepines by Pd(II)-Mediated Cyclization

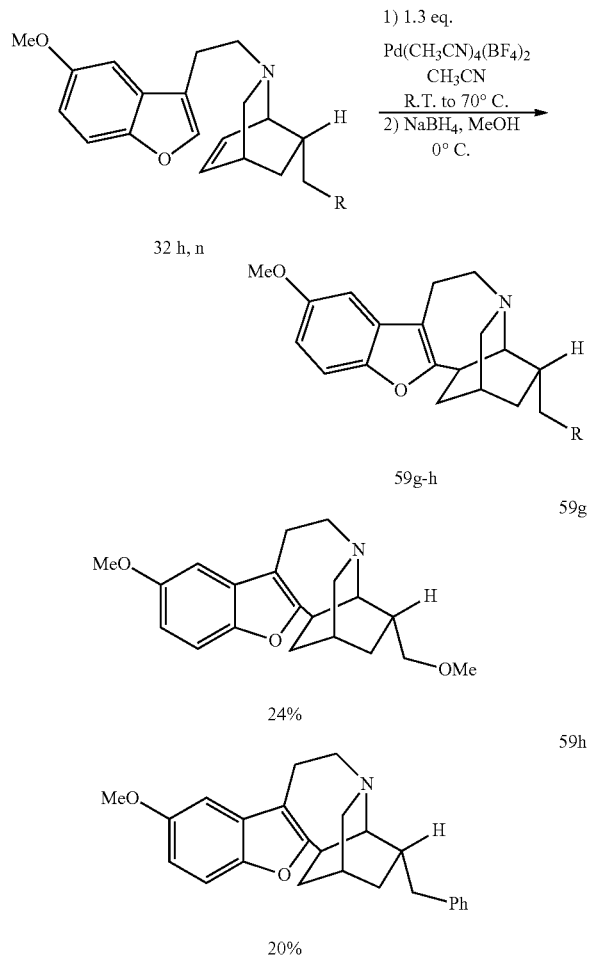

Scheme 26. Synthesis of heteroarylazepines by Pd (II) cyclization

General Procedure for Preparation of Heteroarylazepines by Pd(II) Mediated Cyclization (59g-h). In a glovebox, a Schlenk flask was charged with Pd(CH$_3$CN)$_4$(BF$_4$)$_2$ (1.3 equivalents). It was then sealed and removed from the glovebox and anhydrous CH$_3$CN (0.0929 M, based on Pd(CH$_3$CN)$_4$(BF$_4$)$_2$) was added to form a yellow solution. To this solution was added a solution of the substrate 32h or 32n (1 equivalent) in anhydrous CH$_3$CN (0.0278, M based on substrate) resulting in a color change (yellow to orange). The reaction mixture was stirred for 2 h at room temperature and then warmed to 70° C. and stirred for a further 16 h. At this time, the reaction was cooled to 0° C. and anhydrous MeOH (0.111 M, based on substrate) was added followed by NaBH$_4$ (3.2 equivalents), causing the immediate precipitation of palladium black. The resulting black mixture was stirred for 20 min. at 0° C., then diluted with Et$_2$O, filtered through celite, and the filter cake washed with additional Et$_2$O (4×). The combined filtrate and washings were concentrated to afford the crude product. This material was purified by column chromatography or preparative TLC with an appropriate solvent mixture (as described below for each compound).

Heteroarylazepine (59g). The product 59g was prepared according to the general procedure and purified by column chromatography (6:1 hexanes:EtOAc+2% Et$_3$N, 2 column volumes→4:1 hexanes:EtOAc+2% Et$_3$N, 2 column volumes→2:1 hexanes:EtOAc+2% Et$_3$N, 3 column volumes) to provide a colorless oil (23.2 mg, 24%). $^1$H NMR (400 MHz, CDCl$_3$) δ 7.28 (s, 1H), 6.90 (d, J=2.6 Hz, 1H), 6.84 (dd, J=8.8, 2.6 Hz, 1H), 3.88 (s, 3H), 3.47 (dd, J=5.2, 2.4 Hz, 1H), 3.44 (dd, J=5.2, 2.1 Hz, 1H), 3.39 (s, 3H), 3.35 (d, J=2.0 Hz, 1H), 3.34-3.31 (m, 1H), 3.29-3.27 (m, 1H), 3.26-3.23 (m, 1H), 3.13 (dt, J=9.5, 2.9 Hz, 1H), 3.09 (m, 2H), 2.57-2.48 (m, 2H), 2.02 (ddt, J=22.6, 10.9, 2.8 Hz, 1H), 1.97-1.90 (m, 1H), 1.68 (dq, J=13.4, 3.5 Hz, 1H), 1.13-1.06 (m, 1H), 0.96-0.87 (m, 1H); $^{13}$C NMR (101 MHz, CDCl$_3$) δ 161.4, 156.2, 148.7, 131.6, 112.6, 111.9, 111.3, 102.2, 76.0, 59.3, 56.5, 54.5, 53.6, 49.4, 39.8, 35.1, 34.4, 28.1, 26.3, 19.4; LR-MS calcd. for C$_{20}$H$_{26}$NO$_3^+$ [M+H]$^+$ 328.19, found 328.19.

Heteroarylazepine (59h). The product 59h was purified by column chromatography (10:1 hexanes:EtOAc+2% Et$_3$N, 2 column volumes→6:1 hexanes:EtOAc+2% Et$_3$N, 2 column volumes→2:1 hexanes:EtOAc+2% Et$_3$N, 3 column volumes) followed by preparative TLC (2:1 hexanes:EtOAc+2% Et$_3$N) and obtained as a yellow oil (20.5 mg, 20%). $^1$H NMR (400 MHz, CDCl$_3$) δ 7.32-7.24 (m, 5H), 7.23-7.18 (m, 1H), 6.89 (d, J=2.5 Hz, 1H), 6.85 (ddd, J=8.8, 2.6, 0.9 Hz, 1H), 3.88 (s, 3H), 3.52-3.47 (m, 1H), 3.43-3.37 (m, 1H), 3.27-3.19 (m, 2H), 3.13-3.08 (m, 2H), 2.82 (dd, J=3.3, 1.8 Hz, 1H), 2.76-2.72 (m, 2H), 2.54 (dtd, J=10.6, 5.9, 5.2, 3.1 Hz, 1H), 2.50-2.43 (m, 1H), 2.17 (ddt, J=14.2, 11.9, 2.6 Hz, 1H), 2.03-1.94 (m, 2H), 1.71 (dq, J=13.3, 3.5 Hz, 1H), 0.95-0.87 (m, 1H); $^{13}$C NMR (101 MHz, CDCl$_3$) δ 161.8, 156.2, 148.7, 145.4, 140.8, 131.6, 129.3, 128.9, 126.4, 112.7, 111.9, 111.5, 111.4, 102.1, 56.5, 56.3, 53.8, 49.4, 41.8, 41.7, 34.9, 34.6, 31.8, 26.8, 19.3; LR-MS calcd. for C$_{25}$H$_{28}$NO$_2^+$ [M+H]$^+$ 374.21, found 374.31.

Synthesis of Hydroxyheteroarylazepines by Demethylation

Scheme 27. Demethylation of methoxyaryl analogs

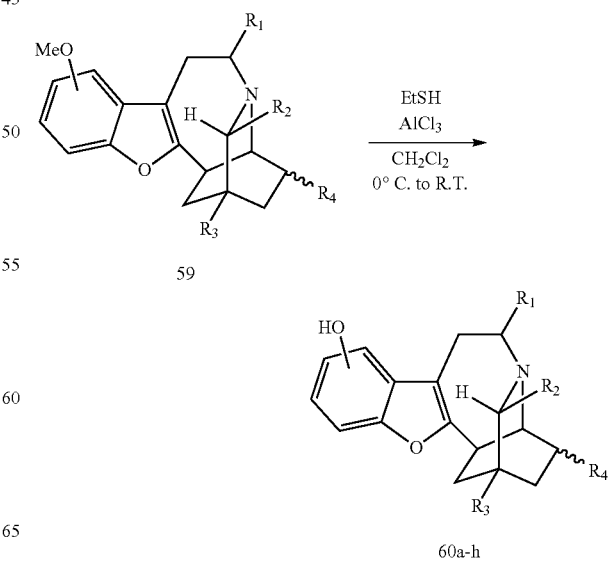

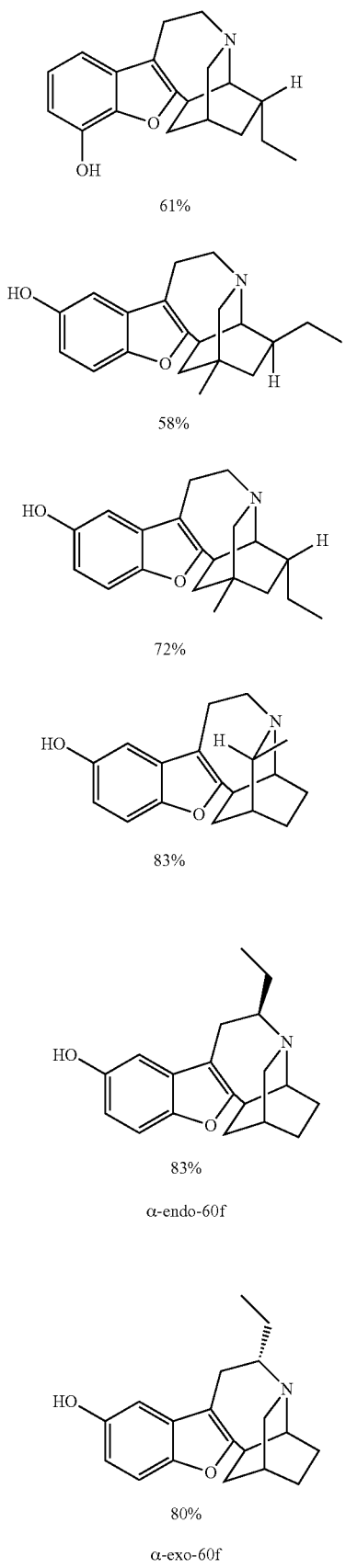

61%

58%

72%

83%

83%

α-endo-60f

80%

α-exo-60f

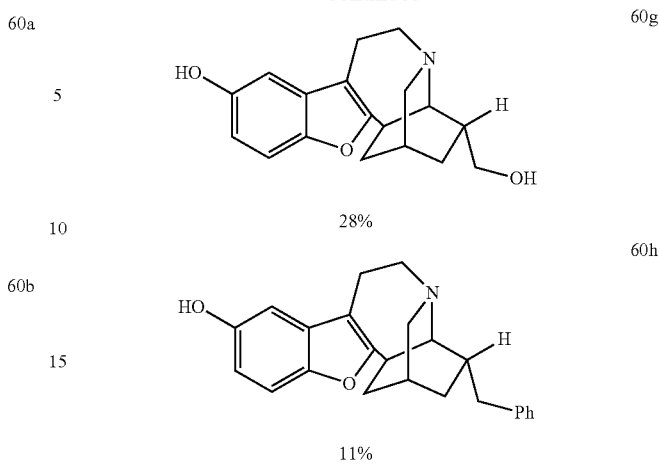

28%

11%

General Procedure for Preparation of Hydroxyheteroarylazepines by Demethylation (60). To a solution of the methoxyoxaibogamine 59 (1 equivalent) in dry dichloromethane (0.125 M, based on 59) at 0° C. was added aluminum chloride (6 equivalents) followed by ethanethiol (18 equivalents), and the resulting mixture was allowed to warm to room temperature and stirred until TLC indicated the complete consumption of starting material (typically <1.5 h). The reaction was then quenched with saturated aqueous NaHCO$_3$ (100 mL per mmol of 59) and extracted with CH$_2$Cl$_2$ (4×-6×, until no further extraction by TLC). The combined organic layers were dried over Na$_2$SO$_4$ and concentrated to provide the crude product. This material was purified by column chromatography with an appropriate solvent mixture as described below for each substrate.

Hydroxyheteroarylazepine (60a). The product 60a was prepared according to the general procedure and purified by column chromatography (10:1 hexanes:EtOAc, 2 column volumes→5:1 hexanes:EtOAc, 2 column volumes 1:1 hexanes:EtOAc, 2 column volumes) and obtained as a white foamy solid (4.9 mg, 61%). $^1$H NMR (500 MHz, CDCl$_3$) δ 7.07 (t, J=7.8 Hz, 1H), 6.94 (d, J=7.8 Hz, 1H), 6.77 (d, J=7.7 Hz, 1H), 3.46 (dt, J=14.1, 4.2 Hz, 1H), 3.43-3.36 (m, 2H), 3.28 (s, 1H), 3.16 (ddd, J=16.7, 11.7, 4.8 Hz, 1H), 3.08-3.00 (m, 2H), 2.63 (d, J=16.9 Hz, 1H), 2.22-2.16 (m, 1H), 2.07 (m, 2H), 1.96 (s, 1H), 1.66-1.61 (m, 1H), 1.44-1.35 (m, 2H), 1.14 (ddt, J=12.9, 5.4, 2.6 Hz, 1H), 0.92 (t, J=7.3 Hz, 3H); $^{13}$C NMR (126 MHz, CDCl$_3$) δ 155.4, 141.3, 123.7, 113.1, 111.0, 110.58, 108.7, 104.6, 77.6, 57.2, 54.2, 53.8, 49.5, 31.2, 28.4, 25.9, 25.9, 18.9, 12.4; LR-MS calcd. for C$_{19}$H$_{24}$NO$_2$$^+$ [M+H]$^+$ 298.18, found 298.01.

Hydroxyheteroarylazepine (60b). The product 60b was prepared according to the general procedure and purified by column chromatography (20:1 CH$_2$Cl$_2$:MeOH) to provide a pale-purple foamy solid (4.5 mg, 58%). $^1$H NMR (500 MHz, CDCl$_3$) δ 7.19 (d, J=8.6 Hz, 1H), 6.81 (d, J=2.5 Hz, 1H), 6.71 (dd, J=8.7, 2.5 Hz, 1H), 3.41 (s, 1H), 3.24-3.09 (m, 3H), 2.84 (s, 1H), 2.77-2.71 (m, 1H), 2.46 (s, 1H), 1.94 (t, J=12.4 Hz, 1H), 1.70-1.42 (m, 4H), 1.38 (dt, J=13.3, 3.2 Hz, 1H), 1.26 (d, J=7.9 Hz, 1H), 1.05 (s, 1H), 0.90 (t, J=7.0 Hz, 3H), 0.83 (s, 3H); $^{13}$C NMR (126 MHz, CDCl$_3$) δ 161.1, 151.4, 148.7, 131.7, 111.7, 111.6, 111.0, 104.1, 57.7, 55.8, 53.0, 41.0, 40.5, 39.9, 39.4, 30.1, 27.5, 25.8, 19.4, 12.0.

Hydroxyheteroarylazepine (60c). The product 60c was prepared according to the general procedure and purified by column chromatography (10:1 CH$_2$Cl$_2$:MeOH) to provide a white foamy solid (50.1 mg, 72%). $^1$H NMR (500 MHz, CDCl$_3$) δ 7.18 (d, J=8.6 Hz, 1H), 6.82 (d, J=2.5 Hz, 1H), 6.75 (dd, J=8.7, 2.5 Hz, 1H), 3.47-3.28 (m, 3H), 3.17-3.06 (m, 1H), 3.03 (s, 1H), 2.96 (dd, J=10.5, 3.1 Hz, 1H), 2.75 (dd, J=10.1, 2.6 Hz, 1H), 2.54 (d, J=17.3, 3.4 Hz, 1H), 2.15 (s, 1H), 1.98-1.88 (m, 1H), 1.88-1.79 (m, 1H), 1.43-1.31 (m, 3H), 1.00-0.94 (m, 1H), 0.92 (t, J=7.3 Hz, 3H), 0.86 (s, 3H); $^{13}$C NMR (126 MHz, CDCl$_3$) δ 160.4, 152.2, 148.2, 131.0, 112.4, 111.9, 111.1, 104.1, 57.3, 55.1, 53.6, 40.4, 39.9, 38.4, 32.9, 29.7, 28.1, 25.6, 18.5, 12.1.

Hydroxyheteroarylazepine (60d). The product 60d was prepared according to the general procedure and purified by column chromatography (20:1 CH$_2$Cl$_2$:MeOH, 2 column volumes→20:1 acetone:MeOH, 4 column volumes) to provide a white solid (7.7 mg, 83%). $^1$H NMR (400 MHz, CDCl$_3$+several drops MeOD) δ 7.15 (d, J=8.7 Hz, 1H), 6.77 (d, J=2.5 Hz, 1H), 6.69 (dd, J=8.6, 2.5 Hz, 1H), 3.54-3.44 (m, 1H), 3.18-3.03 (m, 4H), 3.01 (s, 1H), 2.49-2.37 (m, 1H), 2.19-2.10 (m, 1H), 1.99-1.82 (m, 2H), 1.73-1.66 (m, 1H), 1.62-1.53 (m, 2H), 1.46-1.36 (m, 1H), 1.13 (d, J=6.3 Hz, 3H); $^{13}$C NMR (101 MHz, CDCl$_3$+several drops MeOD) δ 160.8, 152.0, 148.2, 131.4, 111.7, 111.5, 110.8, 103.8, 54.6, 52.0, 51.1, 39.0, 35.5, 30.9, 28.7, 19.0, 18.5, 18.40.

Hydroxyheteroarylazepine (α-endo-60f). The product α-endo-60f was prepared according to the general procedure and purified by column chromatography (20:1 CH$_2$Cl$_2$:MeOH, 2 column volumes→20:1 acetone:MeOH, 2 column volumes) to provide a foamy white solid (24.7 mg, 83%). $^1$H NMR (400 MHz, CDCl$_3$) δ 7.19 (d, J=8.6 Hz, 1H), 6.82 (d, J=2.5 Hz, 1H), 6.70 (dd, J=8.6, 2.5 Hz, 1H), 4.72 (br s, 1H), 3.16 (dt, J=11.5, 2.7 Hz, 1H), 3.05-2.78 (m, 5H), 2.49 (dd, J=16.6, 3.7 Hz, 1H), 2.15-2.02 (m, 2H), 1.84 (s, 1H), 1.80-1.71 (m, 1H), 1.71-1.55 (m, 4H), 1.50-1.37 (m, 1H), 0.98 (t, J=7.3 Hz, 3H); $^{13}$C NMR (101 MHz, CDCl$_3$) δ 161.2, 151.4, 148.4, 131.9, 111.5, 110.9, 110.6, 104.1, 64.8, 54.5, 46.2, 39.8, 34.3, 29.3, 27.7, 25.6, 24.4, 24.2, 11.7.

Hydroxyheteroarylazepine (α-exo-60f). The product α-exo-60f was prepared according to the general procedure and purified by column chromatography (20:1 CH$_2$Cl$_2$:MeOH, 2 column volumes→20:1 acetone:MeOH, 4 column volumes) to provide a foamy white solid (13.2 mg, 80%). $^1$H NMR (400 MHz, CDCl$_3$) δ 7.20 (d, J=8.6 Hz, 1H), 6.82 (d, J=2.5 Hz, 1H), 6.70 (dd, J=8.6, 2.6 Hz, 1H), 4.60 (br s, 1H), 3.36 (d, J=1.9 Hz, 1H), 3.31-3.24 (m, 1H), 3.21-3.13 (m, 1H), 2.99-2.90 (m, 2H), 2.86-2.77 (m, 1H), 2.56 (dd, J=16.1, 7.4 Hz, 1H), 2.16-2.06 (m, 1H), 2.04-1.92 (m, 1H), 1.86-1.67 (m, 4H), 1.65-1.48 (m, 3H), 0.95 (t, J=7.4 Hz, 3H); $^{13}$C NMR (101 MHz, CDCl$_3$) δ 160.4, 151.5, 148.9, 131.5, 111.5, 111.04, 110.98, 104.0, 65.4, 56.0, 45.1, 38.6, 32.9, 29.1, 28.4, 26.4, 24.1, 23.3, 11.7.

Hydroxyheteroarylazepine (60g). The product 60g was prepared according to the general procedure and purified by column chromatography (5% MeOH in CH$_2$Cl$_2$, 2 column volumes→10% MeOH in CH$_2$Cl$_2$, 2 column volumes→20% MeOH in CH$_2$Cl$_2$, 2 column volumes) to provide an off-white solid (5 mg, 28%). $^1$H NMR (500 MHz, Methanol-d4) δ 7.13 (d, J=8.7 Hz, 1H), 6.79 (d, J=2.5 Hz, 1H), 6.67 (dd, J=8.7, 2.5 Hz, 1H), 3.58 (dd, J=11.2, 6.4 Hz, 1H), 3.50 (dd, J=11.2, 9.8 Hz, 1H), 3.41-3.35 (m, 2H), 3.17-3.11 (m, 2H), 3.07-3.03 (m, 1H), 2.55 (dt, J=16.8, 3.2 Hz, 1H), 2.38 (td, J=9.0, 8.6, 4.1 Hz, 1H), 2.06 (ddt, J=14.3, 12.0, 2.7 Hz, 1H), 1.91 (h, J=3.1 Hz, 1H), 1.89-1.84 (m, 1H), 1.63 (dq, J=13.4, 3.6 Hz, 1H), 1.11 (ddt, J=13.0, 4.7, 2.5 Hz, 1H), 0.89 (m, 2H); $^{13}$C NMR (126 MHz, CDCl$_3$) δ 161.6, 154.0, 149.4, 132.3, 112.9, 111.5, 111.0, 104.5, 65.3, 55.3, 54.7, 49.9, 42.3, 34.7, 34.5, 28.1, 26.9, 19.4; LR-MS calcd. for C$_{18}$H$_{22}$NO$_3^+$ [M+H]$^+$ 300.16, found 300.27.

Hydroxyheteroarylazepine (60h). The product 60h was prepared according to the general procedure and purified by column chromatography (10:1 hexanes:EtOAc, 2 column volumes→5:1 hexanes:EtOAc, 2 column volumes→2:1 hexanes:EtOAc, 2 column volumes) to provide an off-white solid (2 mg, 11%). $^1$H NMR (500 MHz, CDCl$_3$) δ 7.22 (m, 5H), 7.20 (m, 1H), 6.82-6.78 (m, 1H), 6.72-6.68 (m, 1H), 3.87-3.83 (m, 1H), 3.48-3.43 (m, 1H), 3.40-3.33 (m, 2H), 3.27-3.19 (m, 2H), 3.05 (s, 1H), 2.78 (s, 1H), 2.72-2.67 (m, 2H), 2.50 (s, 1H), 2.41-2.36 (m, 1H), 2.17-2.11 (m, 1H), 2.05-1.99 (m, 1H), 1.92 (s, 1H), 0.72 (t, J=7.7 Hz, 2H); LR-MS calcd. for C$_{24}$H$_{26}$NO$_2^+$ [M+H]$^+$ 360.20, found 360.38.

EXAMPLE 18

Biological Data of Additional Heteroarylazepines

TABLE 5

Data represents mean EC$_{50}$ of various independent trials. For compounds active as antagonists, IC$_{50}$ for inhibition of a reference antagonist is provided. "—" indicates not active as agonist at 100 micromolar. 60a was not active as agonist at 100 micromolar.

| Compound | Structure | Human KOR | Human MOR | Human DOR |
|---|---|---|---|---|
| 60b | 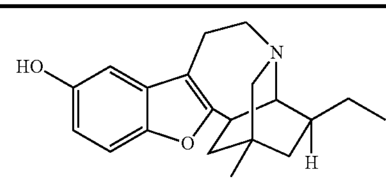 | <10 μM | <10 μM | <10 μM |
| 60c | 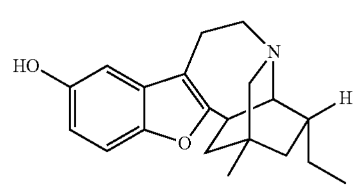 [SMILES: CCC1CC2(C)CC3c4oc5ccc(O)cc5c4CCN(C2)C13] | <10 μM | <10 μM | >10 μM |

TABLE 5-continued

Data represents mean EC$_{50}$ of various independent trials. For compounds active as antagonists, IC$_{50}$ for inhibition of a reference antagonist is provided. "—" indicates not active as agonist at 100 micromolar. 60a was not active as agonist at 100 micromolar.

| Compound | Structure | Human KOR | Human MOR | Human DOR |
| --- | --- | --- | --- | --- |
| 60d | 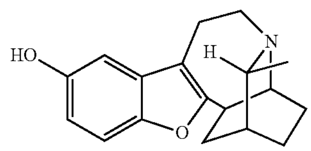 [SMILES: CC1C2CCC3C(C2)c2oc4ccc(O)cc4c2CCN13] | <10 μM | <10 μM | — |
| α-exo-60f | 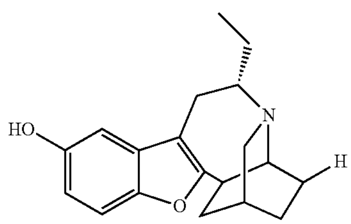 [SMILES: CC[C@H]1Cc2c(oc3ccc(O)cc23)C2CC3CCC2N1C3] | <10 μM | <10 μM | <10 μM |
| α-endo-60f | 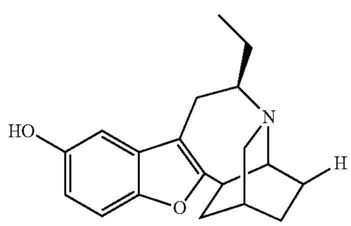 [SMILES: CC[C@@H]1Cc2c(oc3ccc(O)cc23)C2CC3CCC2N1C3] | >10 μM | — | — |
| 60g | 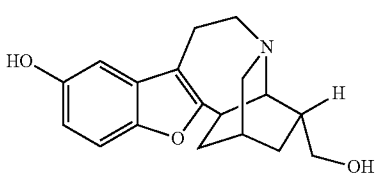 [SMILES: OCC1CC2CC3c4oc5ccc(O)cc5c4CCN(C2)C13] | <10 μM | >10 μM | >10 μM |
| 60h | 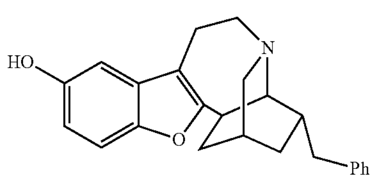 [SMILES: Oc1ccc2oc3c(c2c1)CCN1CC2CC(Cc4ccccc4)C1C3C2] | >10 μM | >10 μM | >10 μM |
| 59g | 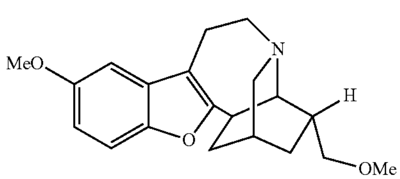 [SMILES: COCC1CC2CC3c4oc5ccc(OC)cc5c4CCN(C2)C13] | <10 μM | — | — |
| 51b | 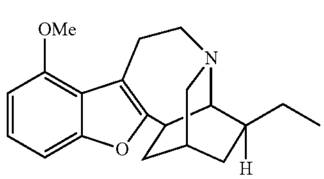 [SMILES: CCC1CC2CC3c4oc5cccc(OC)c5c4CCN(C2)C13] | >10 μM | >10 μM | — |
| 51c | 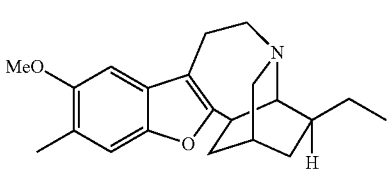 [SMILES: CCC1CC2CC3c4oc5cc(C)c(OC)cc5c4CCN(C2)C13] | >10 μM | >10 μM | >10 μM |

EXAMPLE 19

Activity of Additional Analogs

An additional aspect of the invention provides analogs of the compounds of Table 3 that are KOR, DOR and MOR agonists. Additional benzofuran, benzothiophene and benzimidazole compounds are tested in in vitro human KOR, DOR and MOR assays. These analogs agonize KOR, DOR and/or MOR activity.

An additional aspect of the invention provides analogs of the compounds of Table 4 that are KOR, DOR and MOR agonists. Additional benzofuran, benzothiophene and benzimidazole compounds are tested in in vitro human KOR, DOR and MOR assays. These analogs agonize KOR, DOR and/or MOR activity.

An additional aspect of the invention provides analogs of the compounds of Table 5 that are KOR, DOR and MOR agonists. Additional benzofuran, benzothiophene and benzimidazole compounds are tested in in vitro human KOR, DOR and MOR assays. These analogs agonize KOR, DOR and/or MOR activity.

An additional aspect of the invention provides analogs of the compounds of Table 3 that are KOR, DOR and MOR antagonists. Additional benzofuran, benzothiophene and benzimidazole compounds are tested in in vitro human KOR, DOR and MOR assays. These analogs antagonize KOR, DOR and/or MOR activity.

An additional aspect of the invention provides analogs of the compounds of Table 4 that are KOR, DOR and MOR antagonists. Additional benzofuran, benzothiophene and benzimidazole compounds are tested in in vitro human KOR, DOR and MOR assays. These analogs antagonize KOR, DOR and/or MOR activity.

An additional aspect of the invention provides analogs of the compounds of Table 5 that are KOR, DOR and MOR antagonists. Additional benzofuran, benzothiophene and benzimidazole compounds are tested in in vitro human KOR, DOR and MOR assays. These analogs antagonize KOR, DOR and/or MOR activity.

EXAMPLE 20

Administration of KOR, DOR and MOR Agonists

An amount of any one of compounds of Table 3 is administered to a subject afflicted with depression or major depression. The amount of the compound is effective to treat the subject afflicted with depression or major depression.

An amount of any one of compounds of Table 3 is administered to a subject afflicted with pain. The amount of the compound is effective to treat the subject afflicted with pain.

An amount of any one of compounds of Table 3 is administered to a subject afflicted with an anxiety disorder. The amount of the compound is effective to treat the subject afflicted with the anxiety disorder.

An amount of any one of compounds of Table 3 is administered to a subject afflicted with obsessive-compulsive disorder (OCD). The amount of the compound is effective to treat the subject afflicted with obsessive-compulsive disorder (OCD).

An amount of any one of compounds of Table 3 is administered to a subject afflicted with a stress disorder. The amount of the compound is effective to treat the subject afflicted with the stress disorder.

An amount of any one of compounds of Table 4 is administered to a subject afflicted with depression or major depression. The amount of the compound is effective to treat the subject afflicted with depression or major depression.

An amount of any one of compounds of Table 4 is administered to a subject afflicted with pain. The amount of the compound is effective to treat the subject afflicted with pain.

An amount of any one of compounds of Table 4 is administered to a subject afflicted with an anxiety disorder. The amount of the compound is effective to treat the subject afflicted with the anxiety disorder.

An amount of any one of compounds of Table 4 is administered to a subject afflicted with obsessive-compulsive disorder (OCD). The amount of the compound is effective to treat the subject afflicted with obsessive-compulsive disorder (OCD).

An amount of any one of compounds of Table 4 is administered to a subject afflicted with a stress disorder. The amount of the compound is effective to treat the subject afflicted with the stress disorder.

An amount of any one of compounds of Table 5 is administered to a subject afflicted with depression or major depression. The amount of the compound is effective to treat the subject afflicted with depression or major depression.

An amount of any one of compounds of Table 5 is administered to a subject afflicted with pain. The amount of the compound is effective to treat the subject afflicted with pain.

An amount of any one of compounds of Table 5 is administered to a subject afflicted with an anxiety disorder. The amount of the compound is effective to treat the subject afflicted with the anxiety disorder.

An amount of any one of compounds of Table 5 is administered to a subject afflicted with obsessive-compulsive disorder (OCD). The amount of the compound is effective to treat the subject afflicted with obsessive-compulsive disorder (OCD).

An amount of any one of compounds of Table 5 is administered to a subject afflicted with a stress disorder. The amount of the compound is effective to treat the subject afflicted with the stress disorder.

Discussion

The present invention describes a novel class of heteroarylazepines which are active as modulators of the MOR, DOR, and KOR. The new compounds are structurally and pharmacologically distinct from known opiates. Therefore, they are potentially useful as analgesics with reduced side-effects compared to existing treatments, or as anti-addictive agents. Further, they are useful as antidepressants and anxiolytics, either through direct action or via indirect modulation of glutamate signaling. This invention also describes novel synthetic methods that may be used to access, modify, and encompass chemical space around the heteroarylazepine core structure of the new compounds.

This present invention describes a novel class of heteroarylazepines effective as modulators of opioid receptor activity with submicromolar to micromolar potency. Collectively, the new compounds are full agonists, partial agonists, or antagonists at one or more of the three opioid receptors (MOR, DOR, and/or KOR). The compounds disclosed herein activate MOR, DOR, or KOR, dually activate any of the two receptors, or concomitantly activate all three. Therefore, they are useful as analgesics or as anti-addictive agents. Furthermore, this activity leads to modulation of glutamatergic neurons and signaling, thereby triggering antidepressant and anxiolytic effects. Accordingly, the compounds disclosed herein are also useful as antidepressants and axiolytics.

An additional aspect of the invention provides synthetic methods and chemical intermediates that may be used to access, modify, or encompass chemical space around the polycyclic heteroarylazepine core structure described. The new C—H bond activation methods presented, using Ni(0) and Pd(II) reagents, allow for rapid construction of the polycyclic core of the present compounds by direct formation of the central 7-membered ring. This is a powerful synthetic approach to this structural class and allows for modular and convergent synthesis of a variety of analogs from a diverse set of substituted isoquinuclidines and heteroarylethylhalides. Further, the described methods represent an improvement over existing methodology. Although there are a number of catalytic systems that effect hydroarylation of unactivated alkenes, most of them failed in the specific context of this cyclization. Additional compounds may be synthesized according to the protocols described in Schemes 1-13, and possess analogous biological activity and function to the compounds disclosed in Table 3. Additional compounds may be synthesized according to the protocols described in Schemes 14-27, and possess analogous biological activity and function to the compounds disclosed in Tables 4 and 5.

REFERENCES

Artman, G. D., III; Grubbs, A. W.; Williams, R. M. *J. Am. Chem. Soc.* 2007, 129, 6336-6342 and references cited therein.

Baran, P. S.; Guerrero, C. A.; Corey, E. J. *J. Am. Chem. Soc.* 2003, 125, 5628-5629.

Besson, A.; Privat, A. M.; Eschalier, A.; Fialip, *J. Psychopharmacology* 1996, 123, 71-78.

Bolli, M. et al. (Actelion Pharmaceuticals) Novel pyrazole and imidazole derivatives useful as orexin antagonists. International Patent Application WO 2012/110986 A1, Published: Aug. 23, 2012.

Borne, R. F.; Clark, C. R.; Holbrook, J. M. *J. Med. Chem.* 1973, 16, 853-856.

Campaigne, E.; Neiss, E. S.; Pfeiffer, C. C.; Beck, R. A. *J. Med. Chem.* 1968, 11, 1049-1054.

Chan, J. H-T.; Elix, J. A.; Ferguson, B. A. *Aust. J. Chem.* 1975, 28, 1097-1111.

Chavkin, C. *Neuropsychopharmacology* 2011, 36, 369-370.

Corbett, A. D.; Henderson, G.; McKnight, A. T.; Paterson, S. J.; *Brit. J. Pharmacol.* 2006, 147, S153-S162.

Fujiwara, Y.; Noritani, I.; Danno, S.; Asano, R.; Teranishi, S. *J. Am. Chem. Soc.* 1969, 91, 7166-7169.

Hammond, M. L. et al. *J. Med. Chem.* 1990, 33, 908-918.

Hatzenbuhler, N. T. et al. 3-Amino Choman and 2-Amino Tetralin Derivatives. International Patent Application WO 2005/012291 A1, Published: Feb. 10, 2005.

Hodgson, D. M.; Galano, J-M. *Org. Lett.* 2005, 7, 2221-2224.

Hough, L. B.; Pearl, S. M.; Glick, S. D. *Life Sci.* 1996, 58, PL119-122.

Jutkiewicz, E. M. *Mol. Interv.* 2006, 6, 162-169.

Kozikowski, A. P. et al. *J. Am. Chem. Soc.* 2007, 129, 8328-8332.

Krow, G. R.; Shaw, D. A.; Lynch, B.; Lester, W.; Szczepanski, S. W.; Raghavachari, R. *J. Org. Chem.* 1988, 53, 2258-2262 and references cited therein.

Krow, G. R.; Huang, Q.; Szczepanski, S. W.; Hausheer, F. H.; Carroll, P. J. *J. Org. Chem.* 2007, 72, 3458-3466.

Liu, C.; Bender, C. F.; Han, X.; Widenhoefer, R. A. *Chem. Commun.* 2007, 3607-3618.

Mariano, P. S.; Dunaway-Mariano, D.; Huesmann, P. L. *J. Org. Chem.* 1979, 44, 124-133.

Martins, A.; Lautens, M. *J. Org. Chem.* 2008, 73, 8705-8710.

Mejia-Oneto, J. M.; Padwa, A. *Org. Lett.,* 2004, 6, 3241-3244.

Nakano, H.; Osone, K.; Takeshita, M.; Kwon, E.; Seki, C.; Matsuyama, H.; Takano, N.; Kohari, Y. *Chem. Commun.* 2010, 46, 4827-4829.

Negri, A.; Rives, M.-L.; Caspers, M. J.; Prisinzano, T. E.; Javitch, J. a; Filizola, M. *J. Chem. Inf. Model.* 2013, 53, 521-526.

Negus, S. S.; Mello, N. K.; Portoghese, P. S.; Lin, C. E. *J. Pharmacol. Exp. Ther.* 1997, 282, 44-55.

Pearson, J. R.; Porter, Q. N. *Aust. J. Chem.* 1991, 44, 907-917.

Paul, I. A.; Skolnick, P. *Ann. N. Y. Acad. Sci.* 2003, 1003, 250-272.

Rozenman, M. M.; Kanan, K. M.; Liu, D. R. *J. Am. Chem. Soc.* 2007, 129, 14933-14938.

Rives M-L, Rossillo M, Liu-Chen L-Y, Javitch J A. 6'-Guanidinonaltrindole (6'-GNTI) is a G protein-biased κ-opioid receptor agonist that inhibits arrestin recruitment. J Biol Chem 2012; 287: 27050-27054.

Schenk, S.; Partridge, B.; Shippenberg, T. S. *Psychopharmacology* 2000, 151, 85-90.

Svoboda, K. R.; Adams, C. E.; Lupica, C. R.; *J Neurosci.* 1999, 19, 85-95.

Trost, B. M.; Godleski, S. A.; Genêt, J. P. *J. Am. Chem. Soc.* 1978, 100, 3930-3931.

Trost, B. M.; Godleski, S. A.; Belletire, J. L. *J. Org. Chem.* 1979, 44, 2052-2054.

Trost, B. M.; Fortunak, J. M. *Organometallics* 1982, 1, 7-13.

Wang, M-Z.; Wong, M-K.; Che, C-M. *Chem. Eur. J.* 2008, 14, 8353-8364.

Williams, J. T.; Ingram, S. L.; Henderson, G.; Chavkin, C.; von Zastrow, M.; Schultz, S.; Koch, T.; Evans, C. J.; Christie, M. *J. Pharmacol. Rev.* 2013, 65, 223-254.

Xie, C. W., Lewis D. V. *J Neurophysiol* 1997, 78: 759-766.

Youn, S. W.; Pastine, S. J.; Sames, D. *Org. Lett.* 2004, 6, 581-584.

Zarate, C. A. Jr; Singh, J. B.; Carlson, P. J.; Brutsche, N. E.; Ameli, R.; Luckenbaugh, D. A.; Charney, D. S.; Manji, H. K. *Arch. Gen. Psychiatry* 2006, 63, 856-864.

Zhao, X.; Yu, Z.; Xu, T.; Wu, P.; Yu, H. *Org. Lett.* 2007, 9, 5263-5266.

What is claimed is:

1. A compound having the structure:

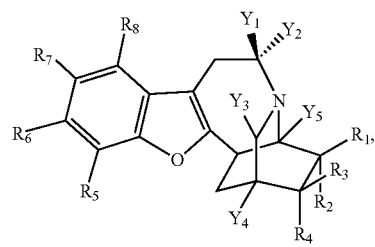

wherein
Y$_1$ is H, -(alkyl), -(alkenyl), -(alkynyl), —(C$_3$-C$_5$ cycloalkyl), -(haloalkyl), -(alkyl)-O-(alkyl) or -(alkyl)-(C$_3$-C$_5$cycloalkyl);
Y$_2$ is H, -(alkyl), -(alkenyl), -(alkynyl), —(C$_3$-C$_5$cycloalkyl), -(haloalkyl), -(alkyl)-O-(alkyl) or -(alkyl)-(C$_3$-C$_5$cycloalkyl);
Y$_3$ is H, -(alkyl), -(alkenyl), -(alkynyl), —(C$_3$-C$_5$cycloalkyl), -(haloalkyl), -(alkyl)-O-(alkyl) or -(alkyl)-(C$_3$-C$_5$cycloalkyl);
Y$_4$ is H, -(alkyl), -(alkenyl), -(alkynyl), —(C$_3$-C$_5$cycloalkyl), -(haloalkyl), -(alkyl)-O-(alkyl) or -(alkyl)-(C$_3$-C$_5$cycloalkyl);
Y$_5$ is H, -(alkyl), -(alkenyl), -(alkynyl), —(C$_3$-C$_5$cycloalkyl), -(haloalkyl), -(alkyl)-O-(alkyl) or -(alkyl)-(C$_3$-C$_5$cycloalkyl);
R$_1$, R$_2$, R$_3$ and R$_4$ are each independently —H, -(alkyl), -(alkenyl), -(alkynyl), -(haloalkyl), —(C$_3$-C$_5$ cycloalkyl), -(phenyl), -(heteroalkyl), -(hydroxyalkyl), benzyl, -(alkyl)-(C$_3$-C$_5$ cycloalkyl), -(alkyl)-OH, -(alkyl)-O-(alkyl), —OH, —NH$_2$, —OAc, —CN, OCF$_3$, halogen, C(O)—NH$_2$, —C(O)—NH-(alkyl), C(O)—NH-(phenyl), —O-alkyl, —O-alkenyl, —O-alkynyl, —O-phenyl, —NH-alkyl, —NH— alkenyl, —NH-alkynyl, —NH-phenyl, or —C(O)—N(alkyl)$_2$; and
R$_5$, R$_6$, R$_7$, R$_8$ are each independently —H, —CN, —CF$_3$, —OCF$_3$, -(alkyl), -(alkenyl), -(alkynyl), -(phenyl), -(heteroalkyl), -(hydroxyalkyl), —NH$_2$, —NH-(alkyl), —NH-(alkenyl), —NH-(alkynyl), —NH-(phenyl), —OH, —OAc, —CO$_2$H, —CO$_2$-(alkyl), —O—C(O)(alkyl), —O-(alkyl), —O-(alkenyl), —O-(alkynyl), —O-(phenyl), C(O)—NH$_2$, C(O)—NH-(alkyl), or C(O)—NH-(phenyl),
or an enantiomer, racemic mixture, or a pharmaceutically acceptable salt thereof.

2. The compound of claim 1, wherein
Y$_1$ is H, -(alkyl), -(alkenyl), -(alkynyl), —(C$_3$-C$_5$ cycloalkyl) or -(alkyl)-(C$_3$-C$_5$cycloalkyl);
Y$_2$ is H, -(alkyl), -(alkenyl), -(alkynyl), —(C$_3$-C$_5$ cycloalkyl) or -(alkyl)-(C$_3$-C$_5$cycloalkyl);
Y$_3$ is H, -(alkyl), -(alkenyl), -(alkynyl), —(C$_3$-C$_5$ cycloalkyl) or -(alkyl)-(C$_3$-C$_5$cycloalkyl);
Y$_4$ is H, -(alkyl), -(alkenyl), -(alkynyl), —(C$_3$-C$_5$ cycloalkyl) or -(alkyl)-(C$_3$-C$_5$cycloalkyl);
Y$_5$ is H, -(alkyl), -(alkenyl), -(alkynyl), —(C$_3$-C$_5$ cycloalkyl) or -(alkyl)-(C$_3$-C$_5$ cycloalkyl); and
R$_1$, R$_2$, R$_3$ and R$_4$ are each independently H, -(alkyl), -(alkenyl), -(alkynyl), -(phenyl), -(heteroalkyl), -(hydroxyalkyl), benzyl, -(alkyl)-OH, -(alkyl)-O-(alkyl), —OH or —NH$_2$.

3. The compound of claim 1, wherein
Y$_1$, Y$_2$, Y$_3$, Y$_4$ and Y$_5$ are each H; and
R$_1$, R$_2$, R$_3$ and R$_4$ are each independently H, -(alkyl), -(alkenyl), -(alkynyl), -(phenyl), -(heteroalkyl), -(hydroxyalkyl), benzyl, -(alkyl)-OH, -(alkyl)-O-(alkyl), —OH or —NH$_2$.

4. The compound of claim 1 having the structure:

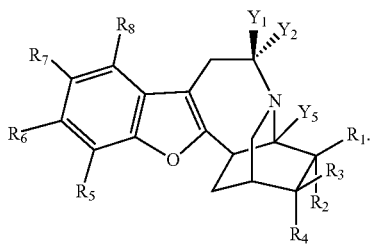

5. The compound of claim 1 having the structure:

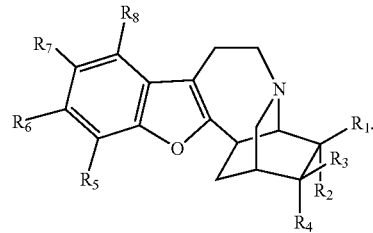

6. The compound of claim 1,
wherein R$_1$ is —H and R$_2$ is -(alkyl), -(alkenyl), -(alkynyl), -(phenyl), -(alkyl)-OH, benzyl, -(alkyl)-O-(alkyl), —OH or —NH$_2$, or
wherein R$_2$ is —H and R$_1$ is -(alkyl), -(alkenyl), -(alkynyl), -(phenyl), -(alkyl)-OH, benzyl, -(alkyl)-O-(alkyl), —OH or —NH$_2$.

7. The compound of claim 1,
wherein R$_3$ is —H and R$_4$ is -(alkyl), -(alkenyl), -(alkynyl), -(phenyl), -(alkyl)-OH, benzyl, -(alkyl)-O-(alkyl), —OH or —NH$_2$, or
wherein R$_4$ is —H and R$_3$ is -(alkyl), -(alkenyl), -(alkynyl), -(phenyl), -(alkyl)-OH, benzyl, -(alkyl)-O-(alkyl), —OH or —NH$_2$.

8. The compound of claim 6,
wherein R$_3$ and R$_4$ are each —H.

9. The compound of claim 7,
wherein R$_1$ and R$_2$ are each —H.

10. The compound of claim 1,
wherein R$_1$, R$_2$, R$_3$ and R$_4$ are each —H.

11. The compound of claim 1,
wherein R$_5$, R$_6$, R$_7$ and R$_8$ are each —H.

12. The compound of claim 1,
wherein R$_5$, R$_6$ and R$_7$ are each —H and R$_8$ is —CN, —CF$_3$, —OCF$_3$, -(alkyl), -(alkenyl), -(alkynyl), -(phenyl), —NH$_2$, —NH-(alkyl), —NH-(alkenyl), —NH-(alkynyl), —NH-(phenyl), —OH, —OAc, —O—C(O)(alkyl), —O-(alkyl), —O-(alkenyl), —O-(alkynyl) or —O-(phenyl); or
wherein R$_5$, R$_6$ and R$_8$ are each —H and R$_7$ is —CN, —CF$_3$, —OCF$_3$, -(alkyl), -(alkenyl), -(alkynyl), -(phenyl), —NH$_2$, —NH-(alkyl), —NH-(alkenyl), —NH-(alkynyl), —NH-(phenyl), —OH, —OAc, —O—C(O)(alkyl), —O-(alkyl), —O-(alkenyl), —O-(alkynyl), or —O-(phenyl); or
wherein R$_5$, R$_7$ and R$_8$ are each —H and R$_6$ is —CN, —CF$_3$, —OCF$_3$, -(alkyl), -(alkenyl), -(alkynyl), -(phenyl), —NH$_2$, —NH-(alkyl), —NH-(alkenyl), —NH-(alkynyl), —NH-(phenyl), —OH, —OAc, —O—C(O)(alkyl), —O-(alkyl), —O-(alkenyl), —O-(alkynyl) or —O-(phenyl); or
wherein R$_6$, R$_7$ and R$_8$ are each —H and R$_5$ is —CN, —CF$_3$, —OCF$_3$, -(alkyl), -(alkenyl), -(alkynyl), -(phenyl), —NH$_2$, —NH-(alkyl), —NH-(alkenyl), —NH-(alkynyl), —NH-(phenyl), —OH, —OAc, —O—C(O)(alkyl), —O-(alkyl), —O-(alkenyl), —O-(alkynyl) or —O-(phenyl); or
wherein R$_5$ and R$_8$ are each —H and R$_6$ and R$_7$ are each independently —CN, —CF$_3$, —OCF$_3$, -(alkyl), -(alkenyl), -(alkynyl), -(phenyl), —NH$_2$, —NH-(alkyl), —NH-(alkenyl), —NH-(alkynyl), —NH-(phenyl), —OH, —OAc, —O—C(O)(alkyl), —O-(alkyl), —O-(alkenyl), —O-(alkynyl) or —O-(phenyl).

13. The compound of claim 1 having the structure:
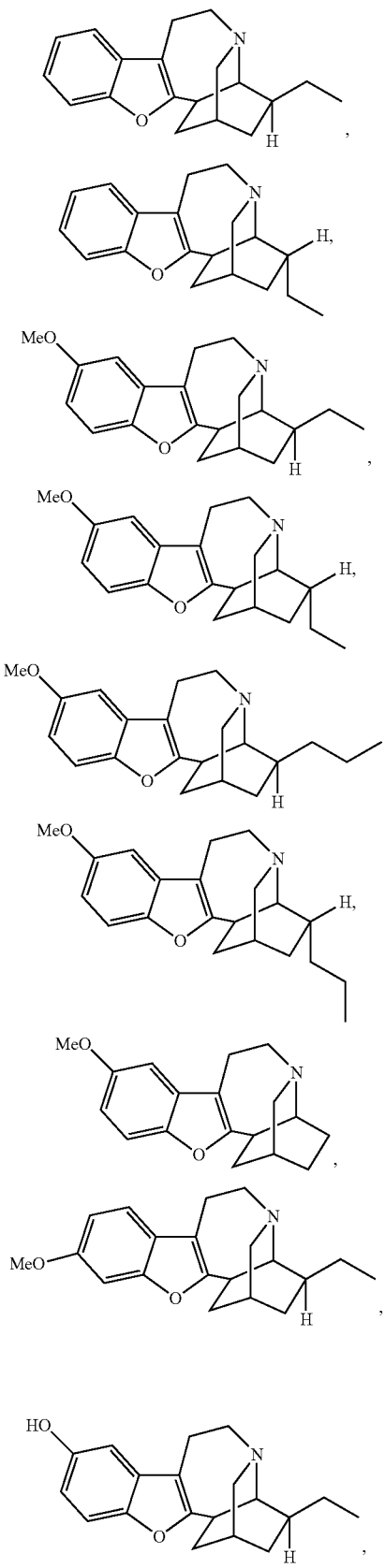
-continued
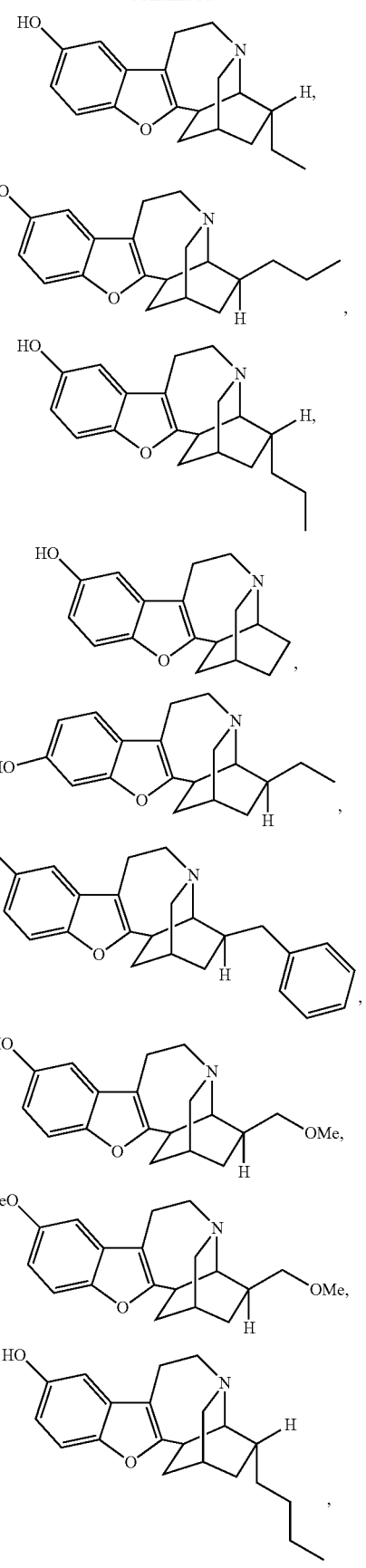

-continued
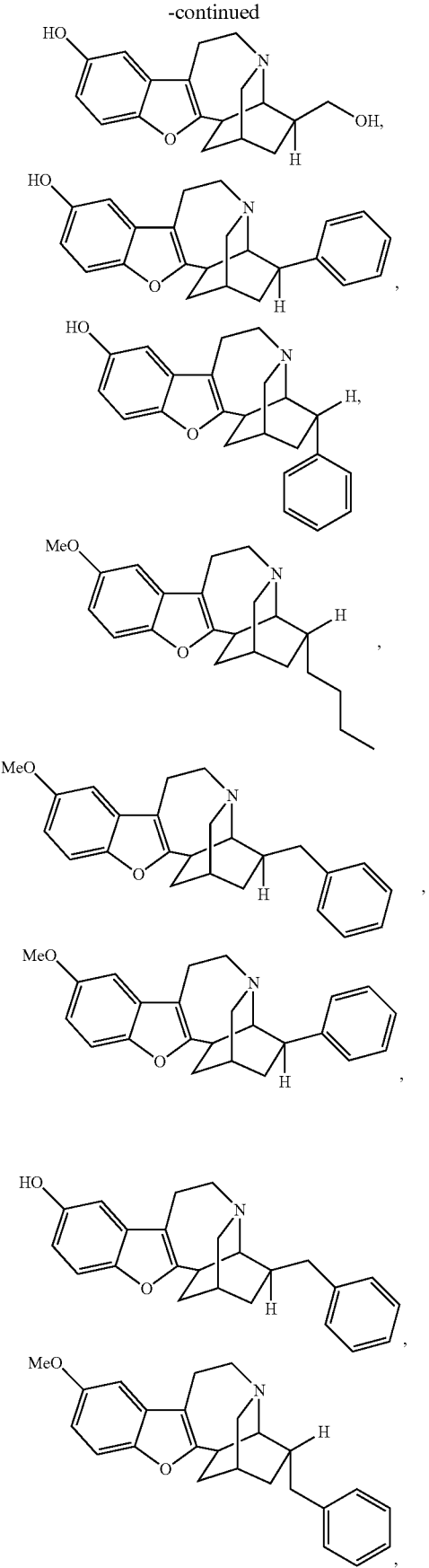
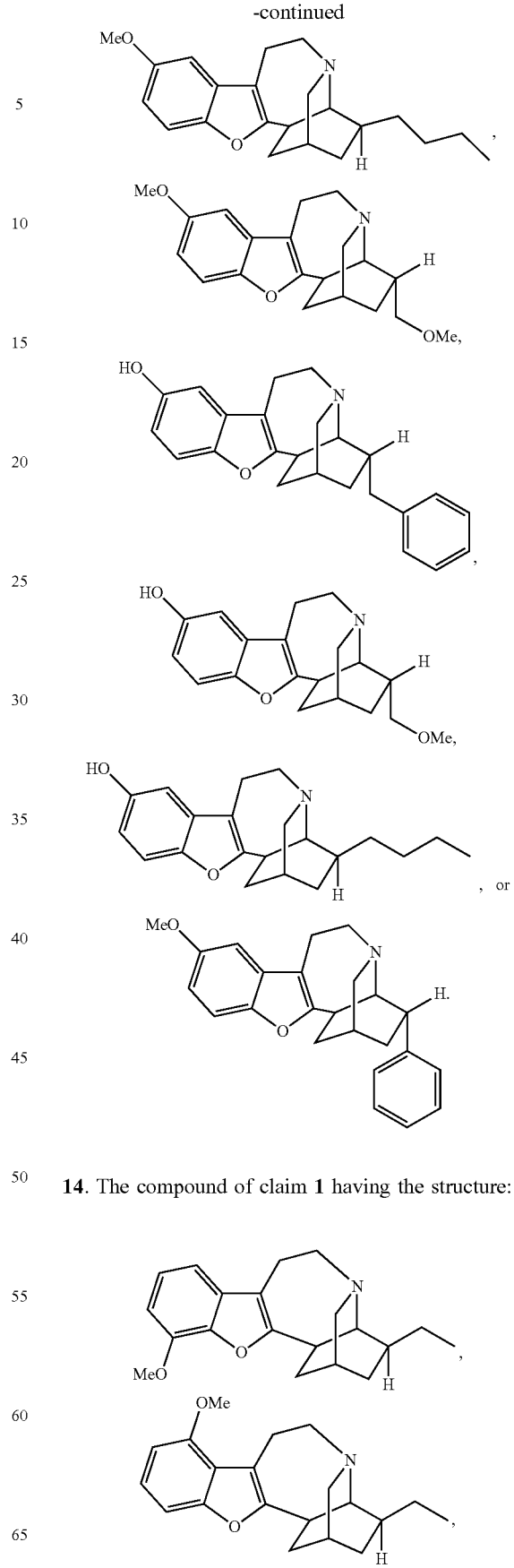
14. The compound of claim 1 having the structure:
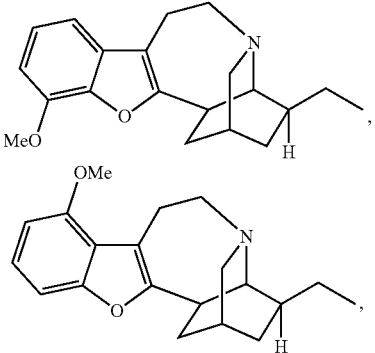

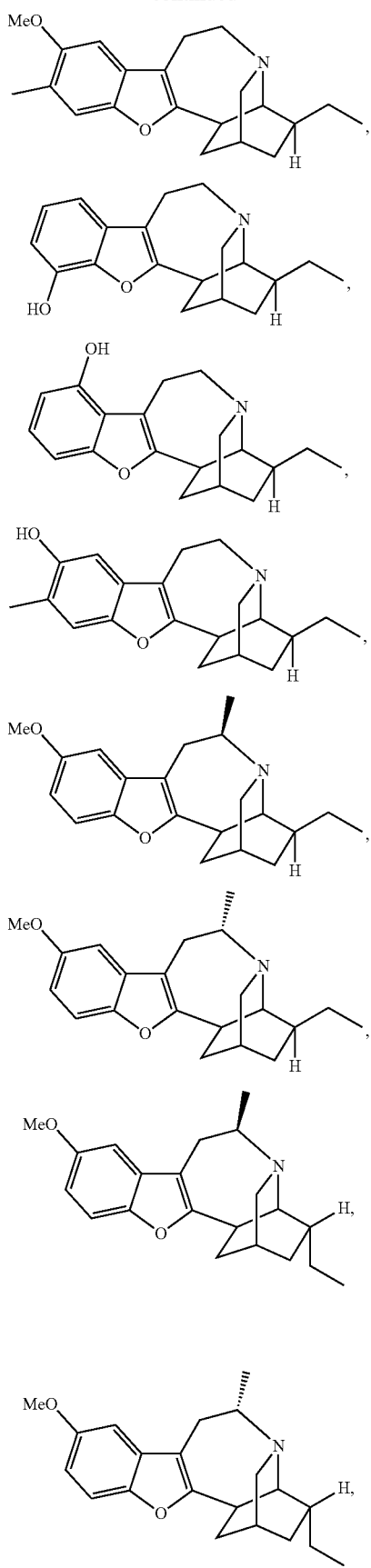
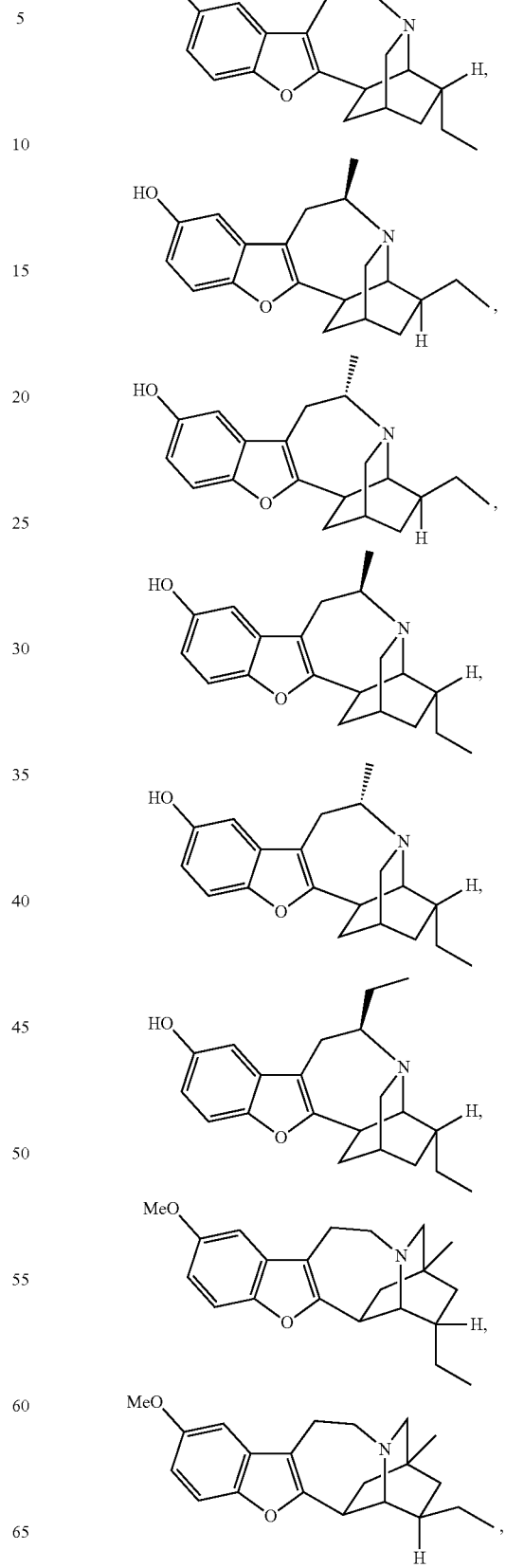

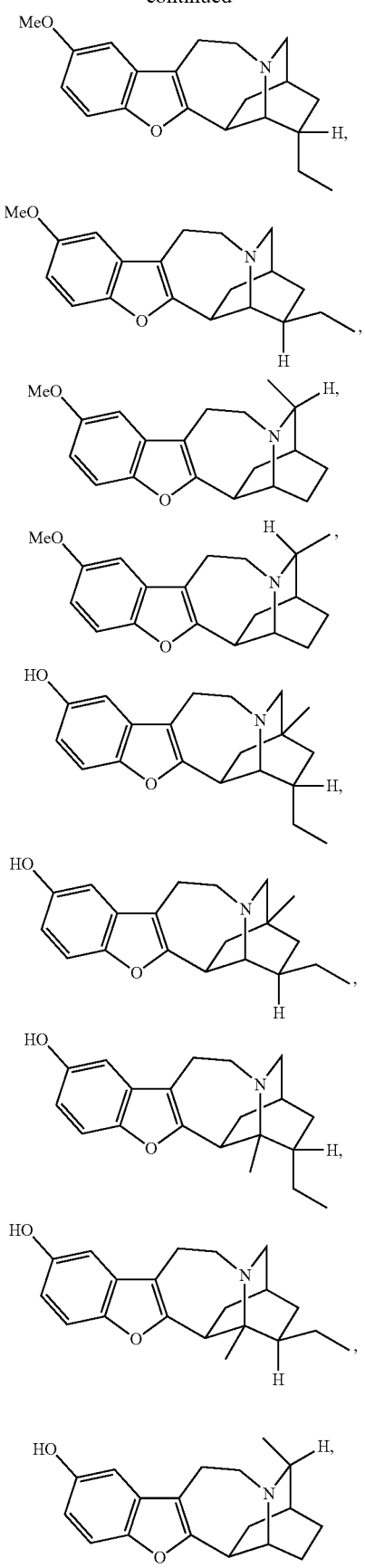

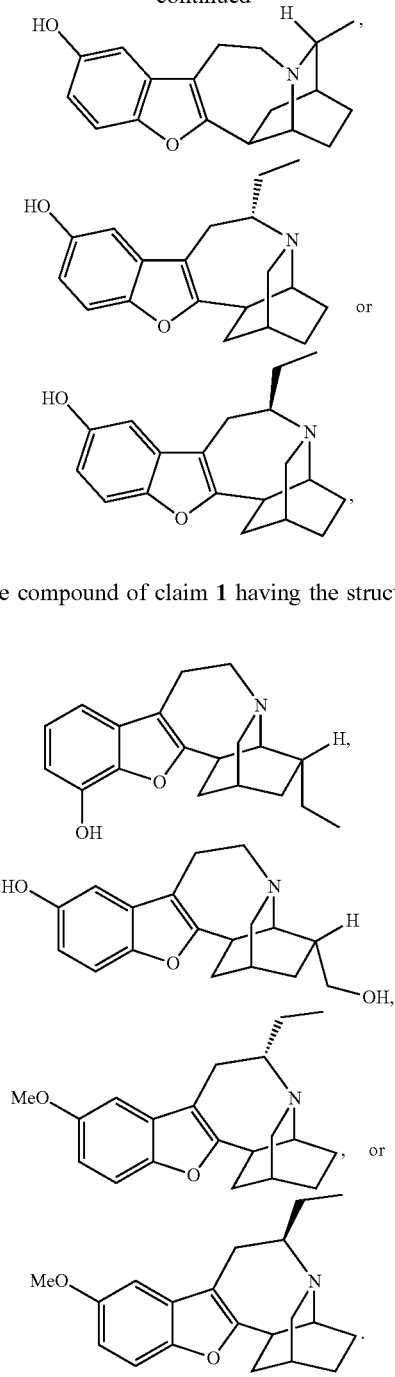

15. The compound of claim 1 having the structure:

16. The compound of claim 1,
wherein
Y$_1$ is H or -(alkyl);
Y$_2$ is H or -(alkyl);
Y$_3$ is H or -(alkyl);
Y$_4$ is H or -(alkyl);
Y$_5$ is H or -(alkyl);
R$_1$, R$_2$, R$_3$ and R$_4$ are each independently H, -(alkyl), -(alkenyl), (alkynyl), -(phenyl), -(heteroalkyl), -(hydroxyalkyl), benzyl, -(alkyl)-OH, -(alkyl)-O-(alkyl), —OH or —NH$_2$; and
R$_5$, R$_8$, R$_7$, R$_8$ are each independently —H, —CN, —CF$_3$, —OCF$_3$, -(alkyl), -(alkenyl), -(alkynyl), -(phenyl), -(heteroalkyl), -(hydroxyalkyl), —NH₂, —NH-(alkyl), —NH-(alkenyl), —NH-(alkynyl), —NH-(phenyl), —OH, —OAc, —CO₂H, —CO₂-(alkyl), —O—C(O)(alkyl), —O-(alkyl), —O-(alkenyl), —O-(alkynyl), —O-(phenyl), C(O)—NH₂, C(O)—NH-(alkyl), or C(O)—NH-(phenyl).

17. The compound of claim 1,
wherein
$Y_1$ is H;
$Y_2$ is -(alkyl), -(alkenyl), -(alkynyl), —($C_3$-$C_5$ cycloalkyl), -(haloalkyl), -(alkyl) -O-(alkyl) or -(alkyl)-($C_3$-$C_5$cycloalkyl);
$Y_3$ is H or -(alkyl);
$Y_4$ is H or -(alkyl);
$Y_5$ is H or -(alkyl);
$R_1$, $R_2$, $R_3$ and $R_4$ are each independently H, -(alkyl), -(alkenyl), (alkynyl), -(phenyl), -(heteroalkyl), -(hydroxyalkyl), benzyl, -(alkyl)-OH, -(alkyl)-O-(alkyl), —OH or —NH₂; and
$R_5$, $R_6$, $R_7$, $R_8$ are each independently —H, —CN, —CF₃, —OCF₃, -(alkyl), -(alkenyl), -(alkynyl), -(phenyl), -(heteroalkyl), -(hydroxyalkyl), —NH₂, —NH-(alkyl), —NH-(alkenyl), —NH-(alkynyl), —NH-(phenyl), —OH, —OAc, —CO₂H, —CO₂-(alkyl), —O—C(O)(alkyl), —O-(alkyl), —O-(alkenyl), —O-(alkynyl), —O-(phenyl), C(O)—NH₂, C(O)—NH-(alkyl), or C(O)—NH-(phenyl).

18. A pharmaceutical composition comprising the compound of claim 1 and a pharmaceutically acceptable carrier.

19. A process for producing the compound of claim 1 having the structure:

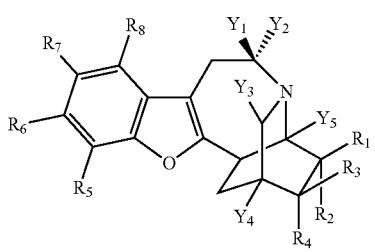

comprising
(a) contacting the compound having the structure:

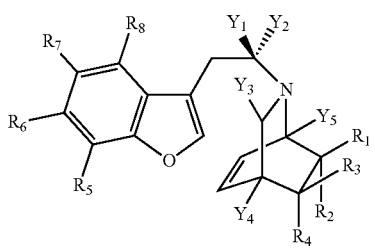

with a nickel (0) catalyst in the presence of an N-heterocyclic carbene in a suitable solvent to produce a compound having the structure:

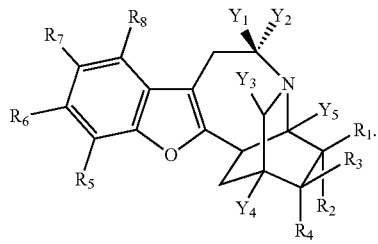

20. The compound of claim 1 having the structure:

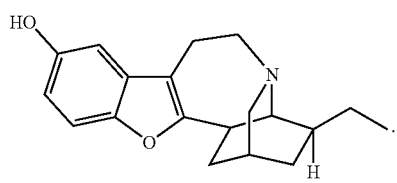 [SMILES: CCC1CC2CC3c4oc5ccc(O)cc5c4CCN(C2)C13]

21. The compound of claim 1 having the structure:

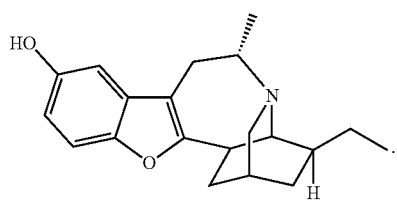 [SMILES: CCC1CC2CC3c4oc5ccc(O)cc5c4C[C@H](C)N(C2)C13]

22. The compound of claim 1 having the structure:

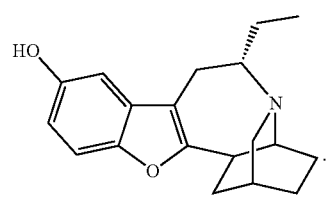 [SMILES: CC[C@H]1Cc2c(oc3ccc(O)cc23)C2CC3CCC2N1C3]

23. The compound of claim 1 having the structure:

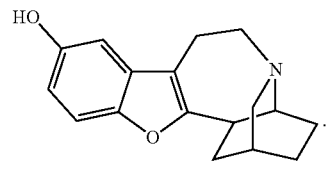 [SMILES: Oc1ccc2oc3c(c2c1)CCN1CC2CCC1C3C2]

24. The compound of claim 1 having the structure:

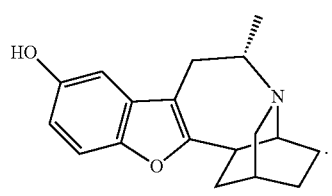 [SMILES: C[C@H]1Cc2c(oc3ccc(O)cc23)C2CC3CCC2N1C3]

25. The compound of claim 1 having the structure:
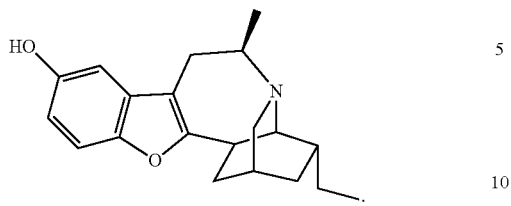
26. The compound of claim 1 having the structure:
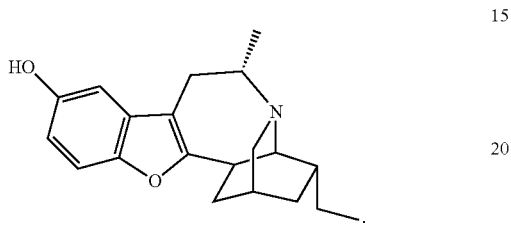
27. The compound of claim 10, wherein
$R_5$, $R_6$ and $R_8$ are each —H and $R_7$ is —OH;
$Y_1$ is H, —CH$_3$ or —CH$_2$CH$_3$; and
$Y_2$ is H, —CH$_3$ or —CH$_2$CH$_3$.
* * * * *